(12) United States Patent
Chen et al.

(10) Patent No.: US 10,035,792 B2
(45) Date of Patent: Jul. 31, 2018

(54) RESORCINOL DERIVATIVE AS HSP90 INHIBITOR

(71) Applicant: Chia Tai Tianqing Pharmaceutical Group Co., Ltd., Lianyungang (CN)

(72) Inventors: Shuhui Chen, Shanghai (CN); Charles Z. Ding, Shanghai (CN); Xiaobing Yan, Shanghai (CN); Wei Huang, Shanghai (CN); Guoping Hu, Shanghai (CN); Jian Li, Shanghai (CN); Xiquan Zhang, Lianyungang (CN); Ling Yang, Lianyungang (CN); Hongjiang Xu, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 0 days.

(21) Appl. No.: 15/545,598

(22) PCT Filed: Jan. 22, 2016

(86) PCT No.: PCT/CN2016/071697
§ 371 (c)(1),
(2) Date: Jul. 21, 2017

(87) PCT Pub. No.: WO2016/116061
PCT Pub. Date: Jul. 28, 2016

(65) Prior Publication Data
US 2018/0009794 A1    Jan. 11, 2018

(30) Foreign Application Priority Data

Jan. 22, 2015 (CN) ............ 2015 1 0033985
Jan. 12, 2016 (CN) ............ 2016 1 0019396
Jan. 19, 2016 (CN) ............ 2016 1 0033498

(51) Int. Cl.
| | | |
|---|---|---|
| *C07D 413/04* | (2006.01) | |
| *C07D 487/08* | (2006.01) | |
| *C07D 495/04* | (2006.01) | |
| *C07D 487/04* | (2006.01) | |
| *C07D 417/04* | (2006.01) | |
| *C07D 471/04* | (2006.01) | |
| *C07D 413/14* | (2006.01) | |

(52) U.S. Cl.
CPC ......... *C07D 413/04* (2013.01); *C07D 413/14* (2013.01); *C07D 417/04* (2013.01); *C07D 471/04* (2013.01); *C07D 487/04* (2013.01); *C07D 487/08* (2013.01); *C07D 495/04* (2013.01)

(58) Field of Classification Search
CPC .. C07D 413/04; C07D 487/08; C07D 495/04; C07D 513/04; C07D 471/04; C07D 417/04; C07D 413/14; A61K 31/4725; A61K 31/422; A61K 31/4365; A61K 31/437
See application file for complete search history.

(56) References Cited

U.S. PATENT DOCUMENTS

| | | |
|---|---|---|
| 7,705,027 B2 | 4/2010 | Drysdale |
| 8,450,310 B2 | 5/2013 | Drysdale |
| 8,507,480 B2 | 8/2013 | Drysdale |
| 2015/0209362 A1 | 7/2015 | Garcia-Echeverria et al. |

FOREIGN PATENT DOCUMENTS

| | | | |
|---|---|---|---|
| CN | 1771235 A | 5/2006 | |
| CN | 102227227 A | 10/2011 | |
| WO | WO 2006/055760 | * 5/2006 | ........... C07D 249/12 |
| WO | WO 2007021966 A1 | 2/2007 | |

OTHER PUBLICATIONS

West, Anthony R., Solid State Chemistry and Its Applications, Wiley, New York, 1988, 358.*
International Search Report corresponding to International Patent Application No. PCT/CN2016/071697, dated Apr. 28, 2016, 3 pages.

* cited by examiner

*Primary Examiner* — Erich A Leeser
(74) *Attorney, Agent, or Firm* — Nixon Peabody LLP

(57) ABSTRACT

The present invention relates to a compound represented by formula (I) of a resorcinol derivative as an HSP90 inhibitor or pharmaceutically accepted salts thereof. The compound in the present invention has the activity of inhibiting heat shock protein HSP90. Therefore, the compound in the present invention is used to treat proliferative diseases such as cancer and neurodegenerative diseases. The present invention further provides the compounds and preparation methods for pharmaceutical compositions comprising the compounds, a method for treating diseases, and pharmaceutical compositions comprising the compounds.

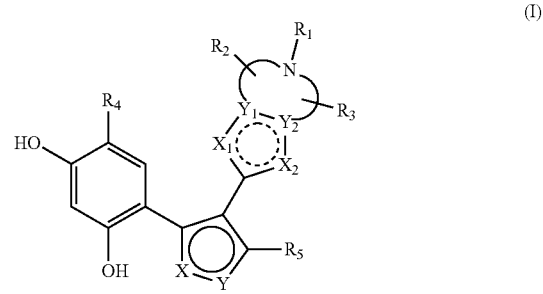

20 Claims, No Drawings

RESORCINOL DERIVATIVE AS HSP90 INHIBITOR

FIELD OF THE INVENTION

The present invention relates to novel resorcinol derivatives, in particular a compound represented by formula (I), and relates to preparation methods thereof, pharmaceutical compositions and the use thereof in preparing an antitumor drug and for treating neurodegenerative diseases.

BACKGROUND OF THE INVENTION

Currently, targeted therapies for cancer treatments are based on the identification of a specific protein contributing to tumor progression, and the identification of a specific agent that is capable of antagonizing the effect of the above proteins. The pharmaceutical industry mostly concentrates efforts on a very limited number of well-validated protein targets. Common defect lies in that the occurrences of drug-resistance mutations are often found in cancer patients treated with these specific inhibitors. Recently, a general view is that simultaneously blocking signaling pathways involving cancer progression may be expected to contribute to a better anti-tumor effect, and reduce the likelihood of drug-resistance development. HSP90 belongs to a small family of proteins that generally have a very specific C-mode (Bergerat fold) linked to adenosine triphosphate (GHKL, derived from DNA gyrase, HSP90, histidine kinase, mutL). HSP90 is one of the most abundant proteins in cells and is essential for the viability of eukaryotes. Human cells contain four HSP90 isotypes: cytosolic β-isotype constitutively expressed, inducible α-form, GRP94/gp96 in endoplasmic reticulum, and TRAP1/HSP75 in mitochondria. The α-form and β-form show 85% sequence homology HSP90 is a key component of chaperoning structure, which catalyzes the folding of proteins referred to as HSP90 clients and control the quality thereof in normal cells and under stress conditions. The molecular chaperone activity, which is strictly dependent on the activity of adenosine triphosphatase, is closely modulated by the binding of other regulatory co-chaperones.

There is strong evidence that, in the case of, for example, cancer or other proliferative diseases, HSP90 becomes critical due to mutations or overexpression of particular oncogenes, or also due to tumors often having overloaded, misfolded proteins (which leads to an increased demand for the molecular chaperone function).

HSP90 is a homodimer consisting of three main domains in structure: a very conserved N-terminal domain, an intermediate domain of the triphosphatase adenylate domain and a C-terminal domain. N-terminal and C-terminal domains can bind to adenosine triphosphate. Most of the known inhibitors, such as geldanamycin, Radicicol, diarylpyrazole and purine derivatives, exhibit competitive binding to the N-terminal adenosine triphosphate binding site with adenosine triphosphate, while novobiocin is a prototype of an inhibitor that binds to the C-terminal pocket.

At present, HSP90 clients reported are increasing (Jolly et al., J. Natl. Cancer Inst. 92; 1564-1572(2000)), belonging to kinase family (Her2, B-RAF V600E, bcr-Abl, FIt3, NPM-ALK, Akt, Npm-Alk, ZAP-70), transcription factor (p53, HIF), telomerase and other molecular chaperones, most of which are closely related to the development of cancer. The ability of HSP90 to inhibit damaged folding or stabilize the client proteins thereof leads to protease-based degradation of these unfolded proteins. The degradation of these client proteins is often used as the indication of HSP90 inhibition, and the typical application is that in Her2 overexpressing cells, such as BT474 breast cancer cells, Her2 is degraded after treatment with compounds.

It has been shown that the natural compound geldanamycin can really block the proliferation of many tumor cells by the abilities of competitively binding to the N-terminal adenosine triphosphate binding site and inhibiting the activity of HSP90 adenosine triphosphatase, which initially caused a substantial amount of researches on the field of HSP90. Surprisingly, this compound is inactive in normal cells, and this may be because HSP90 is present in an active complex (with high affinity to geldanamycin) only existed in tumor cells (Kamal et al., Nature 425, 407-410 (2003)). Another possible reason for the selective sensitivity to tumors is tumor retention exhibited in many HSP90 inhibitors.

A large number of clinical evaluations are ongoing to tanespimycin (17-AAG), a semi-synthetic derivative of geldanamycin (GDA), and other related derivatives (alvespimycin, 17-DMAG, IPI-504), but the effects thereof appear to be limited by a number of factors: complex preparation, dependence on metabolism to produce active metabolites, lack of enrichment of patients, and hepatotoxicity possibly associated with quinone moiety. This leads to a large number of efforts to identify second-generation HSP90 inhibitors with better drug-likeness characters and better tolerability. This results in the identification of purine derivatives and aryl-resorcinol derivatives.

The main cause of neurodegenerative diseases, such as Alzheimer's disease, Parkinson's disease, Huntington's disease and Prion disease, is that the accumulation of misfolded proteins leads to plaque formation. These misfolded proteins rely on molecular chaperones (HSP70, HSP40, etc.) for re-maturation, depolymerization and re-solubilization of protein aggregate. Heat shock protein has been shown to provide this function in a variety of cell culture models. HSF1 can induce HSP, and HSF1 is closely regulated by HSP90 in normal cells. It has been shown that HSP90 inhibitors, such as geldanamycin and 17-AAG derivatives, can disrupt this interaction and lead to HSP induction, resulting in neuroprotective activity as well as re-solubilization and depolymerization of misfolded proteins. HSP90 overexpression can significantly reduce the accumulation of misfolded proteins, and the accumulation of misfolded proteins is the cause of Alzheimer's disease. In fact, it has been shown that there is an inverse correlation between aggregated tau and HSP70/90 levels. Abnormal tau aggregation can be reduced by overexpression of HSP70, HSP27 and HSP40 (by degradation), which is triggered by inhibition of HSP90. Based on the in vivo effect of GDA on neurotoxicity induced by 1-methyl-4-phenyl-1,2,3,6-tetrahydropyridine (MPTP) in mouse models of Parkinson's disease, HSP90 inhibitors were used to treat Parkinson's disease. GDA protects neurons from MPTP-induced toxicity, which is closely related to elevated levels of HSP70. In addition, it has also been shown that HSP90 overexpression can significantly reduce the accumulation of misfolded proteins, which is the cause of motor injury, multiple sclerosis, spinal and bulbar muscular atrophy and other diseases.

GB1,406,345 disclosed a 4,6-disubstituted resorcinol compound having pharmacological activities. Other patent applications describe phenyl-heterocyclic compounds as HSP90 inhibitors, all of which are characterized by having a specific substitution mode of five-membered heterocycles, such as WO2006/101052 of Nippon Kayaku Kabushiki Kaisha; WO2005/000300, WO2004/072051 and WO2004/

056782 of Vernalis; WO2003/055860 of Ribotargets; WO2008/097640 of Synta Pharmaceuticals; and WO2005/063222 of Kyowa Hakko Kogyo.

WO2004072051 relates to a class of HSP90 inhibitors, including Luminespib:

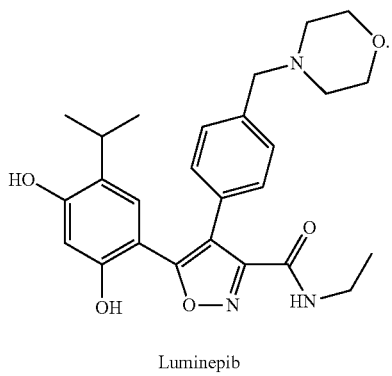 [SMILES: CCNC(=O)c1noc(-c2cc(C(C)C)c(O)cc2O)c1-c1ccc(CN2CCOCC2)cc1]

Luminepib

WO2006055760A1 reported some compounds, such as,

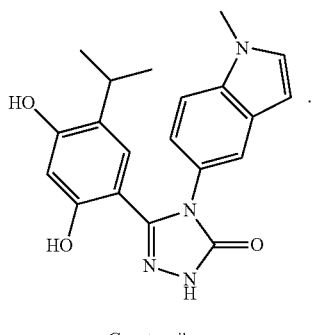

Ganetespib

CN1771235A disclosed some compounds, such as,

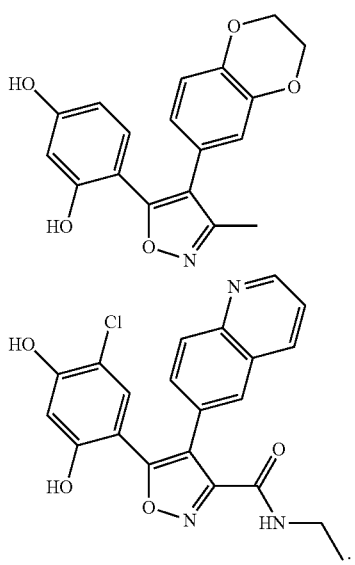

These compounds are not desirable in terms of efficacy, pharmacokinetics, water solubility, druggability and the like.

Despite the above developments, there is still a need to develop more effective HSP90 inhibitors with low side effect.

SUMMARY OF THE INVENTION

An object of the present invention is to provide a compound represented by formula (I), or a pharmaceutically acceptable salt or hydrate thereof,

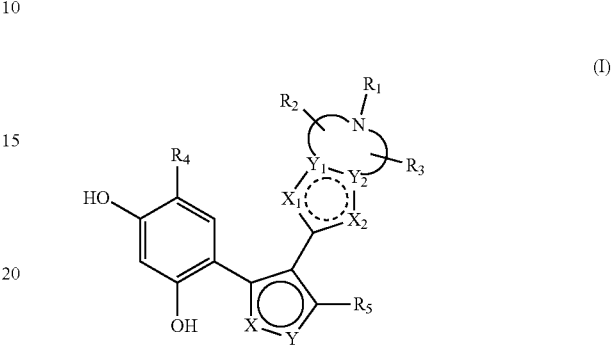

wherein:

X and Y are each independently selected from N, O or S; preferably, X is selected from N, O or S, and Y is selected from N or O;

$X_1$, $X_2$, $Y_1$, $Y_2$ and the carbon atom linking $X_1$ and $X_2$ together form a 5- to 7-membered aromatic ring, aliphatic saturated ring or aliphatic unsaturated ring; preferably, $X_1$, $X_2$, $Y_1$, $Y_2$ and the carbon atom linking $X_1$ and $X_2$ together form a 5- to 6-membered aromatic ring, aliphatic saturated ring or aliphatic unsaturated ring;

$X_1$ and $X_2$ are each independently selected from C, O, S, N, —C=C—, —C=N—; and, C in $X_1$ or $X_2$ may be unsubstituted or may be substituted with $R_{01}$ or $R_{02}$.

$R_{01}$ and $R_{02}$ are each independently selected from halogen, CN, OH, SH, $NH_2$, CHO, COOH, $C_{1-10}$ alkyl, N—$C_{1-10}$ alkylamino, N,N-di($C_{1-10}$ alkyl)amino, $C_{1-10}$ alkoxy, $C_{1-10}$ alkanoyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ cycloalkoxy, $C_{3-10}$ cycloalkyl acyl, $C_{3-10}$ cycloalkoxycarbonyl, $C_{3-10}$ cycloalkylsulfonyl, $C_{3-10}$ cycloalkylsulfinyl, or $C_{1-10}$ alkyl substituted with $C_{3-10}$ cycloalkyl;

$Y_1$ and $Y_2$ are each independently selected from C or N, and both of $Y_1$ and $Y_2$ are preferably C; two substituents on $Y_1$ and $Y_2$ are linked together to form a five-, six- or seven-membered nitrogen-containing saturated hetero ring or aromatic hetero ring having substituents $R_1$, $R_2$ and $R_3$;

$R_1$, $R_2$ and $R_3$ are each independently selected from hydrogen, $C_{1-10}$ alkyl, hydroxyl $C_{1-10}$ alkyl, $C_{1-6}$ alkoxy-$C_{1-6}$ alkyl, halo $C_{1-10}$ alkyl, $C_{1-6}$ alkylsulfonyl-$C_{1-6}$ alkyl, $C_{1-6}$ alkylamido-$C_{1-6}$ alkyl, N, N-di($C_{1-6}$ alkyl)aminoacyl-$C_{1-6}$ alkyl, N, N-di($C_{1-6}$ alkyl)amino-$C_{1-6}$ alkanoyl, morpholinyl-$C_{1-6}$ alkanoyl, N—$C_{1-10}$ alkylamino, N,N-di($C_{1-10}$ alkyl)amino, $C_{1-10}$ alkoxy, $C_{1-10}$ alkanoyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ cycloalkyloxy, $C_{3-10}$ cycloalkyl acyl, $C_{3-10}$ cycloalkoxycarbonyl, $C_{3-10}$ cycloalkylsulfonyl, $C_{3-10}$ cycloalkylsulfinyl, or $C_{3-10}$ cycloalkyl-$C_{1-5}$ alkyl, or substituents of $R_2$ and $R_3$ are linked with each other by a covalent bond to form a five-, six- or seven-membered saturated ring with a substituent $R_{03}$ or without substituents; preferably, $R_1$, $R_2$ and $R_3$ are each independently selected from hydrogen, $C_{1-10}$ alkyl, hydroxy $C_{1-10}$ alkyl, $C_{3-10}$ cycloalkyl, $C_{1-6}$ alkoxy-$C_{1-6}$ alkyl, halo $C_{1-10}$ alkyl, $C_{1-6}$ alkylsulfonyl-$C_{1-6}$ alkyl, $C_{1-6}$ alkylamido-$C_{1-6}$ alkyl, N,N-di($C_{1-6}$ alkyl)aminoacyl-$C_{1-6}$ alkyl, N, N-di($C_{1-6}$ alkyl)amino-$C_{1-6}$ alkanoyl, morpholinyl-$C_{1-6}$ alkanoyl, or $C_{3-10}$ cycloalkyl-$C_{1-5}$ alkyl, or substituents of $R_2$ and $R_3$ are linked with each other by a covalent bond to form a five-, six- or seven-membered saturated ring with a substituent $R_{03}$ or without substituents; more preferably, $R_1$, $R_2$ and $R_3$ are each independently selected from hydrogen, $C_{1-6}$ alkyl, hydroxy $C_{1-6}$ alkyl, $C_{3-10}$ cycloalkyl, $C_{1-4}$ alkoxy-$C_{1-4}$ alkyl, halo $C_{1-4}$ alkyl, $C_{1-4}$ alkylsulfonyl-$C_{1-4}$ alkyl, $C_{1-4}$ alkylamido-$C_{1-4}$ alkyl, N,N-di($C_{1-4}$ alkyl)aminoacyl-$C_{1-4}$ alkyl, N, N-di($C_{1-4}$ alkyl)amino-$C_{1-4}$ alkanoyl, morpholinyl-$C_{1-4}$ alkanoyl, or $C_{3-6}$ cycloalkyl-$C_{1-4}$ alkyl, or substituents of $R_2$ and $R_3$ are linked with each other by a covalent bond to form a five-, six- or seven-membered saturated ring with a substituent $R_{03}$ or without substituents; most preferably, $R_1$ is selected from hydrogen, $C_{1-6}$ alkyl, hydroxy $C_{1-6}$ alkyl, $C_{3-10}$ cycloalkyl, $C_{1-4}$ alkoxy-$C_{1-4}$ alkyl, halo $C_{1-4}$ alkyl, $C_{1-4}$ alkylsulfonyl-$C_{1-4}$ alkyl, $C_{1-4}$ alkylamido-$C_{1-4}$ alkyl, N,N-di($C_{1-4}$ alkyl)aminoacyl-$C_{1-4}$ alkyl, N,N-di($C_{1-4}$ alkyl)amino-$C_{1-4}$ alkanoyl, or morpholinyl-$C_{1-4}$ alkanoyl, $R_2$ and $R_3$ are selected from hydrogen or methyl, or substituents of $R_2$ and $R_3$ are linked with each other by a covalent bond to form a five-, six- or seven-membered saturated ring without substituents;

$R_{03}$ is selected from $C_{1-6}$ alkyl or halogen;

$R_4$ is selected from H, halogen, $C_{1-6}$ alkyl, $C_{3-10}$ cycloalkoxy, phenyl substituted $C_{1-6}$ alkyl, phenyl substituted $C_{2-6}$ alkenyl, phenyl, $C_{1-6}$ alkyl substituted phenyl, or $C_{3-6}$ cycloalkyl; preferably, $R_4$ is selected from H, $C_{1-6}$ alkyl, phenyl substituted $C_{1-6}$ alkyl, halogen, or $C_{3-6}$ cycloalkyl; more preferably, $R_4$ is selected from $C_{1-4}$ alkyl, Cl, Br or cyclopropyl; most preferably, $R_4$ is selected from isopropyl.

$R_5$ is selected from H, cyano, carboxy, $C_{1-6}$ alkoxyacyl, $C_{1-7}$ alkylaminocarbonyl, halo $C_{1-6}$ alkylaminocarbonyl, $C_{1-6}$ alkoxy-$C_{1-6}$ alkylaminocarbonyl, N, N-di($C_{1-6}$ alkyl)amino-$C_{1-6}$ alkylaminocarbonyl, aminocarbonyl, hydroxy $C_{1-6}$ alkylaminocarbonyl, hydroxyl-substituted halo $C_{1-6}$ alkyl, or nitrile group-substituted amidino, or selected from $C_{3-10}$ cycloalkyl, $C_{3-10}$ cycloalkenyl or a 5- to 10-membered aromatic ring, which is optionally substituted with one or more $R_{05}$; wherein $R_{05}$ is selected from $C_{1-6}$ alkyl or $C_{3-10}$ cycloalkyl.

$R_5$ is preferably selected from cyano, $C_{1-6}$ alkylaminocarbonyl, halo $C_{1-4}$ alkylaminocarbonyl, $C_{1-4}$ alkoxy-$C_{1-4}$ alkylaminocarbonyl, N,N-di($C_{1-4}$ alkyl)amino-$C_{1-4}$ alkylaminocarbonyl, aminocarbonyl, hydroxy $C_{1-4}$ alkylaminocarbonyl, hydroxyl-substituted halo $C_{1-4}$ alkyl, or nitrile group substituted amidino, or selected from a 5- to 6-membered nitrogen-containing heteroaromatic ring, which is optionally substituted with one or more $R_{05}$; wherein $R_{05}$ is selected from $C_{1-6}$ alkyl.

In one embodiment of the present invention, the above $R_5$ is selected from

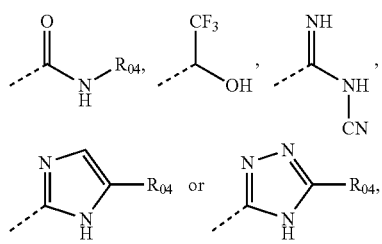

wherein $R_{04}$ is selected from H, $C_{1-6}$ alkyl, halo $C_{1-4}$ alkyl, $C_{1-4}$ alkoxy-$C_{1-4}$ alkyl, N,N-di($C_{1-4}$ alkyl)amino-$C_{1-4}$ alkyl, or hydroxy $C_{1-4}$ alkyl.

In one embodiment of the present invention, the above

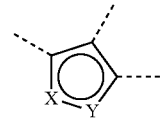

is selected from

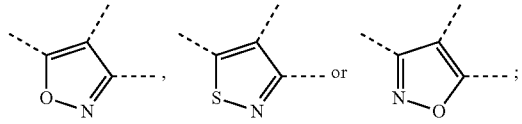

and other variables are defined as those in formula (I).

In one embodiment of the present invention, the above

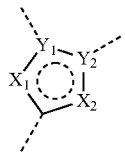

is selected from

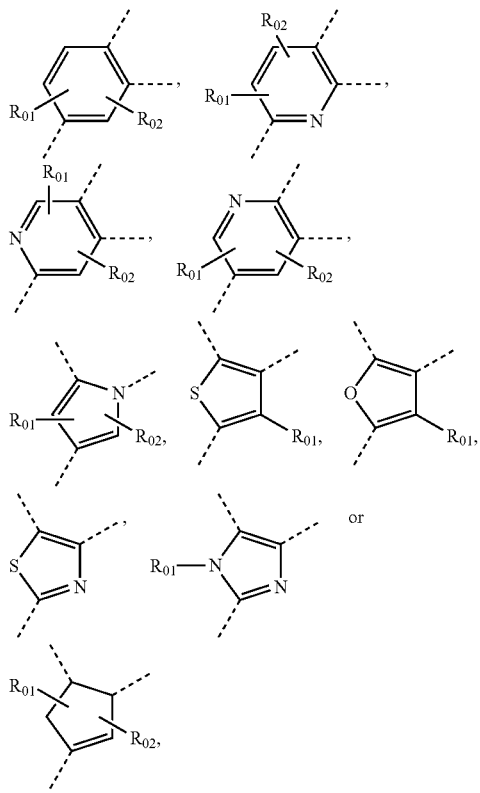

wherein $R_{01}$ and $R_{02}$ are each independently selected from H, halogen, $C_{1-10}$ alkyl, $C_{3-10}$ cycloalkyl, $C_{1-10}$ alkyl substituted with $C_{3-10}$ cycloalkyl; and other variables are defined as those in formula (I).

In one embodiment of the present invention, the above

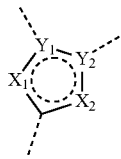

is selected from

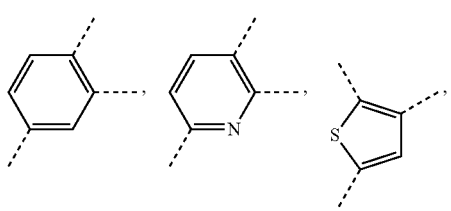

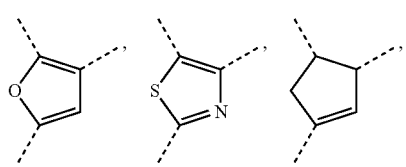

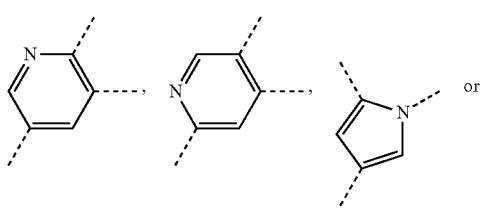

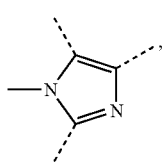

and other variables are defined as those in formula (I).

In one embodiment of the present invention, the above

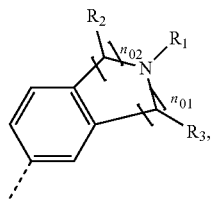

is selected from

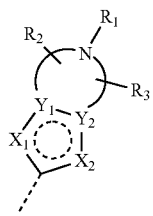

wherein $n_{01}$ and $n_{02}$ are selected from 0, 1, 2 or 3, and the sum of $n_{01}$ and $n_{02}$ is 2, 3 or 4; and, other variables are defined as those in formula (I), and $R_2$ and $R_3$ are not linked to form a ring.

In one embodiment of the present invention, the above

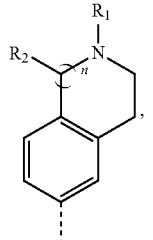

is selected from

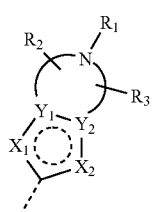

wherein n=1 or 2; and wherein other variables are defined as those in formula (I).

In one embodiment of the present invention, the above

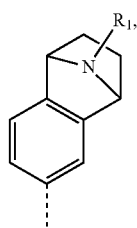

is selected from

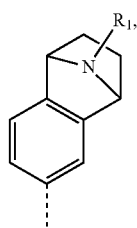

and other variables are defined as those in formula (I).

In one embodiment of the present invention, the above

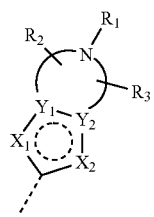

is selected from

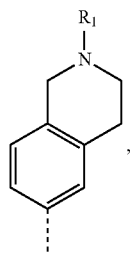 , 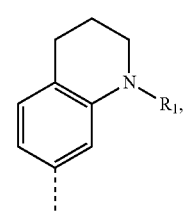 , 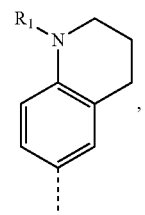 ,

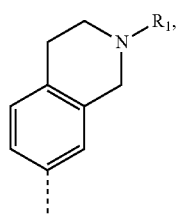 , 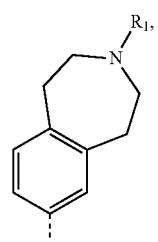 , 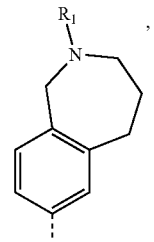 ,

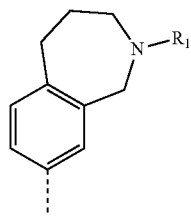 or  , and other variables are defined as those in formula (I).

In one embodiment of the present invention, the above

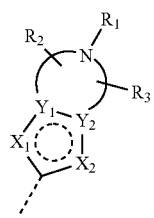

is selected from

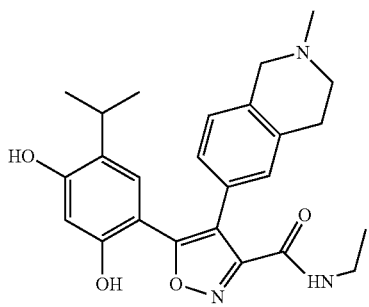

and other variables are defined as those in formula (I).

In one embodiment of the present invention, the above compound or a pharmaceutically acceptable salt or hydrate thereof is selected from the compound or the pharmaceutically acceptable salt or hydrate thereof of the following structural formulas:

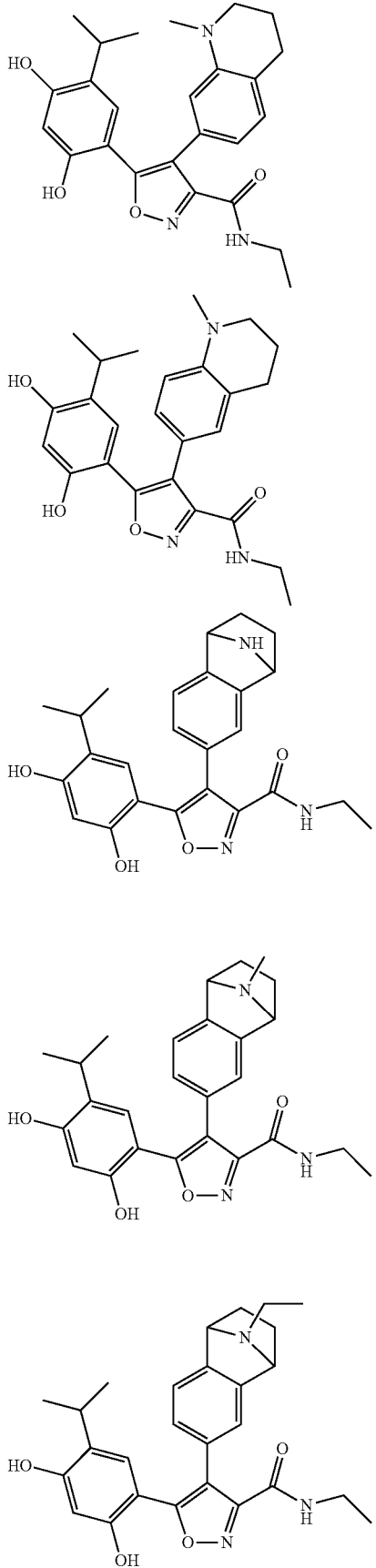

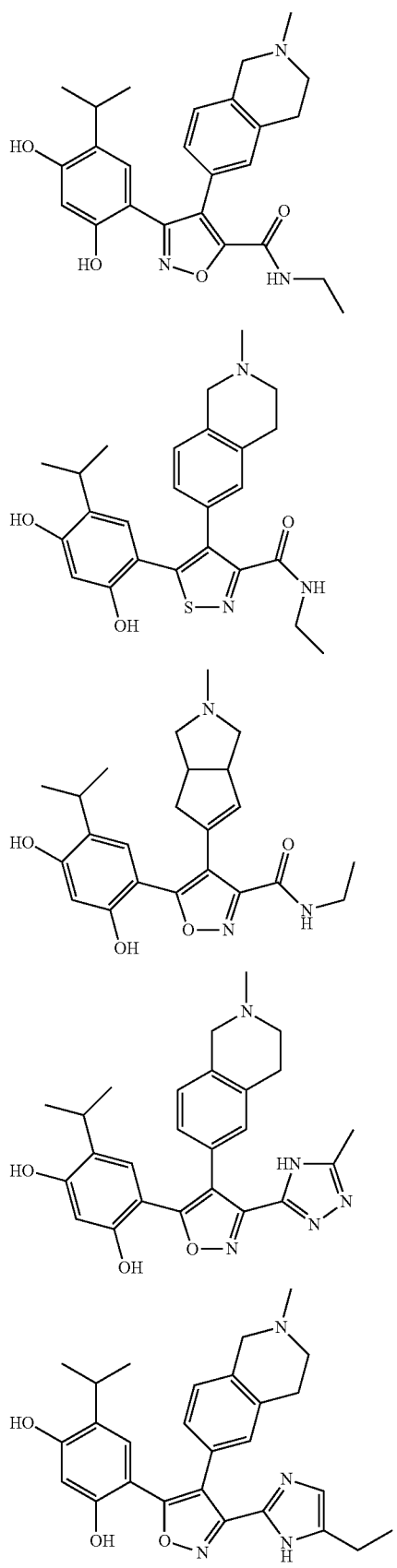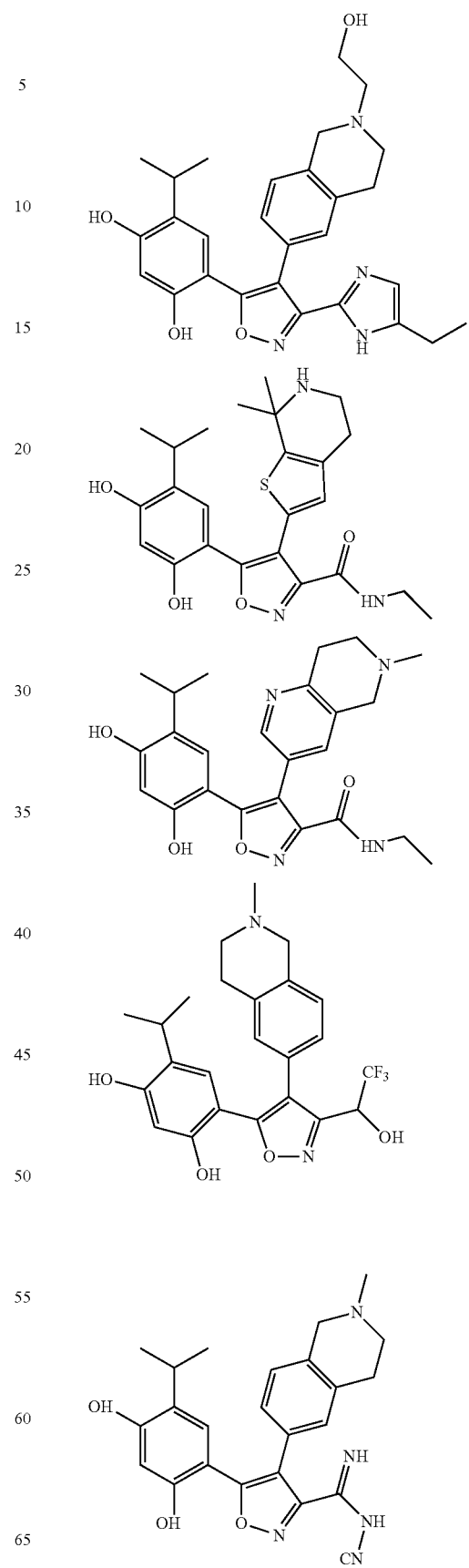

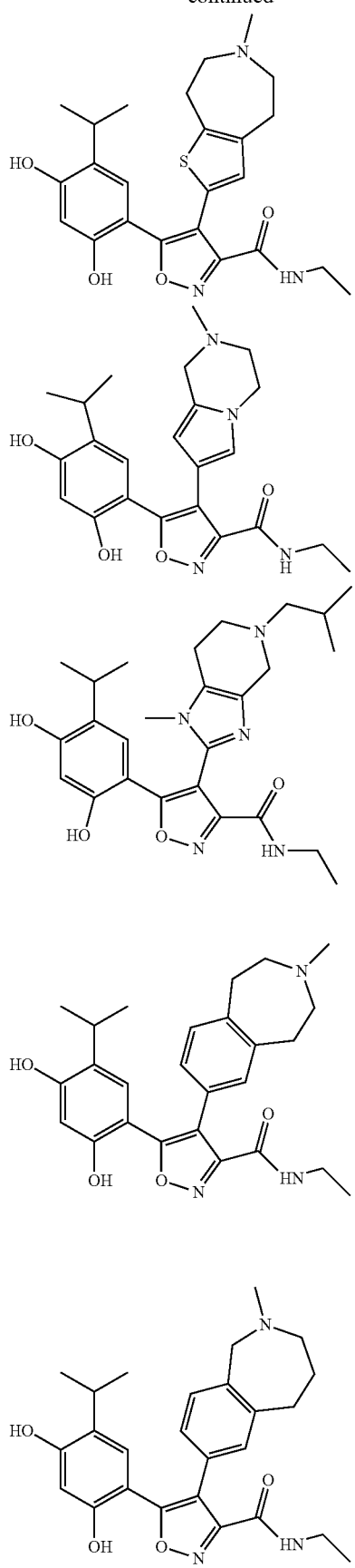
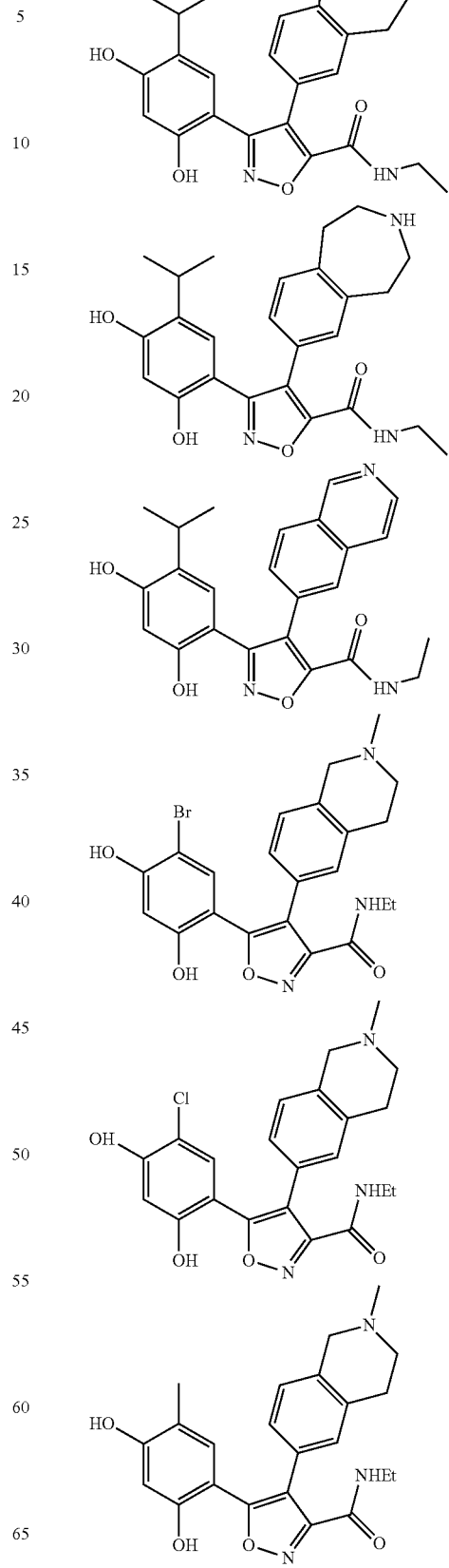

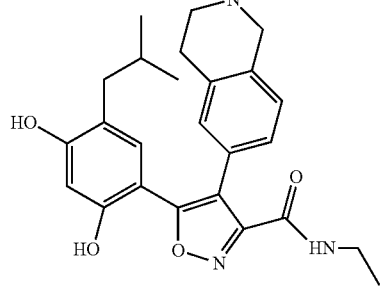
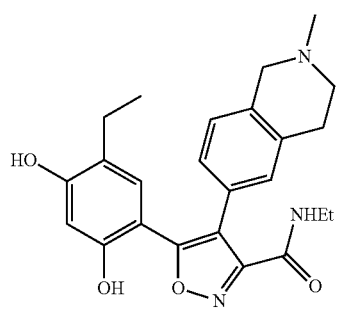
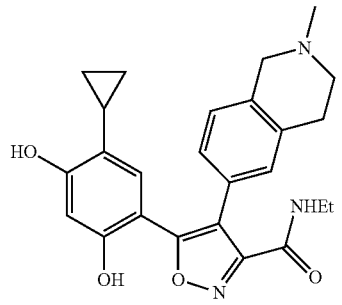
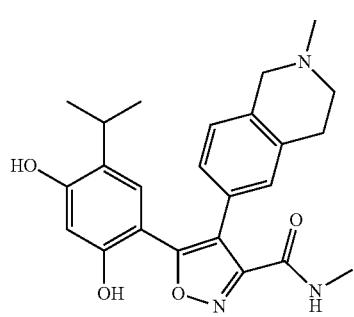
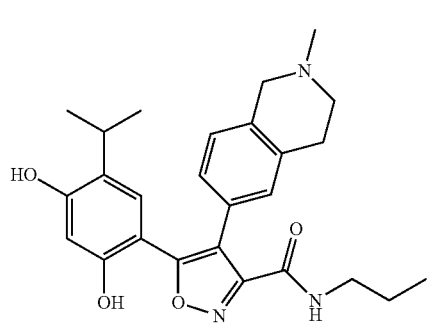
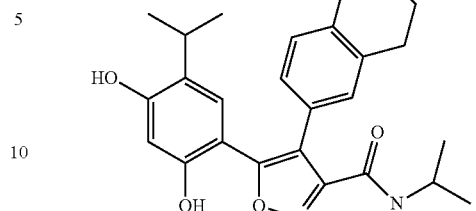
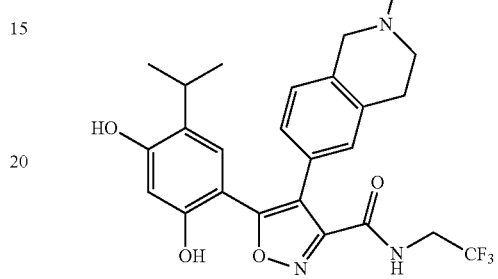
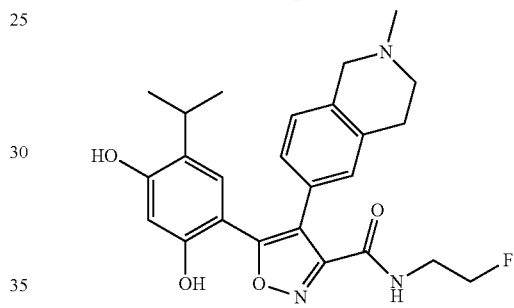
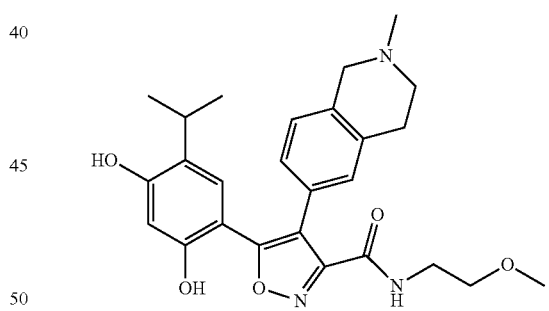
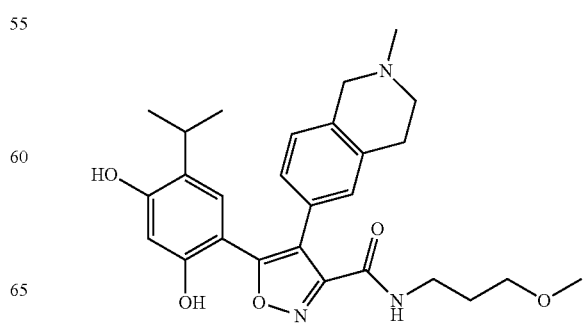

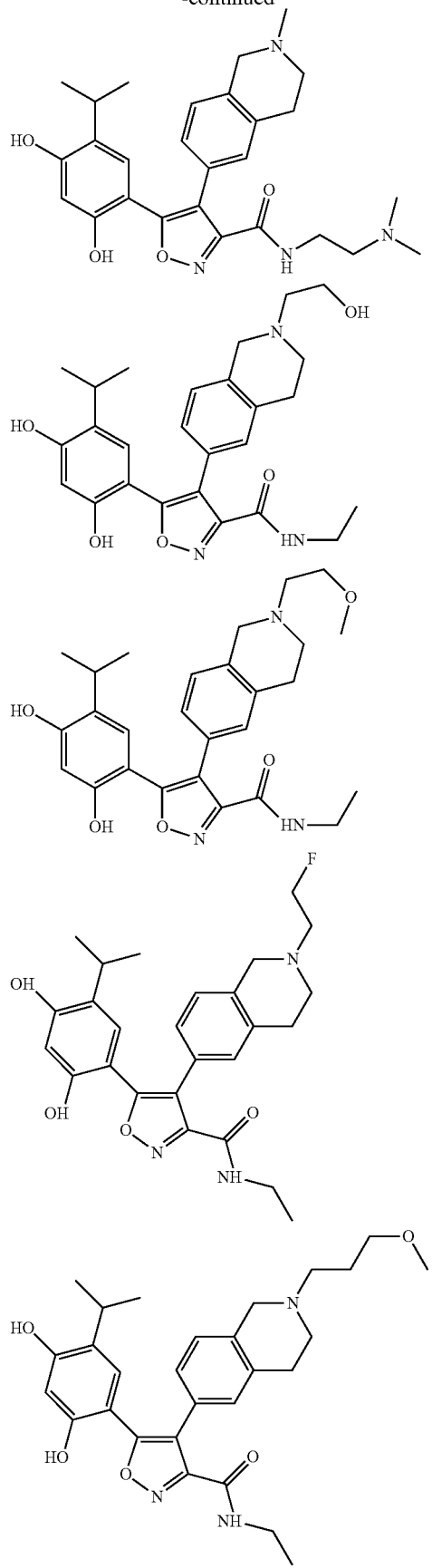
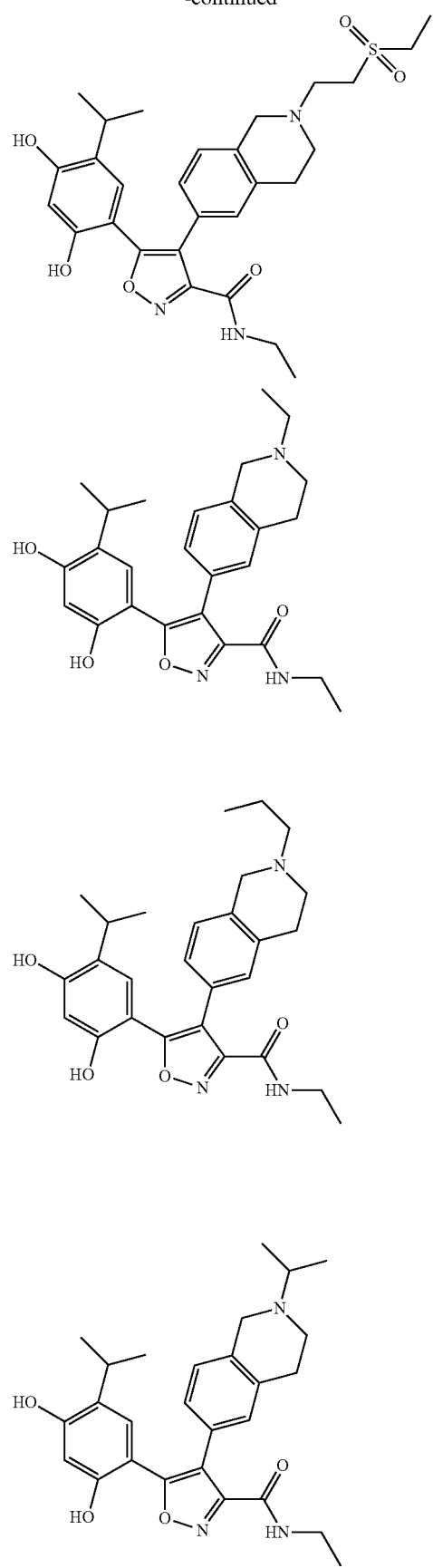

-continued
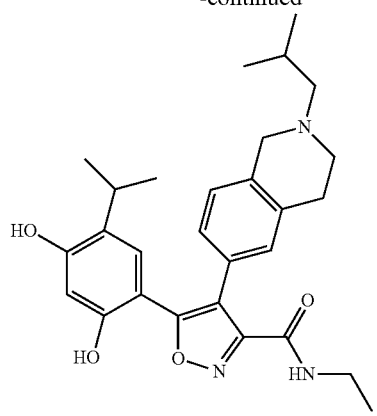
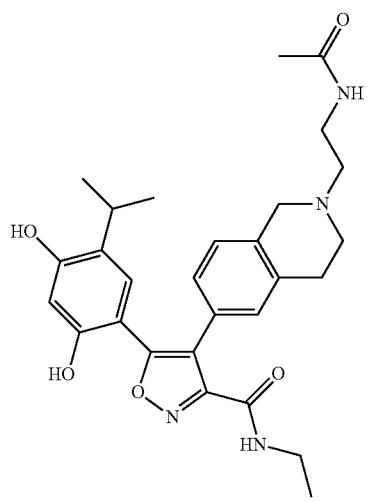
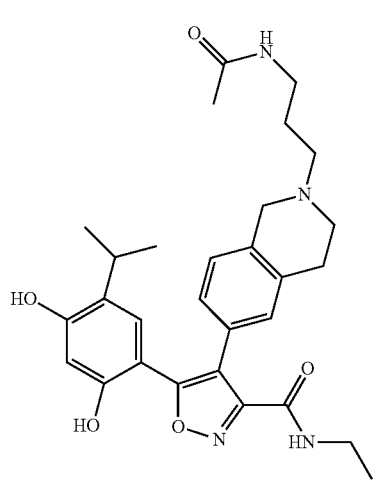
-continued
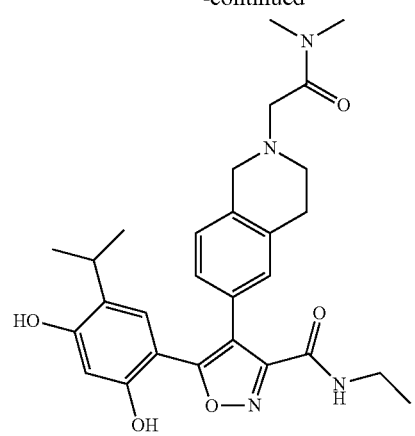
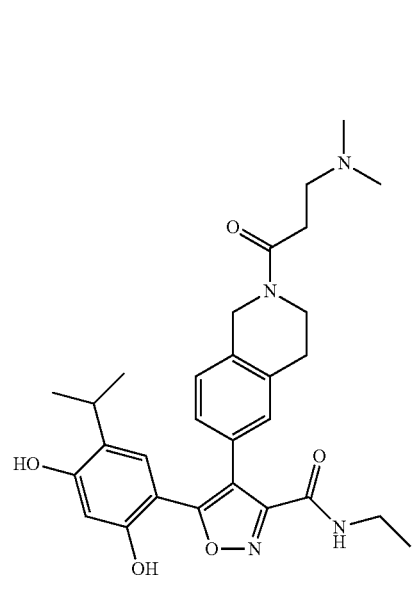

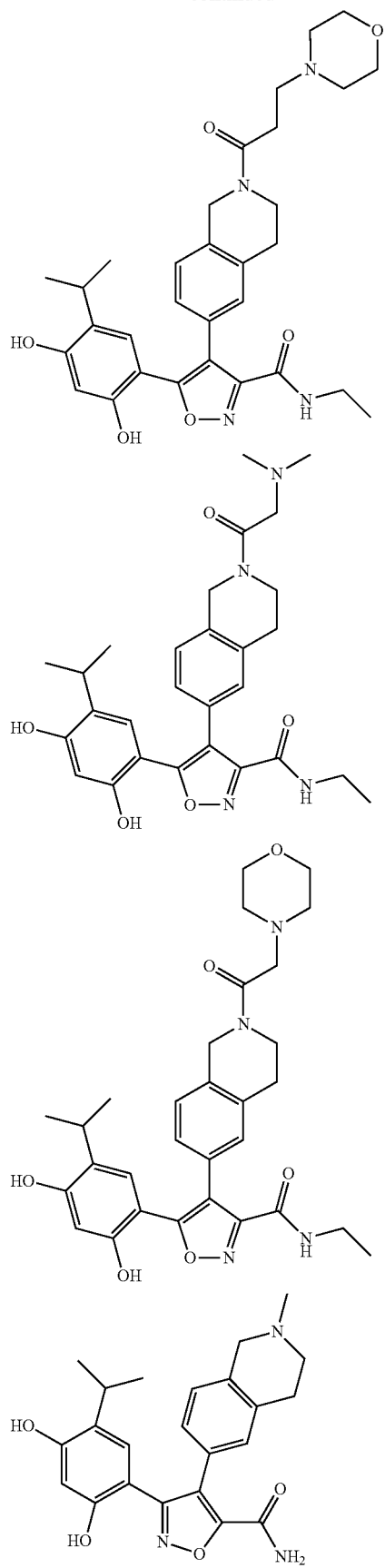
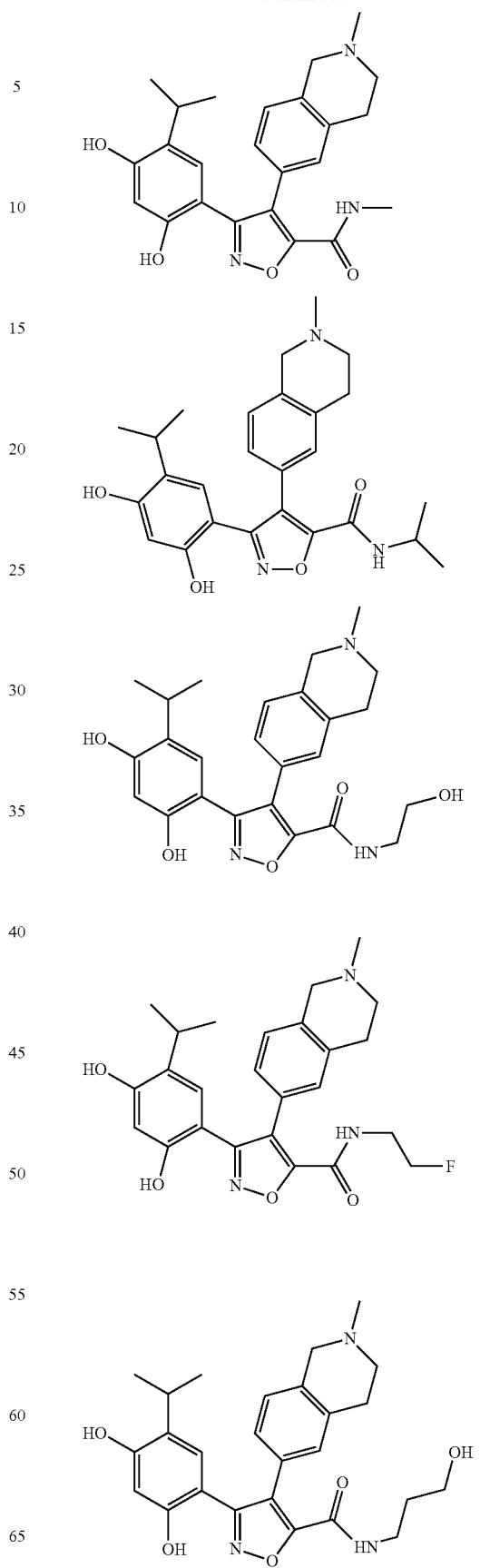

-continued

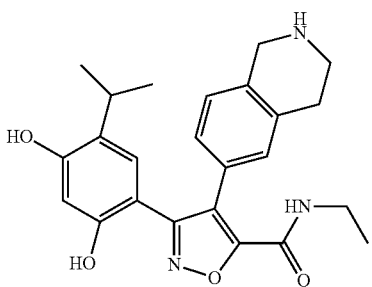
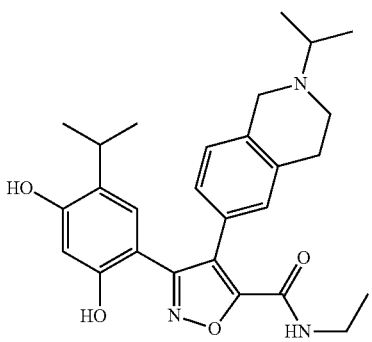
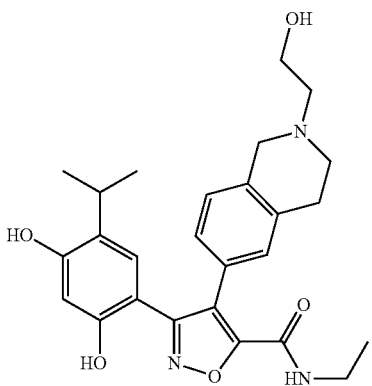
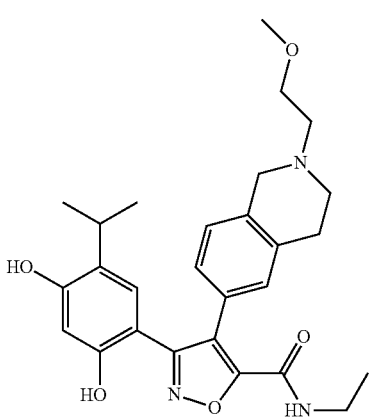

-continued

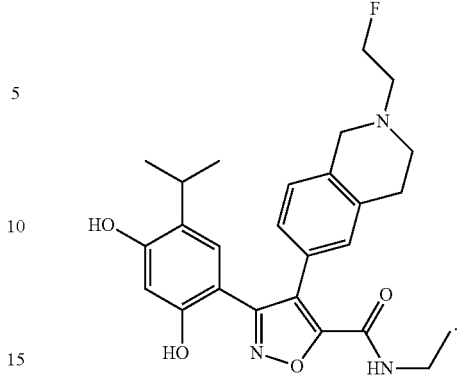

In one embodiment of the present invention, the above compound or the pharmaceutically acceptable salt thereof is selected from:

1) 5-(2,4-dihydroxyl-5-isopropylphenyl)-N-ethyl-4-(2-methyl-1,2,3,4-tetrahydroisoquinolin-6-yl)isoxazole-3-carboxamide or a pharmaceutically acceptable salt thereof;

2) 5-(2,4-dihydroxyl-5-isopropylphenyl)-N-ethyl-4-(1-methyl-1,2,3,4-tetrahydroquinolin-7-yl)isoxazole-3-carboxamide or a pharmaceutically acceptable salt thereof;

3) 5-(2,4-dihydroxyl-5-isopropylphenyl)-N-ethyl-4-(1-methyl-1,2,3,4-tetrahydroquinolin-6-yl)isoxazole-3-carboxamide or a pharmaceutically acceptable salt thereof;

4) 5-(2,4-dihydroxyl-5-isopropylphenyl)-N-ethyl-4-(1,2,3,4-tetrahydro-1,4-epiminonaphth-6-yl)isoxazole-3-carboxamide or a pharmaceutically acceptable salt thereof;

5) 5-(2,4-dihydroxyl-5-isopropylphenyl)-N-ethyl-4-(9-methyl-1,2,3,4-tetrahydro-1,4-epiminonaphth-6-yl)isoxazole-3-carboxamide or a pharmaceutically acceptable salt thereof;

6) 5-(2,4-dihydroxyl-5-isopropylphenyl)-N-ethyl-4-(9-ethyl-1,2,3,4-tetrahydro-1,4-epiminonaphth-6-yl)isoxazole-3-carboxamide or a pharmaceutically acceptable salt thereof;

7) 5-(2,4-dihydroxyl-5-isopropylphenyl)-N-ethyl-4-(9-isopropyl-1,2,3,4-tetrahydro-1,4-epiminonaphth-6-yl)isoxazole-3-carboxamide or a pharmaceutically acceptable salt thereof;

8) 5-(2,4-dihydroxyl-5-isopropylphenyl)-N-ethyl-4-(9-isobutyl-1,2,3,4-tetrahydro-1,4-epiminonaphth-6-yl)isoxazole-3-carboxamide or a pharmaceutically acceptable salt thereof;

9) 5-(2,4-dihydroxyl-5-isopropylphenyl)-N-ethyl-4-(5-methyl-4,5,6,7-tetrahydrothieno[3,2-c]pyridin-2-yl)isoxazole-3-carboxamide or a pharmaceutically acceptable salt thereof;

10) 5-(2,4-dihydroxyl-5-isopropyl-phenyl)-N-ethyl-4-(5-methyl-4,5,6,7-tetrahydrothiazolo[4,5-c]pyridin-2-yl)isoxazole-3-carboxamide or a pharmaceutically acceptable salt thereof;

11) 5-(2,4-dihydroxyl-5-isopropylphenyl)-N-ethyl-4-(6-methyl-5,6,7,8-tetrahydro-1,6-naphthyridin-2-yl)isoxazole-3-carboxamide or a pharmaceutically acceptable salt thereof;

12) 3-(2,4-dihydroxyl-5-isopropylphenyl)-N-ethyl-4-(2-methyl-1,2,3,4-tetrahydroisoquinolin-6-yl)isoxazole-5-carboxamide or a pharmaceutically acceptable salt thereof;

13) 5-(2,4-dihydroxyl-5-isopropyl-phenyl)-N-ethyl-4-(2-methyl-1,2,3,4-tetrahydroisoquinolin-6-yl)isothiazole-3-carboxamide or a pharmaceutically acceptable salt thereof;

14) 5-(2,4-dihydroxyl-5-isopropyl-phenyl)-N-ethyl-4-(2-methyl-1,2,3,3a,4,6a-hexahydrocyclopenta[c]pyrrol-5-yl)isoxazole-3-carboxamide or a pharmaceutically acceptable salt thereof;

15) 4-isopropyl-6-[4-(2-methyl-1,2,3,4-tetrahydroisoquinolin-6-yl)-3-(5-methyl-4H-1,2,4-triazol-3-yl)isoxazol-5-yl]benzene-1,3-diol or a pharmaceutically acceptable salt thereof;

16) 4-(3-(5-ethyl-1H-imidazol-2-yl)-4-(2-methyl-1,2,3,4-tetrahydroisoquinolin-6-yl)isoxazol-5-yl)-6-isopropylbenzene-1,3-diol or a pharmaceutically acceptable salt thereof;

17) 4-(3-(5-ethyl-1H-imidazol-2-yl)-4-(2-(2-hydroxyethyl)-1,2,3,4-tetrahydroisoquinolin-6-yl)isoxazol-5-yl)-6-isopropylbenzene-1,3-diol or a pharmaceutically acceptable salt thereof;

18) 5-(2,4-dihydroxyl-5-isopropylphenyl)-4-(7,7-dimethyl-4,5,6,7-tetrahydrothieno[2,3-c]pyridin-2-yl)-N-ethylisoxazole-3-carboxamide or a pharmaceutically acceptable salt thereof;

19) 5-(2,4-dihydroxyl-5-isopropylphenyl)-N-ethyl-4-(6-methyl-5,6,7,8-tetrahydro-1,6-naphthyridin-3-yl)isoxazole-3-carboxamide or a pharmaceutically acceptable salt thereof;

20) 4-isopropyl-6-(4-(2-methyl-1,2,3,4-tetrahydroisoquinolin-6-yl)-3-(2,2,2-trifluoro-1-hydroxyethyl)isoxazol-5-yl)benzene-1,3-diol or a pharmaceutically acceptable salt thereof;

21) N-cyano-5-(2,4-dihydroxyl-5-isopropylphenyl)-4-(2-methyl-1,2,3,4-tetrahydroisoquinolin-6-yl)isoxazole-3-carboxamidine or a pharmaceutically acceptable salt thereof;

22) 5-(2,4-dihydroxyl-5-isopropylphenyl)-N-ethyl-4-(6-methyl-5,6,7,8-tetrahydro-4H-thieno[2,3-d]azepin-2-yl)isoxazole-3-carboxamide or a pharmaceutically acceptable salt thereof;

23) 5-(2,4-dihydroxyl-5-isopropylphenyl)-N-ethyl-4-(2-methyl-1,2,3,4-tetrahydropyrrolo[1,2-a]pyrazin-7-yl)isoxazole-3-carboxamide or a pharmaceutically acceptable salt thereof;

24) 5-(2,4-dihydroxyl-5-isopropylphenyl)-N-ethyl-4-(5-isobutyl-1-methyl-4,5,6,7-tetrahydro-1H-imidazo[4,5-c]pyridin-2-yl)isoxazole-3-carboxamide or a pharmaceutically acceptable salt thereof;

25) 5-(2,4-dihydroxyl-5-isopropylphenyl)-N-ethyl-4-(3-methyl-2,3,4,5-tetrahydro-1H-benzo[d]azepin-7-yl)isoxazole-3-carboxamide or a pharmaceutically acceptable salt thereof;

26) 5-(2,4-dihydroxyl-5-isopropylphenyl)-N-ethyl-4-(3-methyl-2,3,4,5-tetrahydro-1H-benzo[c]azepin-7-yl)isoxazole-3-carboxamide or a pharmaceutically acceptable salt thereof;

27) 3-(2,4-dihydroxyl-5-isopropylphenyl)-N-ethyl-4-(3-methyl-2,3,4,5-tetrahydro-1H-benzo[d]azepin-7-yl)isoxazole-5-carboxamide or a pharmaceutically acceptable salt thereof;

28) 3-(2,4-dihydroxyl-5-isopropylphenyl)-N-ethyl-4-(2,3,4,5-tetrahydro-1H-3-benzazepin-7-yl)isoxazole-5-carboxamide or a pharmaceutically acceptable salt thereof;

29) 3-(2,4-dihydroxyl-5-isopropylphenyl)-N-ethyl-4-(isoquinolin-6-yl)isoxazole-5-carboxamide or a pharmaceutically acceptable salt thereof;

30) 5-(2,4-dihydroxyl-5-bromo-phenyl)-N-ethyl-4-(2-methyl-1,2,3,4-tetrahydroisoquinolin-6-yl)isoxazole-3-carboxamide or a pharmaceutically acceptable salt thereof;

31) 5-(2,4-dihydroxyl-5-chloro-phenyl)-N-ethyl-4-(2-methyl-1,2,3,4-tetrahydroisoquinolin-6-yl)isoxazole-3-carboxamide or a pharmaceutically acceptable salt thereof;

32) 5-(2,4-dihydroxyl-5-methylphenyl)-N-ethyl-4-(2-methyl-1,2,3,4-tetrahydroisoquinolin-6-yl)isoxazole-3-carboxamide or a pharmaceutically acceptable salt thereof;

33) 5-(5-isobutyl-2,4-dihydroxy-phenyl)-N-ethyl-4-(2-methyl-1,2,3,4-tetrahydroisoquinolin-6-yl)isoxazole-3-carboxamide or a pharmaceutically acceptable salt thereof;

34) 5-(5-ethyl-2,4-dihydroxy-phenyl)-N-ethyl-4-(2-methyl-1,2,3,4-tetrahydroisoquinolin-6-yl)isoxazole-3-carboxamide or a pharmaceutically acceptable salt thereof;

35) 5-(5-cyclopropyl-2,4-dihydroxy-phenyl)-N-ethyl-4-(2-methyl-1,2,3,4-tetrahydroisoquinolin-6-yl)isoxazole-3-carboxamide or a pharmaceutically acceptable salt thereof;

36) 5-(2,4-dihydroxyl-5-isopropylphenyl)-N-methyl-4-(2-methyl-1,2,3,4-tetrahydroisoquinolin-6-yl)isoxazole-3-carboxamide or a pharmaceutically acceptable salt thereof;

37) 5-(2,4-dihydroxyl-5-isopropylphenyl)-N-propyl-4-(2-methyl-1,2,3,4-tetrahydroisoquinolin-6-yl)isoxazole-3-carboxamide or a pharmaceutically acceptable salt thereof;

38) 5-(2,4-dihydroxyl-5-isopropylphenyl)-N-isopropyl-4-(2-methyl-1,2,3,4-tetrahydroisoquinolin-6-yl)isoxazole-3-carboxamide or a pharmaceutically acceptable salt thereof;

39) 5-(2,4-dihydroxyl-5-isopropylphenyl)-N-(2,2, 2-trifluoroethyl)-4-(2-methyl-1,2,3,4-tetrahydroisoquinolin-6-yl)isoxazole-3-carboxamide or a pharmaceutically acceptable salt thereof;
40) 5-(2,4-dihydroxyl-5-isopropylphenyl)-N-(2-fluoroethyl)-4-(2-methyl-1,2,3,4-tetrahydroisoquinolin-6-yl)isoxazole-3-carboxamide or a pharmaceutically acceptable salt thereof;
41) 5-(2,4-dihydroxyl-5-isopropylphenyl)-N-(2-methoxyethyl)-4-(2-methyl-1,2,3,4-tetrahydroisoquinolin-6-yl)isoxazole-3-carboxamide or a pharmaceutically acceptable salt thereof;
42) 5-(2,4-dihydroxyl-5-isopropylphenyl)-N-(3-methoxypropyl)-4-(2-methyl-1,2,3,4-tetrahydroisoquinolin-6-yl)isoxazole-3-carboxamide or a pharmaceutically acceptable salt thereof;
43) 5-(2,4-dihydroxyl-5-isopropylphenyl)-N-[2-(dimethylamino)ethyl]-4-(2-methyl-1,2,3,4-tetrahydroisoquinolin-6-yl)isoxazole-3-carboxamide or a pharmaceutically acceptable salt thereof;
44) 5-(2,4-dihydroxyl-5-isopropylphenyl)-N-ethyl-4-(2-(2-hydroxylethyl)-1,2,3,4-tetrahydroisoquinolin-6-yl)isoxazole-3-carboxamide or a pharmaceutically acceptable salt thereof;
45) 5-(2,4-dihydroxyl-5-isopropylphenyl)-N-ethyl-4-(2-(2-methoxyethyl)-1,2,3,4-tetrahydroisoquinolin-6-yl)isoxazole-3-carboxamide or a pharmaceutically acceptable salt thereof;
46) 5-(2,4-dihydroxyl-5-isopropylphenyl)-N-ethyl-4-(2-(2-fluoroethyl)-1,2,3,4-tetrahydroisoquinolin-6-yl)isoxazole-3-carboxamide or a pharmaceutically acceptable salt thereof;
47) 5-(2,4-dihydroxyl-5-isopropylphenyl)-N-ethyl-4-(2-(3-methoxypropyl)-1,2,3,4-tetrahydroisoquinolin-6-yl)isoxazole-3-carboxamide or a pharmaceutically acceptable salt thereof;
48) 5-(2,4-dihydroxyl-5-isopropylphenyl)-N-ethyl-4-(2-(2-ethylsulfonyl)ethyl-1,2,3,4-tetrahydroisoquinolin-6-yl)isoxazole-3-carboxamide or a pharmaceutically acceptable salt thereof;
49) 5-(2,4-dihydroxyl-5-isopropylphenyl)-N-ethyl-4-(2-ethyl-1,2,3,4-tetrahydroisoquinolin-6-yl)isoxazole-3-carboxamide or a pharmaceutically acceptable salt thereof;
50) 5-(2,4-dihydroxyl-5-isopropylphenyl)-N-ethyl-4-(2-propyl-1,2,3,4-tetrahydroisoquinolin-6-yl)isoxazole-3-carboxamide or a pharmaceutically acceptable salt thereof;
51) 5-(2,4-dihydroxyl-5-isopropylphenyl)-N-ethyl-4-(2-isopropyl-1,2,3,4-tetrahydroisoquinolin-6-yl)isoxazole-3-carboxamide or a pharmaceutically acceptable salt thereof;
52) 5-(2,4-dihydroxyl-5-isopropylphenyl)-N-ethyl-4-(2-isobutyl-1,2,3,4-tetrahydroisoquinolin-6-yl)isoxazole-3-carboxamide or a pharmaceutically acceptable salt thereof;
53) 4-(2-(2-acetylaminoethyl)-1,2,3,4-tetrahydroisoquinolin-6-yl)-5-(2,4-dihydroxyl-5-isopropylphenyl)-N-ethylisoxazole-3-carboxamide or a pharmaceutically acceptable salt thereof;
54) 4-(2-(2-acetylaminopropyl)-1,2,3,4-tetrahydroisoquinolin-6-yl)-5-(2,4-dihydroxyl-5-isopropylphenyl)-N-ethylisoxazole-3-carboxamide or a pharmaceutically acceptable salt thereof;
55) 5-(2,4-dihydroxyl-5-isopropylphenyl)-4-(2-(2-(dimethylamino)-2-oxoethyl)-1,2,3,4-tetrahydroisoquinolin-6-yl)-N-ethylisoxazole-3-carboxamide or a pharmaceutically acceptable salt thereof;
56) 5-(2,4-dihydroxyl-5-isopropylphenyl)-4-(2-(2-(dimethylamino)-3-oxopropyl)-1,2,3,4-tetrahydroisoquinolin-6-yl)-N-ethylisoxazole-3-carboxamide or a pharmaceutically acceptable salt thereof;
57) 5-(2,4-dihydroxyl-5-isopropylphenyl)-4-(2-(3-(dimethylamino)propionyl)-1,2,3,4-tetrahydroisoquinolin-6-yl)-N-ethylisoxazole-3-carboxamide or a pharmaceutically acceptable salt thereof;
58) 5-(2,4-dihydroxyl-5-isopropylphenyl)-N-ethyl-4-(2-(3-morpholino-4-yl-propionyl)-1,2,3,4-tetrahydroisoquinolin-6-yl)isoxazole-3-carboxamide or a pharmaceutically acceptable salt thereof;
59) 5-(2,4-dihydroxyl-5-isopropylphenyl)-4-(2-(2-(dimethylamino)acetyl)-1,2,3,4-tetrahydroisoquinolin-6-yl)-N-ethylisoxazole-3-carboxamide or a pharmaceutically acceptable salt thereof;
60) 5-(2,4-dihydroxyl-5-isopropylphenyl)-N-ethyl-4-(2-(2-morpholino-4-yl-acetyl)-1,2,3,4-tetrahydroisoquinolin-6-yl)isoxazole-3-carboxamide or a pharmaceutically acceptable salt thereof;
61) 3-(2,4-dihydroxyl-5-isopropylphenyl)-4-(2-methyl-1,2,3,4-tetrahydroisoquinolin-6-yl)isoxazole-5-carboxamide or a pharmaceutically acceptable salt thereof;
62) 3-(2,4-dihydroxyl-5-isopropylphenyl)-N-methyl-4-(2-methyl-1,2,3,4-tetrahydroisoquinolin-6-yl)isoxazole-5-carboxamide or a pharmaceutically acceptable salt thereof;
63) 3-(2,4-dihydroxyl-5-isopropylphenyl)-N-isopropyl-4-(2-methyl-1,2,3,4-tetrahydroisoquinolin-6-yl)isoxazole-5-carboxamide or a pharmaceutically acceptable salt thereof;
64) 3-(2,4-dihydroxyl-5-isopropylphenyl)-N-(2-hydroxylethyl)-4-(2-methyl-1,2,3,4-tetrahydroisoquinolin-6-yl)isoxazole-5-carboxamide or a pharmaceutically acceptable salt thereof;
65) 3-(2,4-dihydroxyl-5-isopropylphenyl)-N-(2-fluoroethyl)-4-(2-methyl-1,2,3,4-tetrahydroisoquinolin-6-yl)isoxazole-5-carboxamide or a pharmaceutically acceptable salt thereof;

66) 3-(2,4-dihydroxyl-5-isopropylphenyl)-N-(3-hydroxylpropyl)-4-(2-methyl-1,2,3,4-tetrahydroisoquinolin-6-yl)isoxazole-5-carboxamide or a pharmaceutically acceptable salt thereof;
67) 3-(2,4-dihydroxyl-5-isopropylphenyl)-N-ethyl-4-(1,2,3,4-tetrahydroisoquinolin-6-yl)isoxazole-5-carboxamide or a pharmaceutically acceptable salt thereof;
68) 3-(2,4-dihydroxyl-5-isopropylphenyl)-N-ethyl-4-(2-isopropyl-1,2,3,4-tetrahydroisoquinolin-6-yl)isoxazole-5-carboxamide or a pharmaceutically acceptable salt thereof;
69) 3-(2,4-dihydroxyl-5-isopropylphenyl)-N-ethyl-4-(2-(2-hydroxyethyl)-(1,2,3,4-tetrahydroisoquinolin-6-yl)isoxazole-5-carboxamide or a pharmaceutically acceptable salt thereof;
70) 3-(2,4-dihydroxyl-5-isopropylphenyl)-N-ethyl-4-(2-(2-methoxyethyl)-(1,2,3,4-tetrahydroisoquinolin-6-yl)isoxazole-5-carboxamide or a pharmaceutically acceptable salt thereof;
71) 3-(2,4-dihydroxyl-5-isopropylphenyl)-N-ethyl-4-(2-(2-fluoroethyl)-(1,2,3,4-tetrahydroisoquinolin-6-yl)isoxazole-5-carboxamide or a pharmaceutically acceptable salt thereof.

Another object of the present invention is to provide a pharmaceutical composition comprising a therapeutically effective amount of the compound of formula (I) or the pharmaceutically acceptable salt or hydrate thereof, and pharmaceutically acceptable carriers.

Another object of the present invention is to provide the use of the above compound in preparing a medicament for treating HSP90 protein-mediated diseases.

The diseases mediated by HSP90 protein according to the present invention are preferably selected from cancer and neurodegenerative disorders.

Another object of the present invention is to provide the use of the above compound in preparing a medicament for treating particular types of carcinoma, which includes, but are not limited to, cancer, such as bladder cancer, breast cancer, colon cancer, kidney cancer, liver cancer, lung cancer including small cell lung cancer, esophagus cancer, gallbladder cancer, ovarian cancer, pancreatic cancer, gastric cancer, cervical cancer, thyroid cancer, prostate cancer, and skin cancer including squamous cell carcinoma; lymphoid hematopoietic tumor, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkitt's lymphoma; myeloid hematopoietic tumor, including acute and chronic myeloid leukemia, myelodysplastic syndrome and promyelocytic leukemia; mesenchyme-derived cancer including fibrosarcoma and rhabdomyosarcoma; cancer of the central and peripheral nervous system, including astrocytomas, neurocytomas, gliomas and neurilemmomas; and other cancers, including melanoma, seminoma, teratocarcinoma, osteosarcoma, xeroderma pigmentosum, keratoxanthoma, thyroid follicular carcinoma and Kaposi sarcoma.

Another object of the present invention is to provide the use of the above compound in preparing a medicament for treating particular types of neurodegenerative disorders, the neurodegenerative disorders including, but being not limited to, Alzheimer's disease, Parkinson's disease, Huntington's disease, multiple sclerosis, and spinal and bulbar muscular atrophy.

Another object of the present invention is to provide the use of the compound of formula (I) in preparing a medicament for anticancer therapy, wherein the medicament is used simultaneously, separately or successively with radiotherapy or chemotherapy regimens.

In addition, the present invention provides an in vitro method for inhibiting the activity of HSP90 protein, comprising contacting the protein with an effective amount of a compound of formula (I).

The present invention also provides a pharmaceutical composition comprising one or more compounds of formula (I) or the pharmaceutically acceptable salts thereof, and pharmaceutically acceptable excipients, carriers or diluents.

The present invention also provides a pharmaceutical composition comprising a compound of formula (I) and the following substances: known cell growth inhibitors or cytotoxic drugs, antibiotic agents, alkylating agents, antimetabolites, hormonal agents, immunological agents, interferon agents, cyclooxygenase inhibitors (such as COX-2 inhibitors), matrix metalloproteinase inhibitors, telomerase inhibitors, tyrosine kinase inhibitors, anti-growth factor receptor agents, anti-HER agents, anti-EGFR agents, anti-angiogenesis agents (such as angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors or the like.

In addition, the present invention provides a product or kit, comprising the compound of formula (I) as defined above or the pharmaceutically acceptable salt thereof, or the pharmaceutical composition thereof, and one or more chemotherapeutic drugs, said product or kit is in a form of a combination preparation, and the compound of formula (I) as defined above or the pharmaceutically acceptable salt thereof, or the pharmaceutical composition thereof, and one or more chemotherapeutic drugs are used simultaneously, separately or successively for anticancer therapy.

In still another aspect, the present invention provides the compound of formula (I) as defined above or the pharmaceutically acceptable salt thereof as a drug.

In addition, the present invention provides the use of the compound of formula (I) as defined above or the pharmaceutically acceptable salt thereof in preparing a medicament having antitumor activity.

Finally, the present invention provides the compound of formula (I) as defined above or the pharmaceutically acceptable salt thereof, which is used in preparing a medicament for treating diseases caused by and/or related to activity changes of HSP90, the diseases particularly being cancer or neurodegenerative disorders.

Unless otherwise indicated, when referring to the compounds of formula (I) per se and any pharmaceutical compositions thereof or any therapeutic methods comprising the compounds, the present invention encompasses all isomers, tautomers, hydrates, solvates, complexes, N-oxides and pharmaceutically acceptable salts of the compounds of the present invention.

The pharmaceutically acceptable salts of the compounds of formula (I) include acid addition salts formed with inorganic or organic acids, such as nitric acid, hydrochloric acid, hydrobromic acid, sulfuric acid, perchloric acid, phosphoric acid, acetic acid, trifluoroacetic acid, propionic acid, hydroxyacetic acid, fumaric acid, lactic acid, oxalic acid, malonic acid, malic acid, maleic acid, tartaric acid, citric acid, benzoic acid, cinnamic acid, mandelic acid, methanesulfonic acid, isethionic acid and salicylic acid. The pharmaceutically acceptable salts of the compounds of formula (I) also include salts formed with inorganic or organic bases, such as hydroxides, carbonates or bicarbonates of alkali metals or alkaline earth metals (in particular sodium, potassium, calcium, ammonium or magnesium), and non-cyclic or cyclic amines, preferably methylamine, ethylamine, diethylamine, triethylamine, piperidine and the like.

The term "halogen" means fluorine, chlorine, bromine or iodine.

The term "alkyl" means any saturated hydrocarbons or saturated hydrocarbons substituted with 1-3 heteroatoms, wherein the hydrocarbons may be linear or branched. "Alkyl" includes alkane groups and heteroalkyl. For example, "$C_{1-6}$ alkyl" refers to an alkane comprising 1 to 6 carbon atoms or an alkane of 1 to 6 carbon atoms in which 1 to 3 carbon atoms are substituted with heteroatoms. For example, "$C_{1-10}$ alkyl" refers to an alkane comprising 1 to 10 carbon atoms or an alkane of 1 to 10 carbon atoms in which 1 to 3 carbon atoms are substituted with heteroatoms. Non-limited examples of "alkyl" include methyl, ethyl, n-propyl, isopropyl, n-butyl, isobutyl, t-butyl, sec-butyl, a n-pentyl, n-hexyl and the like.

The term "$C_{2-7}$ alkenyl" means aliphatic $C_{2-7}$ hydrocarbon chains containing at least one double bond and which may be linear or branched, which may be substituted with one or two heteroatoms. Representative examples include, but are not limited to, vinyl, 1-propenyl, 2-propenyl, 1- or 2-butenyl, and the like.

The term "$C_{2-7}$ alkynyl" means aliphatic $C_{2-7}$ hydrocarbon chains containing at least one carbon-carbon triple bond and which may be linear or branched. Representative examples include, but are not limited to, ethynyl, 1-propynyl, 2-propynyl, 1- or 2-butynyl, and the like.

The term "cycloalkyl", unless otherwise indicated, means saturated cyclic hydrocarbons or saturated cyclic hydrocarbons substituted with one or more heteroatoms. "Cycloalkyl" includes cycloalkane groups and hetero cycloalkyl. Non-limited examples of cycloalkyl are cyclopropane, cyclobutane, cyclopentane, cyclohexane, tetrahydrofuran, tetrahydrothiophene and the like. For example, the term "$C_{3-10}$ cycloalkyl" means saturated cyclic hydrocarbons containing 3 to 10 carbon atoms, or saturated cyclic hydrocarbons of 3 to 10 carbon atoms substituted with one or more heteroatoms. Non-limited examples of cycloalkyl are cyclopropane, cyclobutane, cyclopentane, cyclohexane, tetrahydrofuran, tetrahydrothiophene, pyran, pyrrolidine, imidazolidine, pyrazolidine, thiazolidine, 1,3-dioxolane, piperidine, piperazine, morpholine and the like.

The term "cycloalkenyl", unless otherwise indicated, means cyclic hydrocarbons containing a double bond or cyclic hydrocarbons containing a double bond which are substituted with one or more heteroatoms, excluding those containing a completely conjugated π-electron system. "Cycloalkenyl" includes cycloalkene groups and heterocycloalkene groups. Non-limited examples of cycloalkenyl are cyclopentene, cyclohexene, cyclohexadiene, pyrroline, imidazoline, pyrazoline, thiazoline, dihydrofuran and the like.

The term "aryl" or "aromatic ring" includes aromatic hydrocarbyl and heteroaryl.

The term "aromatic hydrocarbyl" means a mono-, di- or poly-carbocyclic hydrocarbon having 1 to 4 ring systems, said ring systems are optionally further fused with each other or linked by a single bond, wherein at least one carbocyclic ring is "aromatic", and wherein the term "aromatic" means a completely conjugated π-electron system.

Non-limited examples of aryl are a phenyl group, an alpha- or beta-naphthyl group, or a biphenyl group.

The term "heteroaryl" means an aromatic heterocyclic ring, and is typically a 5- to 10-membered heterocyclic ring having 1 to 3 heteroatoms selected from N, O or S; and heteroaryl rings may be optionally further fused or linked to aromatic and nonaromatic carbocyclic rings and heterocyclic rings. Non-limited examples of heteroaryl are, for example, pyridyl, pyrazinyl, pyrimidinyl, pyridazinyl, indolyl, imidazolyl, thiazolyl, isothiazolyl, pyrrolyl, phenylpyrrolyl, furanyl, phenyl-furyl, oxazolyl, isoxazolyl, pyrazolyl, thienyl, benzothienyl, isoindolyl, benzimidazolyl, quinolinyl, isoquinolyl, 1,2,3-triazolyl, 1-phenyl-1,2,3-triazolyl, 2,3-dihydroindolyl, 2,3-dihydrobenzofuranyl, 2,3-dihydrobenzothienyl; benzopyranyl, 2,3-dihydrobenzoxazinyl, 2,3-dihydroquinoxalinyl, and the like.

According to the present invention, unless otherwise indicated, any of the above $R_1$ to $R_5$ groups may be optionally substituted at any unoccupied positions thereof with one or more groups, for example, substituted with 1 to 6 groups, wherein the groups are independently selected from: halogen, nitro, oxo group (=O), cyano, $C_1$-$C_6$ alkyl, polyfluoroalkyl, polyfluoroalkoxy, $C_2$-$C_6$ alkenyl, $C_2$-$C_6$ alkynyl, hydroxylalkyl, aryl, arylalkyl, heteroaryl, heteroarylalkyl, heterocyclyl, heterocycloalkyl, $C_3$-$C_7$ cycloalkyl, hydroxyl, alkoxy, aryloxy, heterocyclic oxy, methylenedioxy, alkylcarbonyloxy, arylcarbonyloxy, cycloalkenyloxy, heterocyclylcarbonyloxy, alkyleneaminooxy, carboxy, alkoxycarbonyl, aryloxycarbonyl, cycloalkyloxycarbonyl, heterocyclylalkyloxylcarbonyl-amino, ureido, alkylamino, dialkylamino, arylamino, diarylamino, heterocyclylamino, formamido, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxylcarbonylamino, hydroxylaminocarbonylalkoxyimino, alkylsulfonylamino, arylsulfonylamino, heterocyclyl sulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonates, phosphonic acid, phosphonate radical and alkyl phosphonates. Each of the above substituents in turn may be further substituted by one or more of the aforementioned groups, such as $R_1$, $R_2$, $R_3$, $R_4$ and $R_5$, when appropriate.

The term polyfluoroalkyl or polyfluoroalkoxy means any of the above linear or branched $C_1$-$C_8$ alkyl or alkoxy which is substituted with more than one fluorine atoms, for example, trifluoromethyl, trifluoroethyl, 1,1,1,3,3,3-hexafluoropropyl, trifluoromethoxy and the like.

The term hydroxylalkyl means any of the above $C_1$-$C_8$ alkyl containing hydroxyl, for example, hydroxymethyl, 2-hydroxylethyl, 3-hydroxylpropyl and the like.

By all description as above, it will be appreciated for a skilled person that any groups whose name is a composite name should, by convention, mean to be constituted by moieties deriving the group, for example, arylamino is an amino group which is further substituted with an aryl group, wherein aryl is defined as above.

Similarly, alkyl, alkoxy, aryl, $C_{3-10}$ cycloalkyl and heterocyclyl moieties contained in any terms, for example, alkylthio, alkylamino, dialkylamino, alkoxycarbonyl, alkoxycarbonylamino, heterocyclylcarbonyl, heterocyclylcarbonylamino, cycloalkyloxycarbonyl and the like, are the groups as defined above.

The compounds of the present invention may be prepared by various synthesis methods known to the person skilled in the art, including the specific embodiments listed below, embodiments formed by combining the above specific embodiments with other chemical synthesis methods, and equivalent alternatives known to the person skilled in the art, and the preferred embodiments include, but are not limited to, the Examples of the present invention.

All of the solvents used in the present invention are commercially available and can be used without further purification. Reactions are generally conducted in an anhydrous solvent under inert nitrogen gas. Proton nuclear magnetic resonance data is recorded in a Bruker Avance III 400 (400 MHz) spectrometer, and a chemical shift is represented as δ (ppm) at the low field of tetramethylsilane. Mass spectra are measured on the Agilent 1200 Series plus 6110 (& 1956A). LC/MS or Shimadzu MS contains a DAD: SPD-M20A (LC) and a Shimadzu Micromass 2020 detector. The mass spectrometer is equipped with an electrospray ion source (ESI) operating in positive or negative mode.

In the present invention, the following abbreviations are used: PG represents a protecting group; DMF represents N,N-dimethylcarboxamide; PE represents petroleum ether; EA represents ethyl acetate; NCS represents 1-chloropyrrolidine-2,5-dione; NBS represents 1-bromopyrrolidine-2,5-dione; NIS represents 1-iodopyrrolidine-2,5-dione; eq represents equal-quantitative or equivalent; DCM represents dichloromethane; DMSO represents dimethyl sulfoxide; EtOH represents ethanol; MeOH represents methanol; CBz represents benzyloxycarbonyl and is an amine protecting group; BOC represents t-butyloxycarbonyl, and is an amine protecting group; HOAc represents acetic acid; NaCNBH$_3$ represents sodium cyanoborohydride; THF represents tetrahydrofuran; Boc$_2$O represents di-tert-butyl dicarbonate; TFA represents trifluoroacetic acid; TFAA represents trifluoroacetic anhydride; DIEA represents diisopropylethylamine; DMAP represents N,N-dimethylaminopyridine; TEA represents triethylamine; TMSCl represents trimethylchlorosilane; MTBE represents methyl tert-butyl ether; AIBN represents azobisisobutyronitrile; DME represents dimethyl ether; DCE represents dichloroethane; LDA represents lithium N,N-diisopropylamide; CAN represents cerium ammonium nitrate; mp represents the melting point.

The compounds are named manually or by the ChemDraw® software, and the commercially available compounds use suppliers' catalog names.

High performance liquid chromatography (HPLC) is performed by using Xtimate C18 (a packing material of 3 μm, with a specification of 2.1×300 mm) column with a Shimadzu LC20AB system equipped with a Shimadzu SIL-20A autosampler and a Shimadzu DAD: SPD-M20A detector. A method of 0-60AB_6 minutes: starting the elution with 100% A (A is a 0.0675% TFA solution in water) and terminating it with 60% B (B is a 0.0625% TFA solution in MeCN) by applying a linear gradient, wherein this process costs 4.2 min; then eluting with 60% B for 1 min; and rebalancing the chromatographic column for 0.8 min to 100:0, and the total run time is 6 min. A method of 10-80AB_6 minutes: starting the elution with 90% A (A is a 0.0675% TFA solution in water) and terminating it with 80% B (B is a 0.0625% TFA solution in acetonitrile), wherein this process costs 4.2 min; then eluting with 80% B for 1 min; and rebalancing the chromatographic column for 0.8 min to 90:10, and the total run time is 6 min. The column temperature is 50° C. and the flow rate is 0.8 mL/min. The diode array detector has a scanning wavelength of 200-400 nm.

Thin layer chromatography (TLC) is performed on silica gel GF254 of Sanpont-group. Spots are generally detected using UV lamp irradiation. In some situations, spots are also detected by other methods, and in these situations, thin layer plates are developed with iodine (obtained by adding about 1 g of iodine into 10 g of silica gel and thoroughly mixing), vanillin (obtained by dissolving about 1 g of vanillin in 100 mL of 10% H$_2$SO$_4$), ninhydrin (purchased from Aldrich) or a special developer (obtained by thoroughly mixing (NH$_4$)$_6$Mo$_7$O$_{24}$.4H$_2$O, 5 g of (NH$_4$)$_2$Ce(IV)(NO$_3$)$_6$, 450 mL of H$_2$O and 50 mL of concentrated H$_2$SO$_4$) to detect compounds. Flash column chromatography is performed on Silicycle 40-63 μm (230-400 mesh) silica gel by using the method similar to the technology as disclosed in Still, W. C., Kahn, M., and Mitra, M., Journal of Organic Chemistry, 1978, 43, 2923-2925. The solvents commonly used in flash column chromatography or thin layer chromatography are a mixture of dichloromethane/methanol, ethyl acetate/methanol and hexane/ethyl acetate.

The preparative chromatographic analysis is performed using a Gilson UV/VIS-156 detector in a Gilson-281 Prep LC 322 system, with the chromatographic column of Agella Venusil ASB Prep C18, 5 μm, 150×21.2 mm; Phenomenex Gemini C18, 5 m, 150×30 mm; Boston Symmetrix C18, 5 μm, 150×30 mm; or Phenomenex Synergi C18, 4 μm, 150×30 mm. When the flow rate is about 25 mL/min, the compounds are eluted with acetonitrile/water at low gradient, wherein the water contains 0.05% HCl, 0.25% HCOOH or 0.5% NH$_3$H$_2$O, and the total run time is 8-15 min.

A SFC analysis is performed on an Agilent 1260 Infinity SFC system with an Agilent 1260 autosampler and an Agilent DAD: 1260 detector. The chromatographic column applies Chiralcel OD-H 250×4.6 mm I.D., 5 μm; or Chiralpak AS-H 250×4.6 mm I.D., 5 μm; or Chiralpak AD-H 250×4.6 mm I.D., 5 μm. The chromatographic conditions of OD-H_5_40_2.35ML are: a Chiralcel OD-H chromatographic column (with a specification of 250×4.6 mm I.D., a packing material of 5 μm), a mobile phase of 40% ethanol (0.05% DEA)-CO$_2$, a flow rate of 2.35 mL/min, and a detection wavelength of 220 nm. The chromatographic conditions of AS-H_3_40_2.35ML are: a Chiralpak AS-H chromatographic column (with a specification of 250×4.6 mm I.D., a packing material of 5 μm), a mobile phase of 40% methanol (0.05% DEA)-CO$_2$, a flow rate of 2.35 mL/min, and a detection wavelength of 220 nm. The chromatographic conditions of OD-H_3_40_2.35ML are: a Chiralcel OD-H chromatographic column (with a specification of 250×4.6 mm I.D., a packing material of 5 μm), a mobile phase of 40% methanol (0.05% DEA)-CO$_2$, a flow rate of 2.35 mL/min, and a detection wavelength of 220 nm. The chromatographic conditions of AD-H_2_50_2.35ML are: a Chiralpak AD-H chromatographic column (with a specification of 250×4.6 mm I.D., a packing material of 5 μm), a mobile phase of 50% methanol (0.1% MEA)-CO$_2$, a flow rate of 2.35 mL/min, and a detection wavelength of 220 nm.

A preparative SFC analysis is performed on a Waters Thar 80 Pre-SFC system using a Gilson UV detector, and the chromatographic column applys Chiralcel OD-H (with a specification of 250×4.6 mm I.D., a packing material of 5 μm) or Chiralpak AD-H (with a specification of 250×4.6 mm I.D., a packing material of 5 μm). When the flow rate is approximately 40-80 mL/min, the compounds are eluted with ethanol-carbon dioxide or methanol-carbon dioxide at low gradient, wherein the methanol or ethanol contains 0.05% NH$_3$.H$_2$O, 0.05% DEA or 0.1% MEA, and the total run time is 20-30 min.

Preparation methods for a part of the compounds of the present invention:

The compounds of the present invention may be prepared by various synthesis methods known to the person skilled in the art, including the specific embodiments listed below, embodiments formed by combining the specific embodiments with other chemical synthesis methods, and equivalent replacements known to the person skilled in the art, and the preferred embodiments include, but are not limited to, the Examples of the present invention.

The chemical reactions in the specific embodiments of the present invention are carried out in appropriate solvents, which should be suitable for the chemical changes of the present invention as well as reagents and materials which the chemical changes require. In order to obtain the compounds of the present invention, it is sometimes desirable for the person skilled in the art to make modifications or alternatives to synthetic steps or reaction process on the basis of existing embodiments.

A key consideration in any synthetic route planning in the field is selection of appropriate protecting groups for reactive functional groups (such as amino in the present invention). For trained practitioners, Protective Groups In Organic Synthesis, Wiley and Sons, 1991, by Greene and Wuts is the authority in this respect. All references cited herein are incorporated by reference in their entirety.

The compounds represented by formula (I) in the present invention can be prepared by reaction scheme 1 and standard methods known to the person skilled in the art. Taking a raw material (1-1) of resorcinol with a protecting group for example, it reacts with a substrate of hydroxylamine in a (3+2) cyclization and eliminates a molecule of water to form a five-membered aromatic heterocyclic ring system (1-2), and then an electrophilic halogenation is carried out on the five-membered aromatic heterocyclic ring. The formed halide can react directly with a heterocyclic-fused aromatic borate by Suzuki reaction under palladium catalysis, or the formed halide can firstly be formed to a borate and then undergo Suzuki reaction with a heterocyclic-fused aromatic halide. The two routes can introduce various fused aromatic ring groups on the five-membered aromatic heterocycle to give (1-5). Finally, a resorcinol compound (1-6), i.e., the HSP90 inhibitor of the present invention, is formed by removal of the protecting group.

Reaction Scheme 1

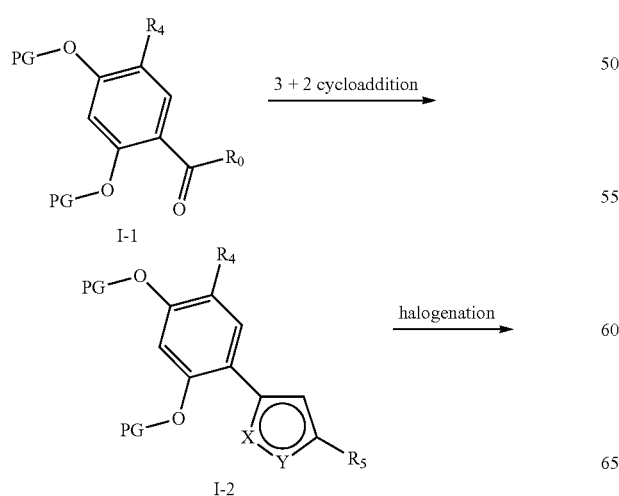

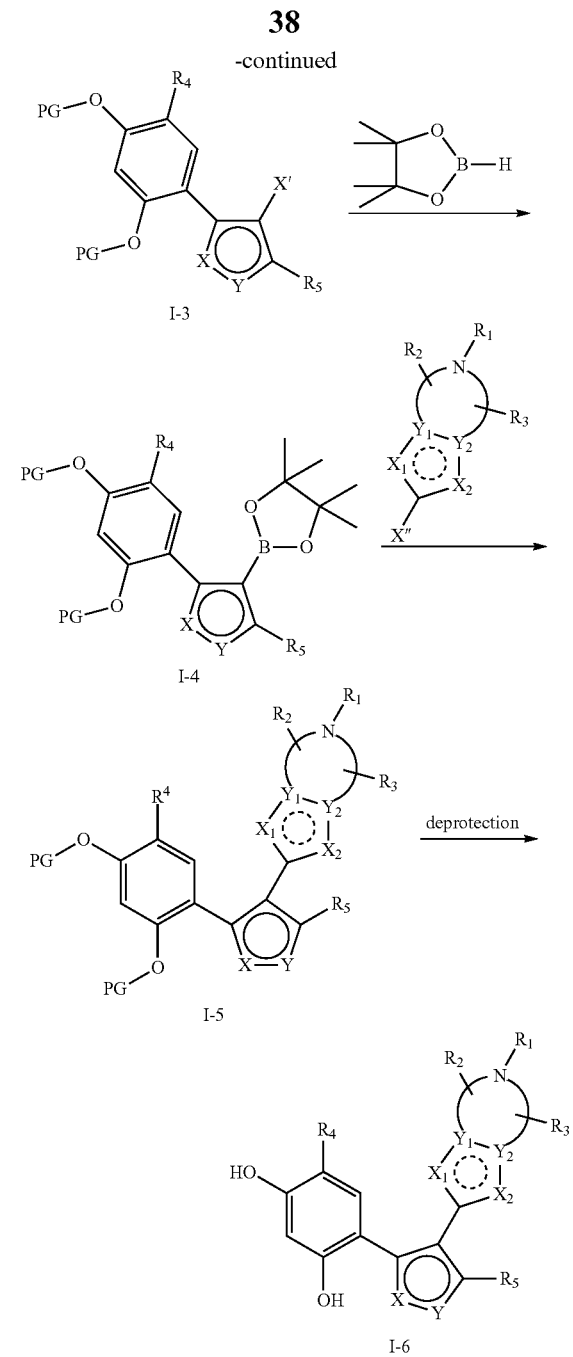

Specifically, the compounds of formula (I) provided in the present invention may be prepared by reaction scheme 1 and standard methods known to the person skilled in the art. It is started from valerolactam (1-1) derivatives which is commercially available, or can be started form other similar derivatives having different modifications of functional groups, wherein $R_0$ is selected from H, halogen, alkyl, heteroatom substituted alkyl, carboxylic acid, alkyl esters of carboxylic acid; PG is a protecting group, selected from methyl (Me), benzyl (Bn), 4-methoxybenzyl (PMB), 3,4-dimethoxybenzyl (DMB), methoxymethyl (MOM), 2-methoxyethoxymethyl (MEM), 2-tetrahydrofuryl (THP), trimethylsilyl (TMS), triethylsilyl (TES), triisopropylsilyl (TIPS), tert-butyldimethylsilyl (TBDMS), tert-butyldiphenylsilyl (TBDPS), acetyl, benzoyl, pivaloyl; X' is halogen; X" is halogen, trifluoromethanesulfonic acid and the like.

Other substituents are the same as those of formula (I). All of these variations, alternatives will be described in detail in the part of DETAILED DESCRIPTION.

It should be appreciated by the person skilled in the art that the order of the reaction steps in Reaction Scheme 1 may vary in order to prepare the compounds of the present invention, which is also within the scope of the present invention.

A series of novel resorcinol compounds represented by formula (I) of the present invention are HSP90 protein inhibitors, which can be used for the treatment of cancer and neurodegenerative disorders. Compared with the prior art, the compounds of the present invention have improved activity and enhanced efficacy. Thus, the compounds of formula (I) could be a therapeutic agent for cancer and neurodegenerative disorders.

DETAILED DESCRIPTION

Hereafter, the present invention will be described in detail by examples, but it is not intended as any disadvantageous limitation of the present invention.

EXAMPLE 1

5-(2,4-dihydroxyl-5-isopropylphenyl)-N-ethyl-4-(2-methyl-1,2,3,4-tetrahydroisoquinolin-6-yl)isoxazole-3-carboxamide

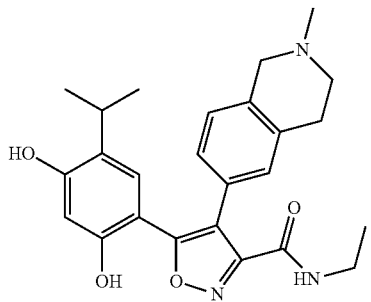 [SMILES: CCNC(=O)c1noc(-c2cc(C(C)C)c(O)cc2O)c1-c1ccc2c(c1)CCN(C)C2]

Reaction scheme:

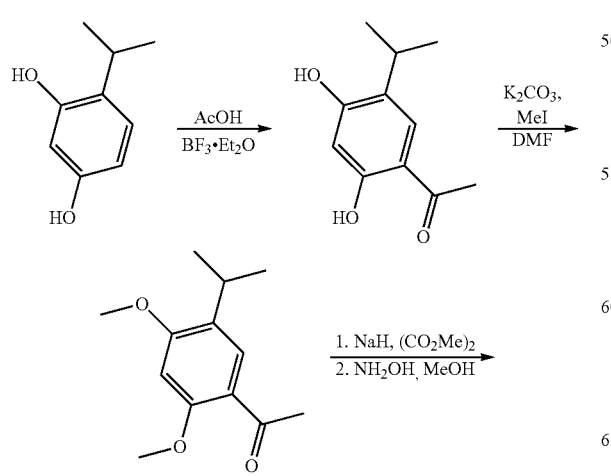

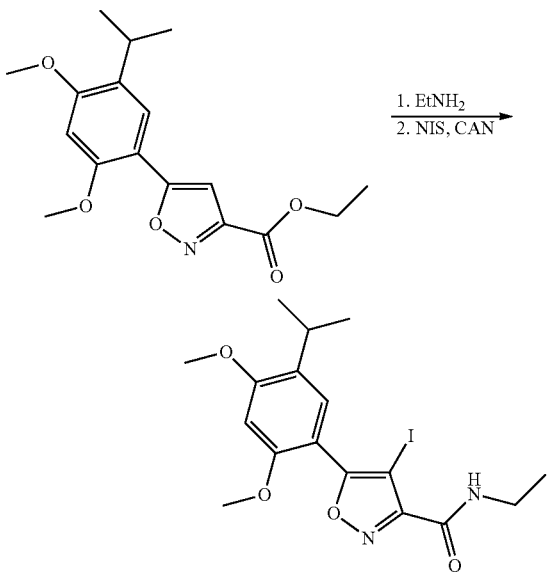

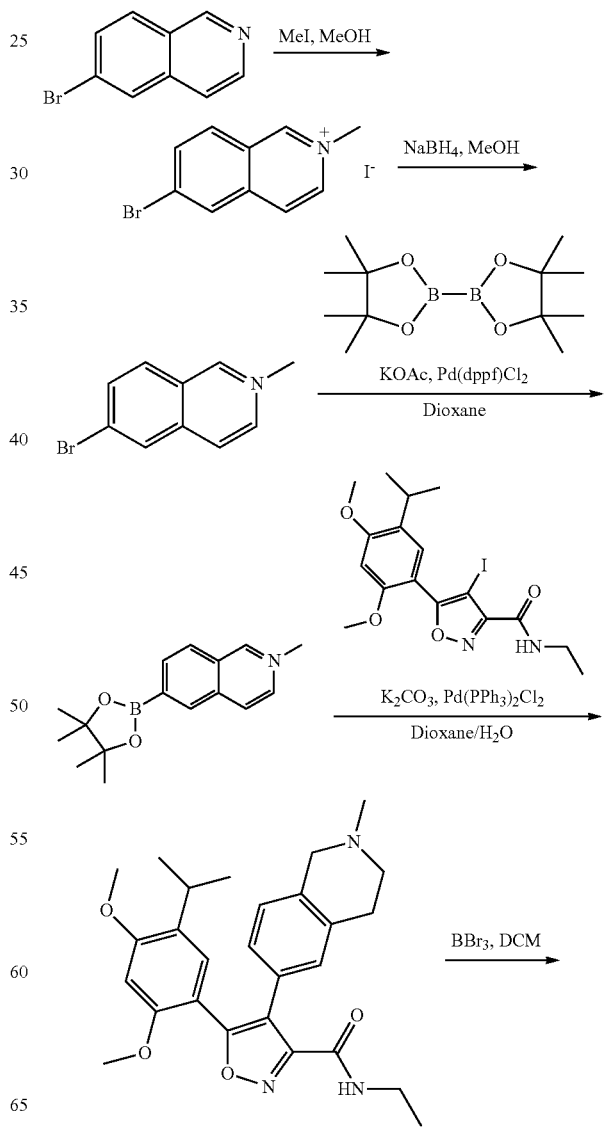

-continued

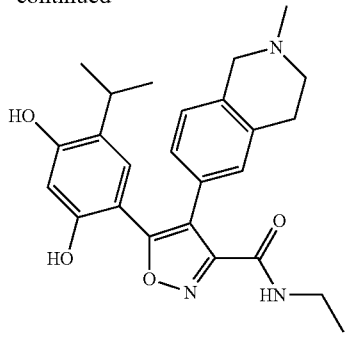

Step A: Under the protection of nitrogen gas, acetic acid (3.26 g, 54.2 mmol, 1.1 eq.) was added dropwise to a solution of 4-isopropylbenzene-1,3-diol (7.5 g, 49.3 mmol, 1.0 eq.) dissolved in $BF_3.Et_2O$ (60 mL) at 20° C. After the addition was completed, the reaction mixture was stirred at 80° C. for 3 hours. The reaction solution was quenched with aqueous potassium acetate solution (120 mL) and then extracted with ethyl acetate (150 mL×3). The combined organic phase was dried over anhydrous sodium sulfate after washed with saturated brine (100 mL), filtered and concentrated in vacuum. The crude product was purified by column chromatography (PE:EA=50:1) to give the product of 1-(2, 4-dihydroxyl-5-isopropylphenyl) ethanone (6.0 g, 30.9 mmol, 62.7% yield) as a yellow solid.

Step B: Cesium carbonate (25.2 g, 77.2 mmol, 2.5 eq.) was added to a mixture of 1-(2,4-dihydroxyl-5-isopropyl-phenyl)ethanone (6.00 g, 30.89 mmol, 1.00 eq.) and MeI (52.6 g, 370.7 mmol, 12.0 eq.) in DMF (80 mL) at 20° C. under the protection of nitrogen gas. The mixture was stirred at 20° C. for 16 hours and then poured into water (80 mL). The aqueous phase was extracted with ethyl acetate (100 mL×2). The combined organic phase was dried over anhydrous sodium sulfate after washed with saturated brine (100 mL), filtered and concentrated in vacuum. The residue was purified by silica gel chromatography (PE/EA=10/1 to 5/1) to give 1-(5-isopropyl-2,4-dimethoxyphenyl)ethanone (3.40 g, 15.3 mmol, 49.5% yield) as a yellow solid.

Step C: NaH (1.22 g, 30.6 mmol, 2.0 eq.) and dimethyl oxalate (5.42 g, 45.9 mmol, 3.0 eq.) were added to a solution of 1-(5-isopropyl-2,4-dimethoxy-phenyl)-ethanone (3.40 g, 15.30 mmol, 1.00 eq.) dissolved in THF (50 mL) at 20° C. under the protection of nitrogen gas. After stirring at 60° C. for an additional hour, the reaction mixture was poured into ammonium chloride aqueous solution (1000 mL) to be quenched, and then extracted with EA (80 mL×2). The combined organic phase was washed with saturated brine (80 mL), and dried over anhydrous sodium sulfate, filtered and concentrated in vacuum, to give the product methyl 2-hydroxyl-4-(5-isopropyl-2,4-dimethoxy-phenyl)-4-oxo-butyrate (4.80 g, crude product) as a yellow solid, which was used directly in the next step.

Step D: $NH_2OH.HCl$ (2.16 g, 31.14 mmol, 2.00 eq.) was added to a solution of methyl 2-hydroxyl-4-(5-isopropyl-2, 4-dimethoxy-phenyl)-4-oxo-butyrate (4.80 g, 15.57 mmol, 1.00 eq.) in MeOH (60 mL) at room temperature under the protection of nitrogen gas. The mixture was heated to 60° C. and stirred for 1 hour. The mixture was cooled down to room temperature and poured into water (50 mL). The aqueous phase was extracted with EA (50 mL×2). After washed with saturated brine (30 mL), the combined organic phase was dried over anhydrous sodium sulfate, filtered and concentrated in vacuum. The residue was purified by silica gel chromatography (PE/EA=6/1 to 3/1) to give ethyl 5-(5-isopropyl-2,4-dimethoxy-phenyl)-isoxazole-3-carboxylate (4.80 g, 15.0 mmol, 96.5% yield) as a yellow solid.

Step E: Ethylamine (3.54 g, 78.6 mmol, 5.0 eq.) was added to a solution of ethyl 5-(5-isopropyl-2,4-dimethoxy-phenyl)isoxazole-3-carboxylate (4.80 g, 15.7 mmol, 1.00 eq.) in MeOH (50 mL) at room temperature. The reaction mixture was stirred at 60° C. for 2 hours. The reaction mixture was concentrated and the crude product was washed by PE/EA=50/1 (100 mL) to give the product N-ethyl-5-(5-isopropyl-2,4-dimethoxyphenyl) isoxazole-3-carboxamide (3.70 g, 11.6 mmol, 73.9% yield) as a yellow solid.

Step F: CAN (301 mg, 549 μmol, 0.05 eq.) and NIS (4.95 g, 22 mmol, 2.00 eq.) were added to a solution of N-ethyl-5-(5-isopropyl-2,4-dimethoxyphenyl) isoxazole-3-carboxamide (3.50 g, 11 mmol, 1.0 eq.) in MeCN (50 mL) at room temperature under $N_2$ protection. The mixture was heated to 80° C. and stirred for 16 hours. The mixture was cooled down to room temperature and poured into water (30 mL), and the aqueous phase was extracted with EA (40 mL×2). The combined organic phase was washed with saturated brine (20 mL×2), dried over anhydrous sodium sulfate, filtered and concentrated in vacuum to dryness. The residue was purified by silica gel chromatography (PE/EA=10/1 to 4/1) to give N-ethyl-4-iodo-5-(5-isopropyl-2,4-dimethoxyphenyl) isoxazole-3-carboxamide (4.10 g, 9.2 mmol, 84.0% yield) as a yellow oil.

Step G: MeI (197.2 g, 1.4 mol) was added to a solution of 6-bromoisoquinoline (17.00 g, 81.7 mmol) dissolved in MeOH (170 mL) in one portion at 0° C. The mixture was stirred at 0° C. for 20 min, and then warmed up to 25° C. and stirred for 16 hours. The mixture was concentrated under reduced pressure to give 6-bromo-2-methylisoquinoline-2-iodonium (28.8 g, crude product) as a yellow solid. $^1H$ NMR (400 MHz, Methanol-$d_4$): δ 9.90 (s, 1H), 8.65-8.61 (m, 2H), 8.45-8.39 (m, 2H), 8.22 (d, J=8.0 Hz, 1 H), 4.55 (s, 1 H).

Step H: $NaBH_4$ (9.31 g, 246.2 mmol) was added to a solution of 6-bromo-2-methylisoquinoline-2-iodonium iodide (28.80 g, 82.1 mmol) in MeOH (350 mL) in one portion at 0° C. After stirring at 25° C. for 2 hours, the mixture was adjusted with an aqueous $NaHCO_3$ solution to pH=9 and extracted with ethyl acetate (50 mL×3). The combined organic phase was washed with saturated brine (100 mL×2), dried over anhydrous sodium sulfate, filtered and concentrated in vacuum. The residue was purified by silica gel chromatography (100~200 mesh of silica gel, dichloromethane/methanol=50/1 to 20/1) to give 6-bromo-2-methyl-1,2,3,4-tetrahydroisoquinoline (16.65 g, 80.8% yield, 90% purity) as a yellow solid.

Step I: Bis(pinacolato)diboron (28.05 g, 110.46 mmol) and KOAc (14.45 g, 147.27 mmol) were added to a solution of 6-bromo-2-methyl-1,2,3,4-tetrahydroisoquinoline (16.65 g, 73.64 mmol) in dioxane (150 mL) at 25° C. under the protection of nitrogen gas, followed by the addition of a catalyst $Pd(dppf)Cl_2.CH_2Cl_2$ (6.01 g, 7.36 mmol). The mixture was stirred at 25° C. for 10 min, and then heated to 90° C. with stirring for 14 hours. The mixture was cooled down to 25° C. and concentrated under reduced pressure. The residue was purified by silica gel chromatography (100~200 mesh of silica gel, dichloromethane/methanol=10/0 to 1/1) to give the title product (31.0 g, crude product) as a black solid, which was used directly in the next step. MS (ESI) M/Z: 274 (M+1).

Step J: $K_2CO_3$ (2.49 g, 18.0 mmol), $H_2O$ (10.0 mL) and $Pd(PPh_3)_4$(1.26 g, 1.80 mmol) were added to a mixed solution of 2-methyl-6-(4,4,5,5-tetramethyl-1,3,2-dioxa-borolan-2-yl)-1,2,3,4-tetrahydroisoquinoline (6.15 g, 13.5 mmol) and N-ethyl-4-iodo-5-(5-isopropyl-2,4-dimethoxyphenyl) isoxazole-3-carboxamide (4.00 g, 9.0 mmol) in dioxane (50 mL) at 25° C. under the protection of nitrogen gas. The mixture was stirred at 25° C. for 10 min and then heated to 110° C. with stirring for 18 hours. The mixture was cooled down to 25° C. and concentrated under reduced pressure. The residue was purified by silica gel chromatography (200~300 mesh of silica gel, petroleum ether/ethyl acetate, dichloromethane/methanol=5/1, 10/1) to give N-ethyl-5-(5-isopropyl-2,4-dimethoxyphenyl)-4-(2-methyl-1,2,3,4-tetrahydroisoquinolin-6-yl)isoxazole-3-carboxamide (2.87 g, 68.8% yield) as a brown solid. MS (ESI) M/Z: 464 (M+1).

Step K: BBr$_3$ (9.19 g, 36.67 mmol) was slowly added to a solution of N-ethyl-5-(5-isopropyl-2,4-dimethoxyphenyl)-4-(2-methyl-1,2,3,4-tetrahydroisoquinolin-6-yl)isoxazole-3-carboxamide (1.70 g, 3.67 mmol) in DCM (16.00 mL) at −78° C. under the protection of nitrogen gas, which lasted for 2 hours. The reaction mixture was allowed to warm up to 0° C. over the course of 1 hour, and the reaction mixture was stirred at 25° C. for an additional 16 hours. The reaction was quenched by the addition of MeOH (10 mL) with stirring at 25° C. for 1 hour, and the mixture was slowly added dropwise to a saturated NaHCO$_3$ aqueous solution and filtered at 0° C. The aqueous phase was extracted with dichloromethane:methanol=10:1 (10 mL×3). The combined organic phase was washed with saturated brine (10 mL×2), dried over anhydrous sodium sulfate, filtered and concentrated in vacuum. The residue was purified by silica gel chromatography (100~200 mesh of silica gel, dichloromethane/methanol=10/0 to 1/1) to give 5-(2,4-dihydroxyl-5-isopropylphenyl)-N-ethyl-4-(2-methyl-1,2,3,4-tetrahydroisoquinolin-6-yl)isoxazole-3-carboxamide (566.0 mg, 35.4% yield). $^1$H NMR (400 MHz, DMSO-d$_6$) δ 11.08 (s, 1H), 9.92-9.78 (m, J=4.0 Hz, 1H), 7.16-7.12 (m, 3H), 6.89 (s, 1H), 6.53 (s, 1H), 4.6-4.42 (d, J=16.0 Hz, 1H), 4.27-4.21 (m, 1H), 3.26-3.22 (m, 4H), 3.05-3.02 (m, 1H), 2.88-2.87 (m, 4H), 1.11-1.08 (t, J=8.0 Hz, 3H), 1.03-0.98 (m, 6H). MS (ESI) m/z: 436 (M+1).

EXAMPLE 2

5-(2,4-dihydroxyl-5-isopropylphenyl)-N-ethyl-4-(1-methyl-1,2,3,4-tetrahydroquinolin-7-yl)isoxazole-3-carboxamide

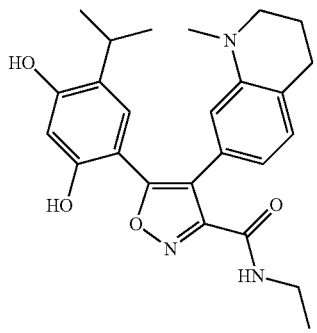 [SMILES: CCNC(=O)c1noc(-c2cc(C(C)C)c(O)cc2O)c1-c1ccc2c(c1)N(C)CCC2]

Reaction scheme:

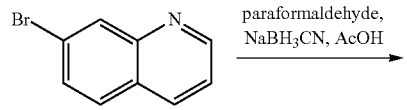

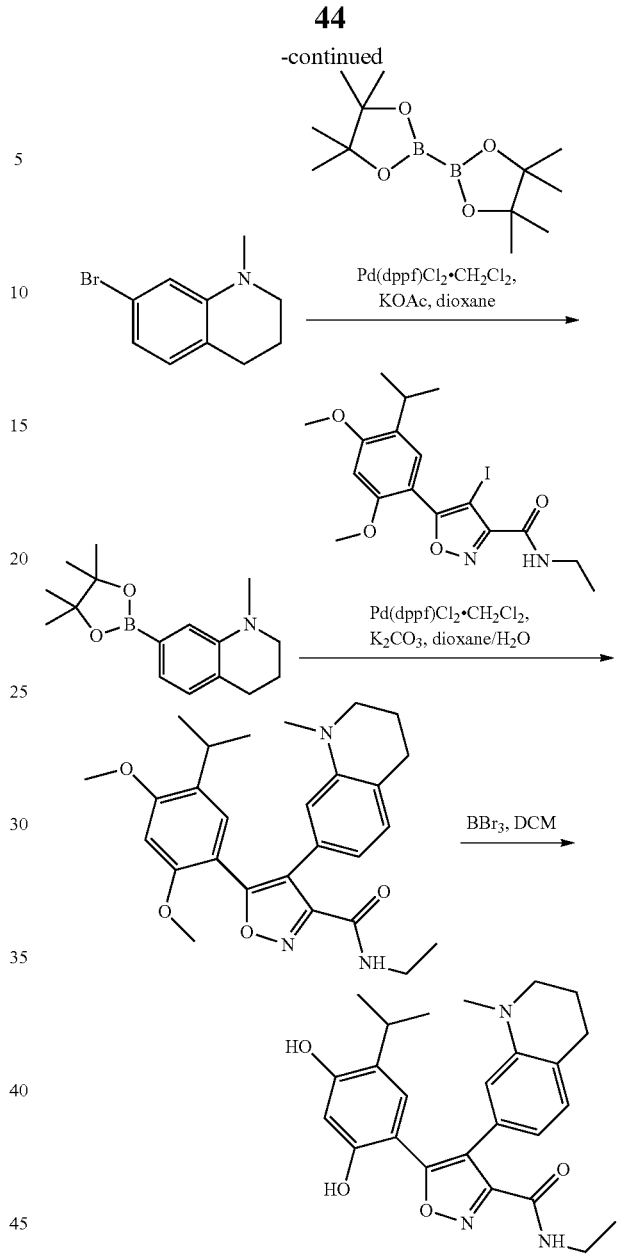

Step A: NaBH$_3$CN (151 mg, 2.4 mmol) was added to a mixture of 7-bromoquinoline (100.00 mg, 480.65 µmol) and paraformaldehyde (433 mg, 4.8 mmol) dissolved in AcOH (3 mL) at 25° C. The mixture was stirred at 25° C. for 40 min and neutralized with NaOH. The whole reaction solution was extracted with DCM (3 mL×3), and the organic phases were combined and washed with saturated brine (3 mL×2), dried over anhydrous sodium sulfate, filtered and concentrated in vacuum. The resulting crude product 7-bromo-1-methyl-1,2,3,4-tetrahydroquinoline (155 mg) was obtained as a brown oil, which was used directly in the next step without further purification. MS (ESI) M/Z: 226 (M+1).

Step B: Bis(pinacolato)diboron (318 mg, 1.25 mmol) and KOAc (144 mg, 1.47 mmol) were added to a solution of 7-bromo-1-methyl-1,2,3,4-tetrahydroquinoline (250 mg, 1.11 mmol) in dioxane (7 mL) at 25° C. under the protection of nitrogen gas, followed by the addition of a catalyst Pd(dppf)Cl$_2$.CH$_2$Cl$_2$ (272 mg, 333 µmol). The mixture was stirred at 25° C. for 10 min and then heated to 90° C. with stirring for 17 hours. The mixture was cooled down to 25°

C. and concentrated under reduced pressure. The residue was purified by silica gel chromatography (100~200 mesh of silica gel, petroleum ether/ethyl acetate=50/1) to give a crude product 1-methyl-7-(4,4,5,5-tetramethyl-1,3,2-dioxaborolan-2-yl)-1,2,3,4-tetrahydroquinoline (316 mg) as a yellow oil. MS (ESI) m/z: 274 (M+1).

Step C: K$_2$CO$_3$ (224 mg, 1.6 mmol) and Pd(dppf)Cl$_2$·CH$_2$Cl$_2$ (66 mg, 81 μmol) were added to a mixed solution of 1-methyl-7-(4,4,5,5-tetramethyl-1,3,2-dioxaborolan-2-yl)-1,2,3,4-tetrahydroquinoline (221 mg, 810.3 μmol) and N-ethyl-4-iodo-5-(5-isopropyl-2,4-dimethoxyphenyl) isoxazole-3-carboxamide (360 mg, 810 μmol) dissolved in dioxane (9.9 mL) and H$_2$O (2.1 mL) at 25° C. under the protection of nitrogen gas. The mixture was stirred at 25° C. for 20 min and then heated to 90° C. with stirring for 17 hours. The mixture was cooled down to 25° C. and concentrated under reduced pressure. The residue was poured into water (5 mL) and stirred for 10 min. The aqueous phase was extracted with ethyl acetate (5 mL×3). The combined organic phase was washed with saturated brine (5 mL×2), dried over anhydrous sodium sulfate, filtered and concentrated in vacuum. The residue was purified by a thin layer chromatography plate (dichloromethane:ethyl acetate=5/1) to give N-ethyl-5-(5-isopropyl-2,4-dimethoxyphenyl)-4-(1-methyl-1,2,3,4-tetrahydroquinolin-7-yl)isoxazole-3-carboxamide (72 mg, 19.2% yield) as a brown oil. MS (ESI) M/Z: 464 (M+1).

Step D: BBr$_3$ (462 mg, 1.85 mmol) was added to a solution of N-ethyl-5-(5-isopropyl-2,4-dimethoxyphenyl)-4-(1-methyl-1,2,3,4-tetrahydroquinolin-7-yl)isoxazole-3-carboxamide (83 mg, 184.6 μmol) in DCM (5 mL) at −78° C. over the course of 15 min. During this course, the temperature was maintained at −78° C. After the addition, the reaction mixture was warmed up to 0° C. and stirred for 30 min. The reaction mixture was then stirred at 25° C. for an additional 16 hours. The reaction was quenched slowly with a saturated aqueous NaHCO$_3$ solution and filtered. The filtrate was removed by distillation in vacuum. The crude product was further purified by preparative HPLC to give 5-(2,4-dihydroxyl-5-isopropylphenyl)-N-ethyl-4-(1-methyl-1,2,3,4-tetrahydroquinolin-7-yl)isoxazole-3-carboxamide (23 mg, 29.8% yield). $^1$H NMR (400 MHz, DMSO-d$_6$): δ 9.73 (s, 1H), 9.63 (s, 1H), 8.83 (t, J=4.0 Hz, 1H), 6.84 (s, 1H), 6.79 (d, J=8.0 Hz, 1H), 6.49 (s, 1H), 6.43-6.42 (m, 2H), 3.27-3.21 (m, 2H), 3.06-2.99 (m, 1H), 2.65-2.63 (m, 5H), 1.88-1.82 (m, 2H), 1.09 (t, J=4.0 Hz, 3H), 1.01 (d, J=4.0 Hz, 6H). MS (ESI) m/z: 436 (M+1).

EXAMPLE 3

5-(2,4-dihydroxyl-5-isopropylphenyl)-N-ethyl-4-(1-methyl-1,2,3,4-tetrahydroquinolin-6-yl)isoxazole-3-carboxamide

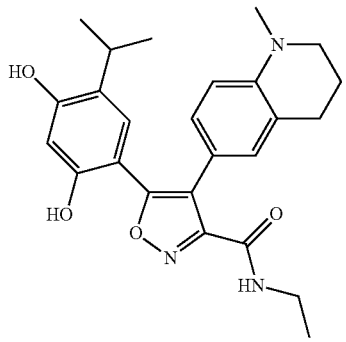 [SMILES: CCNC(=O)c1noc(-c2cc(C(C)C)c(O)cc2O)c1-c1ccc2c(c1)CCCN2C]

Reaction scheme:

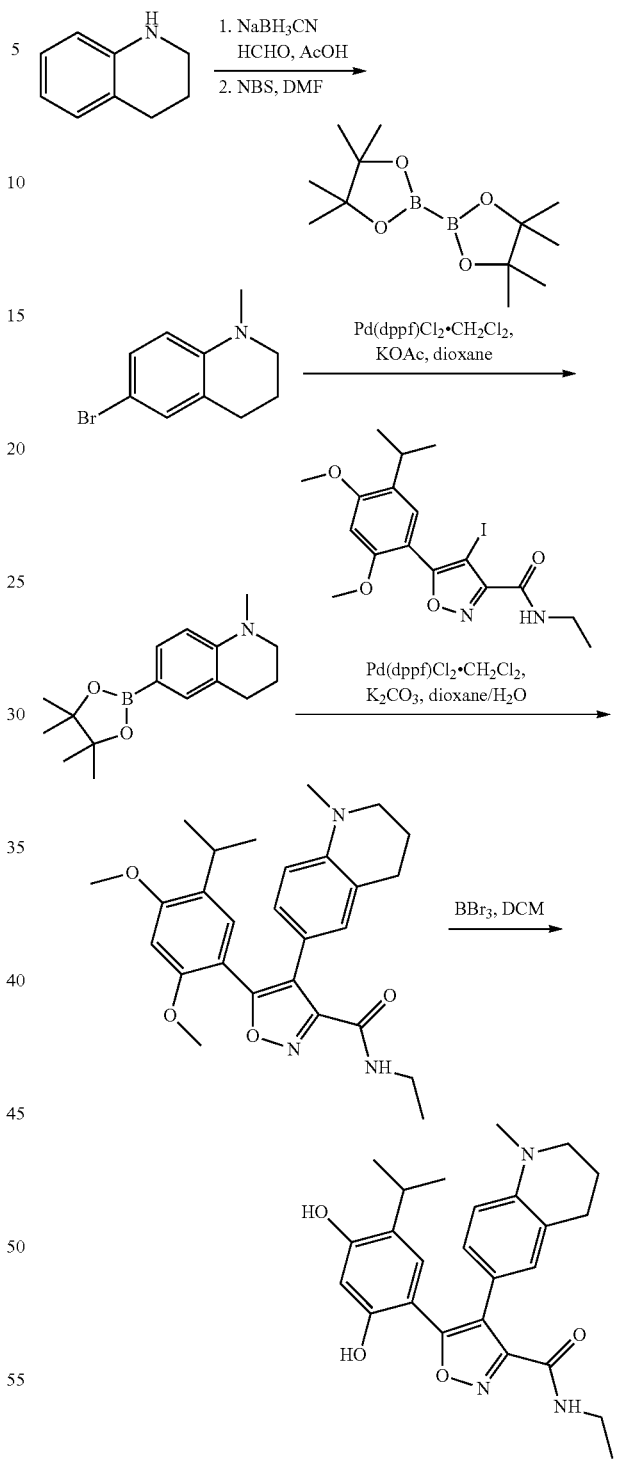

Step A: AcOH (210 mg, 3.5 mmol) was added to a mixture of 1,2,3,4-tetrahydroquinoline (2.0 g, 15.0 mmol) and paraformaldehyde (6.77 g, 75.1 mmol) dissolved in MeOH (20 mL) in one portion at 25° C. The mixture was stirred at 25° C. for 1 hour, followed by the addition of NaBH$_3$CN (1.89 g, 30.0 mmol) and continuous stirring for 16 hours. The mixture was concentrated under reduced pressure. The residue was poured into water (15 mL) and stirred for 10 min. The aqueous phase was extracted with ethyl acetate (10 mL×3). The combined organic phase was washed with saturated brine (10 mL×3), dried over anhydrous sodium sulfate, filtered and concentrated in vacuum, to give 1-methyl-1,2,3,4-tetrahydroquinoline (1.17 g, 52.9%) as a yellow oil. MS (ESI) M/Z: 148 (M+1).

Step B: A solution of 1-methyl-1,2,3,4-tetrahydroquinoline (300 mg, 2.04 mmol) in DMF (5 mL) was cooled down to 0° C. and then added with NBS (363.1 mg, 2.0 mmol). The reaction solution was stirred at 0° C. for 2 hours and then warmed up to 25° C. with stirring for 16 hours. The reaction substances were then poured into 5 mL of water and the suspension was extracted with ethyl acetate (5 mL×3). The combined organic phase was washed with saturated brine (5 mL×2), dried over anhydrous sodium sulfate, filtered and concentrated in vacuum, to give the crude product 6-bromo-1-methyl-1,2,3,4-tetrahydroquinoline (485 mg) as a brown solid, which was used in the next step without further purification. MS (ESI) M/Z: 226 (M+1).

Step C: Pd(dppf)Cl$_2$.CH$_2$Cl$_2$ (271 mg, 331.7 μmol) was added to a solution of 6-bromo-1-methyl-1,2,3,4-tetrahydroquinoline (250 mg, 1.1 mmol), bis(pinacolato)diboron (318 mg, 1.2 mmol) and KOAc (325 mg, 3.3 mmol) dissolved in dioxane (7 mL) at 25° C. under the protection of nitrogen gas. The mixture was stirred at 25° C. for 10 min and then heated to 90° C. with stirring for 17 hours. The mixture was cooled down to 25° C. and concentrated under reduced pressure. The residue was purified by silica gel chromatography (100~200 mesh of silica gel, petroleum ether/ethyl acetate=50/1) to give 1-methyl-6-(4,4,5,5-tetramethyl-1,3,2-dioxaborolan-2-yl)-1,2,3,4-tetrahydroquinoline (187 mg) as a yellow oil. MS (ESI) M/Z: 274 (M+1).

Step D: Pd(PPh$_3$)$_2$Cl$_2$ (15.8 mg, 22.5 μmol) and NaHCO$_3$ (37.8 mg, 450.2 μmol) were added to a mixed solution of 1-methyl-6-(4,4,5,5-tetramethyl-1,3,2-dioxaborolan-2-yl)-1,2,3,4-tetrahydroquinoline (92 mg, 337.6 μmol) and N-ethyl-4-iodo-5-(5-isopropyl-2,4-dimethoxyphenyl) isoxazole-3-carboxamide (100 mg, 225.1 μmol) dissolved in dioxane (6.6 mL) and H$_2$O (1.4 mL) at 25° C. under the protection of nitrogen gas. The mixture was stirred at 25° C. for 10 min and then heated to 90° C. with stirring for 17 hours. The mixture was cooled down to 25° C. and concentrated under reduced pressure. The residue was poured into water (8 mL) and stirred for 10 min. The aqueous phase was extracted with ethyl acetate (5 mL×3). The combined organic phase was washed with saturated brine (5 mL×2), dried over anhydrous sodium sulfate, filtered and concentrated in vacuum. The residue was purified by a thin layer chromatography plate (dichloromethane:ethyl acetate=3/1) to give N-ethyl-5-(5-isopropyl-2,4-dimethoxyphenyl)-4-(1-methyl-1,2,3,4-tetrahydroquinolin-6-yl)isoxazole-3-carboxamide (51 mg, 48.9% yield) as a brown oil. MS (ESI) M/Z: 464 (M+1).

Step E: BBr$_3$ (270 mg, 1.08 mmol, 10.00 eq.) was added to a solution of N-ethyl-5-(5-isopropyl-2,4-dimethoxyphenyl)-4-(1-methyl-1,2,3,4-tetrahydroquinolin-6-yl)isoxazole-3-carboxamide (50 mg, 107.9 μmol, 1.00 eq.) in DCM (5 mL) at −78° C. over the course of 15 min. During this course, the temperature was maintained at −78° C. After the addition, the reaction mixture was warmed up to 0° C. and stirred for 30 min. The reaction mixture was then stirred at 25° C. for an additional 16 hours. The reaction substances were quenched slowly with a saturated aqueous NaHCO$_3$ solution and filtered. The filtrate was removed by distillation under vacuum. The crude product was purified by preparative HPLC to give 5-(2,4-dihydroxyl-5-isopropylphenyl)-N-ethyl-4-(1-methyl-1,2,3,4-tetrahydroquinolin-6-yl)isoxazole-3-carboxamide (26.8 mg, 57.0%). $^1$H NMR (400 MHz, DMSO-d$_6$): δ 9.73 (s, 1H), 9.60 (s, 1H), 8.78 (t, J=8.0 Hz, 1H), 6.87-6.89 (m, 1H), 6.84-6.80 (m, 1H), 6.49 (d, J=8.0 Hz, 1H), 6.43 (s, 1H), 3.27-3.20 (m, 2H), 3.17-3.14 (m, 2 H), 3.06-2.97 (m, 1 H), 2.80 (s, 3 H), 2.56 (t, J=4.0 Hz, 2H), 1.87-1.83 (m, 2H), 1.09 (t, J=4.0 Hz, 3H), 1.02-0.99 (m, 6H). MS (ESI) m/z: 356 (M+1).

EXAMPLE 4

5-(2,4-dihydroxyl-5-isopropylphenyl)-N-ethyl-4-(1,2,3,4-tetrahydro-1,4-epiminonaphth-6-yl)isoxazole-3-carboxamide

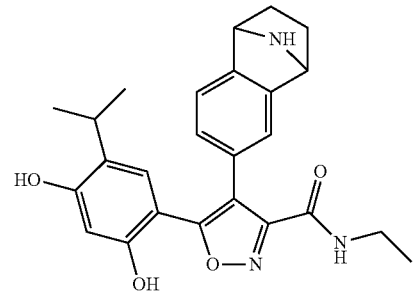 [SMILES: CCNC(=O)c1noc(-c2cc(C(C)C)c(O)cc2O)c1-c1ccc2c(c1)C1CCC2N1]

Reaction scheme:

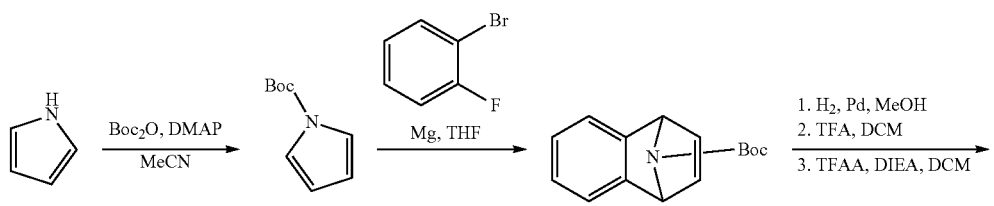

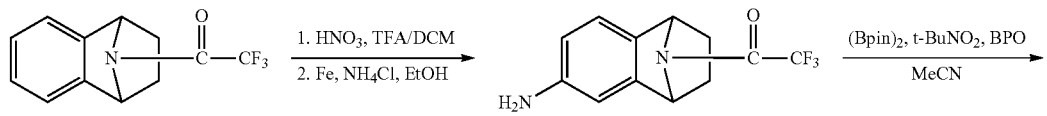

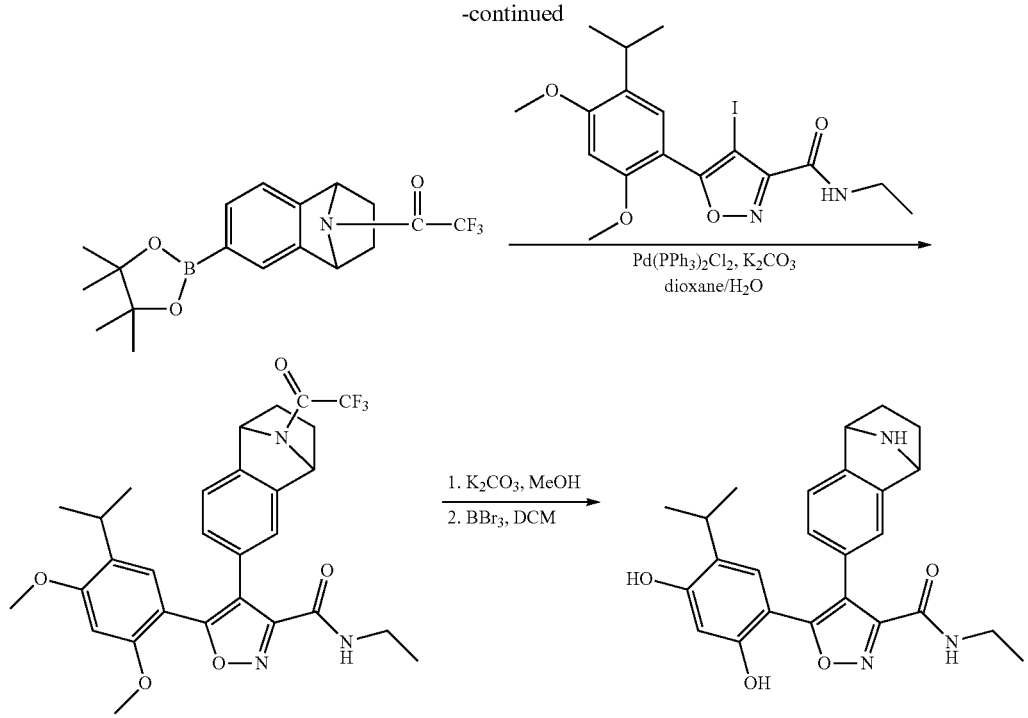

Step A: DMAP (1.00 g, 8.2 mmol, 0.14 eq.) was added to a solution of pyrrole (4.00 g, 59 mmol, 1.00 eq.) and (Boc)$_2$O (15.60 g, 71.5 mmol, 1.20 eq.) dissolved in acetonitrile (200 mL). The mixture was stirred at 25° C. for 2 hours. The mixture was concentrated and the residue was purified by a silica gel column (the eluent is PE) to give t-butyl pyrryl-1-formate (7.80 g, 46.7 mmol, 78.3% yield) as colorless liquid.

Step B: A mixed solution of t-butyl pyrryl-1-formate (4.60 g, 27.5 mmol, 1.00 eq.) and magnesium powder (720 mg, 27.5 mmol, 1.0 eq.) in THF (20 mL) was heated to 66° C. in an oil bath. 1-bromo-2-fluoro-benzene (4.88 g, 27.89 mmol, 1.0 eq.) was added slowly in 20 min, and after the addition, the mixture was stirred at 66° C. for 8 hours. The solvent was removed under reduced pressure and 0.5N HCl aqueous solution was added, followed by extraction with DCM. The organic layer was washed with brine, dried over anhydrous sodium sulfate and concentrated under reduced pressure. The resulting residue was purified by column chromatography (PE/EA=20/1) to give t-butyl 1,4-dihydro-1,4-epiminonaphthyl-9-formate (2.43 g, 10 mmol, 36.3% yield) as yellow liquid.

Step C: A solution of t-butyl 1,4-dihydro-1,4-epiminonaphthyl-9-formate (2.43 g, 10 mmol, 1.00 eq.) and dry Pd/C (200 mg) in MeOH (50 mL) was stirred at 25° C. for 2 hours under H$_2$ atmosphere. The mixture was filtered through a diatomaceous earth pad and the filtrate was concentrated to give t-butyl 1,2,3,4-tetrahydro-1,4-epiminonaphthyl-9-formate (2.33 g, 9.5 mmol, 95.1% yield) as a yellow oil.

Step D: t-Butyl 1,2,3,4-tetrahydro-1,4-epiminonaphthyl-9-formate (2.33 g, 9.5 mmol, 1.0 eq.) was added to a mixed solution of DCM (1.2 mL) and TFA (4.5 mL) at 0° C. The mixture was stirred at 0° C. for 0.5 hour and subsequently stirred at 25° C. for 4.5 hours. After the solvent was removed under reduced pressure, 2N NaOH aqueous solution was added and the aqueous phase was extracted with DCM. The organic layer was dried over anhydrous sodium sulfate and concentrated, to give 1,2,3,4-tetrahydro-1,4-epiminonaphthalene (1.38 g, 9.5 mmol, 100% yield) as a yellow solid.

Step E: A mixture of 1,2,3,4-tetrahydro-1,4-epiminonaphthalene (1.38 g, 9.5 mmol, 1.00 eq.) and DIEA (1.37 g, 10.6 mmol, 1.12 eq.) in anhydrous DCM (20.00 mL) was cooled down to 0° C., and added with TFAA (2.27 g, 10.8 mmol, 1.14 eq.). The reaction mixture was slowly warmed up to 25° C. under the protection of nitrogen gas, and stirred for 5 hours. The resulting reaction mixture was cooled down to 0° C. and added with water (2 mL) to quench the remaining anhydride. The aqueous phase was adjusted to neutral using aqueous NaOH solution (1 N), and then the organic phase was separated out. The aqueous phase was extracted twice with DCM, and the combined organic layer was dried by anhydrous sodium sulfate and concentrated to give 2,2,2-trifluoro-1-(1,2,3,4-tetrahydro-1,4-epiminonaphth-9-yl)ethanone (2.24 g, 9.29 mmol, 97.8% yield) as a brown oil.

Step F: A solution (5.00 mL) of 2,2,2-trifluoro-1-(1,2,3,4-tetrahydro-1,4-epiminonaphth-9-yl)ethanone (2.24 g, 9.29 mmol, 1.00 eq.) in TFA was cooled down to 0° C. and added dropwise with fuming nitric acid (1 mL). The resulting reaction mixture was stirred at 0° C. for 1 hour and then stirred at 25° C. for 1 hour. The mixture was poured into 300 mL of ice water and extracted three times with DCM. The combined organic phase was washed successively with saturated aqueous NaHCO$_3$ solution and saturated aqueous NaCl solution. The organic phase was dried over anhydrous sodium sulfate and concentrated. The residue was purified by silica gel column chromatography (elution with DCM) to give the target product 2,2,2-trifluoro-1-(6-nitro-1,2,3,4-tetrahydro-1,4-epiminonaphth-9-yl)ethanone (1.86 g, 6.50 mmol, 67.0% yield) as a yellow solid.

Step G: NH$_4$Cl (2.63 g, 49.2 mmol, 4.02 eq.) and iron powder (3.43 g, 61.4 mmol, 5.02 eq.) were successively added to a mixed solution of 2,2,2-trifluoro-1-(6-nitro-1,2,3,4-tetrahydro-1,4-epiminonaphth-9-yl)ethanone (3.5 g, 12.23 mmol, 1.00 eq) dissolved in dioxane (20.00 mL)/ ethanol (16.00 mL)/H$_2$O (12.00 mL). The resulting mixture was heated to 80° C. under the protection of nitrogen gas and stirred for 3 hours. The reaction mixture was cooled down to 25° C., diluted with EtOAc and H$_2$O, and filtered through a diatomaceous earth pad. The organic phase was collected by liquid separation, dried over sodium sulfate and concentrated under reduced pressure to give 2,2,2-trifluoro-1-(6-amino-1,2,3,4-tetrahydro-1,4-epiminonaphth-9-yl)ethanone (2.7 g, 10.5 mmol, 86.2% yield), which was used directly in the next step without further purification.

Step H: A solution of 2,2,2-trifluoro-1-(6-amino-1,2,3,4-tetrahydro-1,4-epiminonaphth-9-yl)ethanone (2.7 g, 10.5 mmol, 1.0 eq.), bis(pinacolato)diboron (2.68 g, 10.5 mmol, 1.0 eq.), BPO (76 mg, 316 μmol, 0.03 eq.) and t-butyl nitrite (1.63 g, 15.8 mmol, 1.5 eq.) dissolved in MeCN (15.0 mL) was stirred at 25° C. for 16 hours. The mixture was concentrated under reduced pressure and the crude residue was purified by column chromatography (petroleum ether:ethyl acetate=40:1 to 5:1) to give 2,2,2-trifluoro-1-(6-(4,4,5,5-tetramethyl-1,3,2-dioxaborolan-2-yl)-1,2,3,4-tetrahydro-1,4-epiminonaphth-9-yl)ethanone (2.2 g, 6.0 mmol, 56.9% yield) as a yellow oil.

Step I: A solution of N-ethyl-4-iodo-5-(5-isopropyl-2,4-dimethoxy-phenyl)-isoxazole-3-carboxamide (500 mg, 1.13 mmol, 1.00 eq.), 2,2,2-trifluoro-1-(6-(4,4,5,5-tetramethyl-1,3,2-dioxaborolan-2-yl)-1,2,3,4-tetrahydro-1,4-epiminonaphth-9-yl)ethanone (539 mg, 1.47 mmol, 1.3 eq.), Pd(PPh$_3$)$_2$Cl$_2$ (158 mg, 225.1 μmol, 0.20 eq.) and NaHCO$_3$ (283 mg, 3.38 mmol, 3.0 eq.) added in THF (5.00 mL) was replaced in a nitrogen atmosphere, then heated to 120° C. by microwave and reacted for 30 min. The reaction mixture was poured into water (15 mL). The mixture was extracted with ethyl acetate (10 mL×2). The combined organic phase was washed with saturated brine (15 mL), dried over anhydrous Na$_2$SO$_4$, filtered and concentrated in vacuum to give a residue. The residue was purified by silica gel chromatography (petroleum ether/ethyl acetate=50/1 to 5/1) to give N-ethyl-5-(5-isopropyl-2,4-dimethoxy-phenyl)-4-(9-(2,2,2-trifluoroacetyl)-1,2,3,4-tetrahydro-1,4-epiminonaphth-6-yl)isoxazole-3-carboxamide (500 mg, 807 μmol, 71.4% yield, 90% purity).

Step J: K$_2$CO$_3$ (526 mg, 3.8 mmol, 5.0 eq.) was added to a mixed solution of N-ethyl-5-(5-isopropyl-2,4-dimethoxy-phenyl)-4-(9-(2,2,2-trifluoroacetyl)-1,2,3,4-tetrahydro-1,4-epiminonaphth-6-yl)isoxazole-3-carboxamide (500 mg, 762.3 μmol, 1.0 eq.) in MeOH (4.2 mL) and H$_2$O (1.8 mL) at 30° C. The reaction solution was stirred at 30° C. for 18 hours and poured into water (10 mL). The aqueous phase was extracted with EA (10 mL×3). The combined organic phase was washed with saturated brine (10 mL×2), dried over anhydrous sodium sulfate, filtered and concentrated in vacuum. The residue was purified by thin layer chromatography plate (DCM/methanol=15:1) to give N-ethyl-5-(5-isopropyl-2,4-dimethoxy-phenyl)-4-(1,2,3,4-tetrahydro-1,4-epiminonaphth-6-yl)isoxazole-3-carboxamide (220 mg, 476.7 μmol, 62.5% yield) as a white solid.

Step K: BBr$_3$ (271 mg, 1.08 mmol, 10.00 eq.) was slowly added dropwise to a solution of N-ethyl-5-(5-isopropyl-2,4-dimethoxy-phenyl)-4-(1,2,3,4-tetrahydro-1,4-epiminonaphth-6-yl)isoxazole-3-carboxamide (50 mg, 108.3 μmol, 1.0 eq.) in anhydrous DCM (2.0 mL) at −78° C. After the addition, the solution was warmed up to 30° C. and stirred for 18 hours. The solution was cooled down to −78° C. and added with MeOH (1 mL), followed by addition of saturated aqueous NaHCO$_3$ solution (3 mL). The mixture was stirred at 30° C. for 5 min. The mixture was extracted with DCM (10 mL×3), and the organic layers were combined, washed with brine (10 mL×2), dried with Na$_2$SO$_4$, filtered and concentrated in vacuum to give a residue. The residue was purified by high performance liquid chromatography (formic acid system) to give 5-(2,4-dihydroxyl-5-isopropylphenyl)-N-ethyl-4-(1,2,3,4-tetrahydro-1,4-epiminonaphth-6-yl)isoxazole-3-carboxamide (30 mg, 69.2 μmol, 63.9% yield). $^1$H NMR (400 MHz, DMSO-d$_6$): δ 8.83 (t, J=5.4 Hz, 1H), 8.31 (brs, 1H), 7.25-7.14 (m, 2H), 7.01 (d, J=7.0 Hz, 1H), 6.71 (s, 1H), 6.45 (s, 1H), 4.72-4.57 (m, 2H), 3.28-3.17 (m, 2H), 3.03-2.90 (m, 1H), 1.95 (brs, 2H), 1.18-1.04 (m, 5H), 0.91 (t, J=6.0 Hz, 6H).

EXAMPLE 5

5-(2,4-dihydroxyl-5-isopropylphenyl)-N-ethyl-4-(9-methyl-1,2,3,4-tetrahydro-1,4-epiminonaphth-6-yl)isoxazole-3-carboxamide

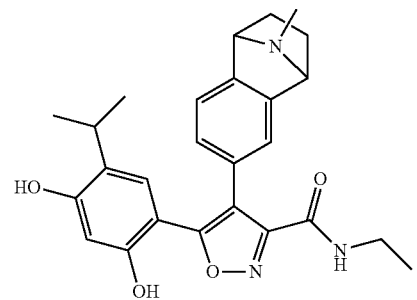 [SMILES: CCNC(=O)c1noc(-c2cc(C(C)C)c(O)cc2O)c1-c1ccc2c(c1)C1CCC2N1C]

Reaction scheme:

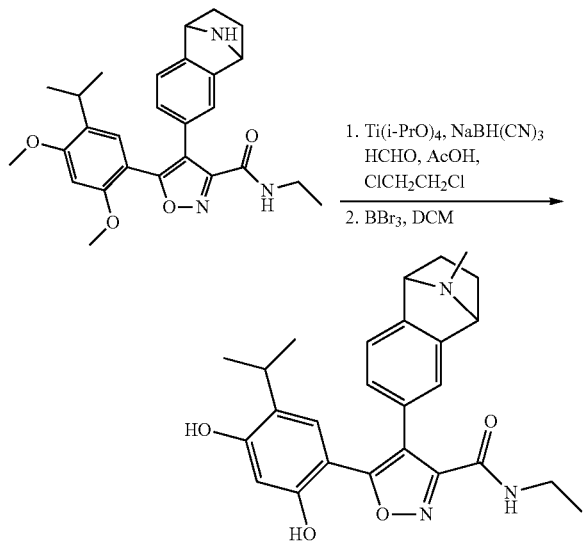

Step A: Paraformaldehyde (39 mg, 433.3 μmol, 10.00 eq.), acetic acid (1.3 mg, 21.7 μmol, 0.50 eq.) and titanium tetraisopropanolate (6.2 mg, 21.7 μmol, 0.50 eq.) were added to a solution of N-ethyl-5-(5-isopropyl-2,4-dimethoxy-phenyl)-4-(1,2,3,4-tetrahydro-1,4-epiminonaphth-6-yl)isoxazole-3-carboxamide (20 mg, 43.3 μmol, 1.0 eq.) in 1,2-dichloroethane (3 mL). The mixed solution was stirred at 30° C. for 18 hours and then added with NaBH$_3$CN (8.2 mg, 130 μmol, 3.00 eq.), and the mixture was stirred for an additional 2 hours. The reaction solution was added with water (10 mL) and filtered, and the filtrate was extracted with DCM (10 mL×3). The organic layers were combined, washed with brine (5 mL×2), dried over anhydrous sodium sulfate, filtered and concentrated in vacuum, to give N-ethyl-5-(5-isopropyl-2,4-dimethoxyphenyl)-4-(9-methyl-1,2,3,4-tetrahydro-1,4-epiminonaphth-6-yl)isoxazole-3-carboxamide (20 mg, 42.1 µmol, 97.1% yield) as a yellow oil.

Step B: BBr$_3$ (158 mg, 630.8 µmol, 10 eq.) was slowly added dropwise to a solution of N-ethyl-5-(5-isopropyl-2,4-dimethoxyphenyl)-4-(9-methyl-1,2,3,4-tetrahydro-1,4-epiminonaphth-6-yl)isoxazole-3-carboxamide (30 mg, 63.1 µmol, 1.0 eq.) in anhydrous DCM (2 mL) at −78° C. After the addition, the solution was warmed up to 30° C. and stirred for 18 hours. The solution was cooled down to −78° C. and slowly added with MeOH (1 mL), followed by the addition of a saturated aqueous NaHCO$_3$ solution (3 mL). The mixture then was stirred at 30° C. for 5 min. The mixture was extracted with DCM (10 mL×3), and the organic layers were combined, washed with brine (10 mL×2), dried over anhydrous Na$_2$SO$_4$, filtered and concentrated in vacuum. The resulting residue was purified by preparative HPLC to give 5-(2,4-dihydroxyl-5-isopropylphenyl)-N-ethyl-4-(9-methyl-1,2,3,4-tetrahydro-1,4-epiminonaphth-6-yl)isoxazole-3-carboxamide (10 mg, 22.3 µmol, 35.4% yield). $^1$H NMR (400 MHz, DMSO-d$_6$) ■δ8.79 (t, J=5.5 Hz, 1H), 7.22-7.12 (m, 2H), 6.99 (d, J=7.3 Hz, 1H), 6.68 (s, 1H), 6.46 (s, 1H), 4.04 (d, J=19.8 Hz, 2H), 3.27-3.16 (m, 2H), 3.01-2.89 (m, 1H), 2.05-1.80 (m, 5H), 1.10-0.97 (m, 6H), 0.89 (d, J=6.8 Hz, 6H).

EXAMPLE 6

5-(2,4-dihydroxyl-5-isopropylphenyl)-N-ethyl-4-(9-ethyl-1,2,3,4-tetrahydro-1,4-epiminonaphth-6-yl)isoxazole-3-carboxamide

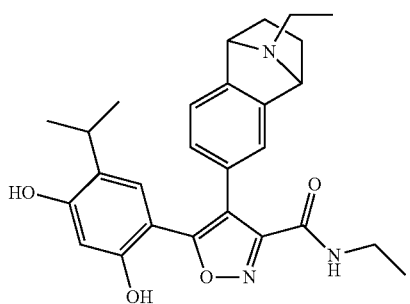 [SMILES: CCNC(=O)c1noc(-c2cc(C(C)C)c(O)cc2O)c1-c1ccc2c(c1)C1CCC2N1CC]

Step A: The title compound of this example was prepared according to the order of steps A and B in Example 5, wherein paraformaldehyde in step A was replaced with acetaldehyde. $^1$H NMR (400 MHz, DMSO-d$_6$) δ 8.80 (t, J=5.5 Hz, 1H), 8.24 (brs, 1H), 7.23-7.11 (m, 2H), 6.98 (d, J=7.5 Hz, 1H), 6.67 (s, 1H), 6.46 (s, 1H), 4.22 (d, J=19.8 Hz, 2H), 3.25-3.15 (m, 2H), 2.95 (td, J=6.8, 13.7 Hz, 1H), 2.17-1.86 (m, 4H), 1.06 (t, J=7.2 Hz, 5H), 0.95-0.84 (m, 9H).

EXAMPLE 7

5-(2,4-dihydroxyl-5-isopropylphenyl)-N-ethyl-4-(9-isopropyl-1,2,3,4-tetrahydro-1,4-epiminonaphth-6-yl)isoxazole-3-carboxamide

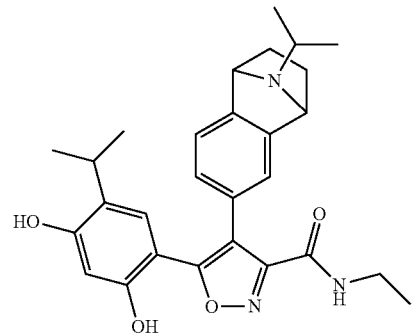 [SMILES: CCNC(=O)c1noc(-c2cc(C(C)C)c(O)cc2O)c1-c1ccc2c(c1)C1CCC2N1C(C)C]

Step A: The title compound of this example was prepared according to the order of steps A and B in Example 5, wherein paraformaldehyde in step A was replaced with acetone. $^1$H NMR (400 MHz, DMSO-d$_6$) δ 8.80 (t, J=5.5 Hz, 1H), 8.21 (s, 1H), 7.23-7.11 (m, 2H), 6.98 (d, J=7.3 Hz, 1H), 6.66 (s, 1H), 6.45 (s, 1H), 4.40 (d, J=16.6 Hz, 2H), 3.22 (q, J=6.7 Hz, 2H), 2.95 (td, J=6.9, 13.6 Hz, 1H), 1.98 (brs, 3H), 1.06 (t, J=7.2 Hz, 5H), 0.96-0.79 (m, 12H).

EXAMPLE 8

5-(2,4-dihydroxyl-5-isopropylphenyl)-N-ethyl-4-(9-isobutyl-1,2,3,4-tetrahydro-1,4-epiminonaphth-6-yl)isoxazole-3-carboxamide

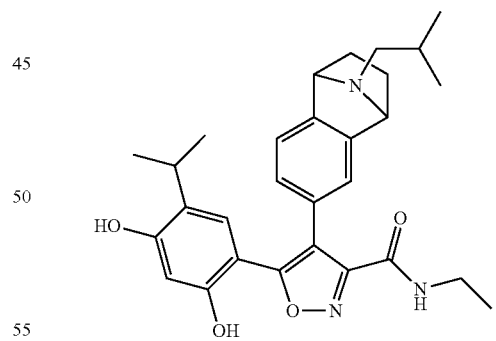

Step A: The title compound of this example was prepared according to the order of steps A and B in Example 5, wherein paraformaldehyde in step A was replaced with isobutyraldehyde. $^1$H NMR (400 MHz, DMSO-d$_6$) δ 8.78 (t, J=5.5 Hz, 1H), 7.19-7.10 (m, 2H), 6.96 (d, J=7.3 Hz, 1H), 6.65 (s, 1H), 6.46 (s, 1H), 4.18-4.04 (m, 2H), 3.26-3.17 (m, 3H), 3.01-2.88 (m, 1H), 1.96 (brs, 2H), 1.83 (d, J=7.0 Hz, 2H), 1.53 (td, J=6.7, 13.3 Hz, 1H), 1.09-0.95 (m, 5H), 0.87 (d, J=6.0 Hz, 6H), 0.80 (dd, J=1.8, 6.3 Hz, 6H).

EXAMPLE 9

5-(2,4-dihydroxyl-5-isopropylphenyl)-N-ethyl-4-(5-methyl-4,5,6,7-tetrahydrothieno[3,2-c]pyridin-2-yl) isoxazole-3-carboxamide

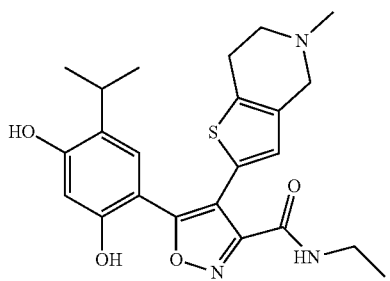 [SMILES: CCNC(=O)c1noc(-c2cc(C(C)C)c(O)cc2O)c1-c1cc2c(s1)CCN(C)C2]

Reaction scheme:

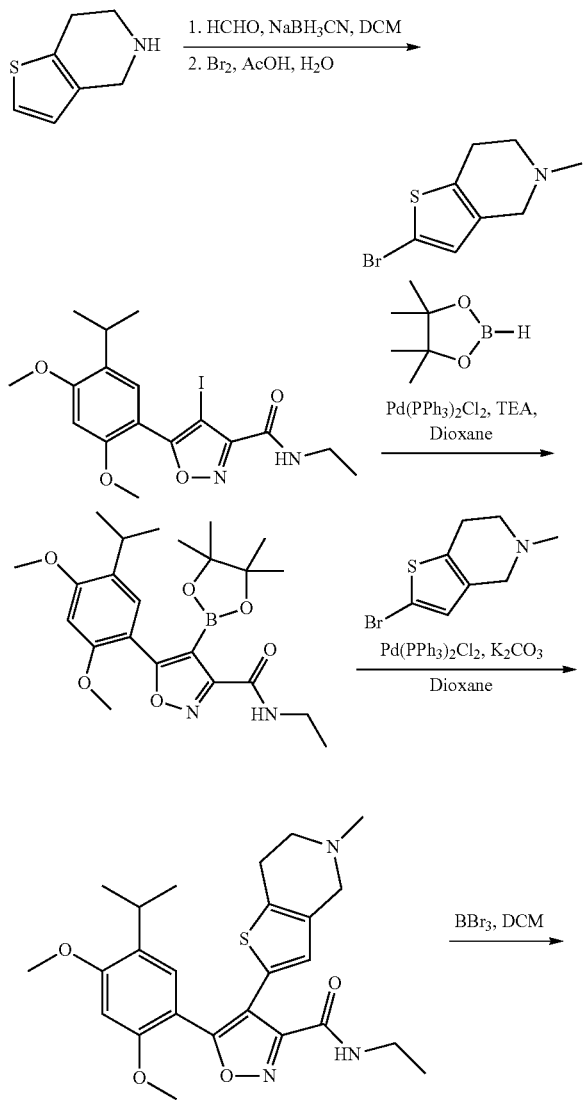

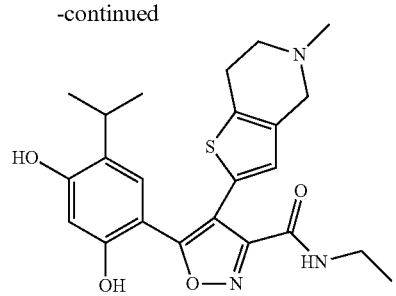

Step A: 4 Å molecular sieve (10.00 g), titanium tetraisopropanolate (1.02 g, 3.59 mmol, 0.05 eq.) and AcOH (215.67 mg, 3.59 mmol, 0.05 eq.) were added to a solution of 4,5,6,7-tetrahydrothieno[3,2-c]pyridine (10.0 g, 71.8 mmol, 1.0 eq.) in DCM (120.0 mL). The mixture was stirred at 25° C. for 16 hours, then added with $NaBH_3CN$ (9.03 g, 143.66 mmol, 2.00 eq.) and stirred at 25° C. for an additional 3 hours. The mixture was poured into water (300 mL) and extracted with EA (100 mL×2). The combined organic layer was dried by anhydrous sodium sulfate, filtered and concentrated. The residue was purified by silica gel chromatography (DCM/methanol=50/1 to 10/1), to give 5-methyl-4,5,6,7-tetrahydrothieno[3,2-c]pyridine (2.50 g, 16.31 mmol, 22.71% yield) as a yellow oil.

Step B: $Br_2$ (1.88 g, 11.75 mmol, 0.90 eq.) was added to a mixed solution of 5-methyl-4,5,6,7-tetrahydrothieno[3,2-c]pyridine (2.00 g, 13.05 mmol, 1.0 eq.) dissolved in AcOH (20.00 mL) and water (20.00 mL) at 0° C. After stirring at 0° C. for 1 hour, the mixture was poured into water (100 mL), basified with NaOH (10 N) to pH=8~9, and then extracted with EA (100 mL×2). The combined organic layer was concentrated to give 2-bromo-5-methyl-4,5,6,7-tetrahydrothieno[3,2-c]pyridine (2.70 g, 11.6 mmol, 89.1% yield), which was used directly in the next step.

Step C: $Pd(PPh_3)_2Cl_2$ (142.5 mg, 203.0 μmol, 0.10 eq.), TEA (616 mg, 6.1 mmol, 3.0 eq.) and 4,4,5,5-tetramethyl-1,3,2-dioxaborolane (779 mg, 6.1 mmol, 3.0 eq.) were added to a solution of N-ethyl-4-iodo-5-(5-isopropyl-2,4-dimethoxy-phenyl) isoxazole-3-carboxamide (900 mg, 2.03 mmol, 0.10 eq.) in dioxane (20.00 mL) under the protection of nitrogen gas. The mixture was stirred at 80° C. for 16 hours. After cooling, the mixture was poured into water (60 mL) and extracted with EA (60 mL×2), and then the organic layers were combined. The organic layer was concentrated to give N-ethyl-5-(5-isopropyl-2,4-dimethoxy-phenyl)-4-(4,4,5,5-tetramethyl-1,3,2-dioxaborolan-2-yl)isoxazole-3-carboxamide (1.0 g, a crude product) as a black-brown oil, which was used directly in the next step.

Step D: $Pd(dppf)Cl_2 \cdot CH_2Cl_2$ (91.9 mg, 112.5 μmol, 0.10 eq.) and $K_2CO_3$ (466 mg, 3.4 mmol, 3.00 eq.) were added to a mixed solution of N-ethyl-5-(5-isopropyl-2,4-dimethoxy-phenyl)-4-(4,4,5,5-tetramethyl-1,3,2-dioxaborolan-2-yl) isoxazole-3-carboxamide (500 mg, 1.13 mmol, 1.00 eq.) and 2-bromo-5-methyl-4,5, 6,7-tetrahydrothieno[3,2-c]pyridine (268 mg, 1.13 mmol, 1.00 eq.) in dioxane (10.00 mL) and water (2.00 mL) under the protection of nitrogen gas. The mixture was stirred at 80° C. for 16 hours. After cooling, the mixture was poured into water (80 mL) and extracted with EA (80 mL×2). The organic layers were combined and concentrated. The residue was purified by silica gel chromatography (PE/EA=1/1 to 0/1). N-ethyl-5-(5-isopropyl-2,4-dimethoxy-phenyl)-4-(5-methyl-4,5,6,7-tetrahydrothieno

[3,2-c]pyridin-2-yl)isoxazole-3-carboxamide (430 mg, 915.7 μmol, 81.0% yield) as a black-brown solid was obtained.

Step E: BBr₃ (1.49 g, 5.96 mmol, 5.0 eq.) was added slowly to a solution of N-ethyl-5-(5-isopropyl-2,4-dimethoxy-phenyl)-4-(5-methyl-4,5,6,7-tetrahydrothieno[3,2-c]pyridin-2-yl)isoxazole-3-carboxamide (560 mg, 1.19 mmol, 1.00 eq.) in DCM (15 mL) at −78° C. The mixture was stirred at 25° C. for 16 hours, added with MeOH (20 mL) and concentrated. The residue was purified by preparative HPLC (formic acid system). The product 5-(2,4-dihydroxyl-5-isopropyl-phenyl)-N-ethyl-4-(5-methyl-4,5,6,7-tetrahydrothieno[3,2-c]pyridin-2-yl)isoxazole-3-carboxamide (243 mg, 550.3 μmol, 46.1% yield) was obtained. ¹HNMR (400 MHz, DMSO-d₆) δ 9.73 (m, 2H), 8.91 (t, J=2.0 Hz, 1H), 8.15 (s, 1H), 6.91 (s, 1H), 6.80 (s, 1H), 6.45 (s, 1H), 3.27-3.24 (m, 2H), 3.07-3.04 (m, 1H), 2.72-2.70 (m, 2H), 2.65-2.63 (m, 2H), 2.34 (s, 3H), 1.16-1.04 (s, 9H).

EXAMPLE 10

5-(2,4-dihydroxyl-5-isopropyl-phenyl)-N-ethyl-4-(5-methyl-4,5,6,7-tetrahydrothiazolo[4,5-c]pyridin-2-yl)isoxazole-3-carboxamide

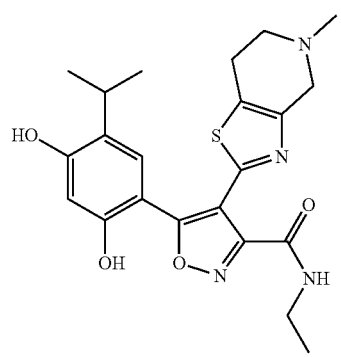 [SMILES: CCNC(=O)c1noc(-c2cc(C(C)C)c(O)cc2O)c1-c1nc2c(s1)CCN(C)C2]

Reaction scheme:

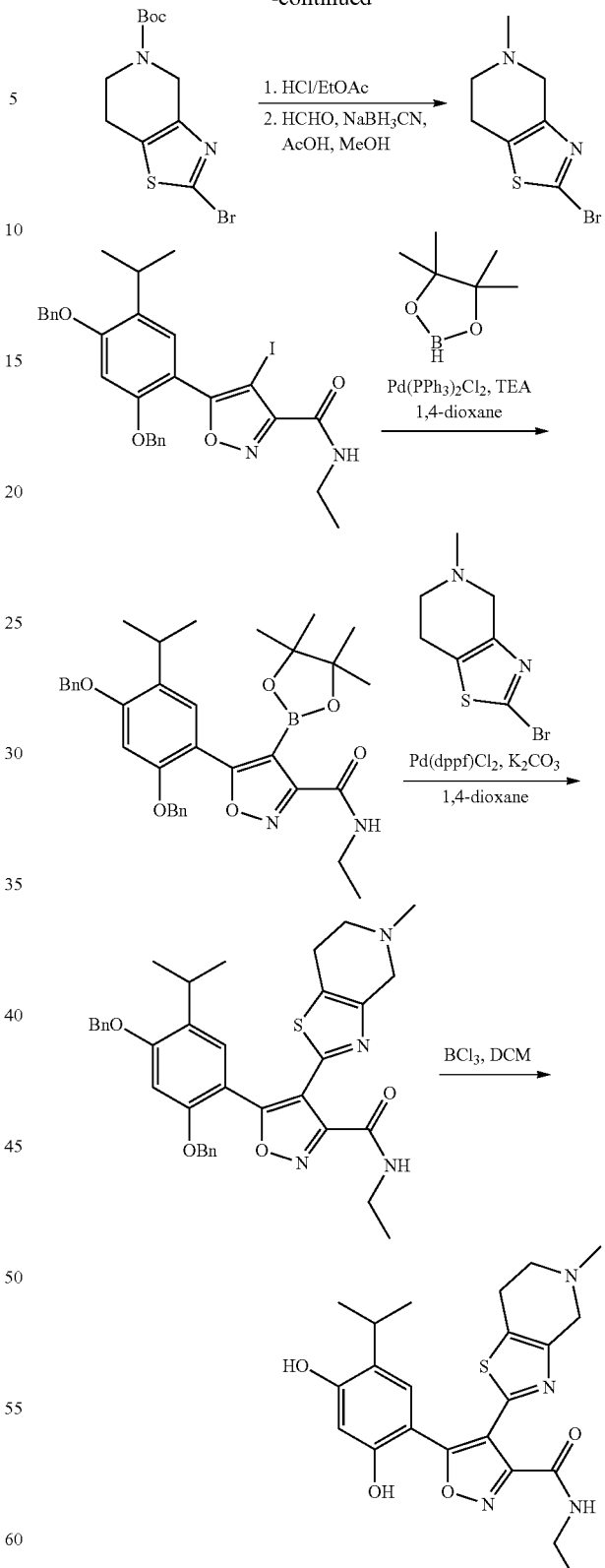

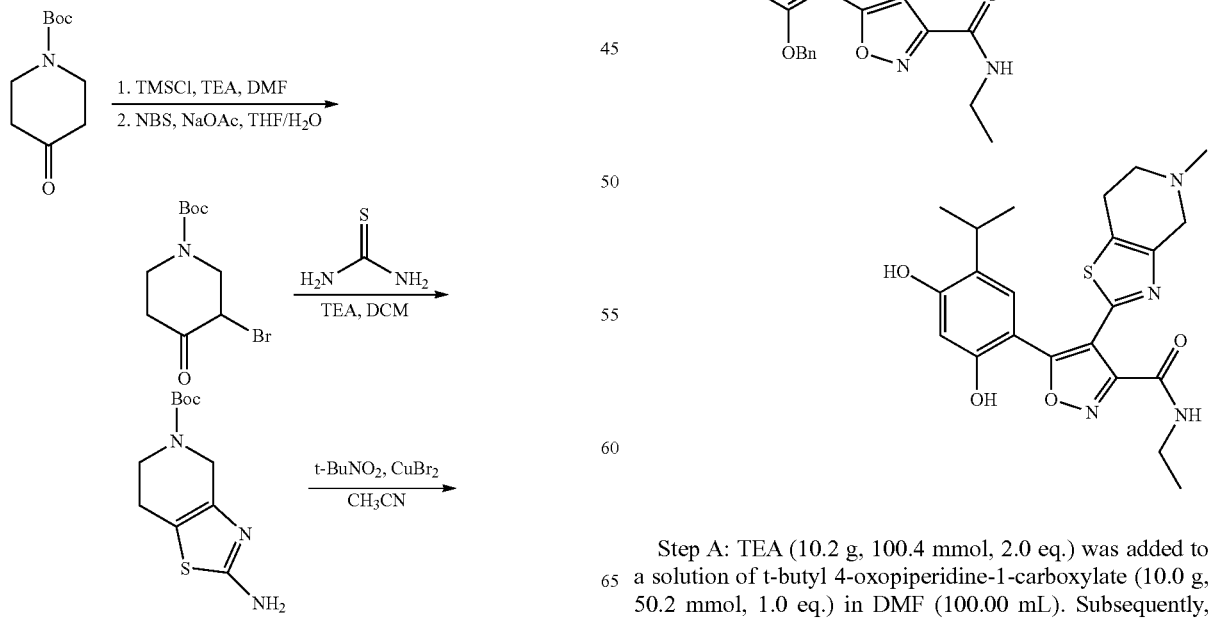

Step A: TEA (10.2 g, 100.4 mmol, 2.0 eq.) was added to a solution of t-butyl 4-oxopiperidine-1-carboxylate (10.0 g, 50.2 mmol, 1.0 eq.) in DMF (100.00 mL). Subsequently, TMSCl (6.27 g, 57.7 mmol, 1.15 eq.) was added dropwise to the solution at 20° C., and the atmosphere was changed to nitrogen atmosphere. After the mixture was stirred at 80° C. for 16 hours, 300 mL of saturated aqueous NaHCO$_3$ solution was added. The mixture was extracted with EA (150 mL×3), and then the combined organic phase was dried with anhydrous sodium sulfate, filtered and concentrated in vacuum, to give a crude product. The crude product was purified by silica gel column chromatography to give t-butyl 4-trimethylsilyl-3,6-dihydro-2H-pyridine-1-carboxylate (9.2 g, 67% yield) as a colorless oil. $^1$H NMR (400 MHz, CDCl$_3$) δ 4.77 (brs, 1H), 3.85 (brs, 2H), 3.5 (t, J=5.6 Hz, 2H), 2.08 (brs, 2H), 1.45 (s, 9H), 0.17 (s, 9H).

Step B: NaOAc (420 mg, 5.1 mmol, 0.1 eq.) and NBS (13.67 g, 76.8 mmol, 1.5 eq.) were added to a mixed solution of t-butyl 4-trimethylsilyl-3,6-dihydro-2H-pyridine-1-carboxylate (13.9 g, 51.2 mmol, 1.0 eq.) in THF (150 mL) and water (150 mL) at 0° C. The mixture was stirred at 20° C. for 12 hours. The reaction was quenched with 100 mL of saturated aqueous solution of sodium thiosulfate, and then washed and neutralized with 200 mL of saturated aqueous NaHCO$_3$ solution. The mixture was extracted with EA (2×500 mL), and the combined organic phase was dried with anhydrous Na$_2$SO$_4$, filtered and concentrated in vacuum to give a crude product. The crude product was purified by silica gel column chromatography to give t-butyl 3-bromo-4-oxopiperidine-1-carboxylate (7 g, 49% yield) as a white solid. $^1$HNMR (400 MHz, CDCl$_3$): δ 4.28-4.31 (m, 1H), 3.96 (m, 2H), 3.57-3.77 (m, 2H), 2.97-3.00 (m, 1H), 2.40-2.46 (m, 1H), 1.48 (s, 9H).

Step C: TEA (7.64 g, 75.5 mmol, 3.0 eq.) and thiourea (2.11 g, 27.7 mmol, 1.1 eq.) were added to a solution of t-butyl 3-bromo-4-oxopiperidine-1-carboxylate (7.0 g, 25.2 mmol, 1.0 eq.) in DMF (70 mL). The mixture was stirred at 110° C. for 12 hours and then poured into 300 mL of water, followed by filtration of solid. The solid was washed with 100 mL of water and 4.5 g of the red crude product t-butyl 2-amino-4,5,6,7-tetrahydrothiazolo[4,5-c]pyridine-5-formate was obtained. The crude product was used directly in the next step. MS (ESI) m/z: 256.0 (M+1).

Step D: CuBr$_2$ (4.52 g, 20.3 mmol, 1.1 eq.) and t-butyl nitrite (2.09 g, 20.3 mmol, 1.1 eq) were added to a solution of t-butyl 2-amino-4,5,6,7-tetrahydrothiazolo[4,5-c]pyridine-5-formate (4.70 g, 18.4 mmol, 1.0 eq.) in CH$_3$CN (50 mL) at 0° C. The mixture was stirred at 0° C. for 1 hour, quenched by the addition of 3 mL of 0.5 mol/L HCl solution, and then neutralized by adding 50 mL of saturated aqueous NaHCO$_3$ solution. The mixture was filtered, and the filtrate was extracted with EA (50 mL×2), dried by anhydrous sodium sulfate and concentrated in vacuum to give a crude product. The crude product was purified by silica gel column chromatography (PE:EA=5:1) to give t-butyl 2-bromo-4,5,6,7-tetrahydrothiazolo[4,5-c]pyridine-5-carboxylate (1.7 g, 29% yield) as a white solid product. MS (ESI) m/z: 318.9, 320.9 (M+1, M+3).

Step E: t-Butyl 2-bromo-4,5,6,7-tetrahydrothiazolo[4,5-c]pyridine-5-carboxylate (1.70 g, 5.33 mmol, 1.00 eq.) was added to hydrochloric acid/ethyl acetate (4 N, 30 mL), and the mixture was stirred at 20° C. for 2 hours. The mixture was concentrated in vacuum to give 1.35 g of a crude product 2-bromo-4,5,6,7-tetrahydrothiazolo[4,5-c]pyridine as a white solid, which was used directly in the next step. $^1$HNMR (400 MHz, DMSO-d$_6$) δ 9.88 (brs, 2H), 4.31 (s, 2H), 3.39-3.41 (m, 2H), 2.99 (t, J=6.0 Hz, 2H).

Step F: Formaldehyde (194 mg, 6.46 mmol, 3.00 eq.) and AcOH (258 mg, 4.3 mmol, 2.0 eq.) were added to a solution of 2-bromo-4,5,6,7-tetrahydrothiazolo[4,5-c]pyridine (550.00 mg, 2.15 mmol, 1.00 eq.) in MeOH (10.00 mL). The mixture was stirred at 20° C. for 1 hour and then added with NaBH$_3$CN (406 mg, 6.5 mmol, 3.0 eq.), and the mixture was further stirred at 20° C. for 4 hours. The reaction was quenched with 0.5 mol/L HCl solution (2 mL), followed by the addition of saturated NaHCO$_3$ (20 mL) to neutralization. The mixture was then extracted with EA (20 mL×2), and the combined organic phase was dried with anhydrous Na$_2$SO$_4$, filtered and concentrated in vacuum to give a product of 2-bromo-5-methyl-4,5,6,7-tetrahydrothiazole[4,5-c]pyridine (490 mg, 97% yield) as a white solid. MS (ESI) m/z: 232.8, 234.8 (M+1, M+3).

Step G: TEA (510 mg, 5.04 mmol, 3.0 eq.) and Pd(PPh$_3$)$_2$Cl$_2$ (117.9 mg, 168.00 μmol, 0.1 eq.) were added to a solution of 5-(2,4-dibenzyloxy-5-isopropyl-phenyl)-N-ethyl-4-iodo-isoxazole-3-carboxamide (1.00 g, 1.68 mmol, 1.0 eq.) in 1,4-dioxane (15 mL) under the protection of nitrogen gas. A solution of 4,4,5,5-tetramethyl-1,3,2-dioxaborolane (1.08 g, 8.4 mmol, 5.0 eq.) was finally added and the mixture was stirred at 90° C. for 12 hours. The reaction mixture was diluted with EA (20 mL) and filtered through diatomaceous earth. The filtrate was washed with 30 mL of water, and the organic phase was dried with anhydrous Na$_2$SO$_4$, filtered and concentrated in vacuum to give an orange gel crude product 5-(2,4-dibenzyloxy-5-isopropyl-phenyl)-N-ethyl-4-(4,4,5,5-tetramethyl-1,3,2-dioxaborolan-2-yl)isoxazole-3-carboxamide (1.7 g, 60% of purity by LCMS), and the crude product was used directly in the next step. MS (ESI) m/z: 597.3 (M+1).

Step H: 2-Bromo-5-methyl-4,5,6,7-tetrahydrothiazolo[4,5-c]pyridine (313 mg, 1.34 mmol, 1.0 eq.) and K$_2$CO$_3$ (371 mg, 2.7 mmol, 2.0 eq.) were added to a mixed solution of 5-(2,4-dibenzyloxy-5-isopropyl-phenyl)-N-ethyl-4-(4,4,5,5-tetramethyl-1,3,2-dioxaborolan-2-yl)isoxazole-3-carboxamide (800 mg, 1.34 mmol, 1.0 eq.) in 1,4-dioxane (20 mL) and water (4 mL). The mixture was replaced with a nitrogen atmosphere and then added with Pd(dppf)Cl$_2$ (196 mg, 268.2 μmol, 0.2 eq.). The mixture was stirred at 95° C. for 8 hours, and the reaction substances were diluted with 20 mL of EA and filtered through diatomaceous earth. The filtrate was extracted with EA (20 mL×2), and the combined organic phase was dried with anhydrous Na$_2$SO$_4$, filtered and concentrated in vacuum to give a crude product. The crude product was purified by silica gel column chromatography (DCM:methanol=20:1) to give 5-(2,4-dibenzyloxy-5-isopropyl-phenyl)-N-ethyl-4-(5-methyl-4,5,6,7-tetrahydrothiazolo[4,5-c]pyridin-2-yl)isoxazole-3-carboxamide (60 mg, 7.2% yield), which is a white solid product. MS (ESI) m/z: 623.3 (M+1).

Step I: BCl$_3$ (34 mg, 289 μmol, 3.0 eq.) was added to a solution of 5-(2,4-dibenzyloxy-5-isopropyl-phenyl)-N-diethyl-4-(5-methyl-4,5,6,7-tetrahydrothiazolo[4,5-c]pyridin-2-yl)isoxazole-3-carboxamide (60 mg, 96.3 μmol, 1.0 eq.) in DCM (2 mL) at 0° C. After the mixture was stirred at 0° C. for 1 hour, 2 mL of MeOH was added to quench and the mixture was poured into 5 mL of saturated aqueous NaHCO$_3$ solution. The mixture was then extracted with DCM (5 mL×3), and the combined organic phase was dried with anhydrous Na$_2$SO$_4$, filtered and concentrated in vacuum to give a crude product. The crude product was purified by preparative HPLC (formic acid, Column: Welch Ultimate AQ-C18 150×30 mm×5 μm, Condition: 0.225% FA-ACN, FlowRate: 25) to give 5-(2,4-dihydroxyl-5-isopropyl-phenyl)-N-ethyl-4-(5-methyl-4,5,6,7-tetrahydrothiazolo[4,5-c]pyridin-2-yl)isoxazole-3-carboxamide (17 mg, 34% yield). $^1$HNMR (400 MHz, DMSO-d$_6$) δ 9.93 (brs, 2H), 9.09 (brs, 1H), 7.07 (s, 1H), 6.47 (s, 1H), 3.54 (s, 2H), 3.26 (m, 2H), 3.07 (m, 1H), 2.71 (brs, 4H), 2.35 (s, 3H), 1.07-1.12 (m, 9H).

EXAMPLE 11

5-(2,4-dihydroxyl-5-isopropylphenyl)-N-ethyl-4-(6-methyl-5,6,7,8-tetrahydro-1,6-naphthyridin-2-yl)isoxazole-3-carboxamide

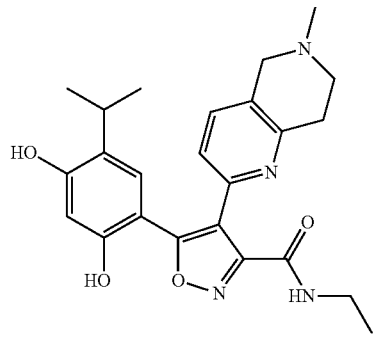 [SMILES: CCNC(=O)c1noc(-c2cc(C(C)C)c(O)cc2O)c1-c1ccc2c(n1)CCN(C)C2]

Reaction scheme:

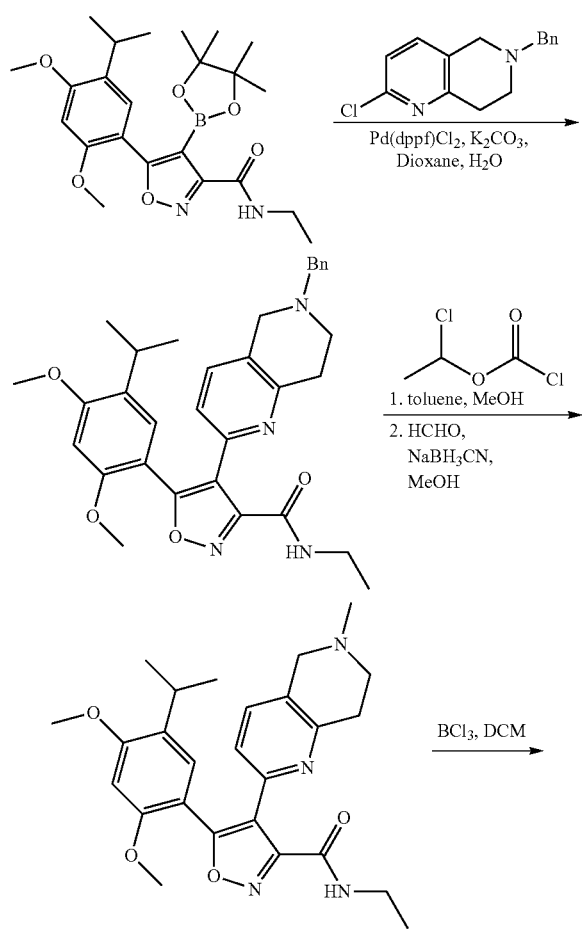

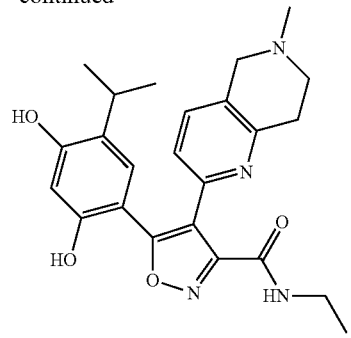

Step A: Pd(dppf)Cl$_2$ (115 mg, 157.5 μmol, 0.1 eq.) and K$_2$CO$_3$ (435 mg, 3.2 mmol, 2.0 eq.) were added to a mixed solution of N-ethyl-5-(5-isopropyl-2,4-dimethoxy-phenyl)-4-(4,4,5,5-tetramethyl-1,3,2-dioxaborolan-2-yl)isoxazole-3-carboxamide (700 mg, 1.58 mmol, 1.0 eq.) and 6-benzyl-2-chloro-5,6,7,8-tetrahydro-1,6-naphthyridine (409 mg, 1.58 mmol, 1.0 eq.) in dioxane (3 mL) and water (500 IL). After the mixture was stirred at 80° C. for 16 hours, the mixture was poured into water (80 mL) and extracted with EA (60 mL×2). The combined organic layer was dried with sodium sulfate, filtered and concentrated, and the resulting crude product was purified by silica gel chromatography (PE/EA=1:1 to EA) to give 4-(6-benzyl-5,6,7,8-tetrahydro-1,6-naphthyridin-2-yl)-N-ethyl-5-(5-isopropyl-2,4-dimethoxy-phenyl)-isoxazole-3-carboxamide (250 mg, 462.4 μmol, 29.3% yield) as a yellow solid.

Step B: 1-Chloroethyl carbonyl chloride (264 mg, 1.85 mmol, 4.0 eq.) was added to a solution of 4-(6-benzyl-5,6,7,8-tetrahydro-1, 6-naphthyridin-2-yl)-N-ethyl-5-(5-isopropyl-2,4-dimethoxy-phenyl)-isoxazole-3-carboxamide (250 mg, 462.4 μmol, 1.00 eq.) in toluene (8 mL) at room temperature, and then the mixture was stirred at 110° C. for 8 hours. The mixture was concentrated, and the residue was dissolved in MeOH (8 mL). The mixture was heated to 80° C. and stirred for 12 hours. The mixture was concentrated to give a crude product N-ethyl-5-(5-isopropyl-2,4-dimethoxy-phenyl)-4-(5, 6,7,8-tetrahydro-1, 6-naphthyridin-2-yl)isoxazole-3-carboxamide (200.00 mg, the crude product) as a yellow solid, which was used directly in the next step.

Step C: Paraformaldehyde (200 mg, 2.2 mmol, 5.0 eq.), titanium tetraisopropoxide (126 mg, 443.9 μmol, 1.0 eq.), acetic acid (27 mg, 444 μmol, 1.0 eq.) and 4 Å molecular sieves (300 mg, 444 μmol, 1.0 eq.) were added to a solution of N-ethyl-5-(5-isopropyl-2,4-dimethoxy-phenyl)-4-(5, 6,7,8-tetrahydro-1,6-naphthyridin-2-yl)isoxazole-3-carboxamide (200 mg, 443.9 μmol, 1.0 eq.) in DCE (8 mL). The mixture was stirred at 25° C. for 8 hours and then added with NaBH$_3$CN (56 mg, 887.8 μmol, 2.0 eq.). The mixture was stirred at 25° C. for an additional 12 hours. The mixture was filtered, the filtrate was concentrated, and the crude product was purified by a thin layer chromatography plate (DCM/MeOH=10:1) to give N-ethyl-5-(5-isopropyl-2,4-dimethoxy-phenyl)-4-(6-methyl-7,8-dihydro-5H-1,6-naphthyridin-2-yl)isoxazole-3-carboxamide (120 mg, 258.3 μmol, 58.2% yield) as a yellow solid.

Step D: BBr$_3$ (323.6 mg, 1.3 mmol, 10.0 eq.) was added slowly to a solution of N-ethyl-5-(5-isopropyl-2,4-dimethoxy-phenyl)-4-(6-methyl-5,6,7,8-tetrahydro-1,6-naphthyridin-2-yl)isoxazole-3-carboxamide (60 mg, 129.2 μmol, 1.0 eq.) in DCM (8 mL) at 0° C. The mixture was stirred at 25° C. for 16 hours and was slowly added to MeOH (15 mL), followed by concentrating the mixture. The crude product was purified by preparative HPLC (Phenomenex Synergi Max-RP 250×80 10 μm, 0.225% FA-ACN) to give 5-(2,4-dihydroxyl-5-isopropylphenyl)-N-ethyl-4-(6-methyl-5,6,7,8-tetrahydro-1,6-naphthyridin-2-yl)isoxazole-3-carboxamide (3.1 mg, 6.4 μmol, 5.0% yield). $^1$HNMR (300 MHz, DMSO-$d_6$) δ 8.99-8.95 (m, 1H), 8.24 (s, 1H), 7.44 (d, J=8.1 Hz, 1H), 7.03 (d, J=7.8 Hz, 1H), 6.98 (s, 1H), 6.43 (s, 1H), 3.26-3.19 (m, 4H), 3.09-3.05 (m, 1H), 2.84-2.81 (m, 2H), 2.72-2.68 (m, 2H), 2.35 (s, 3H), 1.13-1.03 (m, 9H).

EXAMPLE 12

3-(2,4-dihydroxyl-5-isopropylphenyl)-N-ethyl-4-(2-methyl-1,2,3,4-tetrahydroisoquinolin-6-yl)isoxazole-5-carboxamide

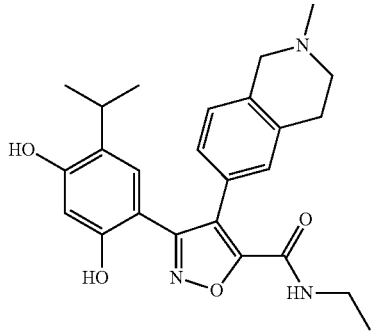 [SMILES: CCNC(=O)c1onc(-c2cc(C(C)C)c(O)cc2O)c1-c1ccc2c(c1)CCN(C)C2]

Reaction scheme:

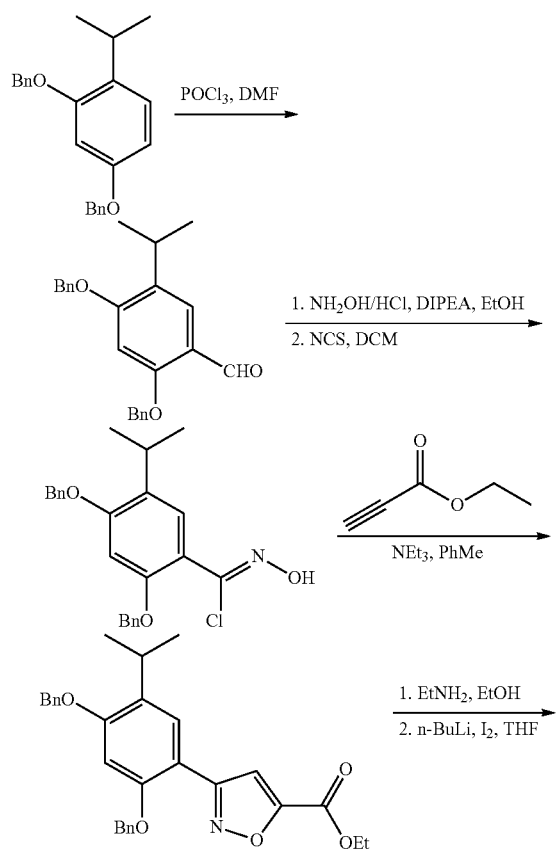

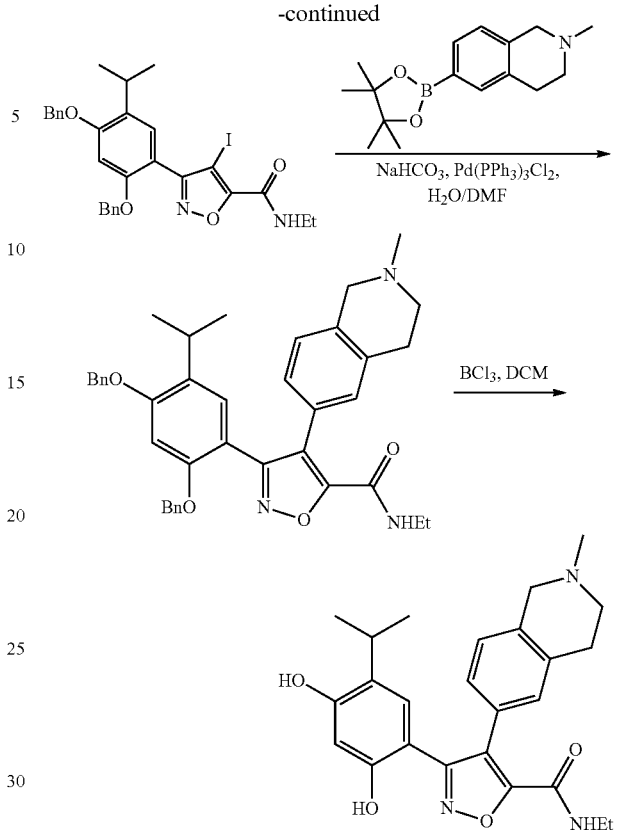

Step A: POCl$_3$ (6.25 g, 40.8 mmol, 1.5 eq) was added to DMF (60 mL) at 0° C. and stirred at 0° C. for 10 min. Then, 2,4-dibenzyloxy-1-isopropylbenzene (9.0 g, 27.1 mmol, 1.0 eq.) was added at 0° C., and after the addition. stirring was continued at 0° C. for 10 min. The temperature was raised to 15~25° C., and after stirring for 10 min, the temperature was further raised to 100° C. with stirring for 2.5 hours. The reaction mixture was cooled down to 15~25° C., poured into ice water (120 mL), adjusted to pH=6 by the addition of 10% aqueous NaOAc solution, and then extracted with EA (120 mL×3). The combined organic layer was dried, filtered and concentrated to give 2,4-dibenzyloxy-5-isopropyl-benzaldehyde (9.70 g, a crude product) as a yellow solid, which was used directly in the next step.

Step B: NH$_2$OH.HCl (3.66 g, 52.7 mmol, 2.0 eq.) was added to a solution of 2,4-dibenzyl-5-isopropyl-benzaldehyde (9.5 g, 26.4 mmol, 1.0 eq.) dissolved in EtOH (100 mL) at 15~25° C., followed by the addition of DIEA (5.11 g, 39.5 mmol, 1.5 eq.), and then the temperature was raised to 80° C. with stirring for 16 hours. The reaction mixture was cooled down to 15~25° C. and concentrated in vacuum to give a residue. The residue was dissolved in EA (80 mL) and washed with water (80 mL). The organic layer was dried, filtered and concentrated to give a crude product. The crude product was purified by silica gel chromatography (PE:EA=10:1 to 5:1). (1E)-2,4-dibenzyl-5-isopropyl-benzaldehyde oxime (7.00 g, 18.6 mmol, 70.7% yield) as a yellow solid was obtained.

Step C: NCS (1.28 g, 9.59 mmol, 1.2 eq.) was added to a solution of (1E)-2,4-dibenzyl-5-isopropyl-benzaldehyde oxime (3.00 g, 7.99 mmol, 1.0 eq.) in DCM (30.00 mL) at 0~5° C., with stirring at 0~5° C. for 2 hours and then stirring at 15~25° C. for an additional 16 hours. The reaction mixture was concentrated to give 2,4-dibenzyloxy-N-hydroxyl-5-isopropylbenzoimidoyl chloride (4.0 g, a crude product) as a yellow oil. The crude product was used directly in the next step.

Step D: Ethyl 2-propiolate (588.60 mg, 6.00 mmol, 1.50 eq.) was added to a solution of 2,4-dibenzyloxy-N-hydroxy-5-isopropylbenzimidoyl chloride (1.64 g, 4.00 mmol, 1.0 eq.) in toluene (15.00 mL) at 15~25° C., followed by adding TEA (445.24 mg, 4.40 mmol, 1.10 eq.) dropwise at 15~25° C. within 0.5 hour. After the addition, the mixture was stirred at 15~25° C. for 0.5 hour, and then stirred at 80° C. for 3 hours. The reaction mixture was cooled down to 15~25° C., poured into water (20 mL) and extracted with EA (20 mL×2). The combined organic layer was dried, filtered and concentrated to give a crude product. The crude product was purified by silica gel chromatography (PE:EA=20:1 to 5:1). Ethyl 3-(2,4-dibenzyloxy-5-isopropyl-phenyl)isoxazole-5-carboxylate (1.20 g, a crude product) as a yellow solid was obtained.

Step E: Ethylamine (573.6 mg, 12.7 mmol, 10.0 eq.) was added to a solution of ethyl 3-(2,4-dibenzyloxy-5-isopropyl-phenyl)isoxazole-5-carboxylate (600 mg, 1.27 mmol, 1.0 eq.) dissolved in EtOH (10.00 mL) at 15~25° C., with stirring at 80° C. for 16 hours. The reaction mixture was cooled down to 15~25° C. and concentrated to give a crude product. The crude product was purified by silica gel chromatography (PE:EA=10:1 to 3:1), 3-(2,4-dibenzyloxy-5-isopropyl-phenyl)-N-ethyl-isoxazole-5-carboxamide (150 mg, 318.8 µmol, 25.1% yield) as a yellow solid was obtained.

Step F: n-Butyllithium (2M, 132 µL, 2.5 eq.) was added to a solution of 3-(2,4-dibenzyloxy-5-isopropyl-phenyl)-N-ethyl-isoxazole-5-carboxamide (50 mg, 106.3 µmol, 1.0 eq.) in THF (2 mL) at −78° C., with stirring at −78° C. for 1 hour after the addition, followed by adding a solution of I₂ (40.5 mg, 159.4 µmol, 1.5 eq.) in THF (1 mL) at −78° C. and stirring continually at −78° C. for 1 hour. The reaction solution was warmed up to 15~25° C. with stirring for 16 hours. The reaction mixture was poured into a saturated aqueous NH₄Cl solution (10 mL) and extracted with EA (10 mL×3). The combined organic layer was dried, filtered and concentrated to give a crude product. The crude product was purified by preparative TLC (PE:EA=3:1) to give 3-(2,4-dibenzyloxy-5-isopropyl-phenyl)-N-ethyl-4-iodo-isoxazole-5-carboxamide (15 mg, 25.2 µmol, 23.7% yield) as a yellow solid. MS (ESI) M/Z: 597 (M+1).

Step G: 2-Methyl-6-(4,4,5,5-tetramethyl-1,3,2-dioxaborolan-2-yl)-1,2,3,4-tetrahydroisoquinoline (13.7 mg, 50.3 µmol, 2.00 eq.), water (500.00 µL) and sodium bicarbonate (6.34 mg, 75.5 µmol, 3.0 eq.) were added to a solution of 3-(2,4-dibenzyloxy-5-isopropyl-phenyl)-N-ethyl-4-iodo-isoxazole-5-carboxamide (15 mg, 25.15 µmol, 1.00 eq.) in DMF (2.5 mL) at 15~25° C. under the protection of nitrogen gas, followed by the addition of Pd(PPh₃)₂Cl₂ (3.5 mg, 5.0 µmol, 0.2 eq.). The mixture was stirred at 80° C. for 16 hours. The reaction mixture was cooled down to 15~25° C., poured into water (10 mL) and extracted with EA (10 mL×3). The combined organic layer was dried, filtered and concentrated to give a crude product. The crude product was purified by preparative TLC (DCM:methanol=15:1). 3-(2,4-dibenzyloxy-5-isopropyl-phenyl)-N-ethyl-4-(2-methyl-1,2,3,4-tetrahydroisoquinolin-6-yl)isoxazole-5-carboxamide (10.00 mg, 16.24 J mol, 64.57% yield) as a yellow solid was obtained. (ESI) M/Z: 616 (M+1).

Step H: A solution of BCl₃ (1 M, 324.81 µL, 20.0 eq.) in DCM was added to a solution of 3-(2,4-dibenzyloxy-5-isopropyl-phenyl)-N-ethyl-4-(2-methyl-1,2,3,4-tetrahydroisoquinolin-6-yl)isoxazole-5-carboxamide (10 mg, 16.2 µmol, 1.0 eq.) in DCM (1 mL) at 0° C., and after stirring at 0° C. for 2 hours, the temperature was raised to 15~25° C. with stirring for 1 hour. The reaction mixture was cooled down to 0° C., added with MeOH (2 mL), and stirred at 0° C. for 0.5 hour and then at 15~25° C. for an additional 0.5 hour. The mixture was concentrated to give a crude product. The crude product was purified by preparative HPLC (0.225% FA-ACN; Phenomenex Synergi Max-RP 250×80 10 µm) to give 3-(2,4-dihydroxyl-5-isopropyl-phenyl)-N-ethyl-4-(2-methyl-1,2,3,4-tetrahydroisoquinolin-6-yl)isoxazole-5-carboxamide (3.5 mg, 8.0 µmol, 49.5% yield). ¹H NMR (400 MHz, DMSO) δ 8.87 (t, J=5.6 Hz, 1 H), 7.00-6.98 (m, 1 H), 6.95-6.90 (m, 2 H), 6.79 (s, 1 H), 6.33 (s, 1 H), 3.26-3.19 (m, 2 H), 3.06-2.98 (m, 1 H), 2.69-2.66 (m, 2 H), 2.55-2.50 (m, 4 H), 2.31 (s, 3 H), 1.07 (t, J=7.2 Hz, 3 H), 1.01 (d, J=6.8 Hz, 6 H). MS (ESI) m/z: 436 (M+1).

EXAMPLE 13

5-(2,4-dihydroxyl-5-isopropyl-phenyl)-N-ethyl-4-(2-methyl-1,2,3,4-tetrahydroisoquinolin-6-yl)isothiazole-3-carboxamide

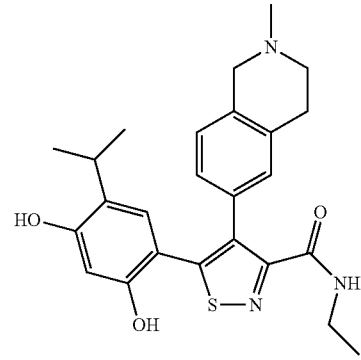 [SMILES: CCNC(=O)c1nsc(-c2cc(C(C)C)c(O)cc2O)c1-c1ccc2c(c1)CCN(C)C2]

Reaction scheme:

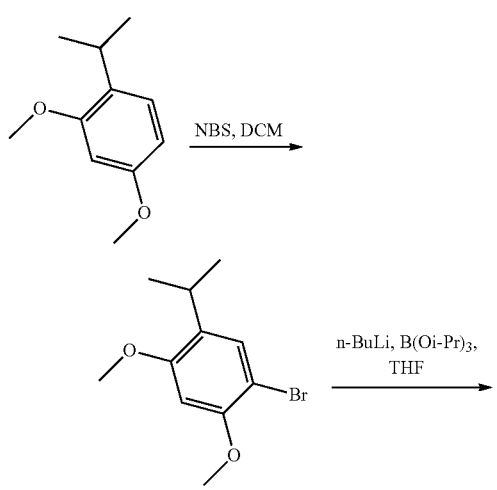

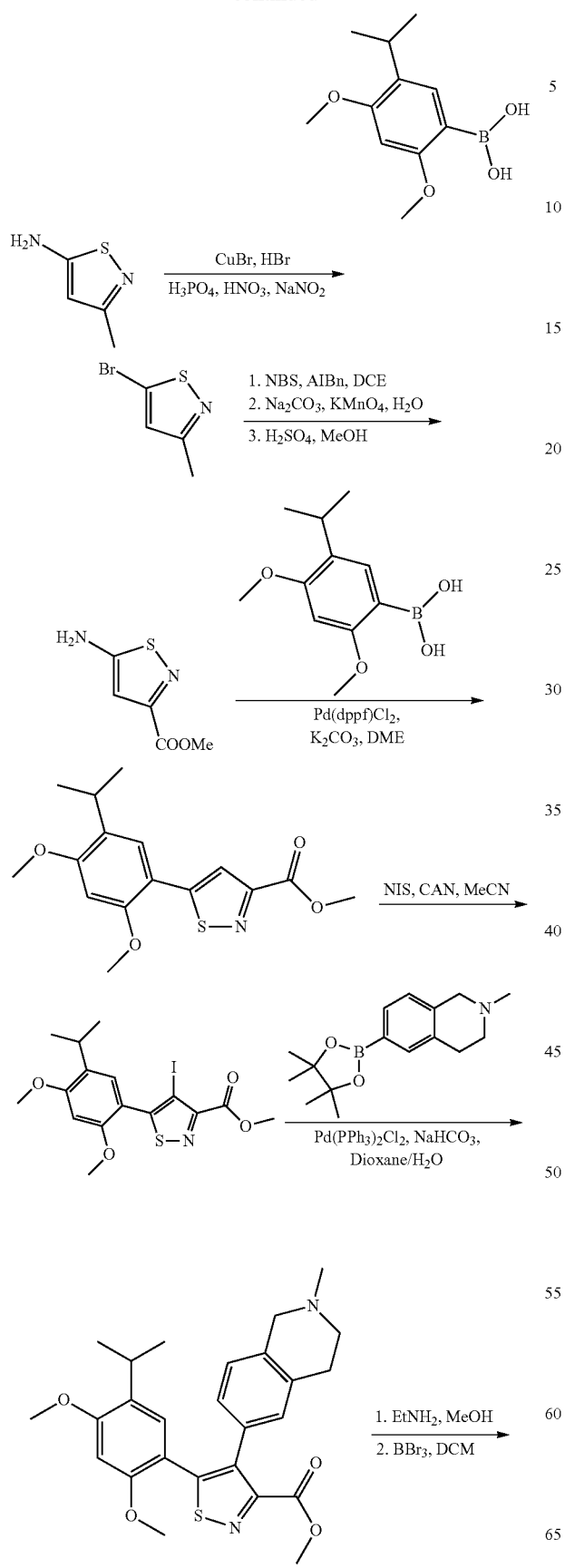

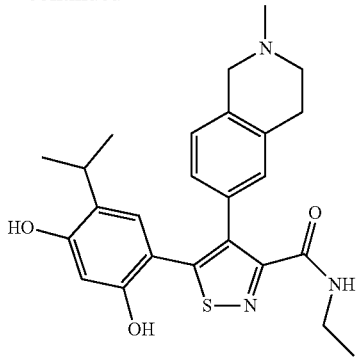

Step A: NBS (2.21 g, 12.42 mmol, 1.12 eq.) was added to a solution of 1-isopropyl-2,4-dimethoxy-benzene (2.0 g, 11.1 mmol, 1.0 eq.) in DCM (40 mL) at 0° C. The mixture was stirred at 0° C. for 3 hours and then stirred at 25° C. for 1 hour. The mixture was concentrated and the residue was purified by column chromatography (PE/EA=10/1) to give 1-bromo-5-isopropyl-2,4-dimethoxy-benzene (2.77 g, 10.69 mmol, 96.30% yield) as a yellow solid.

Step B: n-BuLi (2.5 M, 6.00 mL, 1.40 eq.) was added to a solution of 1-bromo-5-isopropyl-2,4-dimethoxy-benzene (2.77 g, 10.69 mmol, 1.0 eq.) in anhydrous THF (100 mL) at −78° C. The mixture was stirred at −78° C. for 1 hour. Then, a solution of triisopropyl borate (6.03 g, 32.07 mmol, 3.0 eq.) in anhydrous THF (10 mL) was slowly added and the temperature was maintained at −78° C. After the addition, the reaction substances were stirred at 25° C. for 4 hours. The mixture was poured into ice water and adjusted to pH 3~4 with 1N hydrochloric acid. The resulting mixture was extracted three times with EA, and the combined organic layer was washed with brine, dried over anhydrous sodium sulfate and concentrated. The residue was recrystallized in PE to give the target product (5-isopropyl-2,4-dimethoxy-phenyl)-boronic acid (1.60 g, 7.14 mmol, 66.8% yield) as a white solid. MS (ESI) m/z: 225.2 (M+H).

Step C: 3-Methylisoquinoline-5-amine hydrochloride (8.00 g, 53.11 mmol, 1.00 eq.) was added to EA (100 mL) and washed with 10% aqueous sodium carbonate solution. The organic phase was dried and concentrated to give a free base, and the free base was dissolved in phosphoric acid (20 mL) and cooled down to 0° C. The mixture was added dropwise into nitric acid (10 mL), followed by adding dropwise a saturated aqueous sodium nitrite solution (4.17 g, 60.4 mmol, 1.14 eq.), during which the temperature was maintained at 0~5° C. The reaction mixture was stirred at 10° C. for 30 min and then added dropwise into 48% HBr aqueous solution (100 mL) with cuprous bromide (9.50 g, 66.2 mmol, 1.25 eq.) dissolved, and the resulting mixture was stirred at room temperature for 2 hours. The reaction solution was adjusted to pH 6~7 with 4N NaOH aqueous solution and water (200 mL). The aqueous phase was extracted with MTBE, and the organic layer was dried over anhydrous sodium sulfate and concentrated to give 5-bromo-3-methylisothiazole (8.0 g, a crude product), which was used directly in the next step.

Step D: The mixture of 5-bromo-3-methylisothiazole (8.0 g, 44.9 mmol, 1.0 eq.), NBS (16.0 g, 89.9 mmol, 2.0 eq.) and AIBN (1.40 g, 8.53 mmol, 0.19 eq.) in DCE (150 mL) was heated to 90° C., and irradiated by placing under a 150W halogen lamp with stirring for 48 hours. The mixture was washed with a saturated aqueous NaHSO₃ solution and extracted three times with DCM. The combined organic layer was washed with brine, dried over anhydrous sodium sulfate and concentrated. The residue was purified by column chromatography (PE/DCM=100/0 to 1/2) to give the target product 5-bromo-3-(bromomethyl)isothiazole (4.60 g, 17.9 mmol, 39.8% yield).

Step E: A mixture of 5-bromo-3-(bromomethyl)isothiazole (4.10 g, 15.96 mmol, 1.0 eq.) and sodium carbonate (1.92 g, 18.11 mmol, 1.14 eq.) in water (90 mL) was heated to reflux, and then added into potassium permanganate (3.28 g, 20.76 mmol, 1.3 eq.) in several small batches. The reaction mixture was stirred under reflux for 1 hour, cooled and filtered. The filtrate was acidified with 1N HCl and extracted three times with EA. The combined organic layer was dried over anhydrous sodium sulfate and concentrated to give 5-bromoisothiazole-3-carboxylic acid (1.26 g, 6.06 mmol, 38.0% yield) as a white solid.

Step F: Sulfuric acid (0.5 mL) was added to a solution of 5-bromoisothiazole-3-carboxylic acid (1.26 g, 6.06 mmol, 1.0 eq.) in MeOH (50 mL). The reaction mixture was refluxed at 65° C. for 16 hours. The mixture was cooled down to room temperature and quenched with a saturated aqueous NaHCO$_3$ solution, and the aqueous layer was extracted with EA. The organic layer was dried over anhydrous sodium sulfate and concentrated to give methyl 5-bromoisothiazole-3-carboxylate (1.30 g, 5.85 mmol, 96.6% yield) as a yellow oil.

Step G: Methyl 5-bromoisothiazole-3-carboxylate (1.00 g, 4.50 mmol), (5-isopropyl-2,4-dimethoxy-phenyl)-boronic acid (1.20 g, 5.36 mmol, 1.19 eq.), Pd(dppf)Cl$_2$ (340.00 mg, 464.67 μmol, 0.10 eq.) and K$_2$CO$_3$ (1.29 g, 9.33 mmol, 2.07 eq.) were added to a mixed solution of DME (30 mL) and water (0.12 mL). Under a nitrogen atmosphere, the reaction solution was stirred at 100° C. for 16 hours. The mixture was filtered through diatomaceous earth and the filtrate was concentrated. The residue was purified by column chromatography (PE/EA=6/1 to 3/1) to give the target product methyl 5-(5-isopropyl-2,4-dimethoxy-phenyl)isothiazol-3-carboxylate (1.10 g, 3.42 mmol, 76.1% yield) as a white solid. MS (ESI) m/z: 322.1 (M+H).

Step H: Methyl 5-(5-isopropyl-2,4-dimethoxy-phenyl)-isothiazole-3-carboxylate (300 mg, 933 μmol, 1.0 eq.), NIS (24 mg, 1.07 mmol, 1.14 eq.) and CAN (55 mg, 100.3 μmol, 0.11 eq.) were added to MeCN (20 mL). The mixture was stirred at 82° C. for 16 hours. The mixture was concentrated. The residue was dissolved in DCM, and washed with water and brine. The organic phase was dried over anhydrous sodium sulfate and concentrated. The residue was purified by preparative TLC (PE/EA=3/1) to give methyl 4-iodo-5-(5-isopropyl-2,4-dimethoxy-phenyl)isothiazole-3-carboxylate (300 mg, 670.7 μmol, 71.9% yield) as a yellow oil. MS (ESI) m/z: 448.0 (M+H).

Step I: Methyl 4-iodo-5-(5-isopropyl-2,4-dimethoxyphenyl)isothiazole-3-carboxylate (120 mg, 268.3 μmol, 1.00 eq.), 2-methyl-6-(4,4,5,5-tetramethyl-1,3,2-dioxaborolan-2-yl)-1,2,3,4-tetraisoquinoline (100 mg, 366.1 μmol, 1.36 eq.), Pd(PPh$_3$)$_2$Cl$_2$ (30 mg, 57 μmol, 0.21 eq) and NaHCO$_3$ (50 mg, 595.2 μmol, 2.22 eq.) were added to a mixed solution of dioxane (10 mL) and H$_2$O (1 mL) under the protection of nitrogen gas. The mixture was stirred at 80° C. for 16 hours. After cooling, the mixture was filtered through a diatomaceous earth pad and the filtrate was concentrated. The residue was purified by preparative TLC (DCM/methanol=20/1) to give the target product methyl 5-(5-isopropyl-2,4-dimethoxy-phenyl)-4-(2-methyl-1,2,3,4-tetrahydroisoquinolin-6-yl)isothiazole-3-carboxylate (80 mg, 171.5 μmol, 63.9% yield) as a yellow solid. MS (ESI) m/z: 467.2 (M+H).

Step J: Methyl 5-(5-isopropyl-2,4-dimethoxy-phenyl)-4-(2-methyl-1,2,3,4-tetrahydroisoquinolin-6-yl)isothiazole-3-carboxylate (80 mg, 171.5 μmol, 1.0 eq.) and ethylamine (1 mL, 15.3 mmol, 89 eq.) were added to MeOH (10 mL). The mixture was stirred at 65° C. for 16 hours. The mixture was concentrated in vacuum to give the target product N-ethyl-5-(5-isopropyl-2,4-dimethoxy-phenyl)-4-(2-methyl-1,2,3,4-tetrahydroisoquinolin-6-yl)isothiazole-3-carboxamide (82 mg, 171 μmol, 99.7% yield) as a yellow solid. MS (ESI) m/z: 480.2 (M+H).

Step K: BBr$_3$ (1 mL, 10.4 mmol, 62 eq.) was added to a solution of N-ethyl-5-(5-isopropyl-2,4-dimethoxy-phenyl)-4-(2-methyl-1,2,3,4-tetrahydroisoquinolin-6-yl)isothiazole-3-carboxamide (80 mg, 166.8 μmol, 1.0 eq.) in DCM (1 mL) at −78° C. The mixture was stirred at 25° C. for 2 hours. 0.1 mL of water and 1 g of NaHCO$_3$ solid were added to the mixture, and the mixture was stirred at 25° C. for 10 min. The mixture was filtered and the residue was purified by preparative HPLC to give the target product 5-(2,4-dihydroxyl-5-isopropyl-phenyl)-N-ethyl-4-(2-methyl-1,2,3,4-tetrahydroisoquinolin-6-yl)isothiazole-3-carboxamide (16 mg, 35.4 μmol, 21.2% yield). $^1$HNMR (400 MHz, DMSO-d$_6$) δ 8.20 (brs, 1H), 7.06 (d, J=7.6 Hz, 1H), 6.94-6.91 (m, 2H), 6.44 (s, 1H), 6.06 (brs, 1H), 3.52 (s, 2H), 3.13-3.07 (m, 3H), 2.82-2.78 (m, 4H), 2.59 (brs, 2H), 2.36 (s, 3H), 1.00 (t, J=7.2 Hz, 3H), 0.67 (d, J=6.8 Hz, 6H). MS (ESI) m/z: 452.2 (M+H).

EXAMPLE 14

5-(2,4-dihydroxyl-5-isopropyl-phenyl)-N-ethyl-4-(2-methyl-1,2,3,3a,4,6a-hexahydrocyclopenta[c]pyrrol-5-yl)isoxazole-3-carboxamide

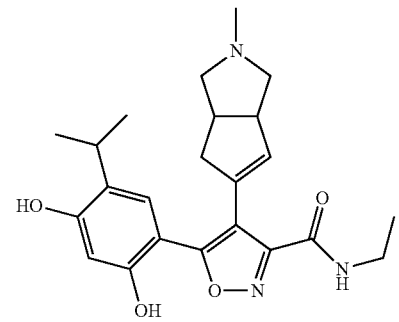 [SMILES: CCNC(=O)c1noc(-c2cc(C(C)C)c(O)cc2O)c1C1=CC2CN(C)CC2C1]

Reaction scheme:

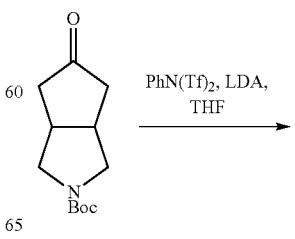

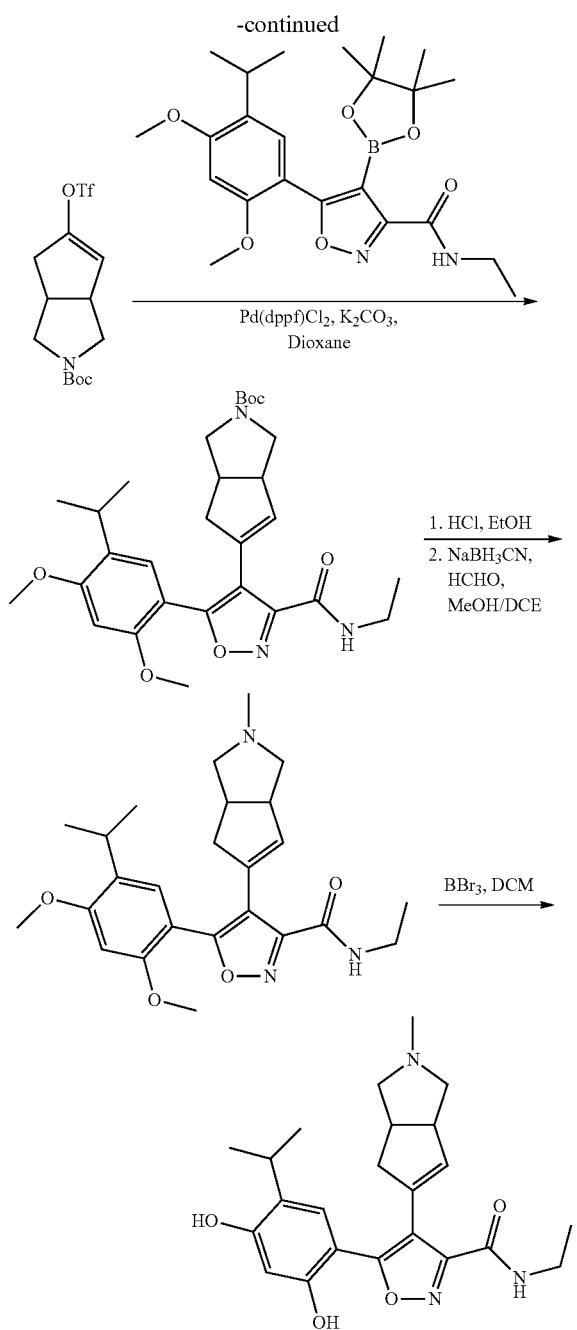

Step A: LDA (2M, 1.0 mL, 2.0 eq.) was added to a solution of t-butyl 5-oxo-1,3,3a,4,6,6a-hexahydrocyclopenta[c]pyrrole-2-carboxylate (226 mg, 1.0 mmol, 1.0 eq.) in anhydrous THF (20 mL) at −78° C. The resulting mixture was stirred at −78° C. for 1 hour and further added with a solution of N,N-bis(trifluoromethanesulfonyl)aniline (467 mg, 1.2 mmol, 1.2 eq.) in anhydrous THF (20 mL). The mixture was then warmed up to room temperature and stirred for 16 hours. The mixture was concentrated to dryness, and the residue was dissolved in DCM, successively, washed with a saturated aqueous NaHCO₃ solution, dried over anhydrous MgSO₄ and concentrated, to give t-butyl 5-(trifluoromethylsulfonyloxy)-3, 3a, 6, 6-tetrahydro-1H-cyclopenta[c]pyrrole-2-carboxylate (360 mg, a crude product) as a brown oil, which was used directly in the next step.

Step B: t-Butyl 5-(trifluoromethylsulfonyloxy)-3, 3a, 6, 6-tetrahydro-1H-cyclopenta[c]pyrrole-2-carboxylate (350 mg, 979.43 μmol, 1.0 eq.), N-ethyl-5-(5-isopropyl-2,4-dimethoxy-phenyl)-4-(4,4,5,5-tetramethyl-1,3,2-dioxaborolan-2-yl)isoxazole-3-carboxamide (440 mg, 990.3 μmol, 1.01 eq.), Pd(dppf)Cl₂ (140 mg, 191.3 μmol, 0.2 eq.) and K₂CO₃ (280 mg, 2.03 mmol, 2.07 eq) were added to a mixed solution of dioxane (20 mL) and water (2 mL) under the protection of nitrogen gas. The mixture was stirred at 80° C. for 16 hours. After cooling, the mixture was filtered through diatomaceous earth and the filtrate was concentrated. The residue was purified by column chromatography (PE/EA=5/1 to 1/1) to give the target product t-butyl 5-[3-(ethylcarbamoyl)-5-(5-isopropyl-2,4-dimethoxy-phenyl)-isoxazol-4-yl]-3,3a,6,6a-tetrahydro-1H-cyclopenta[c] pyrrole-2-carboxylate (290 mg, 551.7 μmol, 56.3% yield) as an off-white solid. MS (ESI) m/z: 426.2 (M-99).

Step C: Hydrochloric acid/ethyl ester (4 N, 1 mL) was added to a solution of t-butyl 5-[3-(ethylcarbamoyl)-5-(5-isopropyl-2,4-dimethoxy-phenyl)-isoxazol-4-yl]-3,3a,6,6a-tetrahydro-1H-cyclopenta[c]pyrrole-2-carboxylate (290 mg, 551.7 μmol, 1.0 eq.) in EA (10 mL). The mixture was stirred at 25° C. for 2 hours. The mixture was concentrated to give the target product 4-(1,2,3,3a,4,6a-hexahydrocyclopenta[c] pyrrol-5-yl)-N-ethyl-5-(5-isopropyl-2,4-dimethoxy-phenyl)-isoxazole-3-carboxamide (234 mg, 549.9 μmol, 99.7% yield) as a yellow solid. MS (ESI) m/z: 426.2 (M+H).

Step D: Formaldehyde (500 μL, 18.2 mmol, 33.00 eq.) was added to a mixed solution of 4-(1,2,3,3a,4,6a-hexahydrocyclopenta[c]pyrrol-5-yl)-N-ethyl-5-(5-isopropyl-2,4-dimethoxy-phenyl)-isoxazole-3-carboxamide (234 mg, 549.9 μmol, 1.00 eq.) in DCE (12 mL) and MeOH (4 mL). The mixture was stirred at 25° C. for 16 hours and then added with NaBH(OAc)₃ (500 mg, 2.36 mmol, 4.3 eq.), and the mixture was further stirred at 25° C. for 2 hours. The reaction was quenched with a saturated aqueous NaHCO₃ solution and extracted three times with DCM. The combined organic phase was dried over anhydrous sodium sulfate, filtered and concentrated. The residue was purified by preparative TLC (DCM/methanol=10/1) to give the target product N-ethyl-5-(5-isopropyl-2,4-dimethoxy-phenyl)-4-(2-methyl-1,2,3,3a,4,6a-hexahydrocyclopenta[c]pyrrol-5-yl) isoxazole-3-carboxamide (160 mg, 364.0 μmol, 66.2% yield). MS (ESI) m/z: 440.2 (M+H).

Step E: BBr₃ (1 mL, 10.4 mmol, 28.5 eq.) was added to a solution of N-ethyl-5-(5-isopropyl-2,4-dimethoxy-phenyl)-4-(2-methyl-1,2,3,3a,4,6a-hexahydrocyclopenta[c]pyrrol-5-yl)isoxazole-3-carboxamide (160 mg, 364.0 μmol, 1.0 eq.) in DCM (1 mL) at −78° C. The mixture was stirred at 25° C. for 2 hours, 0.1 mL of water and 1 g of NaHCO₃ were added to the mixture, and the resulting mixture was stirred at 25° C. for 10 min. The mixture was filtered and the residual liquid was purified by preparative HPLC (formic acid system) to give the target product 5-(2,4-dihydroxyl-5-isopropyl-phenyl)-N-ethyl-4-(2-methyl-1,2,3,3a,4,6a-hexahydrocyclopenta[c]pyrrol-5-yl)isoxazole-3-carboxamide (75.5 mg, 165.0 μmol, 45.3% yield). ¹HNMR (400 MHz, DMSO-d₆) δ 8.82 (t, J=5.2 Hz, 1H), 8.20 (s, 1H), 6.91 (s, 1H), 6.47 (s, 1H), 5.61 (d, J=1.6 Hz, 1H), 3.28-3.23 (m, 4H), 3.11-3.09 (m, 1H), 2.75 (br, 1H), 2.63-2.59 (m, 3H), 2.31-2.26 (m, 5H), 2.15-2.13 (m, 1H), 1.11 (dd, J=7.2, 1.6 Hz, 9H). MS (ESI) m/z: 412.2 (M+H).

EXAMPLE 15

4-isopropyl-6-[4-(2-methyl-1,2,3,4-tetrahydroisoquinolin-6-yl)-3-(5-methyl-4H-1,2,4-triazol-3-yl)isoxazol-5-yl]benzene-1,3-diol

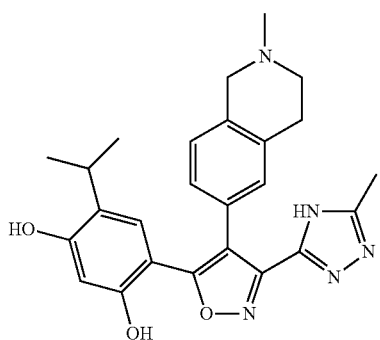 [SMILES: Cc1nnc(-c2noc(-c3cc(C(C)C)c(O)cc3O)c2-c2ccc3c(c2)CCN(C)C3)[nH]1]

Reaction scheme:

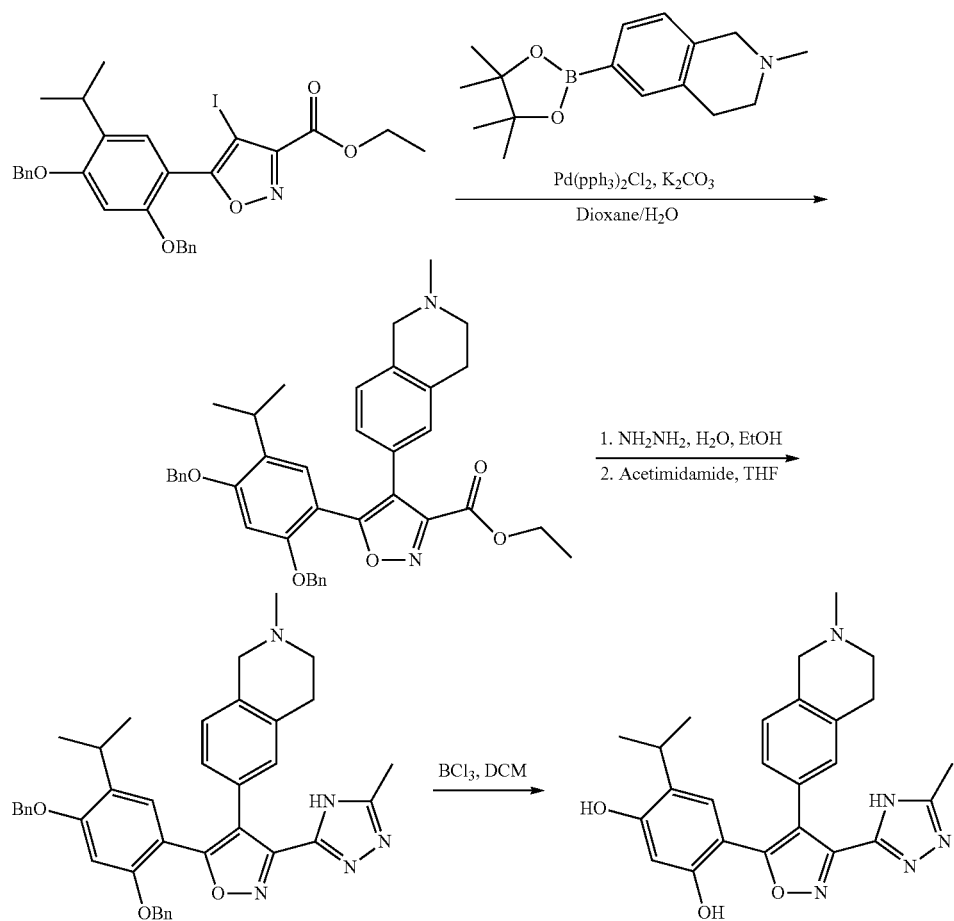

Step A: 2-Methyl-6-(4,4,5,5-tetramethyl-1,3,2-dioxaborolan-2-yl)-1,2,3,4-tetrahydroisoquinoline (3.66 g, 8.7 mmol, 1.3 eq.), ethyl 5-(2,4-dibenzyloxy-5-isopropyl-phenyl)-4-iodo-isoxazole-3-carboxylate (4.00 g, 6.7 mmol, 1.0 eq.), Pd(PPh$_3$)$_2$Cl$_2$ (470 mg, 670.0 µmol, 0.1 eq.) and K$_2$CO$_3$ (1.85 g, 13.4 mmol, 2.0 eq.) were added to a mixed solution of dioxane (30 mL) and water (6 mL) under the protection of nitrogen gas. The mixture was heated to 80° C. under N$_2$ protection and stirred for 18 hours. After cooling, the reaction mixture was poured into water (15 mL) and extracted with ethyl acetate (10 mL×2). The organic phase was washed with saturated brine (15 mL), dried over anhydrous Na$_2$SO$_4$ and concentrated in vacuum to give a residue. The residue was purified by silica gel chromatography (petroleum ether/ethyl acetate=50/1 to 5/1) to give ethyl 5-(2,4-dibenzyloxy-5-isopropyl-phenyl)-4-(2-methyl-1,2,3,4-tetrahydroisoquinolin-6-yl)isoxazole-3-carboxylate (2.90 g, 3.5 mmol, 52.6% yield, 75% purity) as a yellow oil.

Step B: Hydrazine hydrate (1.20 g, 24.1 mmol, 5 eq.) was added to a solution of ethyl 5-(2,4-dibenzyloxy-5-isopropyl-phenyl)-4-(2-methyl-1,2,3,4-tetrahydroisoquinolin-6-yl)isoxazole-3-carboxylate (2.90 g, 4.1 mmol, 1.0 eq.) in EtOH (30 mL). The solution was heated to 90° C. and stirred for 18 hours. The solution was concentrated in vacuum and then added with water (20 mL), and the mixture was extracted with EA (15 mL×3). The organic layers were combined, washed with brine (10 mL×2), dried over anhydrous sodium sulfate, filtered and concentrated to give a residue. The residue was purified by silica gel chromatography (DCM/methanol=60/1, 10/1) to give 5-(2,4-dibenzyloxy-5-isopropyl-phenyl)-4-(2-methyl-1,2,3,4-tetrahydroisoquinolin-6-yl)isoxazole-3-carbohydrazide (1.50 g, 2.5 mmol, 51.7% yield) as a yellow solid.

Step C: NaOH (149.32 mg, 3.73 mmol, 1.50 eq.) was added to a solution of 5-(2,4-dibenzyloxy-5-isopropyl-phenyl)-4-(2-methyl-1,2,3,4-tetrahydroisoquinolin-6-yl)isoxazole-3-carbohydrazide (1.50 g, 2.49 mmol, 1.00 eq.) and acetamidine hydrochloride (352.93 mg, 3.73 mmol, 1.50 eq.) in THF (4.00 mL). The solution was heated to 80° C. and stirred for 18 hours. The solution was cooled, concentrated, and added with ethylene glycol (4.00 mL). The resulting mixture was heated to 120° C. and stirred for 2 hours. After the mixture being cooled, water (10 mL) was added, and the solution was extracted with EA (10 mL×3). The organic layers were combined, washed with brine (10 mL×2), dried over anhydrous sodium sulfate, filtered and concentrated in vacuum to give a residue. The residue was purified by silica gel chromatography (DCM/methanol=60/1, 1/10) to give 5-(2,4-dibenzyloxy-5-isopropyl-phenyl)-4-(2-methyl-1,2,3,4-tetrahydroisoquinolin-6-yl)-3-(5-methyl-4H-1,2,4-triazol-3-yl)isoxazole (1.10 g, 1.76 mmol, 70.6% yield) as a yellow solid.

Step D: A solution of $BCl_3$ in DCM (1 M, 1.92 mL, 10.0 eq.) was added dropwise to a solution of 5-(2,4-dibenzyloxy-5-isopropyl-phenyl)-4-(2-methyl-1,2,3,4-tetrahydroisoquinolin-6-yl)-3-(5-methyl-4H-1,2,4-triazol-3-yl)isoxazole (120 mg, 191.77 μmol, 1.0 eq.) in DCM (2.0 mL) at 0° C., which took 5 min. The suspension was stirred at 0° C. for 30 min, then warmed up to 25° C. and stirred for 2 hours. The mixture was cooled down to −78° C., quenched by slowly adding MeOH (2 mL), basified to pH=8 with a saturated aqueous $NaHCO_3$ solution and then extracted with DCM (10 mL×3). The organic phases were combined, washed with brine (10 mL×2), dried over anhydrous sodium sulfate, filtered and concentrated in vacuum, to give a residue. The residue was purified by preparative TLC (DCM/methanol=5/1) to give 4-isopropyl-6-[4-(2-methyl-1,2,3,4-tetrahydroisoquinolin-6-yl)-3-(5-methyl-4H-1,2,4-triazol-3-yl)isoxazol-5-yl]benzene-1,3-diol (30 mg, 67.3 μmol, 35.1% yield). $^1$H NMR (400 MHz, DMSO-$d_6$) δ 9.74 (s, 1H), 9.63 (s, 1H), 7.06-6.95 (m, 3H), 6.86 (s, 1H), 6.44 (s, 1H), 3.17 (d, J=5.0 Hz, 1H), 3.06-2.95 (m, 1H), 2.77 (brs, 4H), 2.38 (s, 3H), 0.97 (d, J=7.0 Hz, 7H).

EXAMPLE 16

4-(3-(5-ethyl-1H-imidazol-2-yl)-4-(2-methyl-1,2,3,4-tetrahydroisoquinolin-6-yl)isoxazol-5-yl)-6-isopropylbenzene-1,3-diol

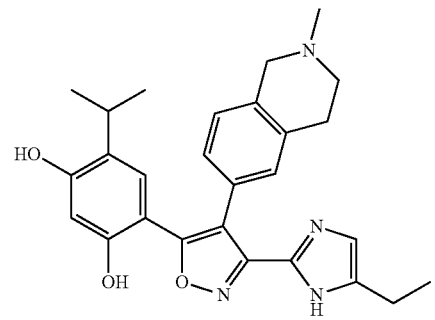 [SMILES: CCc1cnc(-c2noc(-c3cc(C(C)C)c(O)cc3O)c2-c2ccc3c(c2)CCN(C)C3)[nH]1]

Reaction scheme:

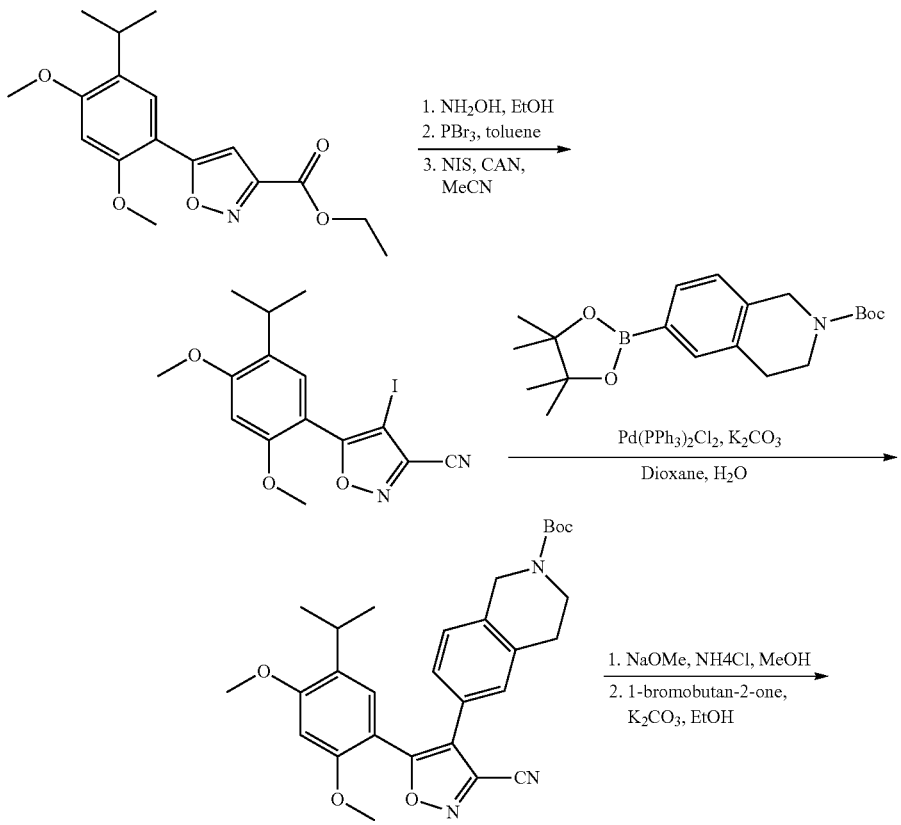

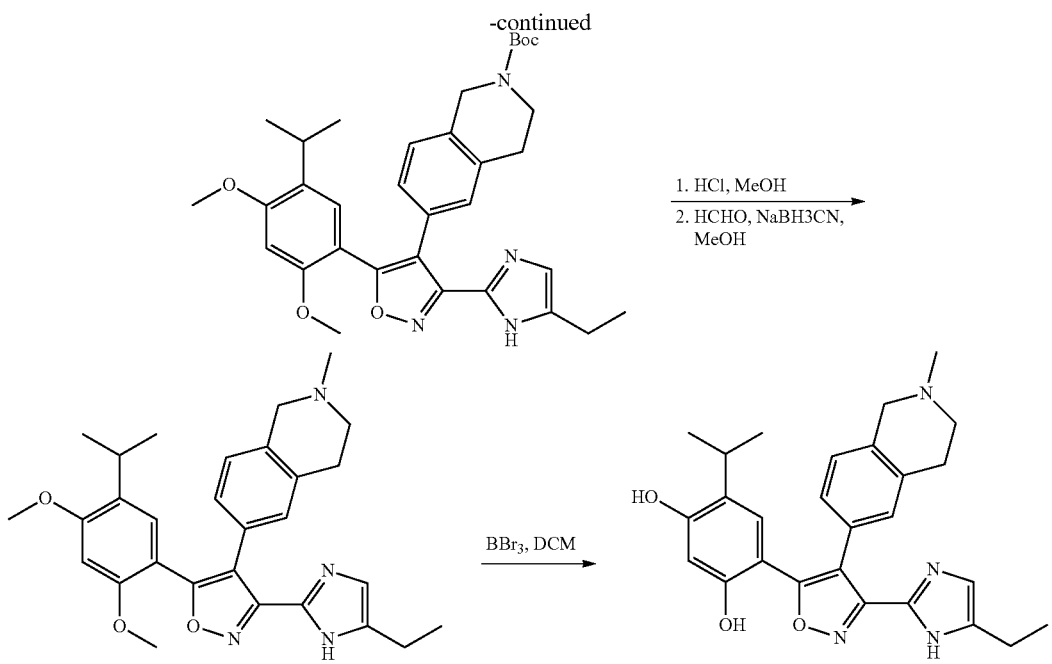

Step A: A solution of KOH (1.41 g, 25.1 mmol, 150 eq.) in MeOH (3 mL) was added dropwise to a solution of NH₂OH.HCl (1.16 g, 16.74 mmol, 100 eq.) dissolved in MeOH (6 mL) at 0° C. The mixture was stirred at 0° C. for 30 min and then the solid was filtered out. The remaining methanol solution was added with ethyl 5-(5-isopropyl-2,4-dimethoxyphenyl)isoxazole-3-formate (100.00 mg, 333.38 μmol, 1.0 eq.) and stirred at 5° C. for 30 min. The mixture was adjusted to pH 4 with 1.2 M dilute hydrochloric acid, concentrated under reduced pressure, added with water and extracted with EA (10 mL×3). The combined organic phase was washed with saturated brine (10 mL×2), dried over anhydrous sodium sulfate, filtered and concentrated to give a crude product N-ethyl-5-(5-isopropyl-2,4-dimethoxyphenyl)isoxazole-3-carboxamide (97 mg, 330 μmol, 98% yield) as a white solid, which was used directly in the next step.

Step B: PBr₃ (6.01 g, 22.2 mmol, 2.0 eq.) was added to a solution of N-hydroxyl-5-(5-isopropyl-2,4-dimethoxyphenyl)isoxazole-3-carboxamide (3.40 g, 11.1 mmol, 1.0 eq.) in toluene (80 mL) in one portion at 29° C. under the protection of nitrogen gas. The mixture was stirred at 29° C. for 10 min and then heated to 110° C. with stirring for 8 hours. The mixture was cooled down to 29° C. and then poured into saturated aqueous NaHCO₃ solution (60 mL) with stirring for 5 min. The aqueous phase was extracted with EA (100 mL×3), and the organic phase was combined, washed with brine (30 mL×2), dried over anhydrous sodium sulfate, filtered and concentrated in vacuum. The crude product obtained was purified by column chromatography (PE/EA=10/1 to 5/1) to give 5-(isopropyl-2,4-dimethoxyphenyl)isoxazole-3-carbonitrile (1.0 g, 3.67 mmol, 33.1% yield) as a white solid.

Step C: NIS (1.93 g, 8.59 mmol, 1.3 eq.) and CAN (362 mg, 661 μmol, 0.1 eq.) were added to a solution of 5-(isopropyl-2,4-dimethoxyphenyl)isoxazole-3-carbonitrile (1.80 g, 6.6 mmol, 1.0 eq) in MeCN (32 mL) at 28° C. under the protection of nitrogen gas. The mixture was stirred at 28° C. for 10 min and then heated to 80° C. with stirring for 4 hours. The mixture was cooled down to 28° C. and then concentrated under reduced pressure. The residue was poured into saturated aqueous NaHCO₃ solution (50 mL) and stirred for 5 min. The aqueous phase was extracted with ethyl acetate (5 mL×3), and the combined organic phase was washed with saturated brine (10 mL×2), dried over anhydrous sodium sulfate, filtered and concentrated in vacuum. The resulting crude product was purified by column chromatography (PE/EA=20/1 to 10/1) to give 4-iodo-5-(isopropyl-2,4-dimethoxyphenyl)isoxazole-3-nitrile (1.30 g, 3.26 mmol, 49.4% yield) as a pale yellow solid.

Step D: 4-iodo-5-(5-isopropyl-2,4-dimethoxy-phenyl)isoxazole-3-nitrile (2.04 g, 5.12 mmol, 0.80 eq.), Pd(PPh₃)₂Cl₂ (314.45 mg, 448.00 μmol, 0.07 eq.) and K₂CO₃ (1.77 g, 12.80 mmol, 2.0 eq.) were added to a solution of t-butyl 6-(4,4,5,5-tetramethyl-1,3,2-dioxaborolan-2-yl)-1,2,3,4-tetrahydroisoquinolin-2-carboxylate (2.30 g, 6.40 mmol, 1.0 eq.) in dioxane (30 mL) under the protection of nitrogen gas. The mixture was stirred at 80° C. for 16 hours. The mixture was poured into water (100 mL) and extracted with EA (100 mL×2). The combined organic layer was concentrated, and the residue was purified by silica gel chromatography (PE/EA=5/1, 2/1) to give t-butyl 6-[3-cyano-5-(5-isopropyl-2,4-di methoxy-phenyl)isoxazol-4-yl]-1,2,3,4-tetrahydroisoquinoline-2-carboxylate (2.00 g, 3.97 mmol, 62.1% yield) as a black-brown solid.

Step E: Sodium methoxide (2.14 g, 39.7 mmol, 10 eq.) was added to a solution of t-butyl 6-[3-cyano-5-(5-isopropyl-2,4-dimethoxy-phenyl)-isoxazol-4-yl]-1,2,3,4-tetrahydroisoquinoline-2-carboxylate (2.00 g, 3.97 mmol, 1.0 eq.) in MeOH (15 mL) at 25° C. The mixture was stirred at 25° C. for 2 hours and then added with ammonium chloride (2.12 g, 39.71 mmol, 10 eq.). The reaction mixture was stirred at 25° C. for 14 hours. The mixture was poured into water (80 mL) and extracted with EA (60 mL×2), and the organic layers were combined and concentrated. The crude product was purified by column chromatography (PE/EA=30/1) to give t-butyl 6-[3-form am idinyl-5-(5-isopropyl-2,4-dimethoxy-phenyl)isoxazol-4-yl]-1, 2,3,4-tetrahydroisoquinoline-2-carboxylate (1.50 g, 2.88 mmol, 72.6% yield) as a white solid.

Step F: K₂CO₃ (265 mg, 1.92 mmol, 1.0 eq.) and 1-bromo-2-butanone (290 mg, 1.92 mmol, 1.0 eq.) were added to a solution of t-butyl 6-[3-form am idinyl-5-(5-isopropyl-2,4-dimethoxy-phenyl)isoxazol-4-yl]-1,2,3,4-tetrahydroisoquinoline-2-carboxylate (1.00 g, 1.92 mmol, 1.0 eq.) in EtOH (15 mL). The mixture was stirred at 80° C. for 10 hours, poured into water (80 mL) and extracted with EA (60 mL×2), and the organic layers were combined and concentrated. The residue was purified by silica gel chromatography (PE/EA=5/1, 2/1) to give t-butyl 6-[3-(5-ethyl-1H-imidazol-2-yl)-5-(5-isopropyl-2,4-dimethoxy-phenyl) isoxazol-4-yl]-1,2,3,4-tetrahydroisoquinoline-2-carboxylate (850 mg, 1.48 mmol, 77.3% yield) as a white solid.

Step G: A mixture of t-butyl 6-[3-(5-ethyl-1H-imidazol-2-yl)-5-(5-isopropyl-2,4-dimethoxy-phenyl)isoxazol-4-yl]-1,2,3,4-tetrahydroisoquinoline-2-carboxylate (600 mg, 1.05 mmol, 1.00 eq.) in HCl/MeOH (4 M, 15.00 mL) was stirred at 25° C. for 30 min. The mixture was concentrated at 40° C., to give 3-(5-ethyl-1H-imidazol-2-yl)-5-(5-isopropyl-2,4-dimethoxyphenyl)-4-(1,2,3,4-tetrahydroisoquinolin-6-yl) isoxazole (50 mg, 982.2 μmol, 93.6% yield) as a yellow solid.

Step H: Paraformaldehyde (476 mg, 5.29 mmol, 5.0 eq.) and AcOH (63.7 mg, 1.06 mmol, 1.0 eq.) were added to a solution of 3-(5-ethyl-1H-imidazol-2-yl)-5-(5-isopropyl-2,4-dimethoxyphenyl)-4-(1,2,3,4-tetrahydroisoquinolin-6-yl) isoxazole (500 mg, 1.06 mmol, 1.0 eq.) in MeOH (8 mL). The mixture was stirred at 25° C. for 2 hours and then added with NaBH₃CN (133 mg, 2.12 mmol, 2.0 eq.). The reaction was continuously stirred at 25° C. for 14 hours, the mixture was poured into water (80 mL) and extracted with EA (80 mL×2), and the organic layers were combined and concentrated to give 3-(5-ethyl-1H-imidazol-2-yl)-5-(5-isopropyl-2,4-dimethoxy-phenyl)-4-(2-methyl-1,2,3,4-tetrahydroisoquinolin-6-yl)isoxazole (450 mg, 924.8 μmol, 87.2% yield) as a yellow solid.

Step I: BBr₃ (1.54 g, 6.15 mmol, 5.0 eq.) was added to a solution of 3-(5-ethyl-1H-imidazol-2-yl)-5-(5-isopropyl-2,4-dimethoxy-phenyl)-4-(2-methyl-1,2,3,4-tetrahydroisoquinolin-6-yl)isoxazole (600 mg, 1.23 mmol, 1.0 eq.) in DCM (12 mL) at −78° C. The mixture was stirred at 25° C. for 16 hours and quenched by slowly adding MeOH (20 mL). The mixture was concentrated and the residue was purified by preparative HPLC (formic acid system) to give the product 4-[3-(5-ethyl-1H-imidazol-2-yl)-4-(2-methyl-1,2,3,4-tetrahydroisoquinolin-6-yl)isoxazol-5-yl]-6-isopropyl-benzene-1,3-diol (262 mg, 571.4 μmol, 46.5% yield). ¹HNMR (400 MHz, DMSO-d₆) δ 12.55 (m, 1H), 9.65 (m, 1H), 8.16 (s, 1H), 7.07-6.81 (brs, 5H), 6.41 (d, 1H), 3.52-3.50 (m, 4H), 3.11-2.97 (m, 1H), 2.70-2.61 (m, 4H), 2.36 (s, 3H), 1.15 (t, J=3.6 Hz, 3H), 0.96-0.94 (m, 6H).

EXAMPLE 17

4-(3-(5-ethyl-1H-imidazol-2-yl)-4-(2-(2-hydroxy-ethyl)-1,2,3,4-tetrahydroisoquinolin-6-yl)isoxazol-5-yl)-6-isopropylbenzene-1,3-diol

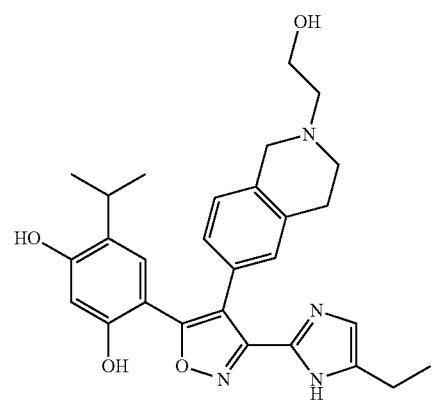 [SMILES: CCc1cnc(-c2noc(-c3cc(C(C)C)c(O)cc3O)c2-c2ccc3c(c2)CCN(CCO)C3)[nH]1]

Reaction scheme:

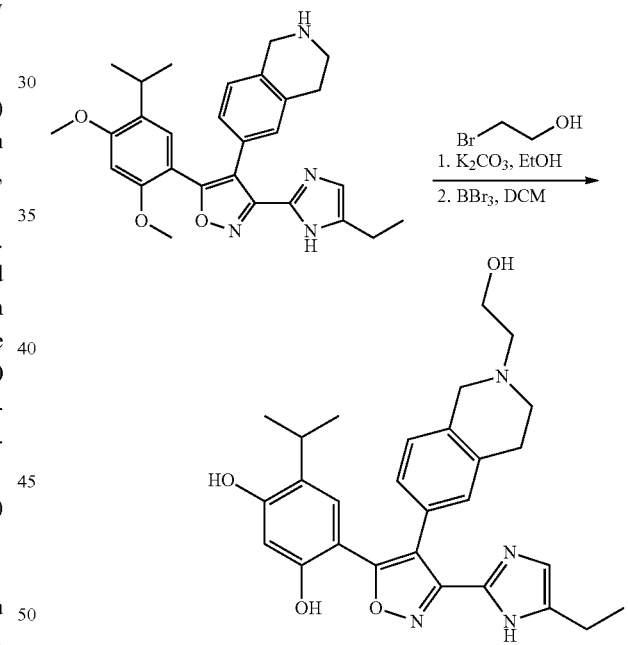

Step A: 2-bromoethanol (137.5 mg, 1.1 mmol, 4.0 eq.) and K₂CO₃ (114 mg, 825.3 μmol, 3.0 eq.) were added to a solution of 3-(5-ethyl-1H-imidazol-2-yl)-5-(5-isopropyl-2,4-dimethoxy-phenyl)-4-(1,2,3,4-tetrahydroisoquinolin-6-yl) isoxazole (130 mg, 275.1 μmol, 1.0 eq.) in EtOH (6 mL). The mixture was stirred at 50° C. for 16 hours, then poured into water (30 mL) and extracted with EA (30 mL×2). The organic layers were combined and concentrated. The crude product was purified by preparative TLC (DCM/MeOH=10:1) to give 2-[6-[3-(5-ethyl-1H-imidazol-2-yl)-5-(5-isopropyl-2,4-dimethoxy-phenyl)-isoxazol-4-yl]-1,2,3,4-tetrahydroisoquinolin-2-yl]ethanol (80 mg, 154.9 μmol, 56.3% yield) as a yellow solid.

Step B: BBr₃ (387.9 mg, 1.55 mmol, 10.0 eq.) was added to a solution of 2-[6-[3-(5-ethyl-1H-imidazol-2-yl)-5-(5-isopropyl-2,4-dimethoxy-phenyl)-isoxazol-4-yl]-1,2,3,4-tetra-hydroisoquinolin-2-yl]ethanol (80 mg, 154.9 μmol, 1.0 eq.) in DCM (8 mL) at 0° C. The mixture was stirred at 25° C. for 16 hours and quenched by adding MeOH (15 mL), and the mixture was concentrated. The crude product was purified by preparative HPLC (Phenomenex Synergi C18 250× 21.2 mm×4 μm, 0.05% HCl-ACN) to give 4-(3-(5-ethyl-1H-imidazol-2-yl)-4-(2-(2-hydroxyethyl)-1,2,3,4-tetrahydroisoquinolin-6-yl)isoxazol-5-yl)-6-isopropylbenzene-1,3-diol (24.5 mg, 50.2 J mol, 32.4% yield). $^1$HNMR (300 MHz, DMSO-$d_6$) δ 11.01 (brs, 1H), 10.05-9.99 (m, 2H), 7.62 (s, 1H), 7.18-7.03 (m, 3H), 6.91 (s, 1H), 6.57 (s, 1H), 4.55-4.34 (m, 2H), 4.30-4.28 (m, 2H), 3.27-3.01 (m, 7H), 2.88-2.82 (m, 2H), 1.23 (t, J=4.5 Hz, 3H), 1.00 (d, J=6.9 Hz, 6H).

EXAMPLE 18

5-(2,4-dihydroxyl-5-isopropylphenyl)-4-(7,7-dimethyl-4,5,6,7-tetrahydrothieno[2,3-c]pyridin-2-yl)-N-ethyl-isoxazole-3-carboxamide

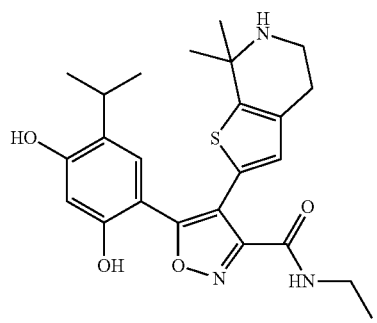 [SMILES: CCNC(=O)c1noc(-c2cc(C(C)C)c(O)cc2O)c1-c1cc2c(s1)C(C)(C)NCC2]

Reaction scheme:

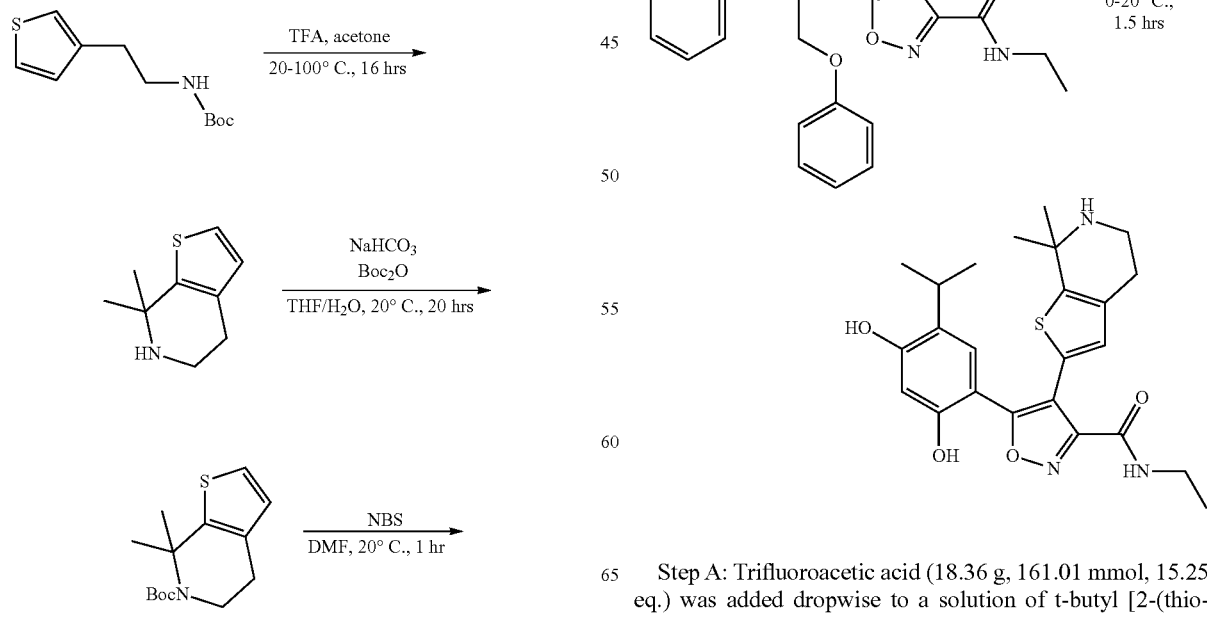

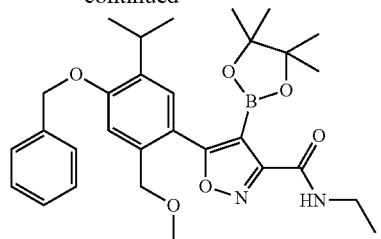

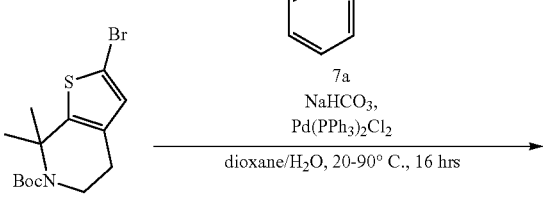

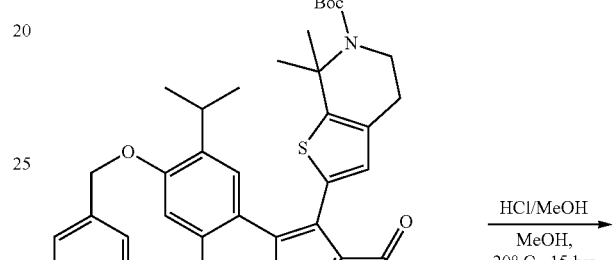

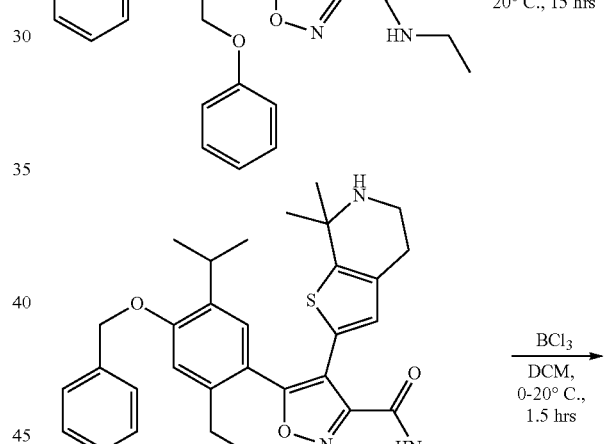

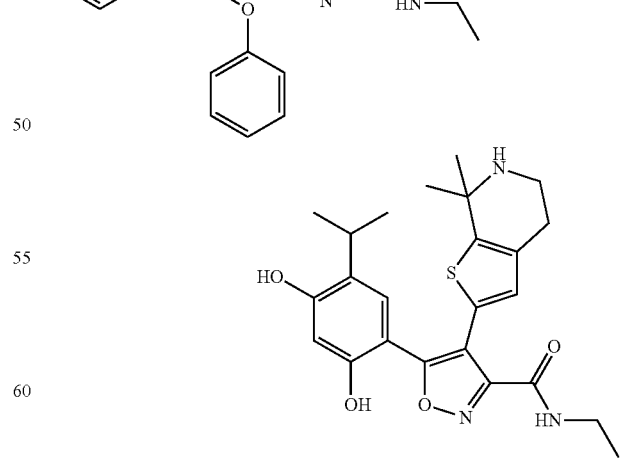

Step A: Trifluoroacetic acid (18.36 g, 161.01 mmol, 15.25 eq.) was added dropwise to a solution of t-butyl [2-(thiophen-3-yl)ethyl]carbamate (2.40 g, 10.56 mmol, 1.0 eq.)

dissolved in acetone (9.48 g, 163.22 mmol, 15.46 eq.) at 20° C. under the protection of nitrogen gas. After the addition, the reaction mixture was stirred at 100° C. for 16 hours. The reaction solution was cooled down to 20° C. and then concentrated at 50° C. to give 7,7-dimethyl-4,5,6,7-tetrahydrothieno[2,3-c]pyridine (10.05 g, a crude product). The resulting crude product was adjusted to pH=10 with 2M NaOH solution and the solution after alkalization was used for the next step of the reaction.

Step B: Boc$_2$O (2.31 g, 10.57 mmol, 1 eq.) was added dropwise to a solution of 7,7-dimethyl-4,5,6,7-tetrahydrothieno[2,3-c]pyridine (10.05 g, a crude product) dissolved in tetrahydrofuran (10 mL) at 20° C. under the protection of nitrogen gas. After the addition, the reaction mixture was stirred at 20° C. for 20 hours. The reaction solution was poured into 20 mL of water and stirred for 5 min. The aqueous phase was extracted three times with each 10 mL of ethyl acetate, and the organic phase was washed three times with each 10 mL of brine, dried over anhydrous sodium sulfate, filtered and concentrated, to give a crude product. The crude residue was purified by silica gel chromatography (100~200 mesh of silica gel, petroleum ether/ethyl acetate=400/1 to 90/1) to give t-butyl 7,7-dimethyl-4,5-dihydrothieno[2,3-c]pyridine-6(7H)-carbamate (733 mg, 2.74 mmol, 25.93% yield) as a yellow oil.

Step C: NBS (487.67 mg, 2.74 mmol, 1 eq.) was added in batch to a solution of t-butyl 7,7-dimethyl-4,5-dihydrothieno[2,3-c]pyridine-6(7H)-carbamate (733 mg, 2.74 mmol, 1 eq.) dissolved in N,N-dimethylcarboxamide (7 mL) at 20° C. under the protection of nitrogen gas. The reaction solution was allowed to react at 20° C. for one hour. The reaction solution was poured into 20 mL of water and stirred for 5 min. The aqueous phase was extracted three times with each 10 mL of ethyl acetate, and the organic phase was washed three times with each 10 mL of brine. Then, the organic phase was dried over anhydrous sodium sulfate, filtered and concentrated to give t-butyl 2-bromo-7,7-dimethyl-4,5-dihydrothieno[2,3-c]pyridine-6(7H)-carbamate (840 mg, 2.43 mmol, 88.53% yield) as a yellow oil.

Step D: Sodium bicarbonate (743.49 mg, 8.85 mmol, 3 eq.) and Pd(PPh$_3$)$_2$Cl$_2$ (414.12 mg, 590.00 μmol, 0.20 eq.) were added to a solution of t-butyl 2-bromo-7,7-dimethyl-4,5-dihydrothieno[2,3-c]pyridine-6(7H)-carbamate (1.02 g, 2.95 mmol, 1 eq.) and 5-(2,4-dibenzyloxy-5-isopropyl-phenyl)-N-ethyl-4-(4,4,5,5-tetramethyl-1, 3,2-dioxaborolan-2-yl)isoxazole-3-carboxamide (1.76 g, 2.95 mmol, 1 eq.) in dioxane (20 mL) and water (4 mL) at 25° C. under the protection of nitrogen gas. The reaction solution was reacted at 90° C. for 16 hours. The reaction solution was cooled down to room temperature and then concentrated to give a crude product. The crude residue was purified by silica gel chromatography (100~200 mesh of silica gel, petroleum ether/ethyl acetate=100/1 to 3/1) to give t-butyl 2-[5-(2,4-dibenzyloxy-5-isopropyl-phenyl)-3-(ethylcarboxamide)isoxazol-4-yl]-7,7-dimethyl-4,5-dihydrothieno[2,3-c]pyridine-6(7H)-carbamate (841.00 mg, 719.95 μmol, 24.40% yield, 63% purity) as a brown solid.

Step D: HCl/MeOH (4 mol/L, 8 mL, 44.50 eq.) was added dropwise to a solution of t-butyl 2-[5-(2,4-dibenzyloxy-5-isopropyl-phenyl)-3-(ethylcarboxamide)isoxazol-4-yl]-7,7-dimethyl-4,5-dihydrothieno[2,3-c]pyridine-6(7H)-carbamate (840 mg, 719.09 μmol, 1 eq.) in methanol (8 mL) at 20° C. The reaction solution was stirred at 20° C. for 15 hours. The reaction solution was concentrated to give a crude product, and then the crude product was purified by silica gel chromatography (100~200 mesh of silica gel, dichloromethane/methanol=1/0 to 10/1) to give 5-(2,4-dibenzyloxy-5-isopropylphenyl)-4-(7,7-dimethyl-4,5,6,7-tetrahydrothieno[2,3-c]pyridin-2-yl)-N-ethyl-isoxazole-3-carboxamide (442.00 mg, 695.18 μmol, 96.67% yield) as a light brown solid.

Step E: Boron trichloride (1 mol/L, 4.72 mL, 10 eq.) was slowly added dropwise to a solution of 5-(2,4-dibenzyloxy-5-isopropylphenyl)-4-(7,7-dimethyl-4,5,6,7-tetrahydrothieno[2,3-c]pyridin-2-yl)-N-ethyl-isoxazole-3-carboxamide (300 mg, 471.84 mol, 1 eq.) in anhydrous dichloromethane (20 mL) at 0° C. under nitrogen gas atmosphere. The reaction solution was reacted at 0° C. for one hour and then warmed up to 20° C. for 0.5 hour. After the completion of the reaction, the reaction solution was cooled down to 0° C., and slowly added dropwise with methanol (30 mL), followed by stirring for 0.5 hour. The organic phase was concentrated to give a crude product. The crude product was purified by pre-HPLC (Phenomenex Synergi Max-RP 250× 80 10 μm, 0.225% FA-ACN) to give 5-(2,4-dihydroxyl-5-isopropyl-phenyl)-4-(7,7-dimethyl-4,5,6,7-tetrahydrothieno[2,3-c]pyridin-2-yl)-N-ethyl-isoxazole-3-carboxamide (150.00 mg, 311.43 mol, 66.0% yield) as a white solid. $^1$H NMR (400 MHz, DMSO-d$_6$): δ 8.94 (t, J=5.5 Hz, 1 H), 8.28 (s, 1 H), 6.90 (s, 1 H), 6.82 (s, 1 H), 6.50 (s, 1 H), 3.31-3.24 (m, 2 H), 3.09-3.03 (m, 3 H), 2.56-2.54 (m, 2 H), 1.38 (s, 6 H), 1.11 (t, J=7.2 Hz, 3 H), 1.04 (d, J=7 Hz, 6 H).

EXAMPLE 19

5-(2,4-dihydroxyl-5-isopropylphenyl)-N-ethyl-4-(6-methyl-5,6,7,8-tetrahydro-1,6-naphthyridin-3-yl)isoxazole-3-carboxamide

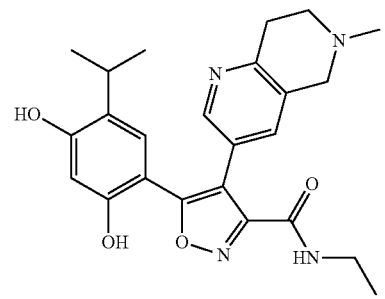 [SMILES: CCNC(=O)c1noc(-c2cc(C(C)C)c(O)cc2O)c1-c1cnc2c(c1)CN(C)CC2]

Reaction scheme:

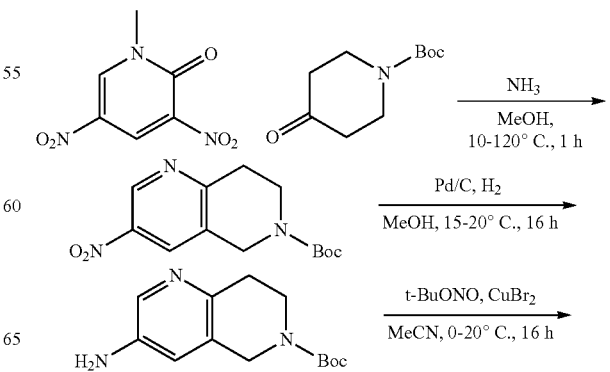

-continued

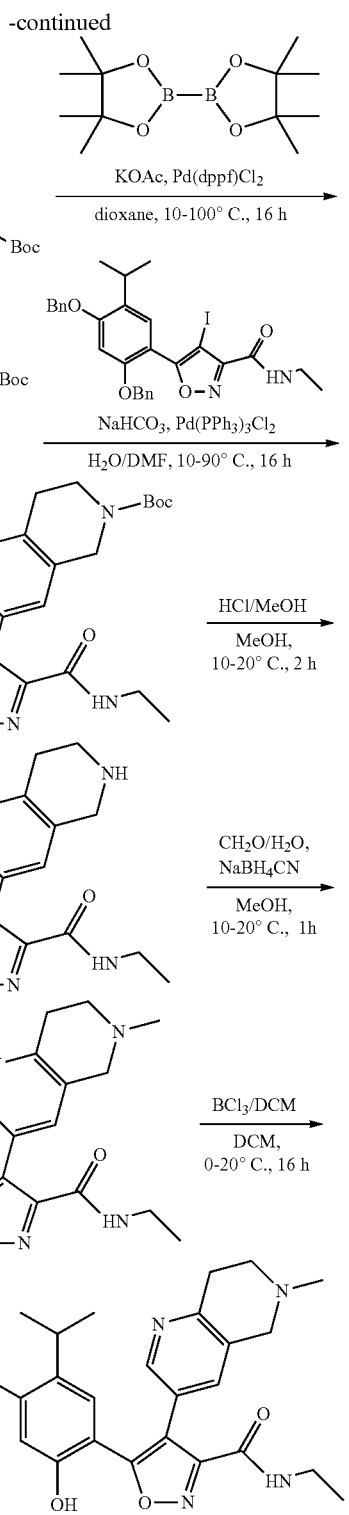

Step A: Ammonia gas (1.37 g, 80.32 mmol, 8 eq.) was added to a solution of 1-methyl-3,5-dinitro-pyridin-2-one (2 g, 10.04 mmol, 1 eq.) and t-butyl 4-piperidone-1-carboxylate in methanol (50 mL) at room temperature. The reaction solution was stirred in a sealed tank at 120° C. for 1 hour. The reaction solution was cooled down to room temperature and concentrated to give a crude product. The crude product was purified by a silica gel chromatography column (PE/ EA=10/1 to 3/1) to give t-butyl 3-nitro-7,8-dihydro-5H-1, 6-naphthyridine-6-carboxylate (1.9 g, 6.8 mmol, 67.76% yield) as a gray-white solid.

Step B: Pd/C (1.00 g) was added to a solution of t-butyl 3-nitro-7,8-dihydro-5H-1,6-naphthyridine-6-carboxylate (3 g, 10.74 mmol, 1 eq.) in methanol (100 mL) at room temperature under hydrogen gas environment (40 Psi). The reaction solution was stirred at room temperature for 16 hours. After the completion of the reaction, the reaction solution was filtrated and concentrated to give t-butyl 3-amino-7,8-dihydro-5H-1,6-naphthyridine-6-carboxylate (2.5 g, 10.03 mmol, 93.37% yield) as a white solid.

Step C: CuBr$_2$ (402.03 mg, 1.8 mmol, 1.5 eq.) was added to a solution of t-butyl 3-amino-7,8-dihydro-5H-1,6-naphthyridine-6-carboxylate (300 mg, 1.2 mmol, 1 eq.) in acetonitrile (6 mL) at room temperature, followed by dropwise adding t-butyl nitrite (148.49 mg, 1.44 mmol, 1.2 eq.) at 0-5° C. to react for 1 hour. The temperature was raised to room temperature with stirring for 15 hours. The reaction solution was poured into water (20 mL), filtered, and extracted three times with each 20 mL of ethyl acetate. The organic phase was washed twice with 30 mL of water each time, dried over anhydrous sodium sulfate, filtrated and concentrated to give a crude product. The crude product was purified by a silica gel chromatography column (PE/ EA=10/1 to 3/1) to give t-butyl 3-bromo-7,8-dihydro-5H-1, 6-naphthyridine-6-carboxylate (180 mg, 534.5 µmol, 44.54% yield, 93% of purity) as a colorless and transparent oil.

Step D: Bis(pinacolato)diboron (194.60 mg, 766.31 µmol, 1.50 eq.) and KOAc (150.41 mg, 1.53 mmol, 3 eq.) were added to a solution of t-butyl 3-bromo-7,8-dihydro-5H-1,6-naphthyridine-6-carboxylate (160 mg, 510.87 µmol, 1 eq.) in dioxane (3 mL) at 25° C. under the protection of nitrogen gas, followed by the addition of a catalyst Pd(dppf) Cl$_2$.CH$_2$Cl$_2$ (74.76 mg, 102.17 µmol, 0.20 eq.). The mixture was stirred at 25° C. for 10 min, and then heated to 100° C. with stirring for 16 hours. The mixture was cooled down to 25° C. and concentrated under reduced pressure to give a crude product, which was used directly in the next step.

Step E: NaHCO$_3$ (63.38 mg, 754.46 µmol, 3.00 eq.), H$_2$O (1 mL) and Pd(PPh$_3$)$_2$Cl$_2$ (35.30 mg, 50.30 µmol, 0.2 eq.) were added to a mixture solution of t-butyl 3-(4,4,5,5-tetramethyl-1,3,2-dioxaborolan-2-yl)-7,8-dihydro-5H-1,6-naphthyridine-6-carboxylate (181.20 mg, 502.98 µmol, 2.00 eq.) and N-ethyl-4-iodo-5-(5-isopropyl-2,4-dimethoxyphenyl) isoxazole-3-carboxamide (150.00 mg, 251.49 µmol, 1.00 eq.) in dioxane (5 mL) at 25° C. under the protection of nitrogen gas. The mixture was stirred at 25° C. for 10 min, then heated to 90° C. and stirred for 16 hours. The mixture was cooled down to 25° C. and concentrated under reduced pressure. The residue was purified by silica gel chromatography (200~300 mesh of silica gel, petroleum ether/ethyl acetate, dichloromethane/methanol=30/1, 1/15) to give t-butyl 3-[5-(2,4-dibenzyloxy-5-isopropyl-phenyl)-3-(ethylcarboxamide)isoxazol-4-yl]-7,8-dihydro-5H-1,6-naphthyridine-6-carboxylate (90.00 mg, a crude product) as a yellow solid.

Step F: HCl/MeOH (4 mol/L, 2.00 mL, 62.4 eq.) was added dropwise to a solution of t-butyl 3-[5-(2,4-dibenzyloxy-5-isopropyl-phenyl)-3-(ethylcarboxamide)isoxazol-4-yl]-7,8-dihydro-5H-1,6-naphthyridine-6-carboxylate (90 mg, 128.05 µmol, 1 eq.) in methanol (2 mL) at 20° C. The reaction solution was stirred at room temperature for 2 hours. The reaction solution was concentrated under reduced pressure to give a crude product, and the crude product was dissolved in dichloromethane (10 mL) at room temperature and then sodium bicarbonate (1 g) was added. The mixture was stirred at room temperature for 1 hour, filtrated and concentrated. The crude product was separated and purified by a TLC large plate (dichloromethane/methanol=20/1) to give 5-(2,4-dibenzyloxy-5-isopropyl-phenyl)-N-ethyl-4-(5,6,7,8-tetrahydro-1,6-naphthyridin-3-yl)isoxazole-3-carboxylate (50.00 mg, 82.96 μmol, 64.79% yield) as a yellow solid.

Step G: A solution of formaldehyde in water (62.28 mg, 829.6 μmol, 10 eq.) was added dropwise to a solution of 5-(2,4-dibenzyloxy-5-isopropyl-phenyl)-N-ethyl-4-(5,6,7,8-tetrahydro-1,6-naphthyridin-3-yl)isoxazole-3-carboxylate (50.00 mg, 82.96 mol, 1.00 eq.) in methanol (5 mL) at 20° C. under the protection of nitrogen gas. The reaction solution was stirred at room temperature for 10 min, and then added with NaBH$_3$CN (15.64 mg, 248.88 μmol, 3.00 eq.) at room temperature with stirring for 50 min. The reaction solution was directly concentrated to give a rude product, and the crude product was separated and purified by a TLC large plate (dichloromethane/methanol=10/1) to give 5-(2,4-dibenzyloxy-5-isopropyl-phenyl)-N-ethyl-4-(6-methyl-5,6,7,8-tetra hydro-1,6-naphthyridin-3-yl)isoxazole-3-carboxylate (40.00 mg, 64.86 μmol, 78.18% yield) as a white solid.

Step H: Boron trichloride (1 mol/L, 0.648 mL, 10 eq.) was slowly added dropwise to a solution of 5-(2,4-dibenzyloxy-5-isopropyl-phenyl)-N-ethyl-4-(6-methyl-5,6,7,8-tetra hydro-1,6-naphthyridin-3-yl)isoxazole-3-carboxylate (40 mg, 64.86 μmol, 1 eq.) in anhydrous dichloromethane (2.5 mL) at 0° C. under nitrogen gas environment. The reaction solution was allowed to react at 0° C. for one hour, and then warmed up to 20° C. and reacted for 14 hours. After the completion of the reaction, the reaction solution was cooled down to 0° C. and slowly added dropwise methanol (1 mL), followed by stirring for 0.5 hour. The organic phase was concentrated to give a crude product. The crude product was purified by pre-HPLC (Phenomenex Synergi Max-RP 250× 80 10 μm, 0.225% FA-ACN) to give 5-(2,4-dihydroxyl-5-isopropyl-phenyl)-N-ethyl-4-(6-methyl-5,6,7,8-tetrahydro-1,6-naphthyridin-3-yl)isoxazole-3-carboxamide formate (18 mg, 37.3 μmol, 57.00% yield). $^1$H NMR (400 MHz, DMSO): 8.88 (t, J=5.6 Hz, 1 H), 8.12 (d, J=1.6 Hz, 1 H), 7.32 (d, J=1.6 Hz, 1 H), 6.91 (s, 1 H), 6.41 (s, 1 H), 3.42 (s, 2 H), 3.27-3.19 (m, 2 H), 3.07-2.99 (m, 1 H), 2.85 (t, J=6.0 Hz, 2 H), 2.67 (t, J=6.0 Hz, 2 H), 2.34 (s, 3 H), 1.10 (t, J=7.2 Hz, 3 H), 1.01 (d, J=6.8 Hz, 6 H). MS (ESI) m/z: 437 (M+1).

EXAMPLE 20

4-isopropyl-6-(4-(2-methyl-1,2,3,4-tetrahydroisoquinolin-6-yl)-3-(2,2,2-trifluoro-1-hydroxyethyl)isoxazol-5-yl)benzene-1,3-diol

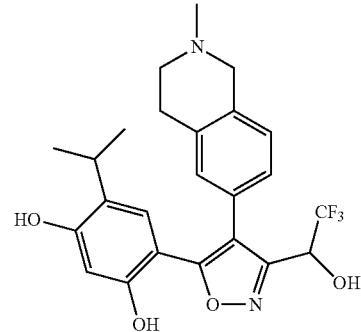 [SMILES: CC(C)c1cc(-c2onc(C(O)C(F)(F)F)c2-c2ccc3c(c2)CCN(C)C3)c(O)cc1O]

Reaction scheme:

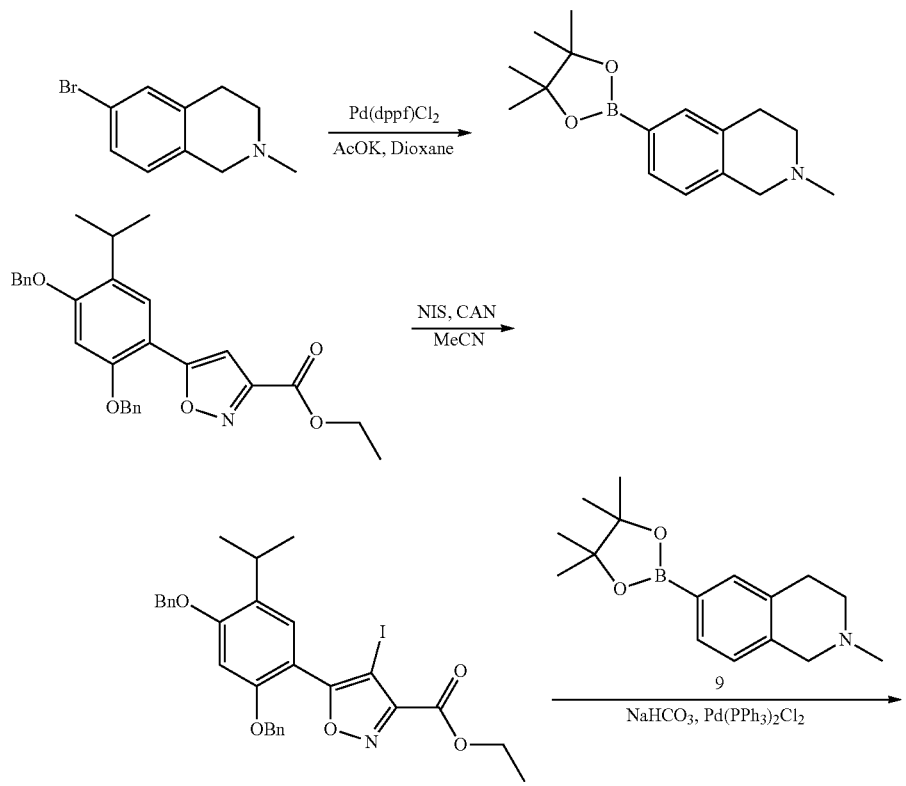

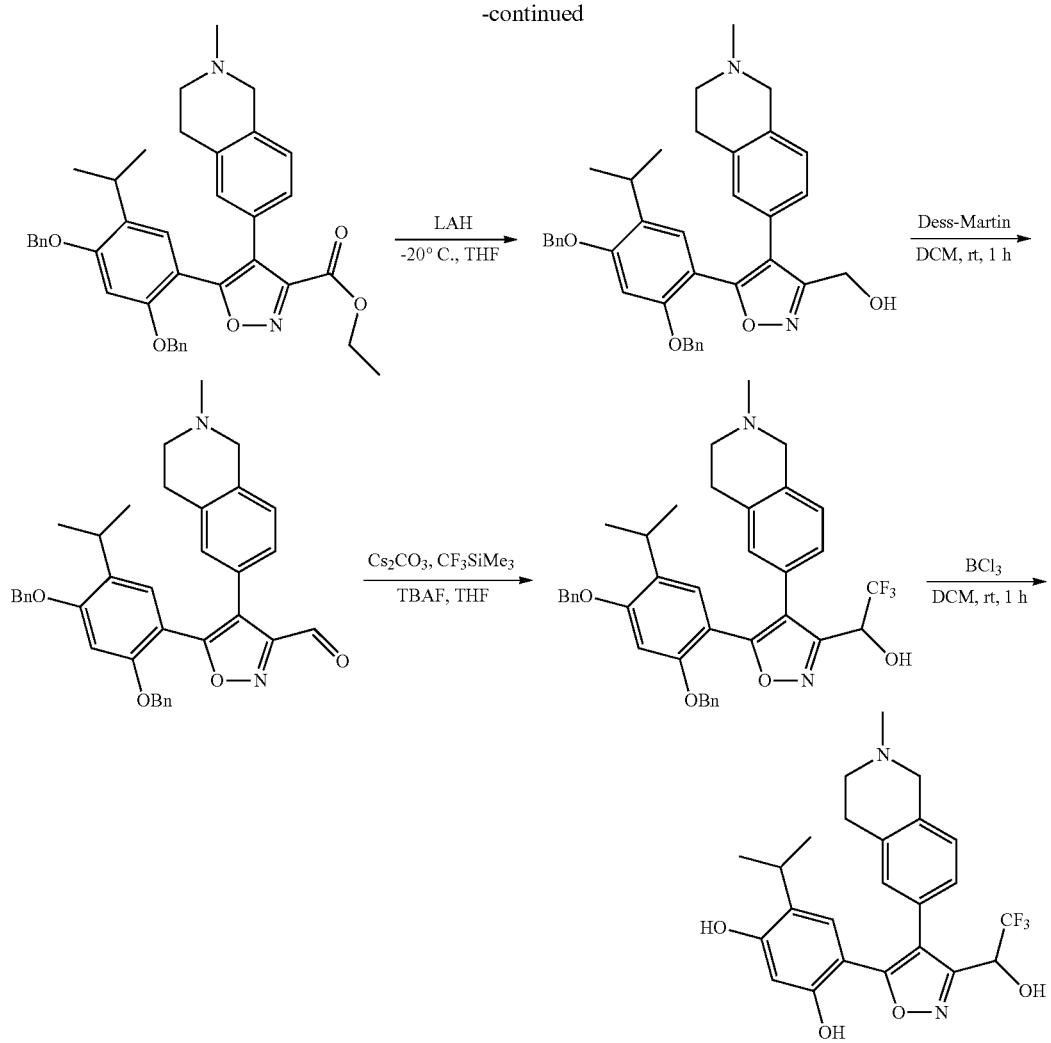

Step A: Bis(pinacolato)diboron (1.68 g, 6.63 mmol, 1.5 eq.) and KOAc (1.30 g, 13.26 mmol, 3.0 eq.) were added to a solution of 6-bromo-2-methyl-1,2,3,4-tetrahydroisoquinoline (1.00 g, 4.42 mmol, 1.0 eq.) in dioxane (10 mL) at 25° C. under the protection of nitrogen gas, followed by the addition of a catalyst Pd(dppf)Cl$_2$ (323.41 mg, 442.00 µmol). The mixture was heated to 90° C. with stirred for 2 hours. The mixture was filtered through diatomaceous earth and concentrated under reduced pressure. The residue was purified by silica gel chromatography (petroleum ether/ethyl acetate=1/1 to 0/1) to give 2-methyl-6-(4,4,5,5-tetramethyl-1,3,2-dioxaborolan-2-yl)-1,2,3,4-tetrahydroisoquinoline (1.0 g, 3.66 mmol, 82.82% yield) as a yellow oil.

Step B: CAN (232.52 mg, 549 µmol, 0.10 eq.) and NIS (2.83 g, 8.48 mmol, 2.00 eq.) were added to a solution of ethyl 5-(2,4-dibenzyloxy-5-isopropyl-phenyl)-isoxazole-3-carboxylate (2.00 g, 4.24 mmol, 1.0 eq.) in MeCN (25 mL) at room temperature under N$_2$ protection. The mixture was heated to 80° C. with stirring for 16 hours. The mixture was cooled down to room temperature and poured into water (40 mL), and the aqueous phase was extracted with EA (40 mL×3). The combined organic phase was dried with anhydrous sodium sulfate, filtered and concentrated in vacuum. Ethyl 5-(2,4-dibenzyloxy-5-isopropyl-phenyl)-4-iodo-isoxazole-3-carboxylate (2.00 g, 3.35 mmol, 78.95% yield) as a yellow solid was obtained.

Step C: NaHCO$_3$ (632.60 mg, 7.53 mmol, 3.0 eq.), H$_2$O (3.00 mL) and Pd(PPh$_3$)$_2$Cl$_2$ (176.18 mg, 251.00 mmol, 0.10 eq.) were added to a solution of 2-methyl-6-(4,4,5,5-tetramethyl-1,3,2-dioxaborolan-2-yl)-1,2,3,4-tetrahydroisoquinoline (6.15 g, 13.5 mmol) and ethyl 5-(2,4-dibenzyloxy-5-isopropyl-phenyl)-4-iodo-isoxazole-3-carboxylate (1.50 g, 2.51 mmol, 1.0 eq.) in dioxane (15 mL) at 25° C. under the protection of nitrogen gas. The mixture was heated to 90° C. with stirring for 1.5 hours. The mixture was filtered through diatomaceous earth and concentrated under reduced pressure. The residue was purified by silica gel chromatography (dichloromethane/methanol=20/1) to give ethyl 5-(2,4-dibenzyloxy-5-isopropylbenzene-4-(2-methyl-1,2,3,4-tetrahydroisoquinolin-6-yl)isoxazole-3-carboxylate (600 mg, 972.86 µmol, 38.76% yield) as a yellow solid, which was used directly in the next step. MS (ESI) M/Z: 617.2 (M+1).

Step D: Lithium tetrahydroaluminate (153.83 mg, 4.05 mmol, 5.0 eq.) was added to a solution of ethyl 5-(2,4-dibenzyloxy-5-isopropylbenzene-4-(2-methyl-1,2,3,4-tetrahydroisoquinolin-6-yl)isoxazole-3-carboxylate (500.00 mg, 810.71 µmol, 1.0 eq.) in tetrahydrofuran (2.0 mL) at −20° C. under the protection of nitrogen gas. The mixture was cooled down to −20° C. with stirring for 0.5 hour. 15% NaOH solution (0.3 mL) was added dropwise to the mixture, and then the mixture was filtered to give an organic phase. The organic phase was concentrated under reduced pressure. The residue was purified by prep-TLC (dichloromethane/methanol=10/1), to give (5-(2,4-dibenzyloxy)-5-isopropylbenzene)-4-(2-methyl-1,2,3,4-tetrahydroisoquinolin-6-yl)isoxazole-3-methanol (300 mg, 522.00 μmol, 64.39% yield) as a yellow solid, which was used directly in the next step. MS (ESI) M/Z: 575.2 (M+1).

Step E: Dess-Martin (221.40 mg, 522.00 μmol, 1.5 eq.) was added to a solution of (5-(2,4-dibenzyloxy)-5-isopropylbenzene)-4-(2-methyl-1,2,3,4-tetrahydroisoquinolin-6-yl)isoxazole-3-methanol (200.00 mg, 348.00 μmol, 1.0 eq.) in dichloromethane (5.0 mL) at 5° C. under $N_2$ protection. The mixture was stirred at 5° C. for 1 hour. A saturated $NaHCO_3$ solution (1.0 mL) and a saturated aqueous $Na_2SO_3$ solution (1.0 mL) were added to the mixture with stirring for 5 min. 15 mL of water was added for dilution, and the aqueous phase was extracted with dichloromethane (15 mL×2). The combined organic phase was dried with anhydrous sodium sulfate, filtered and concentrated in vacuum to dryness. (5-(2,4-dibenzyloxy)-5-isopropylbenzene)-4-(2-methyl-1,2,3,4-tetrahydroisoquinolin-6-yl)isoxazole-3-carbaldehyde (200 mg, a crude product) as a yellow solid was obtained. MS (ESI) M/Z: 573.2 (M+1).

Step F: Cesium carbonate (5.69 mg, 17.465 μmol, 0.05 eq.) and trimethyl(trifluoromethyl) silane (60 mg, 419 μmol, 1.2 eq.) were added to a solution of (5-(2,4-dibenzyloxy)-5-isopropylbenzene)-4-(2-methyl-1,2,3,4-tetrahydroisoquinolin-6-yl)isoxazole-3-carbaldehyde (200.00 mg, 349.23 μmol, 1.0 eq.) in tetrahydrofuran (5.0 mL) at 5° C. under $N_2$ protection. The mixture was stirred at 5° C. for 4 hours. Tetra-butylammonium fluoride (136.96 mg, 523.85 μmol, 1.50 eq.) was added to the mixture at 5° C. and stirred for 12 hours. The mixture was poured into water (15 mL) and the aqueous phase was extracted with dichloromethane (15 mL×2). The combined organic phase was dried with anhydrous sodium sulfate, filtered and concentrated in vacuum to dryness. The residue was purified by thin layer chromatography (DCM/MeOH=8/1) to give 1-(5-(2,4-dibenzyloxy)-5-isopropylbenzene)-4-(2-methyl-1,2,3,4-tetrahydroisoquinolin-6-yl)isoxazol-3-yl)-2,2,2-trifluoroethanol (100.0 mg, 155.59 mmol, 44.55% yield) as a yellow solid. MS (ESI) M/Z: 643.2 (M+1).

Step G: 1 mol/L of $BCl_3$.DCM (2 mL) was added to a solution of 1-(5-(2,4-dibenzyloxy)-5-isopropylbenzene)-4-(2-methyl-1,2,3,4-tetrahydroisoquinolin-6-yl)isoxazol-3-yl)-2,2,2-trifluoroethanol (100.00 mg, 155.59 μmol, 1.0 eq.) in DCM (8 mL) at −20° C. The mixture was stirred at −20° C. for 1 hour, quenched by adding 1 mL of MeOH and concentrated in vacuum to give a crude product. The crude product was purified twice by thin layer chromatography (DCM/MeOH=8/1) to give 4-isopropyl-6-(4-(2-methyl-1,2,3,4-tetrahydroisoquinolin-6-yl)-3-(2,2,2-trifluoro-1-hydroxyethyl)isoxazol-5-yl)benzene-1,3-diol (20.10 mg, 27.93% yield). $^1$H NMR B000139948 EW2407-16-P1A (400 MHz, DMSO-$d_6$): δ 9.77 (s, 1H), 9.65 (s, 1H), 7.28 (d, J=7.2 Hz, 1H), 7.05-7.15 (m, 3H), 6.82 (s, 1H), 6.42 (s, 1H), 5.15 (t, J=7.2 Hz, 2H), 3.87 (brs, 2H), 2.85-3.05 (m, 5H), 2.59 (s, 3H), 0.95 (d, J=6.8 Hz, 9H). MS (ESI) m/z: 623 (M+1)

EXAMPLE 21

N-cyano-5-(2,4-dihydroxyl-5-isopropylphenyl)-4-(2-methyl-1,2,3,4-tetrahydroisoquinolin-6-yl)isoxazole-3-carboxamidine

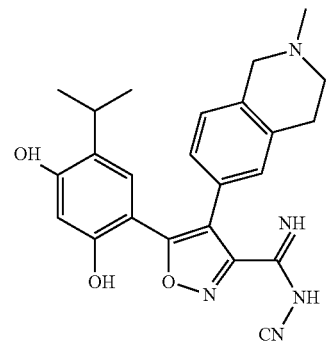

Reaction scheme:

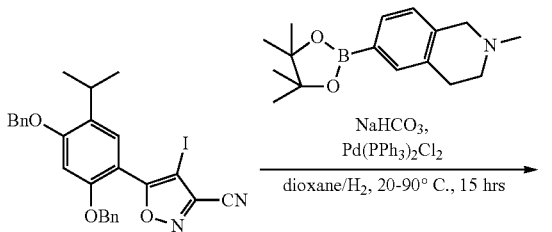

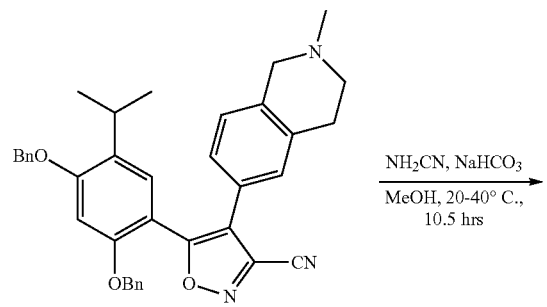

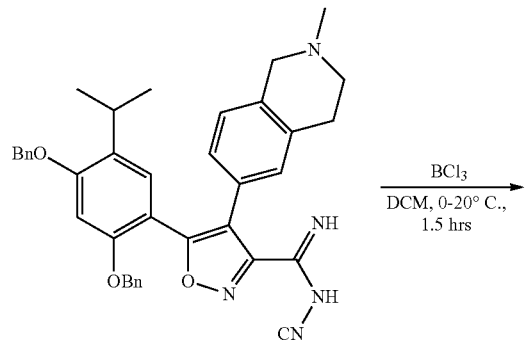

-continued

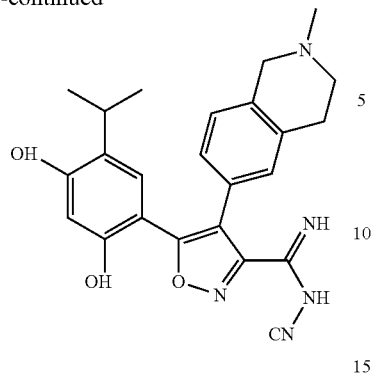

Step A: 2-methyl-6-(4,4,5,5-tetramethyl-1, 3,2-dioxaborolan-2-yl)-1,2,3,4-tetrahydroisoquinoline (372 mg, 818 μmol, 1.5 eq), water (900.00 μL) and sodium bicarbonate (224 mg, 2.7 mmol, 4.9 eq.) were added to a solution of 5-(2,4-dihydroxyl-5-isopropylphenyl)-4-iodo-isoxazole-3-carbonitrile (300 mg, 545 μmol, 1.00 eq.) in dioxane (4.5 mL) at 15-25° C. under the protection of nitrogen gas, followed by the addition of Pd(PPh$_3$)$_2$Cl$_2$ (77 mg, 109 μmol, 0.2 eq). The mixture was stirred at 90° C. for 15 hours. The reaction mixture was cooled down to 15-25° C., poured into water (50 mL) and extracted with EA (50 mL×L). The combined organic layer was dried, filtered and concentrated to give a crude product. The crude product was purified by column chromatography (DCM:methanol=20:1). 5-(2,4-dihydroxyl-5-isopropylphenyl)-4-(2-methyl-1,2,3,4-tetrahydroisoquinolin-6-yl)isoxazole-3-carbonitrile (306 mg, 376 μmol, 70% yield) as a yellow solid was obtained. (ESI) M/Z: 570 (M+1).

Step B: NaHCO$_3$ (221 mg, 2.6 mmol, 10.0 eq.) was added to a solution of 5-(2,4-dihydroxyl-5-isopropylphenyl)-4-(2-methyl-1,2,3,4-tetrahydroisoquinolin-6-yl)isoxazole-3-carbonitrile (150 mg, 263 μmol, 1.0 eq.) in MeOH (4 mL). The mixture was stirred at 40° C. for 6.5 hours. Subsequently, aminonitrile (221 mg, 5 mmol, 20.0 eq.) was added with stirring at 40° C. for 4 hours. The reaction solution was poured into water (20 mL) and extracted with EA (10 mL×3). The combined organic layer was dried with Na$_2$SO$_4$, filtered and concentrated to give a crude product. The crude product was purified by preparative TLC (DCM/MeOH=15:1) to give N-cyano-5-(2,4-dibenzyloxy-5-isopropylphenyl)-4-(2-methyl-1,2,3,4-tetrahydroisoquinolin-6-yl)isoxazole-3-carboxamidine (125 mg, 204 μmol, 77% yield) as a white solid. MS (ESI) m/z: 612 (M+1).

Step C: A solution of BCl$_3$ (1 M, 1.3 mL, 10.0 eq.) in DCM was added to a solution of N-cyano-5-(2,4-dibenzyloxy-5-isopropylphenyl)-4-(2-methyl-1,2,3,4-tetrahydroisoquinolin-6-yl)isoxazole-3-carboxamidine (78 mg, 127 μmol, 1.0 eq.) in DCM (6 mL) at 0° C. After stirring at 0° C. for 2 hours, the temperature was raised to 15-25° C. with stirring for 1 hour. The reaction mixture was cooled down to 0° C. and added with MeOH (3 mL), followed by stirring at 0° C. for 0.5 hour and stirring at 15-25° C. for an additional 0.5 hours. The mixture was concentrated to give a crude product. The crude product was purified by preparative HPLC (0.225% FA-ACN; Phenomenex Synergi Max-RP 250×80 10 μm) to give N-cyano-5-(2,4-dihydroxyl-5-isopropylphenyl)-4-(2-methyl-1,2,3,4-tetrahydroisoquinolin-6-yl)isoxazole-3-carboxamidine (17 mg, 39 μmol, 30% yield). $^1$H NMR (400 MHz, DMSO-d$_6$): δ 8.26 (s, 1 H), 7.05-6.83 (m, 4 H), 6.44 (s, 1 H), 3.02-2.98 (m, 1 H), 2.72-2.55 (m, 6 H), 2.33 (s, 1 H), 0.96 (d, J=6.5 Hz, 6 H). MS (ESI) m/z: 432 (M+1).

EXAMPLE 22

5-(2,4-dihydroxyl-5-isopropylphenyl)-N-ethyl-4-(6-methyl-5,6,7,8-tetrahydro-4H-thieno[2, 3-d]azepin-2-yl) isoxazole-3-carboxamide

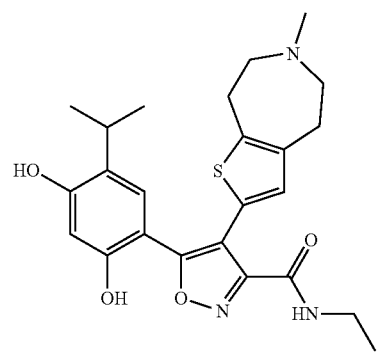 [SMILES: CCNC(=O)c1noc(-c2cc(C(C)C)c(O)cc2O)c1-c1cc2c(s1)CCN(C)CC2]

Reaction scheme:

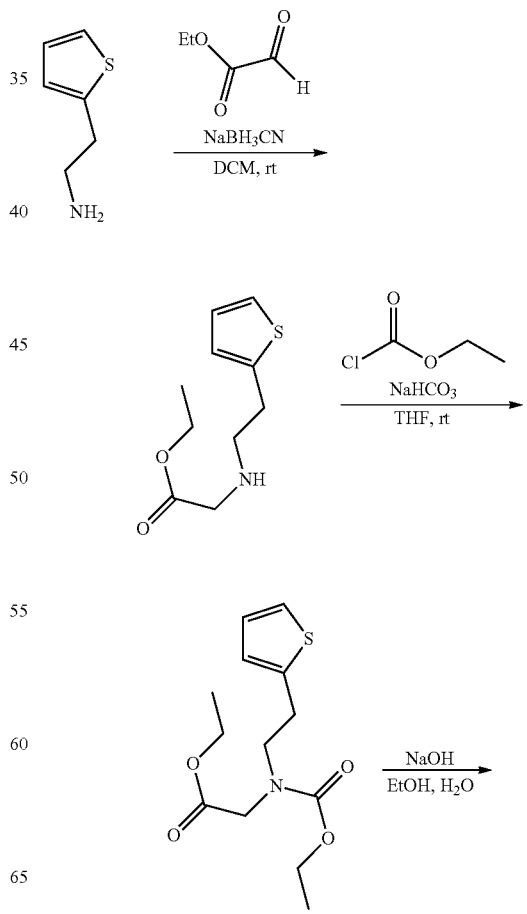

95
-continued

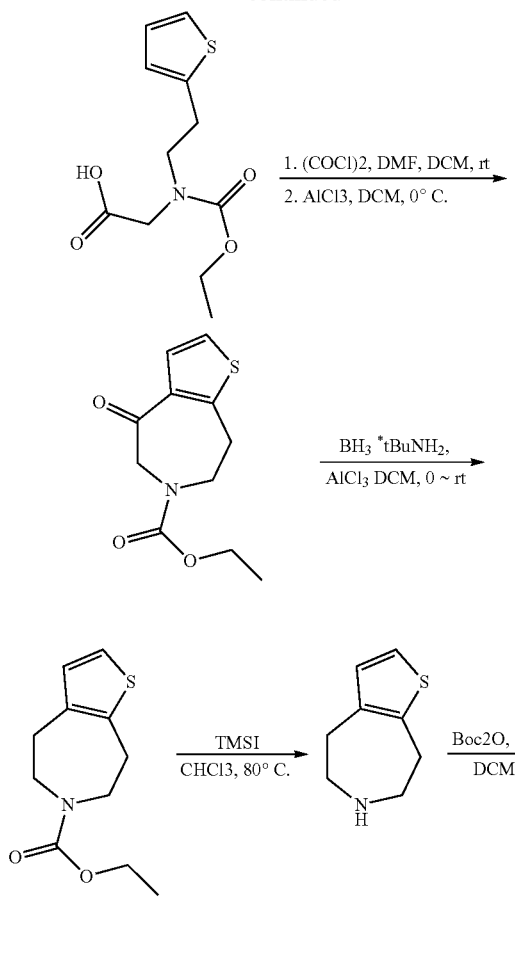

96
-continued

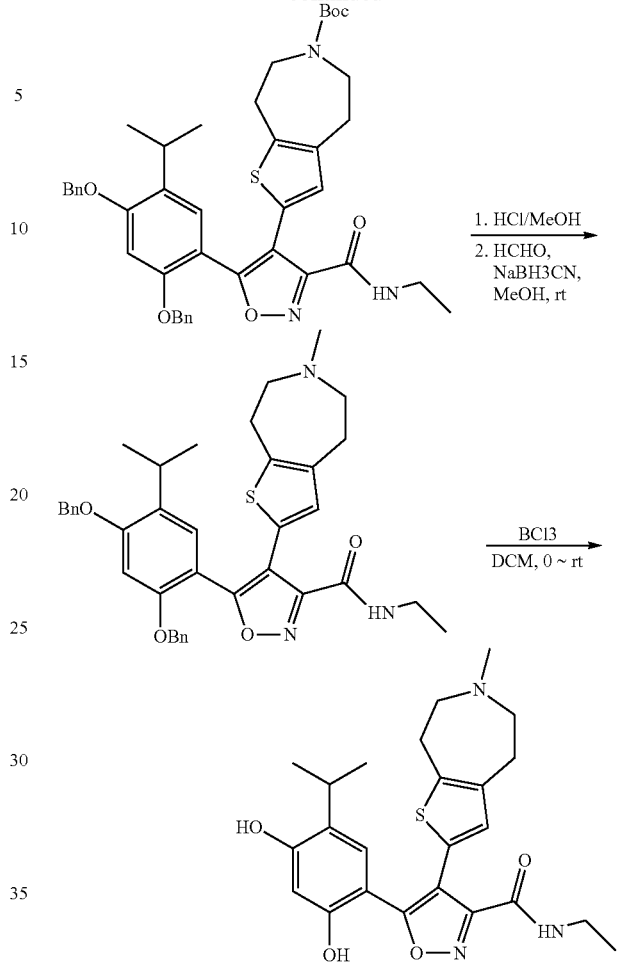

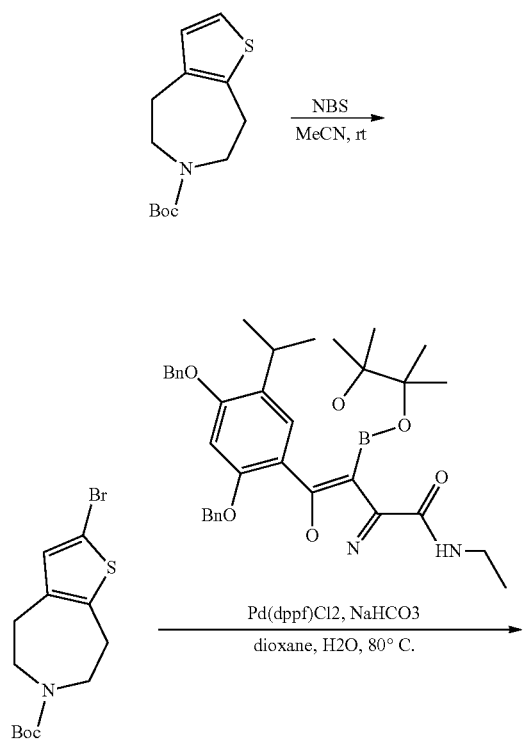

Step A: Acetic acid (1.4 g, 23.6 mmol, 1.0 eq.) and NaBH(OAc)₃ (10.0 g, 47.2 mmol, 2.0 eq.) were added to a solution of 2-(thiophen-2-yl)ethylamine (3.0 g, 23.6 mmol, 1.00 eq.) and ethyl 2-carbaldehyde formate (4.8 g, 23.6 mmol, 1.00 eq.) in DCM (40.0 mL) at 15-25° C. The mixture was stirred at 25° C. for 16 hours. The reaction mixture was poured into water (60 mL) and extracted with EA (50 mL×2). The combined organic layer was dried, filtered and concentrated to give ethyl 2-((2-(thiophen-2-yl)ethyl) amino)acetate (5.0 g, a crude product), which was directly used for the next step.

Step B: Ethyl chloroformate (1.6 g, 15.0 mmol, 1.00 eq.) was added dropwise to a solution of ethyl 2-((2-(thiophen-2-yl)ethyl)amino)acetate (3.2 g, 15.0 mmol, 1.00 eq.) and NaHCO₃ (3.8 g, 45.0 mmol, 3.00 eq.) in THF (40.0 mL) at 0° C. The mixture was stirred at 25° C. for 16 hours. The reaction mixture was poured into saturated aqueous NaHCO₃ solution (80 mL) and extracted with EA (60 mL×L). The combined organic layer was dried, filtered and concentrated to give a crude product. The crude product was purified by column chromatography (PE:EA=5:1 to 1:1) to give ethyl 2-((ethoxyformyl)(2-(thiophen-2-yl)ethyl)amino) acetate (2.9 g, 10.2 mmol, 68% yield) as a yellow oil.

Step C: NaOH/H₂O (20.3 mL, 20.4 mmol, 2.00 eq., 1 M) was added dropwise to a solution of ethyl 2-((ethoxyformyl) (2-(thiophen-2-yl)ethyl)amino)acetate (2.9 g, 10.2 mmol, 1.00 eq.) in EtOH (20.0 mL) at 0° C. The mixture was stirred at 25° C. for 16 hours. The reaction mixture was poured into water (80 mL), adjusted to pH=1 with 1 M aqueous hydrochloric acid solution and extracted with EA (80 mL×L). The combined organic layer was dried, filtered and concentrated to give 2-((ethoxyformyl)(2-(thiophen-2-yl)ethyl)amino) acetic acid (2.0 g, a crude product) as a white solid.

Step D: DMF (14 mg, 195 µmol, 0.05 eq.) and $(COCl)_2$ (987 mL, 7.8 mmol, 2.00 eq.) were added to a solution of 2-((ethoxyformyl)(2-(thiophen-2-yl)ethyl)amino)acetic acid (1.0 g, 3.9 mmol, 1.00 eq.) in DCM (15.0 mL) at 0° C. The mixture was stirred at 25° C. for 16 hours. The reaction mixture was concentrated to give ethyl (2-chloro-2-ethoxy)(2-(thiophen-2-yl)ethyl)carbamate (1.1 g, a crude product) as a yellow oil.

Step E: $AlCl_3$ (5.8 g, 43 mmol, 2.5 eq) was added to a solution of ethyl (2-chloro-2-ethoxy)(2-(thiophen-2-yl) ethyl)carbamate (4.8 g, 17 mmol, 1.00 eq.) in DCM (50.0 mL) at 0° C. The mixture was stirred at 25° C. for 1 hour. To the reaction solution, EtOH (5.0 mL) was added, and the reaction mixture was poured into ice and stirred for 1 hour. The mixture was extracted with DCM (60 mL×L). The combined organic layer was dried with anhydrous $Na_2SO_4$, filtered and concentrated to give a crude product. The crude product was purified by column chromatography (PE:EA=5:1 to 1:1) to give ethyl 4-oxo-7,8-dihydro-4H-thieno [2,3-d]azepine-6(5H)-formate (1.1 g, 4.6 mmol, 26% yield) as a yellow oil.

Step F: Borane/2-methylpropan-2-amine (2.6 g, 30 mmol, 6.0 eq.) was added to a solution of $AlCl_3$ (2.0 g, 15 mmol, 3.0 eq.) in DCM (20.0 mL) at 0° C. The mixture was stirred at 0° C. for 5 min, followed by the addition of a solution of ethyl 4-oxo-7,8-dihydro-4H-thieno[2,3-d]azepine-6(5H)-formate (1.2 g, 5.0 mmol, 1.0 eq.) in DCM (10.0 mL). The reaction mixture was stirred at 25° C. for 12 hours. The reaction mixture was poured into an aqueous HCl solution (60 mL, 1 M) and the mixed solution was extracted with DCM (50 mL×3). The combined organic layer was dried over anhydrous $Na_2SO_4$, filtered and concentrated to give a crude product. The crude product was purified by column chromatography (PE:EA=10:1 to 5:1) to give ethyl 7,8-dihydro-4H-thieno[2,3-d]azepine-6(5H)-formate (700 mg, 3.1 mmol, 62% yield) as a yellow oil.

Step G: TMSI (12.4 g, 62 mmol, 20.0 eq) was added to a solution of ethyl 7,8-dihydro-4H-thieno[2,3-d]azepine-6 (5H)-formate (700 mg, 3.1 mmol, 1.00 eq.) in $CHCl_3$ (15.0 mL) at 25° C. The mixture was stirred at 80° C. for 12 hours. The reaction mixture was added with NaOH (10.0 mL, 2 M) and poured into a saturated aqueous $NaHCO_3$ solution (100 mL), and the mixed solution was extracted with DCM (60 mL×L). The combined organic layer was dried over anhydrous $Na_2SO_4$, filtered and concentrated to give a product 5,6,7,8-tetrahydro-4H-thieno[2,3-d]azepine (550 mg, a crude product) as a yellow solid.

Step H: $Et_3N$ (1.1 g, 11 mmol, 3.0 eq.) and $Boc_2O$ (1.2 g, 5.4 mmol, 1.5 eq.) were added to a solution of 5,6,7,8-tetrahydro-4H-thieno[2,3-d]azepine (550 mg, 3.6 mmol, 1.00 eq.) in DCM (10.0 mL) at 25° C. The mixture was stirred at 25° C. for 12 hours. The reaction mixture was poured into water (60 mL) and the mixed solution was extracted with DCM (60 mL×2). The combined organic layer was dried over anhydrous $Na_2SO_4$, filtered and concentrated to give a crude product. The crude product was purified by column chromatography (PE:EA=5:1) to give a product t-butyl 7,8-dihydro-4H-thieno[2,3-d]azepine-6(5)-formate (500 mg, 2.0 mmol, 55% yield) as a yellow oil.

Step I: NBS (245 mg, 1.4 mmol, 0.7 eq.) was added to a solution of t-butyl 7,8-dihydro-4H-thieno[2,3-d]azepine-6 (5)-formate (500 mg, 2.0 mmol, 1.00 eq.) in MeCN (5.0 mL) at 25° C. The mixture was stirred at 25° C. for 2 hours. The reaction mixture was poured into a saturated aqueous $NaHSO_3$ solution (30 mL) and the mixed solution was extracted with DCM (30 mL×L). The combined organic layer was dried over anhydrous $Na_2SO_4$, filtered and concentrated to give a crude product. The crude product was purified by column chromatography (PE:EA=10:1 to 6:1) to give a product t-butyl 2-bromo-7,8-dihydro-4H-thieno[2,3-d]azepine-6(5H)-formate (470 mg, 1.4 mmol, 72% yield) as a yellow oil.

Step J: $Pd(PPh_3)_2Cl_2$ (88 mg, 126 µmol, 0.10 eq.) and $NaHCO_3$ (212 mg, 2.5 mmol, 2.00 eq.) were added to a mixed solution of N-ethyl-5-(5-isopropyl-2,4-dibenzyloxy-phenyl)-4-(4,4,5,5-tetramethyl-1,3,2-dioxaborolan-2-yl) isoxazole-3-carboxamide (1.1 g, 1.8 mmol, 1.40 eq.) and t-butyl 2-bromo-7,8-dihydro-4H-thieno[2,3-d]azepine-6 (5H)-formate (420 mg, 1.3 mmol) in dioxane (20.00 mL) and water (4.00 mL) under the protection of nitrogen gas. The mixture was stirred at 80° C. for 12 hours. The mixture was cooled, then poured into water (100 mL) and extracted with EA (80 mL×L). The organic layers were combined and concentrated. The residue was purified by silica gel chromatography (PE/EA=10/1 to 3/1). t-Butyl 2-(5-(2,4-dibenzyloxy-5-isopropyl-phenyl)-3-(ethylformamyl)isoxazol-4-yl)-4,5,7,8-tetrahydrothieno[2,3-d]azepine-formate (800 mg, 1.1 mmol, 88.0% yield) as a yellow solid was obtained.

Step K: HCl/MeOH (4M, 10.00 mL) was added to a solution of t-butyl 2-(5-(2,4-dibenzyloxy-5-isopropyl-phenyl)-3-(ethylformamyl)isoxazol-4-yl)-4,5,7,8-tetrahydrothieno[2,3-d]azepine-formate (880 mg, 1.2 mmol, 1.00 eq.) in MeOH (10.00 mL), with stirring at 25° C. for 1 hour. The mixture was concentrated at 40° C. to give a product 5-(2,4-dibenzyloxy-5-isopropyl-phenyl)-N-ethyl-4-(5,6,7,8-tetrahydro-4H-thieno[2,3-d]azepin-2-yl)isoxazole-3-formate (800 mg, 1.2 µmol, 99% yield) as a yellow solid.

Step L: Paraformaldehyde (7.93 g, 98 mmol, 83.5 eq.) and AcOH (70 mg, 1.2 mmol, 1.0 eq.) were added to a solution of 5-(2,4-dibenzyloxy-5-isopropyl-phenyl)-N-ethyl-4-(5,6,7,8-tetrahydro-4H-thieno[2,3-d]azepin-2-yl)isoxazole-3-carboxamide (730 mg, 1.2 mmol, 1.0 eq.) in MeOH (15 mL). The mixture was stirred at 25° C. for 2 hours and then added with $NaBH_3CN$ (147 mg, 2.3 mmol, 2.0 eq.). The reaction was further stirred at 25° C. for 12 hours. The mixture was poured into water (80 mL) and extracted with EA (80 mL×2). The organic layers were combined and concentrated to give a crude product. The crude product was purified by column chromatography (PE/EA=1/1, 0/1) to give a product 5-(2,4-dibenzyloxy-5-isopropyl-phenyl)-N-ethyl-4-(6-methyl-4,5,7,8-tetrahydrothieno[2,3-d]azepin-2-yl)isoxazole-3-carboxamide (340 mg, 535 µmol, 46% yield) as a yellow solid.

Step M: A solution of $BCl_3$ (1M, 0.8 mL, 5.0 eq.) in DCM was added to a solution of 5-(2,4-dibenzyloxy-5-isopropyl-phenyl)-N-ethyl-4-(6-methyl-4,5,7,8-tetrahydrothieno[2,3-d]azepin-2-yl)isoxazole-3-carboxamide (100 mg, 157 µmol, 1.0 eq.) in DCM (8 mL) at 0° C. After stirring at 0° C. for 2 hours, the temperature was raised to 15-25° C. with stirring for 1 hour. The reaction mixture was cooled down to 0° C. and added with MeOH (3 mL), followed by stirring at 0° C. for 0.5 hour and stirring at 15-25° C. for an additional 0.5 hour. The mixture was concentrated to give a crude product. The crude product was purified by preparative HPLC (0.225% FA-ACN; Phenomenex Synergi Max-RP 250×80 10 µm) to give 5-(2,4-dihydroxyl-5-isopropyl-phenyl)-N-ethyl-4-(6-methyl-4,5,7,8-tetrahydrothieno[2,3-d]azepin-2-yl)isoxazole-3-carboxamide (20 mg, 44 µmol, 28% yield).
$^1$H NMR (400 MHz, DMSO-d$_6$): δ 11.05 (m, 1H), 9.92 (s, 1H), 9.81 (s, 1H), 8.97-8.94 (m, 1H), 6.92-6.90 (m, 2H), 6.52 (s, 1H), 6.43 (s, 1H), 3.48-3.36 (m, 2H), 3.28-3.23 (m, 3H), 3.08-3.03 (m, 1H), 2.82-2.81 (m, 3H), 1.13-1.05 (m, 9H). MS (ESI) m/z: 456 (M+1).
EXAMPLE 23
5-(2,4-dihydroxyl-5-isopropylphenyl)-N-ethyl-4-(2-methyl-1,2,3,4-tetrahydropyrrolo[1,2-a]pyrazin-7-yl)isoxazole-3-carboxamide
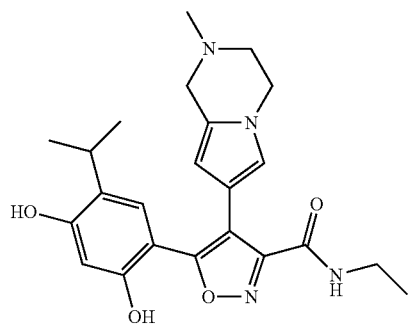 [SMILES: CCNC(=O)c1noc(-c2cc(C(C)C)c(O)cc2O)c1-c1cc2n(c1)CCN(C)C2]
Reaction scheme:
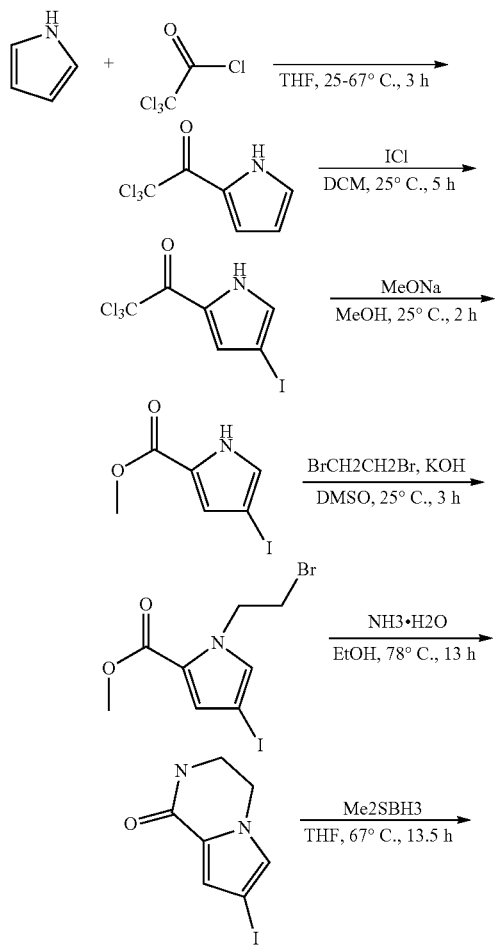
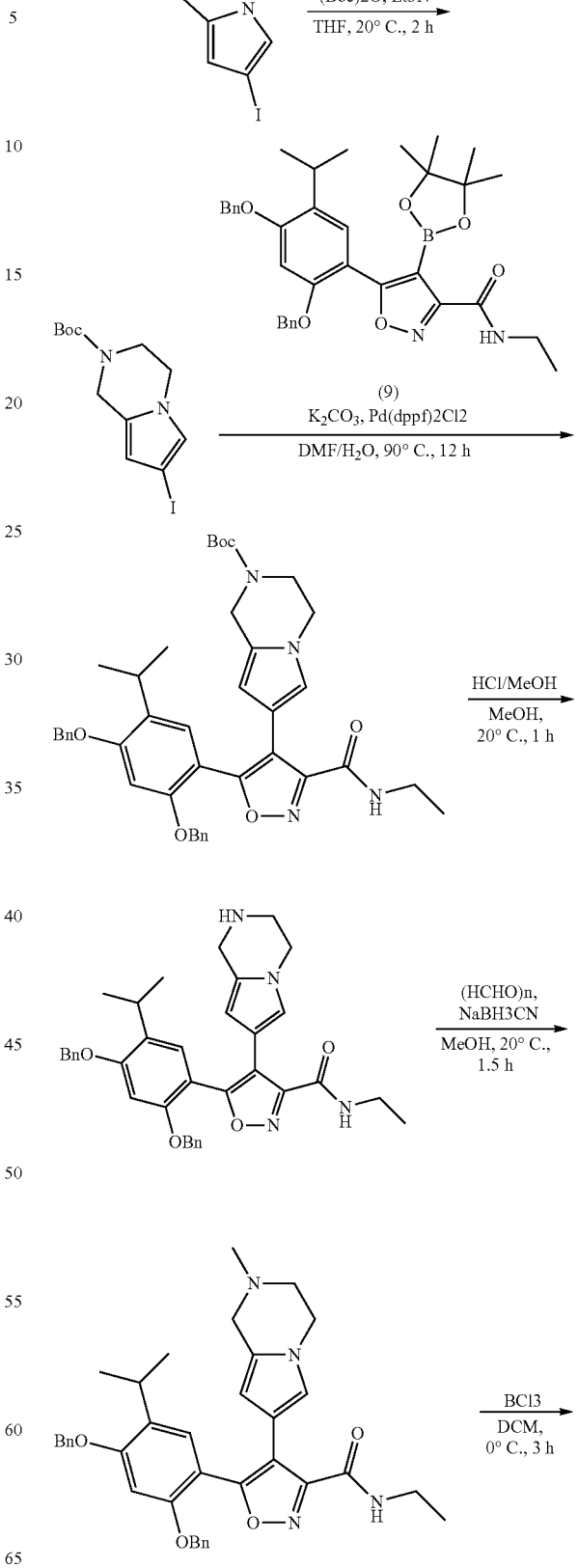

-continued

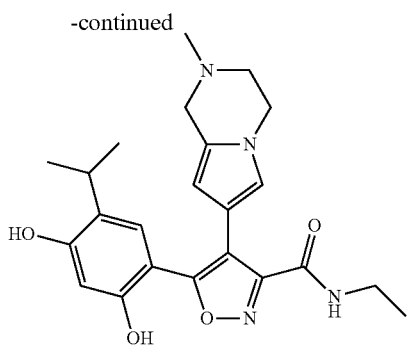

Step A: A solution of pyrrole (6.00 g, 89.43 mmol, 1.00 eq.) dissolved in tetrahydrofuran (120 mL) was slowly added dropwise to a solution of 2,2,2-trichloroacetyl chloride (19.51 g, 107.32 mmol, 1.20 eq.) in tetrahydrofuran (36 mL) at 25° C. under the protection of nitrogen gas. The reaction solution was stirred at 25° C. for 5 min and then warmed up to 67° C. with stirring for 2 hours. The reaction solution was cooled down to room temperature, and a solution of sodium bicarbonate (10 g) in water (50 mL) was slowly added dropwise to the reaction solution. The aqueous phase was extracted three times with ethyl acetate (50 mL each). The organic phases were combined, washed three times with water (80 mL), washed twice with saturated brine (40 mL), dried over anhydrous sodium sulfate, filtered and concentrated to give 2,2,2-trichloro-1-(1H-pyrrol-2-yl)ethanone (18.00 g, 84.72 mmol, 94.74% yield).

Step B: Iodine chloride (16.81 g, 103.55 mmol, 1.00 eq.) was added dropwise to a solution of 2,2,2-trichloro-1-(1H-pyrrol-2-yl)ethanone (22.00 g, 103.55 mmol, 1.00 eq.) in dichloromethane (250 mL) at 20° C. under the protection of nitrogen gas, and the reaction solution was stirred at 20° C. for 5 hours. The reaction solution was washed with 10% $K_2CO_3$ solution (100 mL) and extracted three times with dichloromethane (300 mL). The organic phases were combined, washed with water (50 mL), 1 mol/L sodium thiosulfate (100 mL) and saturated brine (100 mL), dried over anhydrous sodium sulfate, filtered and concentrated to give 2,2,2-trichloro-1-(4-iodo-1H-pyrrol-2-yl)ethanone (33.00 g, 97.53 mmol, 94.19% yield) as a white solid.

Step C: A solution of sodium methoxide (6.63 g) in methanol (50 mL) was added dropwise to a solution of 2,2,2-trichloro-1-(4-iodo-1H-pyrrol-2-yl)ethanone (34.60 g, 102.26 mmol, 1.0 eq.) in methanol (200 mL) at 25° C. under the protection of nitrogen gas. The reaction solution was allowed to react at 25° C. for 2 hours. After the completion of the reaction, the reaction solution was poured into water (150 mL) and the aqueous phase was extracted three times with ethyl acetate (600 mL). The organic phases were combined, washed twice with saturated brine (200 mL), dried over anhydrous sodium sulfate, filtered and concentrated under reduced pressure to give methyl 4-iodo-1H-pyrrole-2-carboxylic acid methyl ester (24.00 g, 95.61 mmol, 93.50% yield) as an gray-white solid.

Step D: Potassium hydroxide (14.08 g, 250.95 mmol, 7.00 eq.) was added to a solution of methyl 4-iodo-1H-pyrrole-2-carboxylic acid methyl ester (9.00 g, 35.85 mmol, 1.00 eq.) in dimethyl sulfoxide (80 mL) at 20° C. under the protection of nitrogen gas. The reaction solution was reacted at 20° C. for 3 hours, and then dibromoethane (53.88 g, 286.80 mmol, 8.00 eq.) was added dropwise to the reaction solution. The reaction solution was reacted at 20° C. for 10 hours. After the completion of the reaction, the reaction solution was poured into water (100 mL) and extracted three times with ethyl acetate (450 mL). The organic phases were combined, washed three times with water (150 mL), dried over anhydrous sodium sulfate, filtered and concentrated to give a crude product. The crude product was purified by silica gel chromatography (100~200 mesh of silica gel, petroleum ether/ethyl acetate=30/1 to 20/1) to give methyl 1-(2-bromoethyl)-4-iodo-1H-pyrrole-2-carboxylate (9.50 g, 26.54 mmol, 74.03% yield) as a yellow oil.

Step E: Aqueous ammonia (14.56 g, 124.55 mmol, 11.15 eq.) was added dropwise to a solution of methyl 1-(2-bromoethyl)-4-iodo-1H-pyrrole-2-carboxylate (4.00 g, 11.17 mmol, 1.00 eq.) in ethanol (20 mL) at 20° C. under the protection of nitrogen gas. The reaction solution was stirred at 20° C. for 1 hour. The reaction solution was then warmed up to 78° C. with stirring for 12 hours. After the completion of the reaction, the reaction solution was concentrated under reduced pressure, and the crude product was diluted with water (20 mL) and then extracted three times with ethyl acetate (150 mL). The combined organic phase was washed twice with saturated brine (40 mL), dried over anhydrous sodium sulfate, filtered and concentrated. The crude product was purified by silica gel chromatography (100~200 mesh of silica gel, dichloromethane/methanol=10/1) to give 7-iodo-3,4-dihydropyrrolo[1,2-a]pyrazin-1(2H)-one (1.00 g, 3.82 mmol, 34.16% yield) as a white solid.

Step F: $BH_3$-$Me_2S$ (10 M, 7.25 mL, 10.00 eq.) was added dropwise to a solution of 7-iodo-3,4-dihydropyrrolo[1,2-a]pyrazin-1(2H)-one (1.90 g, 7.25 mmol, 1.00 eq.) in tetrahydrofuran (40 mL) at 0° C. under the protection of nitrogen gas. The reaction solution was stirred at 0° C. for 30 min and then warmed up to 20° C. with stirring for 1 hour. The temperature was finally raised to 67° C. with stirring for 12 hours. After the completion of the reaction, the reaction solution was cooled down to 0° C., quenched with methanol (5 mL), and then refluxed at 67° C. for 4 hours. The reaction solution was concentrated under reduced pressure to give 7-iodo-1,2,3,4-tetrahydropyrrolo[1,2-a]pyrazine (1.80 g, a crude product) as a yellow solid.

Step G: Triethylamine (3.67 g, 36.30 mmol, 5.0 eq.) and $(Boc)_2O$ (3.17 g, 14.52 mmol, 2.00 eq.) were added to a solution of 7-iodo-1,2,3,4-tetrahydropyrrolo[1,2-a]pyrazine (1.80 g, 7.26 mmol, 1.00 eq.) in tetrahydrofuran (20 mL) at 20° C. under the protection of nitrogen gas. The reaction solution was stirred at 20° C. for 2 hours. After the completion of the reaction, the reaction solution was poured into water (30 mL) and extracted three times with ethyl acetate (150 mL). The combined organic phase was washed twice with saturated brine (20 mL). The organic phase was dried with anhydrous sodium sulfate, filtered and concentrated. The crude product was purified by silica gel chromatography (100~200 mesh of silica gel, petroleum ether/ethyl acetate=20/1 to 10/1) to give t-butyl 7-iodo-3,4-dihydropyrrolo[1,2-a]pyrazine-2(1H)-formate (800.00 mg, 2.30 mmol, 31.65% yield) as a yellow oil.

Step H: The title compound of this Example was prepared according to the order of steps J, K, L and M in Example 22, wherein t-butyl 2-bromo-7,8-dihydro-4H-thieno[2,3-d]azepine-6(5H)-formate in step J was replaced with t-butyl 7-iodo-3,4-dihydropyrrolo[1,2-a]pyrazine-2(1H)-formate.

$^1$H NMR (400 MHz, DMSO-$d_6$): δ 1.01-1.15 (m, 9 H); 2.29 (s, 3 H); 2.64 (t, J=5.40 Hz, 2 H); 3.19-3.30 (m, 5 H); 3.83 (t, J=5.46 Hz, 2 H); 5.61 (s, 1 H); 6.47 (s, 1 H); 6.69 (d, J=1.51 Hz, 1 H); 6.90 (s, 1 H); 8.79 (t, J=5.52 Hz, 1 H); 9.56 (s, 1 H); 9.70 (s, 1 H). m/z: 425.1 [M+1].

EXAMPLE 24
5-(2,4-dihydroxyl-5-isopropylphenyl)-N-ethyl-4-(5-isobutyl-1-methyl-4,5,6,7-tetrahydro-1H-imidazo[4,5-c]pyridin-2-yl)isoxazole-3-carboxamide
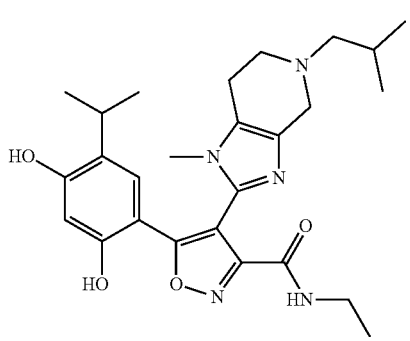 [SMILES: CCNC(=O)c1noc(-c2cc(C(C)C)c(O)cc2O)c1-c1nc2c(n1C)CCN(CC(C)C)C2]
Reaction scheme:
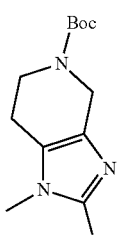
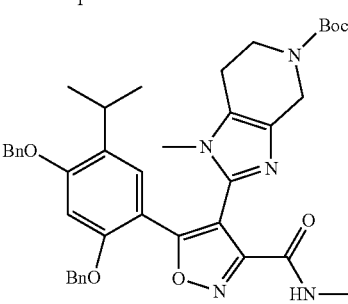
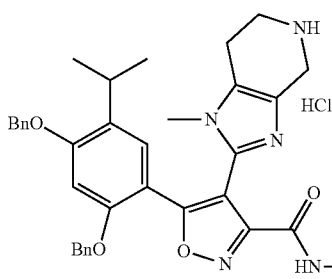
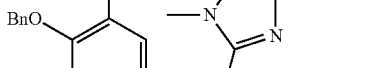
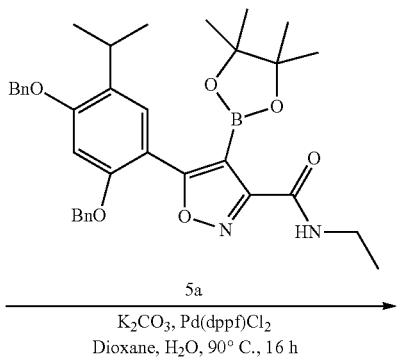
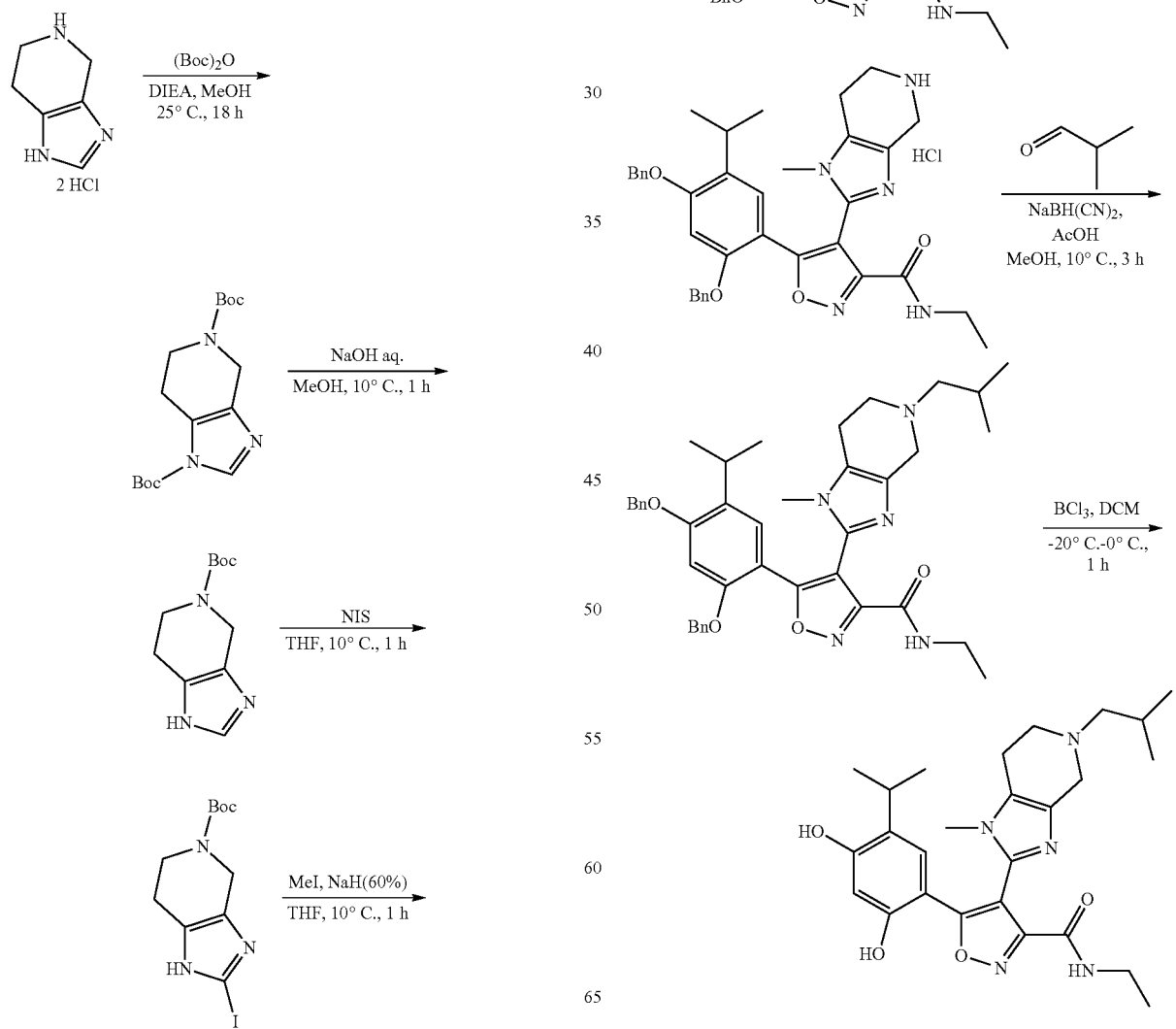
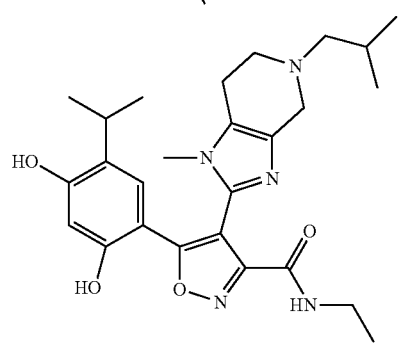

Step A: DIPEA (7.42 g, 57.37 mmol, 2.50 eq.) and (Boc)₂O (12.52 g, 57.37 mmol, 2.50 eq.) were added to a solution of 4,5,6,7-tetrahydro-1H-imidazo[4,5-c]pyridine (4.5 g, 22.95 mmol, 1.00 eq.) dissolved in methanol (50.00 mL) at 25° C. under the protection of nitrogen gas. After the addition, the reaction mixture was stirred at 25° C. for 18 hours. The reaction solution was diluted with water (20 mL) and then extracted with ethyl acetate (20 mL×L). The combined organic phase was dried over anhydrous sodium sulfate, filtered and concentrated in vacuum. The crude product was purified by column chromatography (PE:EA=2:1) to give the product bis-t-butyl 6,7-dihydro-1H-imidazo[4,5-c]pyridine-1,5(4H)-diformate (5.4 g, 16.70 mmol, 72.76% yield) as a white solid.

Step B: 1 mol/L NaOH (20 mL) was added to a solution of bis-t-butyl 6,7-dihydro-1H-imidazo[4,5-c]pyridine-1,5(4H)-diformate (5.40 g, 16.70 mmol, 1.00 eq.) dissolved in methanol (40.00 mL) at 25° C. under the protection of nitrogen gas. After the addition, the reaction mixture was stirred at 25° C. for 1 hour. The reaction solution was diluted with water (50 mL) and then extracted with ethyl acetate (50 mL×L). The combined organic phase was dried over anhydrous sodium sulfate, filtered and concentrated in vacuum. A product t-butyl 1,4,6,7-tetrahydro-imidazo[4,5-c]pyridine-5-formate (3.30 g, 14.78 mmol, 88.50% yield) was obtained as a yellow solid.

Step C: NIS (4.99 g, 22.17 mmol, 1.50 eq.) was added to a solution of 1,4,6,7-tetrahydro-imidazo[4,5-c]pyridine-5-formate (3.30 g, 14.78 mmol, 1.00 eq.) dissolved in tetrahydrofuran (30.00 mL) at 10° C. under the protection of nitrogen gas. After the addition, the reaction mixture was stirred at 10° C. for 1 hour. The reaction solution was diluted with a saturated aqueous sodium bicarbonate solution (15 mL) and then extracted with ethyl acetate (15 mL×L). The combined organic phase was washed with water (10 mL), dried over anhydrous sodium sulfate, filtered and concentrated in vacuum. A product t-butyl 2-iodo-1,4,6,7-tetrahydro-imidazo[4,5-c]pyridine-5-formate (4.30 g, 12.31 mmol, 83.32% yield) was obtained as a yellow solid.

Step D: Sodium hydride (34.37 mg, 859.18 μmol, 2.00 eq.) and methyl iodide (630.00 mg, 4.44 mmol, 10.33 eq.) were added to a solution of t-butyl 2-iodo-1,4,6,7-tetrahydro-imidazo[4,5-c]pyridine-5-formate (150 mg, 429.59 mmol, 1.00 eq.) dissolved in tetrahydrofuran (3.00 mL) at 10° C. under the protection of nitrogen gas. After the addition, the reaction mixture was stirred at 10° C. for 16 hours. The reaction solution was diluted with water (20 mL) and then extracted with ethyl acetate (20 mL×L). The combined organic phase was dried with anhydrous sodium sulfate, filtered and concentrated in vacuum. A product t-butyl 2-iodo-1-methyl-6,7-dihydro-4H-imidazo[4,5-c]pyridine-5-formate (150.00 mg, a crude product) was obtained as a yellow solid. The crude product was used directly in the next step. MS (ESI) M/Z: 363.9 (M+1).

Step E: The title compound of this Example was prepared according to the order of steps J, K, L and M in Example 22, wherein t-butyl 2-bromo-7,8-dihydro-4H-thieno[2,3-d]azepine-6(5H)-formate in step J was replaced with t-butyl 2-iodo-1-methyl-6,7-dihydro-4H-imidazo[4,5-c]pyridine-5-formate. ¹H NMR (400 MHz, DMSO-d₆) δ 10.26 (brs, 2H), 9.96 (s, 1H), 9.96-10.03 (m, 1H), 6.87 (s, 1H), 6.48 (s, 1H), 3.23-3.26 (m, 2H), 3.15-3.23 (m, 5H), 3.00 (t, J=6.8 Hz, 1H), 2.60-2.70 (m, 2H), 2.50-2.55 (m, 2H), 2.20-2.35 (m, 2H), 1.75-1.90 (brs, 1H), 1.08 (t, J=7.2 Hz, 1H), 0.99 (d, J=3.6 Hz, 6H), 0.83 (d, J=3.6 Hz, 6H). m/z: 482[M+1].

EXAMPLE 25

5-(2,4-dihydroxyl-5-isopropylphenyl)-N-ethyl-4-(3-methyl-2,3,4, 5-tetrahydro-1H-benzo[d]azepin-7-yl) isoxazole-3-carboxamide

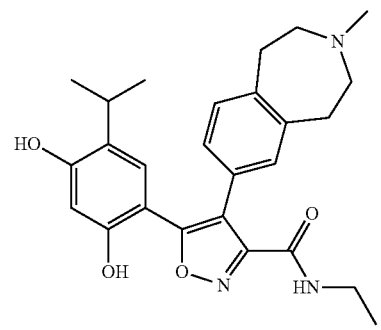 [SMILES: CCNC(=O)c1noc(-c2cc(C(C)C)c(O)cc2O)c1-c1ccc2c(c1)CCN(C)CC2]

Reaction scheme:

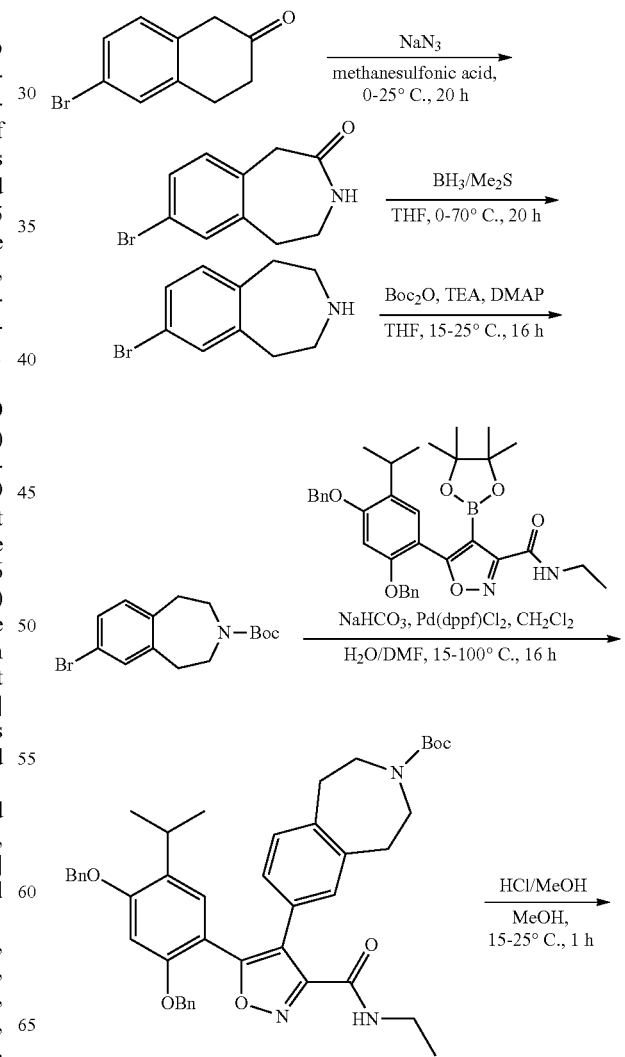

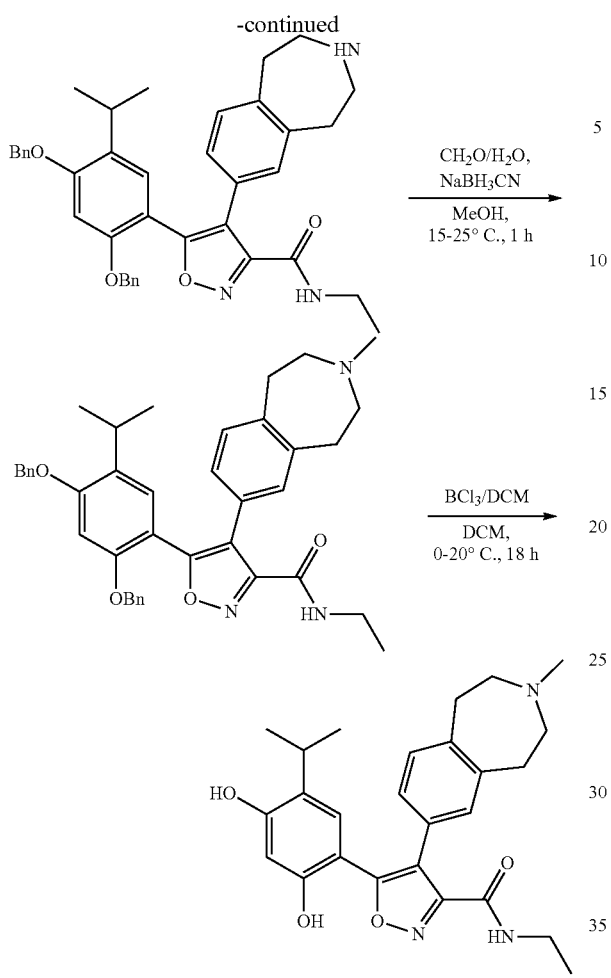

CH₂O/H₂O,
NaBH₃CN
---
MeOH,
15-25° C., 1 h

BCl₃/DCM
---
DCM,
0-20° C., 18 h mg, 3.54 mmol) in THF (16.00 mL) at 25° C., followed by addition of Boc₂O (1.16 g, 10.6 mmol). The reaction mixture was stirred at 25° C. for 16 hours. The reaction mixture was concentrated in vacuum to give a crude product. The residue was purified by silica gel chromatography (200~300 mesh of silica gel, petroleum ether/ethyl acetate=30/1 to 10/1), to give t-butyl 7-bromo-4,5-dihydro-1H-benzo[d]azepine-3 (2H)-formate (500 mg, 43% yield) as a yellow oil. MS (ESI) m/z: 270, 272 (M-56+1).

Step D: The title compound of this Example was prepared according to the order of steps J, K, L and M in Example 22, wherein t-butyl 2-bromo-7,8-dihydro-4H-thieno[2,3-d] azepine-6(5H)-formate in step J was replaced with t-butyl 7-bromo-4,5-dihydro-1H-benzo[d]azepine-3(2H) formate, and the product is a white solid. ¹H NMR (400 MHz, DMSO): δ 8.82 (t, J=5.6 Hz, 1 H), 7.04 (d, J=8.0 Hz, 1 H), 7.01 (s, 1 H), 7.04 (dd, J=1.6, 8.0 Hz, 1 H), 6.76 (s, 1 H), 6.42 (s, 1 H), 3.25-3.18 (m, 2 H), 3.02-2.94 (m, 1 H), 2.86-2.76 (m, 2 H), 2.76-2.66 (m, 2 H), 2.49-2.40 (m, 4 H), 2.26 (s, 3 H), 1.07 (t, J=7.2 Hz, 3 H), 0.94 (d, J=6.8 Hz, 6 H). MS (ESI) m/z: 450 (M+1).

EXAMPLE 26

5-(2,4-dihydroxyl-5-isopropylphenyl)-N-ethyl-4-(2-methyl-2,3,4,5-tetrahydro-1H-benzo[c]azepin-7-yl) isoxazole-3-carboxamide

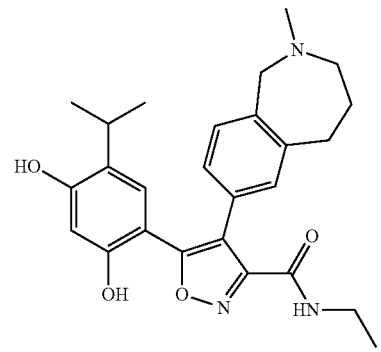 [SMILES: CCNC(=O)c1noc(-c2cc(C(C)C)c(O)cc2O)c1-c1ccc2c(c1)CCCN(C)C2]

Step A: NaN₃ (1.06 g, 16 mmol) was slowly added in batch to a solution of 6-bromo-3,4-dihydronaphthalen-2 (1H)-one (2.25 g, 10 mmol) in methanesulfonic acid (20.00 mL) at 0° C. over a course of 0.5 hour. The reaction mixture was stirred at 0° C. for 3.5 hours and then the reaction mixture was stirred at 25° C. for an additional 16 hours. The mixture was then slowly added dropwise to a saturated aqueous NaHCO₃ solution (100 mL), followed by extraction with ethyl acetate (100 mL×3). The combined organic phase was dried with anhydrous sodium sulfate, filtered and concentrated in vacuum. The residue was purified by silica gel chromatography (100~200 mesh of silica gel, dichloromethane/methanol=50/1 to 20/1) to give 7-bromo-4,5-dihydro-1H-3-benzo[d]azepin-2(3H)-one (800 mg, 33% yield) as a yellow solid.

Step B: BH₃-Me₂S (3.3 mL, 10 M) was added dropwise to a solution of 7-bromo-4,5-dihydro-1H-3-benzo[d]azepin-2(3H)-one (800 mg, 3.3 mmol) in THF (8.00 mL) at 0° C. The reaction mixture was stirred at 0° C. for 1 hour and stirred at 25° C. for 3 hours, and then the reaction mixture was stirred at 70° C. for an additional 16 hours. The mixture was then cooled down to 0° C., and MeOH (4 mL) was slowly added dropwise to the reaction solution at 0° C. and stirred at 25° C. for 0.5 hour. The reaction mixture was concentrated in vacuum to give a crude product 7-bromo-2,3,4,5-tetrahydro-1H-3-benzo[d]azepine (800 mg, a crude product) as a yellow oil.

Step C: TEA (1.07 g, 10.6 mmol) was added to a solution of 7-bromo-2,3,4,5-tetrahydro-1H-3-benzo[d]azepine (800

Reaction scheme:

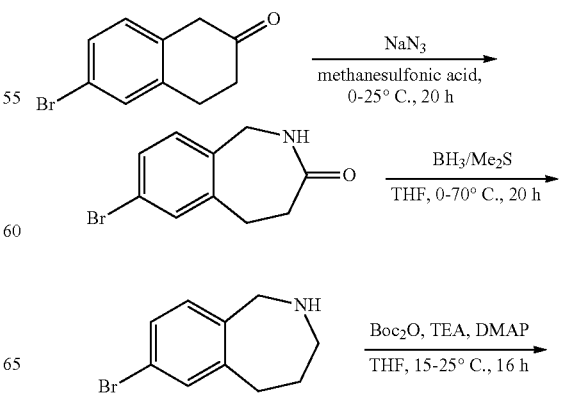

NaN₃
---
methanesulfonic acid,
0-25° C., 20 h

BH₃/Me₂S
---
THF, 0-70° C., 20 h

Boc₂O, TEA, DMAP
---
THF, 15-25° C., 16 h

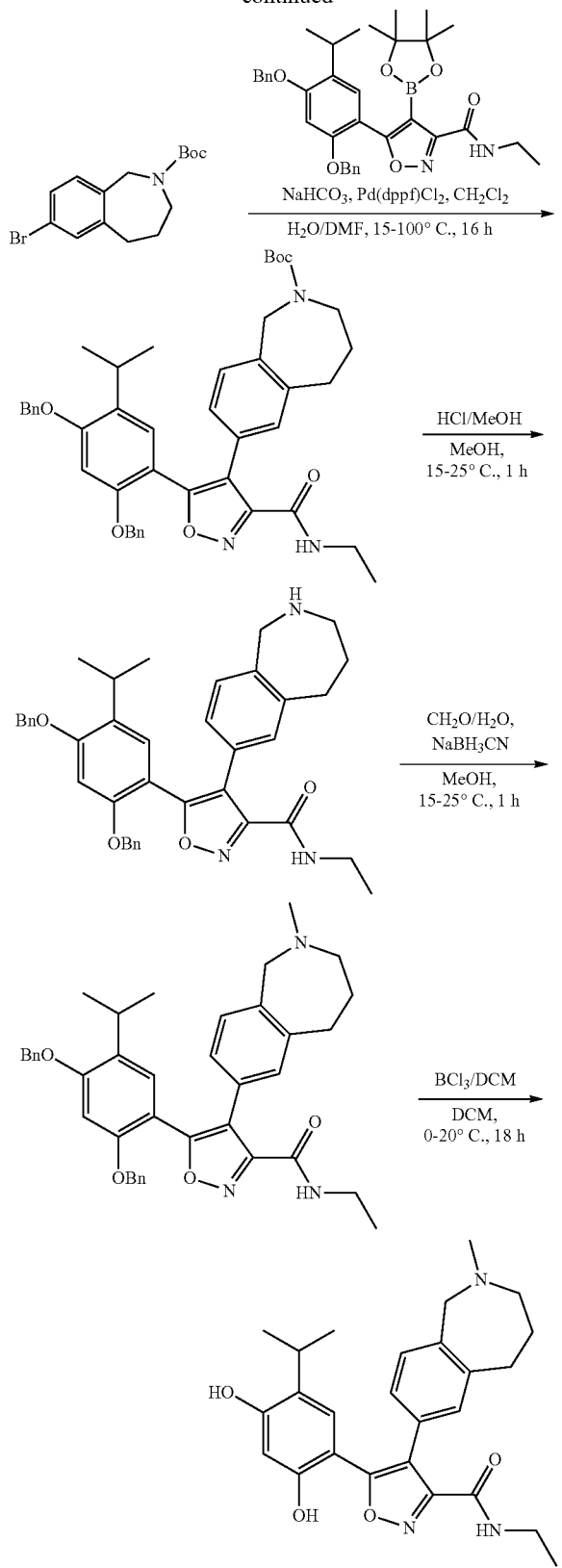

mL) at 0° C. over a course of 0.5 hour. The reaction mixture was stirred at 0° C. for 3.5 hours and then the reaction mixture was stirred at 25° C. for an additional 16 hours. The mixture was then slowly added dropwise to a saturated aqueous NaHCO₃ solution (100 mL), followed by extraction with ethyl acetate (100 mL×3). The combined organic phase was dried with anhydrous sodium sulfate, filtered and concentrated in vacuum. The residue was purified by silica gel chromatography (100~200 mesh of silica gel, dichloromethane/methanol=50/1 to 20/1) to give 7-bromo-4,5-dihydro-1H-benzo[c]azepin-3(2)-one (400 mg, 17% yield) as a yellow solid.

Step B: BH₃-Me₂S (1.7 mL, 10 M) was added dropwise to a solution of 7-bromo-4,5-dihydro-1H-benzo[c]azepine-3(2)-one (400 mg, 1.7 mmol) in THF (4.00 mL) at 0° C. The reaction mixture was stirred at 0° C. for 1 hour and stirred at 25° C. for 3 hours, and then the reaction mixture was stirred at 70° C. for an additional 16 hours. The mixture was then cooled down to 0° C., and MeOH (2 mL) was slowly added dropwise to the reaction solution at 0° C., followed by stirring at 25° C. for 0.5 hour. The reaction mixture was concentrated in vacuum to give a crude product 7-bromo-2,3,4,5-tetrahydro-1H-benzo[c]azepine (400 mg, a crude product) as a yellow oil.

Step C: TEA (537 mg, 5.3 mmol) was added to a solution of 7-bromo-2,3,4,5-tetrahydro-1H-benzo[c]azepine (400 mg, 1.7 mmol) in THF (8.00 mL) at 25° C., followed by addition of Boc₂O (579 mg, 5.3 mmol). The reaction mixture was stirred at 25° C. for 16 hours. The reaction mixture was concentrated in vacuum to give a crude product. The residue was purified by silica gel chromatography (200~300 mesh of silica gel, petroleum ether/ethyl acetate=30/1 to 10/1), to give t-butyl 7-bromo-4,5-dihydro-1H-benzo[c]azepine-2(3H)-formate (210 mg, 36% yield) as a yellow oil. MS (ESI) m/z: 270, 272 (M-56+1).

Step D: The title compound of this Example was prepared according to the order of steps J, K, L and M in Example 22, where t-butyl 2-bromo-7,8-dihydro-4H-thieno[2,3-d]azepine-6(5H)-formate in step J was replaced with t-butyl 7-bromo-4,5-dihydro-1H-benzo[c]azepine-2(3H)-formate.

¹H NMR (400 MHz, DMSO): δ 8.83 (t, J=4.8 Hz, 1 H), 7.08-7.00 (m, 2 H), 6.97-6.97 (m, 1 H), 6.80-6.75 (m, 1 H), 6.44-6.42 (m, 1 H), 3.71 (s, 2 H), 3.26-3.16 (m, 2 H), 3.02-2.95 (m, 1 H), 2.93-2.87 (m, 1.4 H), 2.85-2.80 (m, 0.7 H), 2.77-2.68 (m, 2 H), 2.68-2.66 (m, 0.5 H), 2.26-2.16 (m, 3 H), 1.65-1.55 (m, 1.4 H), 1.07 (t, J=7.2 Hz, 3 H), 0.96-0.92 (m, 6 H). MS (ESI) m/z: 450 (M+1).

EXAMPLE 27

3-(2,4-dihydroxyl-5-isopropylphenyl)-N-ethyl-4-(3-methyl-2, 3,4, 5-tetrahydro-1H-benzo[d]azepin-7-yl)isoxazole-5-carboxamide

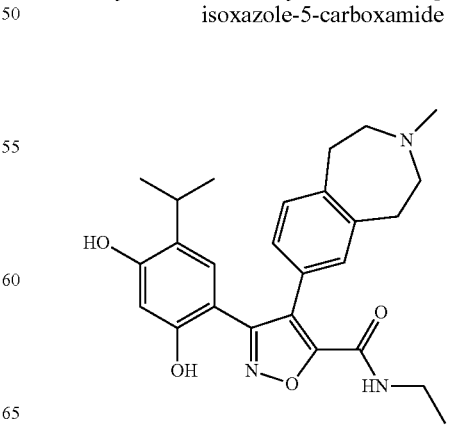

Step A: NaN₃ (1.06 g, 16 mmol) was slowly added in batch to a solution of 6-bromo-3,4-dihydronaphthalen-2(1H)-one (2.25 g, 10 mmol) in methanesulfonic acid (20.00

Reaction scheme:

Step A: t-Butyl

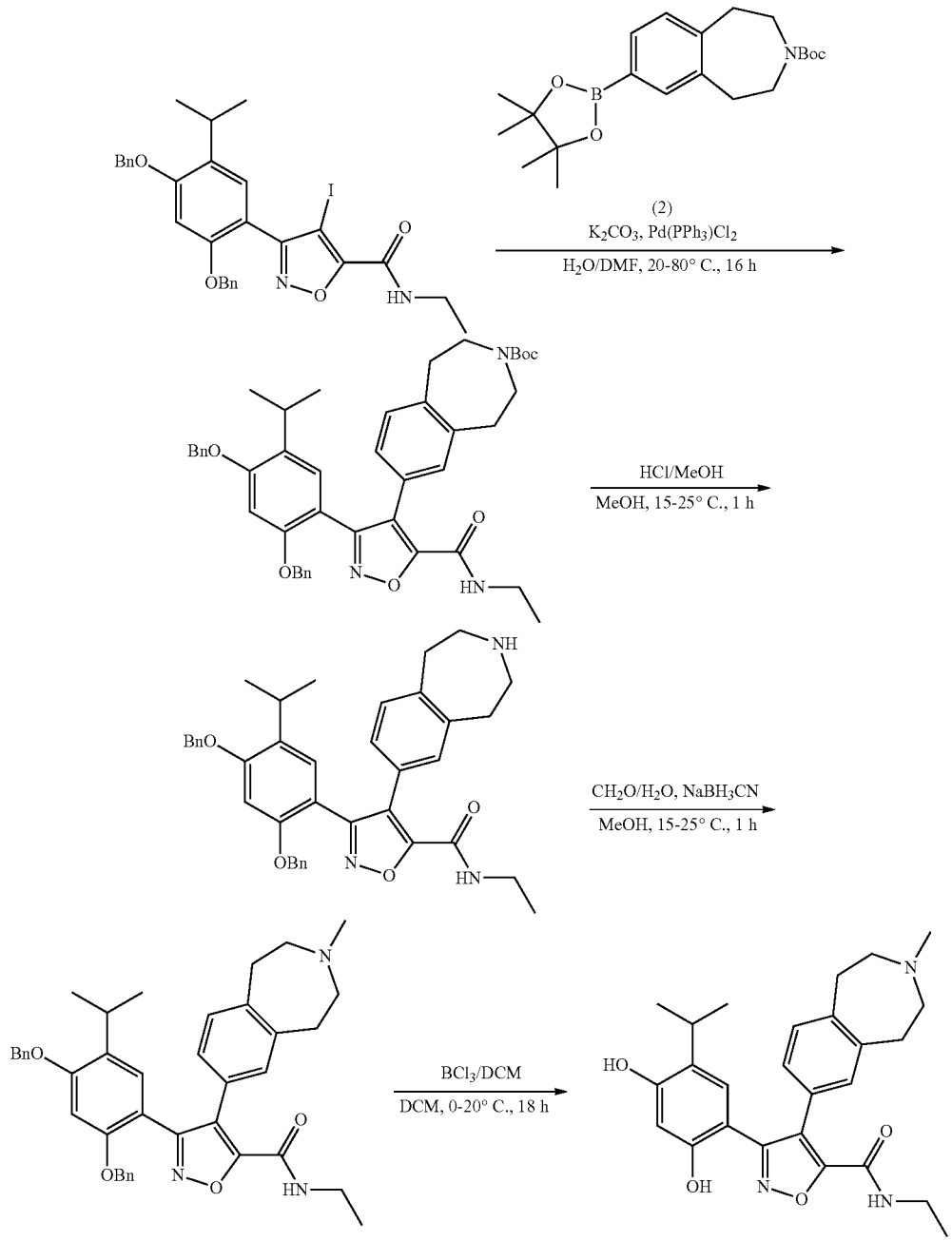

7-(4,4,5,5-tetramethyl-1,3,2-dioxaborolan-2-yl)-1,2,4,5-tetrahydro-benzazepine-3-formate (282 mg, 754 μmol, 1.5 eq.), water (1.5 mL) and potassium carbonate (348 mg, 2.5 mmol, 5.0 eq.) were added to a solution of 3-(2,4-dibenzyloxy-5-isopropyl-phenyl)-N-ethyl-4-iodo-isoxazole-5-carboxamide (300 mg, 503 μmol, 1.00 eq.) in DMF (7.5 mL) at 15-25° C. under the protection of nitrogen gas, followed by addition of Pd(PPh$_3$)$_2$Cl$_2$ (71 mg, 101 μmol, 0.2 eq.). The mixture was stirred at 80° C. for 2 hours. The reaction mixture was cooled down to 15-25° C. and poured into water (30 mL), followed by extraction with EA (30 mL×L). The combined organic layer was dried, filtered and concentrated to give a crude product. The crude product was purified by column chromatography (PE:EA=10:1 to 3:1) to give t-butyl-7-(3-(2,4-dibenzyloxy-5-isopropylphenyl)-5-(ethylcarbamoyl)isoxazol-4-yl)-1,2,4,5-tetrahydro-3-benzazepine-3-formate (200 mg, 179 μmol, 36% yield) as a yellow oil. (ESI) M/Z: 716 (M+1), 660 (M−56+1).

Step B: HCl/MeOH (4M, 2.00 mL) was added to a solution of t-butyl-7-(3-(2,4-dibenzyloxy-5-isopropylphenyl)-5-ethylcarbamoyl)isoxazol-4-yl)-1,2,4,5-tetrahydro-3-benzazepine-3-formate (200 mg, 279 μmol, 1.0 eq.) in MeOH (2.00 mL) at 25° C. The mixture was stirred at 25° C. for 1 hour. The mixture was concentrated at 40° C. to give a crude product. The crude product was dissolved in DCM (10 mL), and the solution was added with NaHCO₃ (1 g) with stirring for 1 hour. The mixture was filtered and concentrated to give a crude product. The crude product was purified by preparative TLC (DCM:MeOH=10:1) to give a product 3-(2,4-dibenzyloxy-5-isopropylphenyl)-N-ethyl-4-(2,3,4,5-tetrahydro-1H-3-benzazepin-7-yl)isoxazole-5-carboxamide (100 mg, 162 μmol, 58% yield) as a yellow oil. MS (ESI) m/z: 616 (M+1).

Step C: An aqueous solution of formaldehyde (211 mg, 162 μmol, 1.0 eq., 40% of content) and AcOH (10 mg, 16 μmol, 1.0 eq.) were added to a solution of 3-(2,4-dibenzyloxy-5-isopropylphenyl)-N-ethyl-4-(2,3,4,5-tetrahydro-1H-3-benzazepin-7-yl)isoxazole-5-carboxamide (100 mg, 162 μmol, 1.0 eq.) in MeOH (5 mL). The mixture was stirred at 25° C. for 10 min and then added with NaBH₃CN (31 mg, 487 μmol, 3.0 eq.). The reaction was further stirred at 25° C. for 50 min and the mixture was concentrated to give a crude product. The crude product was purified by preparative TLC (DCM:MeOH=10:1) to give a product 3-(2,4-dibenzyloxy-5-isopropylphenyl)-N-ethyl-4-(3-methyl-2,3,4, 5-tetrahydro-1H-benzo[d]azepin-7-yl)isoxazole-5-carboxamide (80 mg, 127 μmol, 78% yield) as a colorless oil. MS (ESI) m/z: 630 (M+1).

Step D: A solution of BCl₃ (1 M, 952 μL, 10.0 eq.) in DCM was added to a solution of 3-(2,4-di benzyloxy-5-isopropyl phenyl)-N-ethyl-4-(3-methyl-2, 3,4, 5-tetrahydro-1H-benzo[d]azepin-7-yl)isoxazole-5-carboxamide (60 mg, 95 μmol, 1.0 eq.) in DCM (5 mL) at 0° C. After stirring at 0° C. for 2 hours, the temperature was raised to 15-25° C. with stirring for 1 hour. The reaction mixture was cooled down to 0° C. and added with MeOH (2 mL), followed by stirring at 0° C. for 0.5 hour and at 15-25° C. for an additional 0.5 hour. The mixture was concentrated to give a crude product. The crude product was purified by preparative HPLC (0.225% FA-ACN; Phenomenex Synergi Max-RP 250×80 10 μm) to give 3-(2,4-dihydroxyl-5-isopropylphenyl)-N-ethyl-4-(3-methyl-2,3,4, 5-tetrahydro-1H-benzo[d]azepin-7-yl)isoxazole-5-carboxamide (20 mg, 41 μmol, 43% yield). ¹H NMR (400 MHz, DMSO): δ 10.84 (brs, 1 H), 9.59 (s, 1 H), 9.27 (s, 1 H), 8.91-8.89 (m, 1 H), 7.14-7.10 (m, 2 H), 7.03 (d, J=7.2 Hz, 1 H), 6.79 (s, 2 H), 6.37 (s, 1 H), 3.71 (s, 2 H), 3.25-3.16 (m, 5 H), 3.04-2.80 (m, 5 H), 2.78 (s, 3 H), 1.08 (t, J=6.8 Hz, 3 H), 1.01 (d, J=6.8 Hz, 6 H). MS (ESI) m/z: 450 (M+1).

EXAMPLE 28

3-(2,4-dihydroxyl-5-isopropylphenyl)-N-ethyl-4-(2,3,4,5-tetrahydro-1H-3-benzazepin-7-yl) isoxazole-5-carboxamide Reaction scheme:

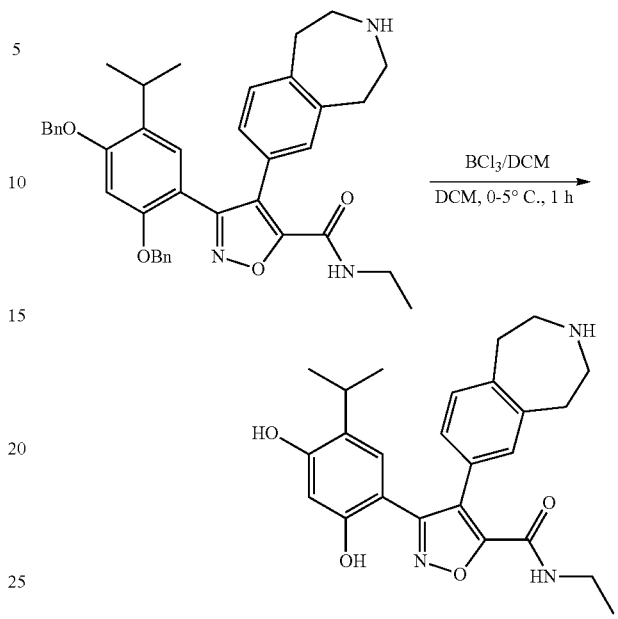

Step A: A solution of BCl₃ (1 M, 2.1 mL, 10.0 eq.) in DCM was added to a solution of 3-(2,4-dibenzyloxy-5-isopropylphenyl)-N-ethyl-4-(2,3,4,5-tetrahydro-1H-3-benzazepin-7-yl)isoxazole-5-carboxamide (130 mg, 211 μmol, 1.0 eq.) in DCM (10 mL) at 0° C. After stirring at 0° C. for 2 hours, the temperature was raised to 15-25° C. with stirring for 1 hour. The reaction mixture was cooled down to 0° C. and added with MeOH (4 mL), with stirring at 0° C. for 0.5 hour and at 15-25° C. for an additional 0.5 hour. The mixture was concentrated to give a crude product. The crude product was purified by preparative HPLC (0.225% FA-ACN; Phenomenex Synergi Max-RP 250×80 10 μm) to give 3-(2,4-dihydroxyl-5-isopropylphenyl)-N-ethyl-4-(2,3,4,5-tetrahydro-1H-3-benzo[d]azepin-7-yl)isoxazole-5-carboxamide (54 mg, 113 μmol, 54% yield). ¹H NMR (400 MHz, DMSO): δ 9.58 (s, 1 H), 9.29 (brs, 2 H), 9.26 (s, 1 H), 8.90 (t, J=5.6 Hz, 1 H), 7.12-7.10 (m, 2 H), 7.03 (d, J=7.6 Hz, 1 H), 6.76 (s, 1 H), 6.38 (s, 1 H), 3.26-3.21 (m, 2 H), 3.12-3.00 (m, 9 H), 1.09 (t, J=7.2 Hz, 3 H), 1.00 (d, J=6.8 Hz, 6 H). MS (ESI) m/z: 436 (M+1).

EXAMPLE 29

3-(2,4-dihydroxyl-5-isopropylphenyl)-N-ethyl-4-(isoquinolin-6-yl)isoxazole-5-carboxamide

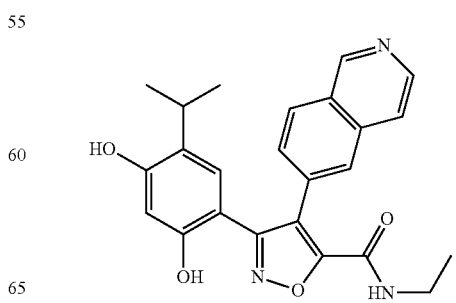

Reaction scheme:

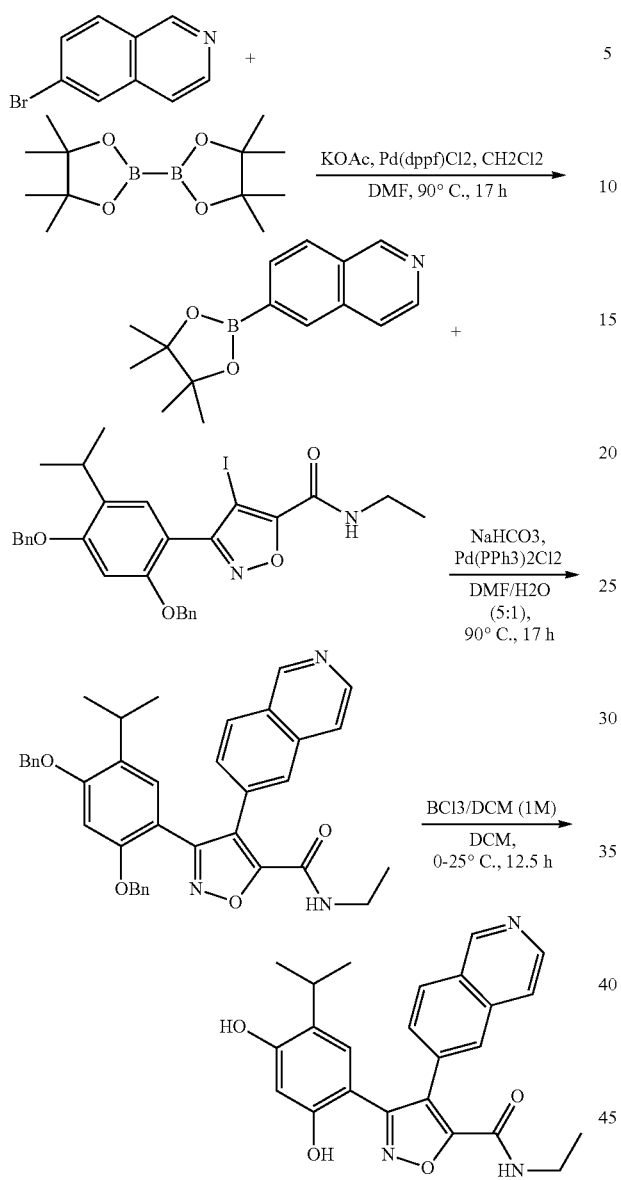

Step A: Bis(pinacolato)diboron (366 mg, 1.4 mmol) and KOAc (354 mg, 3.6 mmol) were added to a solution of 6-bromoisoquinoline (250 mg, 1.2 mmol) in dioxane (150 mL) at 25° C. under the protection of nitrogen gas, followed by adding a catalyst Pd(dppf)Cl$_2$CH$_2$Cl$_2$ (294 mg, 360 µmol). The mixture was stirred at 25° C. for 10 min and then heated to 90° C. with stirring for 17 hours. The mixture was cooled down to 25° C. and concentrated under reduced pressure to give 6-(4,4,5,5-tetramethyl-1,3,2-dioxaborolan-2-yl)isoquinoline (300 mg, a crude product) as a black solid, which was used directly in the next step. MS (ESI) M/Z: 274 (M+1).

Step B: K$_2$CO$_3$ (231 mg, 1.7 mmol), H$_2$O (5.0 mL) and Pd(PPh$_3$)$_2$Cl$_2$ (71 mg, 101 µmol) were added to a mixed solution of 6-(4,4,5,5-tetramethyl-1,3,2-dioxaborolan-2-yl)isoquinoline (128 mg, 503 µmol) and 3-(2,4-dibenzyloxy-5-isopropyl-phenyl)-N-ethyl-4-iodo-isoxazole-5-carboxamide (200 mg, 335 µmol) in DMF (20 mL) at 25° C. under the protection of nitrogen gas. The mixture was stirred at 25° C. for 10 min and then heated to 90° C. with stirring for 17 hours. The mixture was cooled down to 25° C., poured into water (50 mL) and extracted with EA (100 mL×L). The combined organic layer was dried, filtered and concentrated to give a crude product. The crude product was purified by column chromatography (PE:EA=5:1 to 2:1) to give 3-(2,4-dibenzyloxy-5-isopropylphenyl)-N-ethyl-4-(isoquinolin-6-yl)isoxazole-5-carboxamide (180 mg, 90% yield) as a brown solid.

Step C: A solution of BCl$_3$ (1 M, 3.1 mL, 10.0 eq.) in DCM was added to a solution of 3-(2,4-dibenzyloxy-5-isopropylphenyl)-N-ethyl-4-(isoquinolin-6-yl)isoxazole-5-carboxamide (180 mg, 301 µmol, 1.0 eq.) in DCM (10 mL) at 0° C. After stirring at 0° C. for 2 hours, the temperature was raised to 15-25° C. with stirring for 12 hours. The reaction mixture was cooled down to 0° C. and added with MeOH (6 mL), followed by stirring at 0° C. for 0.5 hour and at 15-25° C. for an additional 0.5 hour. The mixture was concentrated to give a crude product. The crude product was purified by preparative TLC (PE:EA=1:1) to give 3-(2,4-dihydroxyl-5-isopropylphenyl)-N-ethyl-4-(isoquinolin-6-yl)isoxazole-5-carboxamide (15 mg, 32 µmol, 10% yield). $^1$H NMR (400 MHz, DMSO-d$_6$) ■ ppm: 0.83 (d, J=6.90 Hz, 10 H); 2.95-3.06 (m, 1 H); 3.36 (q, J=7.28 Hz, 2 H); 6.27 (s, 1 H); 6.79 (s, 1 H); 7.58-7.64 (m, 1 H); 7.74 (d, J=5.77 Hz, 1 H); 7.87 (s, 1 H); 8.07 (d, J=8.53 Hz, 1 H); 8.41 (d, J=5.90 Hz, 1 H); 9.23 (s, 1 H). MS (ESI) m/z: 418 (M+1).

EXAMPLE 30

5-(2,4-dihydroxyl-5-bromo-phenyl)-N-ethyl-4-(2-methyl-1,2,3,4-tetrahydroisoquinolin-6-yl)isoxazole-3-carboxamide

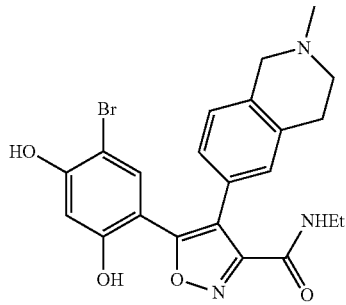

Reaction scheme:

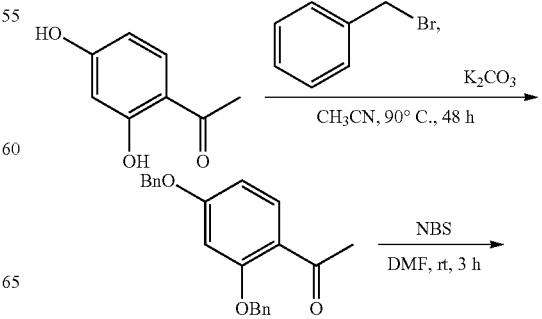

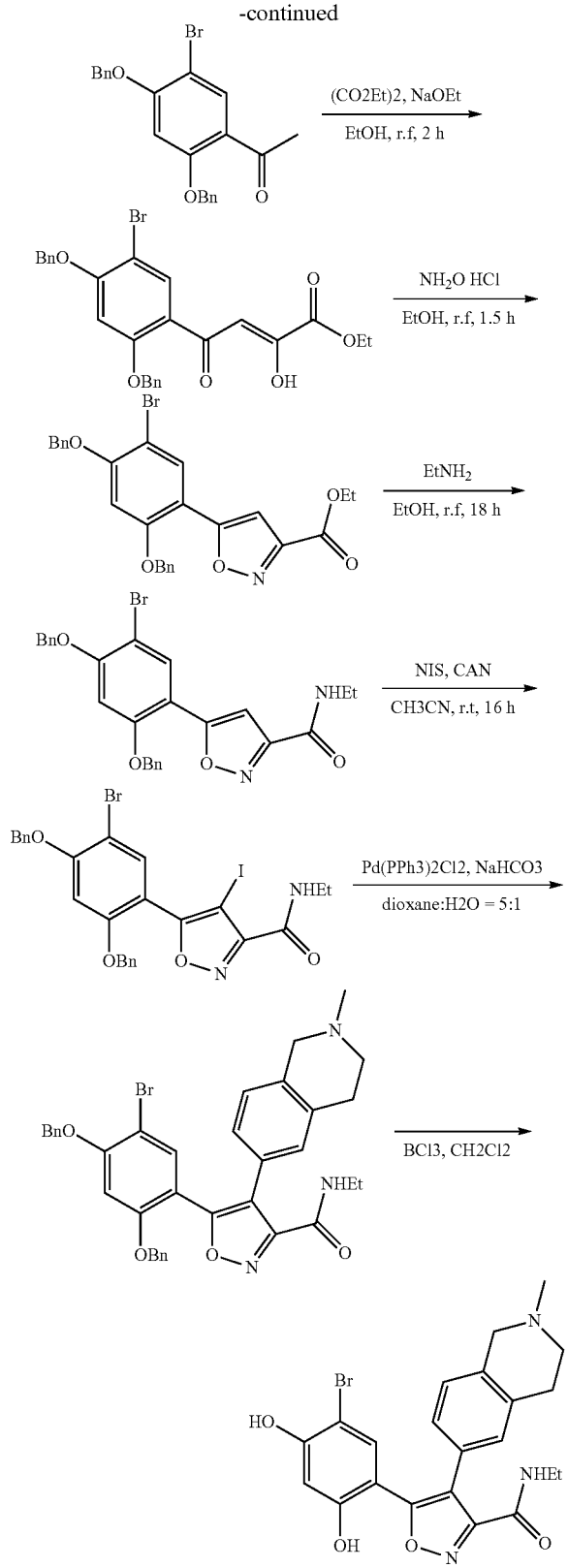

Step A: Potassium carbonate (100 g, 723 mmol, 2.2 eq.) was added to a mixture of 1-(2,4-dihydroxyphenyl)ethanone (50.00 g, 329 mmol, 1.00 eq.) and benzyl bromide (124 g, 723 mmol, 2.2 eq.) in CH₃CN (500 mL) at 20° C. under the protection of nitrogen gas. The mixture was stirred at 80° C. for 18 hours. The reaction solution was cooled down to room temperature, then filtered and concentrated under reduced pressure, to give a crude product. The crude product was beaten in petroleum ether for 30 min. The solid was collected by filtration and dried to give 1-(2,4-dibenzyloxyphenyl)ethanone (105 g, 316 mmol, 96% yield) as a white solid. (MS: (M+1)=333.0).

Step B: NBS (27 g, 150 mmol, 1.0 eq.) was added to a mixture of 1-(2,4-dibenzyloxyphenyl)ethanone (50.00 g, 150 mmol, 1.00 eq.) in DMF (150 mL) at 0° C. under the protection of nitrogen gas. The mixture was stirred at 25° C. for 3 hours. The reaction solution was poured into water (200 mL), and the solid was collected by filtration and dried to give 1-(2,4-dibenzyloxy-5-bromo-phenyl)ethanone (61 g, 148 mmol, 98% yield) as a white solid. (MS: (M+1)=411.1, 413.1).

Step C: Sodium metal (10.2 g, 445 mmol, 3.0 eq.) was added in batch to ethanol (400 mL) at 20° C. under the protection of nitrogen gas with stirring for 1 hour. Subsequently, 1-(2,4-dibenzyloxy-5-bromo-phenyl)ethanone (61.0 g, 148 mmol, 1.0 eq.) was added in batch, followed by adding dimethyl oxalate (32.5 g, 222 mmol, 1.5 eq.). After stirring at 80° C. for 2 hours, the reaction mixture was cooled down to 65° C. and added with glacial acetic acid (30 mL), and the reaction solution was poured into ice water (800 mL) with stirring to cool. The solid was collected by filtration, washed once with water (500 mL) and dried in vacuum to give a product ethyl 2-hydroxyl-4-(5-bromo-2,4-dimethoxy-phenyl)-4-oxo-butyrate (32 g, 63 mmol, 42% yield) as a yellow solid.

Step D: NH₂OH HCl (5.2 g, 75 mmol, 1.2 eq.) was added to a solution of ethyl 2-hydroxyl-4-(5-bromo-2,4-dimethoxy-phenyl)-4-oxo-butyrate (32 g, 63 mmol, 1.00 eq.) in EtOH (320 mL) at room temperature under the protection of nitrogen gas. The mixture was heated to 80° C. and stirred for 3 hours. The mixture was cooled down to room temperature, and the solid was collected by filtration, washed with water (150 mL×2) and ethanol (150 mL×2) and dried in vacuum, to give ethyl 5-(5-bromo-2,4-dimethoxy-phenyl)-isoxazole-3-carboxylate (23 g, 45 mmol, 72% yield) as a yellow solid. (MS: (M+1)=508.1, 510.2).

Step E: Ethylamine (17 g, 384 mmol, 8.5 eq.) was added to a solution of ethyl 5-(5-bromo-2,4-dimethoxy-phenyl)-isoxazole-3-carboxylate (23 g, 45 mmol, 1.00 eq.) in EtOH (200 mL) at room temperature. The reaction mixture was stirred at 80° C. for 12 hours. The reaction mixture was cooled down to room temperature and the solid was precipitated. The solid was collected by filtration, washed with ethanol (50 mL×2) and dried in vacuum to give a product N-ethyl-5-(5-bromo-2,4-dimethoxyphenyl)isoxazole-3-carboxamide (13 g, 26 mmol, 58% yield) as a yellow solid.

Step F: CAN (432 mg, 788 µmol, 0.1 eq.) and NIS (1.3 g, 2.9 mmol, 1.5 eq.) were added to a solution of 5-(2,4-dibenzyloxy-5-bromo-phenyl)-N-ethyl-isoxazole-3-carboxamide (2.0 g, 3.9 mmol, 1.0 eq.) in MeCN (20 mL) at room temperature under N₂ protection. The mixture was heated to 50° C. and stirred for 12 hours. The mixture was cooled down to room temperature and poured into a saturated aqueous Na₂S₂O₃ solution (40 mL), and the aqueous phase was extracted with EA (20 mL×3). The combined organic phase was washed with saturated brine (50 mL×), dried over anhydrous sodium sulfate, filtered and concentrated in vacuum to dryness. The residue was purified by silica gel chromatography (PE/EA=3/1) to give 5-(2,4-dibenzyloxy 5-bromo-phenyl)-N-ethyl-4-iodo-isoxazole-3-carboxamide (2.4 g, 3.8 mmol, 98% yield) as a brown oil. MS: [M+1]= 633.0, 635.0).

Step G: NaHCO$_3$ (1.3 g, 15.5 mmol), H$_2$O (2.5 mL) and Pd(PPh$_3$)$_2$Cl$_2$ (407 mg, 580 μmol) were added to a mixed solution of 2-methyl-6-(4,4,5,5-tetramethyl-1,3,2-dioxaborolan-2-yl)-1,2,3,4-tetrahydroisoquinoline (1.8 g, 4 mmol) and 5-(2,4-dibenzyloxy-5-bromo-phenyl)-N-ethyl-4-iodo-isoxazole-3-carboxamide (2.5 g, 3.9 mmol) in DMF (25.0 mL) at 25° C. under the protection of nitrogen gas. The mixture was stirred at 25° C. for 10 min and then heated to 80° C. with stirring for 12 hours. The mixture was cooled down to 25° C. and poured into water (50 mL), and the aqueous phase was extracted with EA (30 mL×2). The combined organic phase was washed with saturated brine (50 mL), dried with anhydrous sodium sulfate, filtered and concentrated under reduced pressure. The residue was purified by silica gel chromatography (200~300 mesh of silica gel, DCM/MeOH=100:1 to 20:1) to give 5-(2,4-dibenzyloxy-5-bromo-phenyl)-N-ethyl-4-(2-methyl-1,2,3,4-tetrahydroisoquinolin-6-yl)isoxazole-3-carboxamide (2.0 g, 60% yield) as a yellow solid.

Step H: BCl$_3$/DCM (1.3 mL, 1.0 mol/L) was added dropwise to a mixed solution of 5-(2,4-dibenzyloxy-5-bromo-phenyl)-N-ethyl-4-(2-methyl-1,2,3,4-tetrahydroisoquinolin-6-yl)isoxazole-3-carboxamide (300 mg, 345 μmol) in dichloromethane (20.00 mL) at 0° C. under the protection of nitrogen gas. The mixture was stirred at 0° C. for 1 hour. The mixture was added dropwise with methanol (3 mL) and concentrated under reduced pressure. The residue was purified by preparative HPLC (formic acid, Column: Phenomenex Synergi Max-RP 250×80 10 μm, Condition: 0.225% FA-ACN) to give 5-(2,4-dihydroxyl-5-bromo-phenyl)-N-ethyl-4-(2-methyl-1,2,3,4-tetrahydroisoquinolin-6-yl)isoxazole-3-carboxamide (96 mg, 59% yield). $^1$H NMR (DMSO-d$_6$, 300 MHz) δ: $^1$H NMR (400 MHz, DMSO-d$_6$) δ=10.81 (s, 1 H), 10.73 (br. s., 1 H), 10.29 (s, 1 H), 8.94 (t, J=5.65 Hz, 1 H), 7.29 (s, 1 H), 7.06-7.19 (m, 3 H), 6.70 (s, 1H), 4.38-4.50 (m, 1 H), 4.25 (dd, J=15.43, 8.16 Hz, 1 H), 3.59 (br. s., 1 H), 3.19-3.32 (m, 3 H), 3.07-3.19 (m, 1 H), 2.83-2.97 (m, 4 H), 1.09 (t, J=7.15 Hz, 3 H). MS (ESI) M/Z: 472, 474 (M+1).

EXAMPLE 31

5-(2,4-dihydroxyl-5-chloro-phenyl)-N-ethyl-4-(2-methyl-1,2,3,4-tetrahydroisoquinolin-6-yl)isoxazole-3-carboxamide

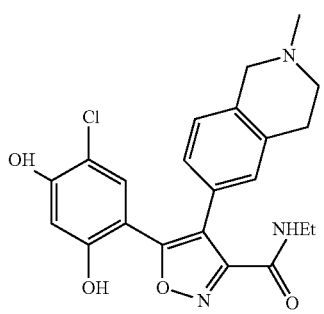

Reaction scheme:

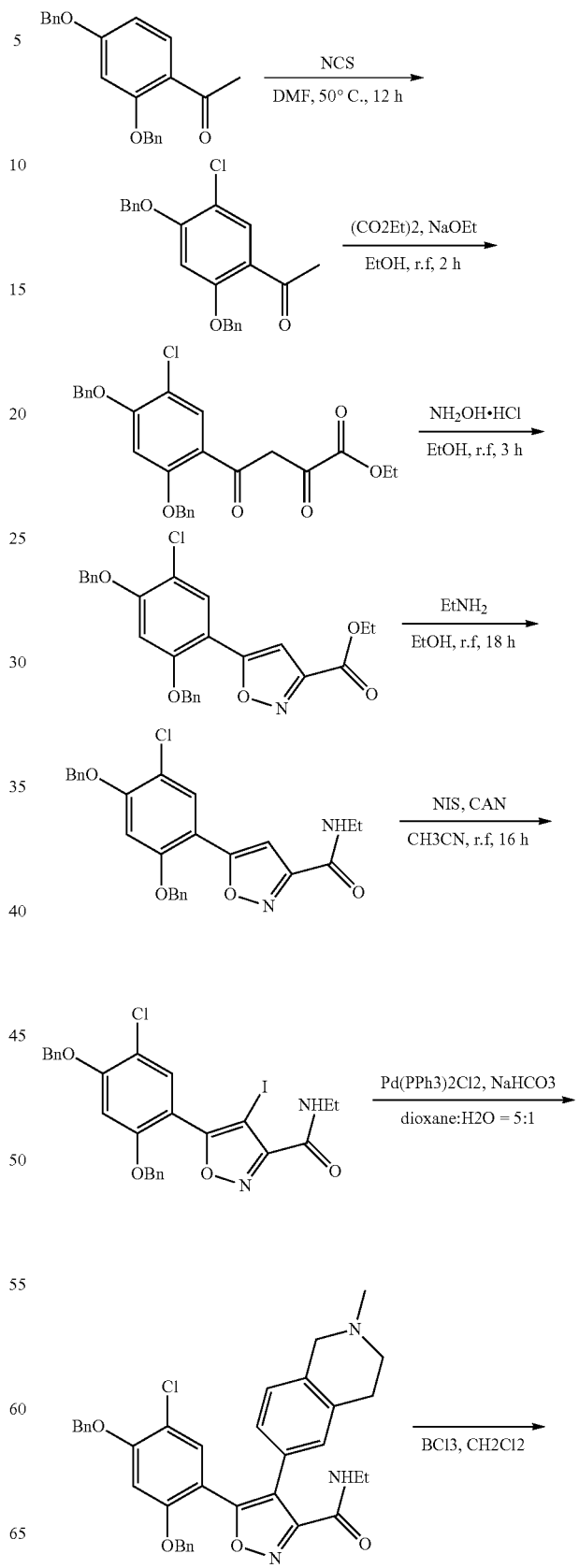

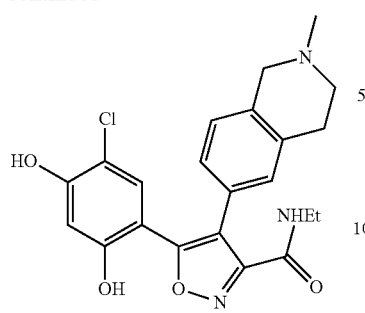

Step A: The title compound of this Example was prepared according to the order of steps B, C, D, E, F, G and H in Example 30, wherein NBS in step B was replaced with NCS, and the product was a white solid. $^1$H NMR (400 MHz, DMSO-$d_6$) δ=10.72 (br. s., 1 H), 10.23 (br. s., 1 H), 8.95 (t, J=5.65 Hz, 1 H), 7.05-7.18 (m, 4 H), 6.67 (br. s., 1 H), 4.45 (d, J=14.31 Hz, 1 H), 4.25 (dd, J=15.43, 8.41 Hz, 1 H), 3.60 (br. s., 1 H), 3.18-3.34 (m, 3 H), 3.10 (br. s., 1 H), 2.89 (br. s., 4 H), 1.09 (t, J=7.15 Hz, 3 H). MS: [M+1]=428.

EXAMPLE 32

5-(2,4-dihydroxyl-5-methylphenyl)-N-ethyl-4-(2-methyl-1,2,3,4-tetrahydroisoquinolin-6-yl)isoxazole-3-carboxamide

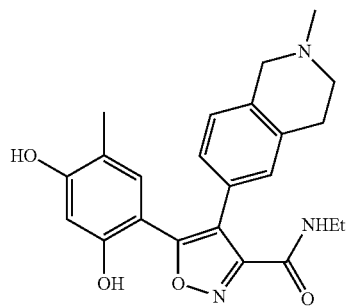

Reaction scheme:

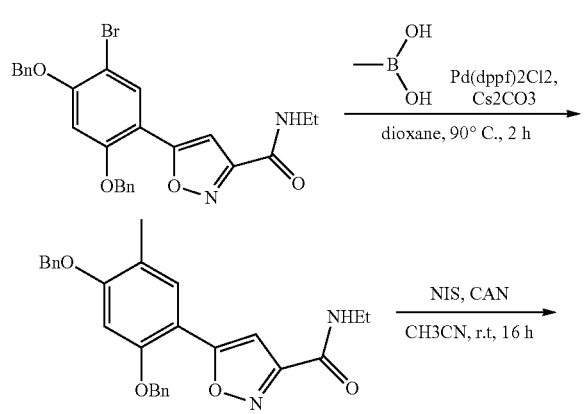

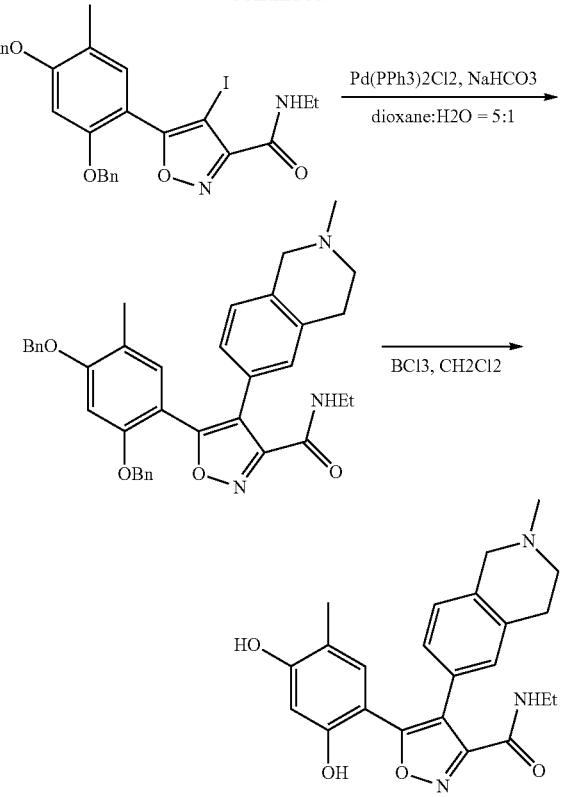

Step A: Cs$_2$CO$_3$ (1.3 g, 4 mmol) and Pd(dppf)$_2$Cl$_2$ (288 mg, 400 μmol) were added to a mixed solution of N-ethyl-5-(5-bromo-2,4-dimethoxyphenyl)isoxazole-3-carboxamide (1.0 g, 2.0 μmol) and methylboronic acid (177 mg, 3.0 mmol) in dioxane (10.0 mL) at 25° C. under the protection of nitrogen gas. The mixture was stirred at 25° C. for 10 min and then heated to 90° C. with stirring for 2 hours. The mixture was cooled down to 25° C. and poured into water (10 mL), and the aqueous phase was extracted with EA (5 mL×3). The combined organic phase was washed with saturated brine (50 mL), dried with anhydrous sodium sulfate, filtered and concentrated under reduced pressure. The residue was purified by silica gel chromatography (200~300 mesh of silica gel, petroleum ether/ethyl acetate=3/1) to give 5-(5-methyl-2,4-dibenzyloxyphenyl)-N-ethyl-isoxazole-3-carboxamide (740 mg, 85% yield) as a yellow solid. MS (ESI) M/Z: 443 (M+1).

Step B: CAN (92 mg, 167 mol, 0.1 eq.) and NIS (488 mg, 2.2 mmol, 1.3 eq.) were added to a solution of 5-(5-methyl-2,4-dibenzyloxyphenyl)-N-ethyl-isoxazole-3-carboxamide (740 mg, 1.7 mmol, 1.0 eq.) in MeCN (30 mL) at room temperature under N$_2$ protection. The mixture was heated to 80° C. with stirring for 12 hours. The mixture was cooled down to room temperature and poured into water (30 mL), and the aqueous phase was extracted with EA (20 mL×3). The combined organic phase was washed with saturated brine (50 mL×3), dried with anhydrous sodium sulfate, filtered and concentrated in vacuum to dryness. The residue was purified by silica gel chromatography (PE/EA=3/1) to give 5-(5-methyl-2,4-dibenzyloxyphenyl)-N-ethyl-4-iodo-isoxazole-3-carboxamide (450 mg, 792 mmol, 47.0% yield) as a yellow oil.

Step C: NaHCO$_3$ (228 mg, 2.7 mmol), H$_2$O (1.0 mL) and Pd(PPh$_3$)$_2$Cl$_2$ (71 mg, 102 μmol) were added to a mixed solution of 2-methyl-6-(4,4,5,5-tetramethyl-1,3,2-dioxaborolan-2-yl)-1,2,3,4-tetrahydroisoquinoline (309 mg, 679 μmol) and 5-(5-methyl-2,4-dibenzyloxyphenyl)-N-ethyl-4-iodo-isoxazole-3-carboxamide (450 mg, 721 μmol) in dioxane (5.0 mL) at 25° C. under the protection of nitrogen gas. The mixture was stirred at 25° C. for 10 min and then heated to 80° C. with stirring for 12 hours. The mixture was cooled down to 25° C. and poured into water (50 mL), and the aqueous phase was extracted with EA (40 mL×3). The combined organic phase was washed with saturated brine (50 mL), dried with anhydrous sodium sulfate, filtered and concentrated under reduced pressure. The residue was purified by silica gel chromatography (200~300 mesh of silica gel, petroleum ether/ethyl acetate=50/1, 3/1) to give 5-(5-methyl-2,4-dibenzyloxyphenyl)-N-ethyl-4-(2-methyl-1,2,3,4-tetrahydroisoquinolin-6-yl)isoxazole-3-carboxamide (280 mg, 70% yield) as a yellow oil. MS (ESI) M/Z: 588 (M+1).

Step D: BCl$_3$/DCM (1.8 mL, 1.0 mol/L) was added dropwise to a mixed solution of 5-(5-methyl-2,4-dibenzyloxyphenyl)-N-ethyl-4-(2-methyl-1,2,3,4-tetrahydroisoquinolin-6-yl)isoxazole-3-carboxamide (280 mg, 476 μmol) in dichloromethane (10.00 mL) at 0° C. under the protection of nitrogen gas. The mixture was stirred at 0° C. for 1 hour. The mixture was added dropwise with methanol (4 mL) and concentrated under reduced pressure. The residue was purified by preparative HPLC (formic acid, Column: Phenomenex Synergi Max-RP 250×80 10 μm, Condition: 0.225% FA-ACN) to give 5-(5-methyl-2,4-dihydroxyphenyl)-N-ethyl-4-(2-methyl-1,2,3,4-tetrahydroisoquinolin-6-yl)isoxazole-3-carboxamide (57 mg, 29% yield). $^1$H NMR (DMSO-d$_6$, 400 MHz) δ: $^1$H NMR (400 MHz, DMSO-d$_6$) δ=8.90 (t, J=5.52 Hz, 1 H), 8.17 (s, 1 H), 7.01-7.10 (m, 1 H), 6.95 (s, 2 H), 6.90 (s, 1 H), 6.42 (s, 1 H), 3.47 (s, 2 H), 3.23 (quin, J=6.78 Hz, 2 H), 2.67-2.75 (m, 2 H), 2.57-2.63 (m, 2 H), 2.34 (s, 3 H), 1.98 (s, 3 H), 1.09 (t, J=7.15 Hz, 3 H). MS (ESI) M/Z: 408 (M+1).

EXAMPLE 33

5-(5-isobutyl-2,4-dihydroxyl-phenyl)-N-ethyl-4-(2-methyl-1,2,3,4-tetrahydroisoquinolin-6-yl)isoxazole-3-carboxamide

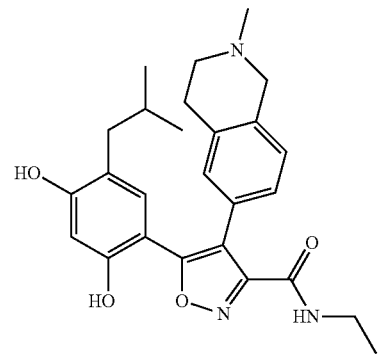 [SMILES: CCNC(=O)c1noc(-c2cc(CC(C)C)c(O)cc2O)c1-c1ccc2c(c1)CCN(C)C2]

Reaction scheme:

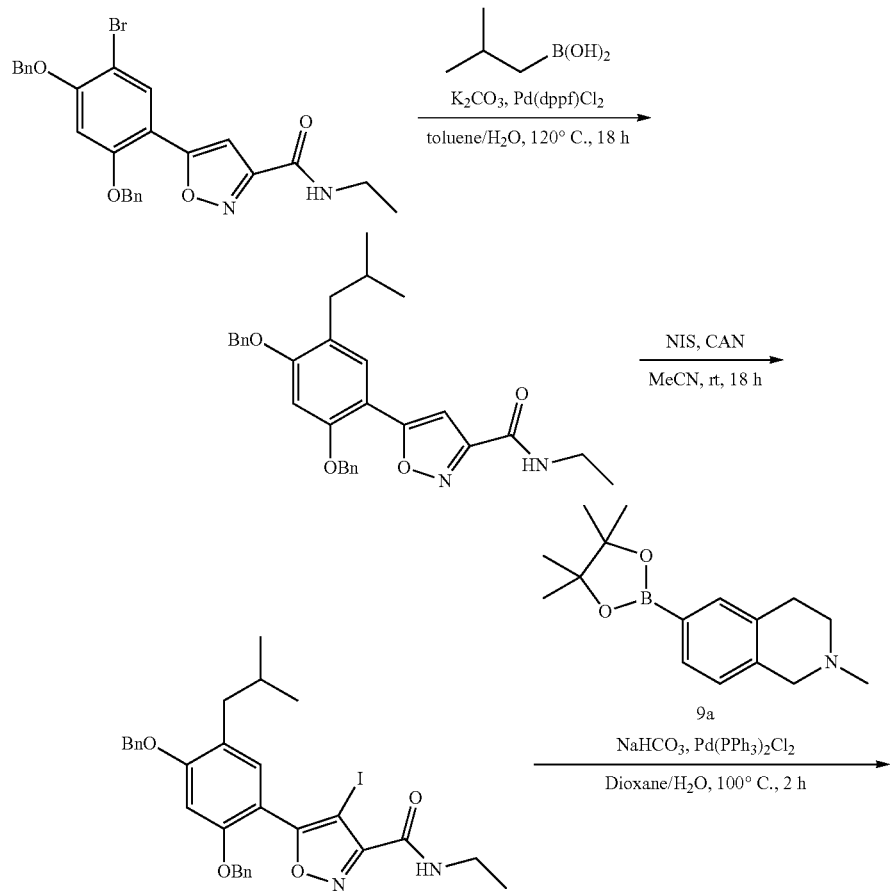

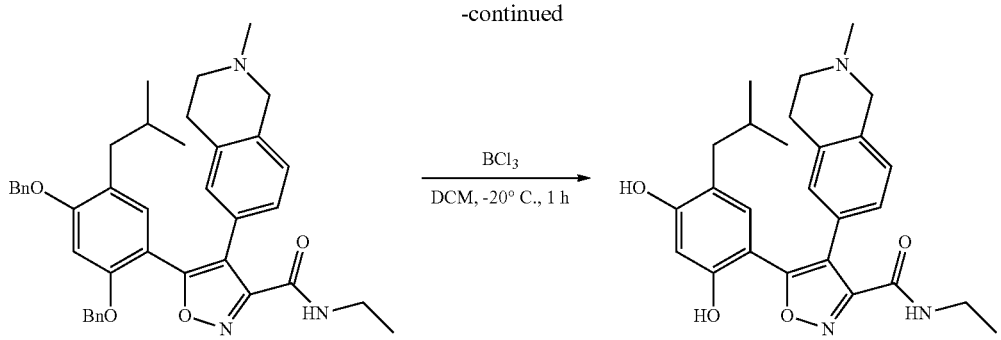

Step A: Na₂CO₃ (835.60 mg, 7.88 mmol, 2 eq), H₂O (2.0 mL) and Pd(dppf)₂Cl₂ (576.86 mg, 788.00 mmol, 0.2 eq) were added to a mixed solution of 5-(2,4-dibenzyloxy-5-bromo-phenyl)-N-ethyl-isoxazole-3-carboxamide (2.00 g, 3.94 mmol, 1 eq.) and isobutylboronic acid (803.67 mg, 7.88 mmol, 2 eq.) in toluene (50 mL) at 25° C. under the protection of nitrogen gas. The mixture was heated to 120° C. with stirring for 18 hours. The mixture was filtered through diatomaceous earth and concentrated under reduced pressure. The residue was purified by silica gel chromatography (petroleum ether/ethyl acetate=6/1) to give 5-(2,4-dibenzyloxy-5-isobutyl-phenyl)-N-ethyl-isoxazole-3-carboxamide (500.00 mg, 26.19% yield) as a white solid.

Step B: CAN (54.67 mg, 103.001 mol, 0.10 eq.) and NIS (463.46 mg, 2.06 mmol, 2.00 eq.) were added to a solution of 5-(2,4-dibenzyloxy-5-isobutyl-phenyl)-N-ethyl-isoxazole-3-carboxamide (500.00 mg, 1.03 mmol, 1.0 eq.) in MeCN (50 mL) at room temperature under N₂ protection. The mixture was heated to 10° C. with stirring for 18 hours. The mixture was cooled down to room temperature and poured into an aqueous Na₂SO₃ solution (40 mL), and the aqueous phase was extracted with EA (30 mL×3). The combined organic phase was dried with anhydrous sodium sulfate, filtered and concentrated in vacuum to dryness. The residue was purified by silica gel chromatography (petroleum ether/ethyl acetate=3/1) to give 5-(2,4-dibenzyloxy-5-isobutyl-phenyl)-N-ethyl-4-iodo-isoxazole-3-carboxamide (400.00 mg, 655.22 μmol, 63.61% yield) as a white solid.

Step C: NaHCO₃ (165.14 mg, 7.88 mmol, 2 eq), H₂O (0.5 mL) and Pd(PPh₃)₂Cl₂ (45.99 mg, 65.52 μmol, 0.10 eq.) were added to a mixed solution of 5-(2,4-dibenzyloxy-5-isobutyl-phenyl)-N-ethyl-4-iodo-isoxazole-3-carboxamide (400 mg, 655.22 mmol, 1 eq.) and 2-methyl-6-(4,4,5,5-tetramethyl-1,3,2-dioxaborolan-2-yl)-1,2,3,4-tetrahydroisoquinoline (268.49 mg, 982.83 μmol, 1.5 eq.) in dioxane (2.50 mL) at 25° C. under the protection of nitrogen gas. The mixture was heated to 90° C. with stirring for 3 hours. The mixture was filtered through diatomaceous earth and concentrated under reduced pressure. The residue was purified by silica gel chromatography (dichloromethane/methanol=6/1) to give 5-(5-isobutyl-2,4-dibenzyloxy-phenyl)-N-ethyl-4-(2-methyl-1,2,3,4-tetrahydroisoquinolin-6-yl)isoxazole-3-carboxamide (300.00 mg, a crude product) as a yellow solid.

Step D: BCl₃/DCM (1 mL, 1.0 mol/L) was added dropwise to a mixed solution of 5-(5-isobutyl-2,4-dibenzyloxy-phenyl)-N-ethyl-4-(2-methyl-1,2,3,4-tetrahydroisoquinolin-6-yl)isoxazole-3-carboxamide (150.00 mg, 238.17 μmol) in dichloromethane (10.00 mL) at −20° C. under the protection of nitrogen gas. The mixture was stirred at −20° C. for 1 hour. The mixture was added dropwise with methanol (2 mL) and concentrated under reduced pressure. The residue was purified by preparative HPLC (formic acid, Column: Phenomenex Synergi Max-RP 250×80 10 μm, Condition: 0.225% FA-ACN) to give 5-(5-isobutyl-2,4-dihydroxyl-phenyl)-N-ethyl-4-(2-methyl-1,2,3,4-tetrahydroisoquinolin-6-yl)isoxazole-3-carboxamide (28.20 mg, 26.34% yield). ¹H NMR (DMSO-d₆, 400 MHz) δ8.87 (t, J=5.6 Hz, 1H), 6.95 (d, J=4.4 Hz, 1H), 6.71 (s, 1H), 6.42 (s, 1H), 6.82 (s, 1H), 6.42 (s, 1H), 3.45 (s, 2H), 3.20-3.25 (m, 2H), 2.68 (d, J=5.2 Hz, 2H), 2.53-2.60 (m, 2H), 2.50 (s, 3H), 2.18-2.35 (m, 2H), 1.68 (dd, J=6.8 Hz, 2H), 1.07 (t, J=7.2 Hz, 3H), 0.72 (d, J=6.8 Hz, 6H). MS (ESI) M/Z: 450.3 (M+1)

EXAMPLE 34

5-(5-ethyl-2,4-dihydroxyl-phenyl)-N-ethyl-4-(2-methyl-1,2,3,4-tetrahydroisoquinolin-6-yl)isoxazole-3-carboxamide

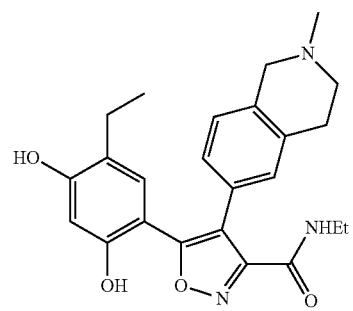

Reaction scheme:

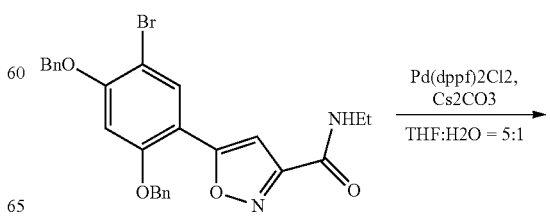

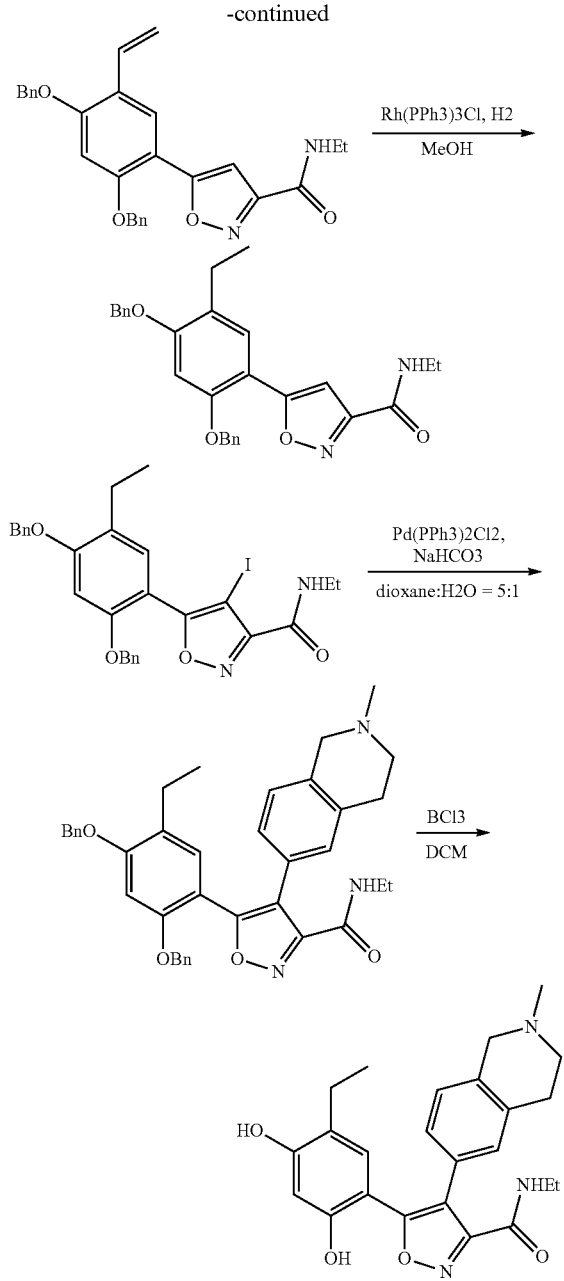

Step A: Potassium vinyltrifluoroborate (316.81 mg, 2.36 mmol) and cesium carbonate (1.93 g, 5.91 mmol) were added to a solution of 5-(2,4-dibenzyloxy-5-bromo-phenyl)-N-ethyl-isoxazole-3-carboxamide (1 g, 1.97 mmol) in tetrahydrofuran (40 mL) and water (4 mL) at 25° C. under the protection of nitrogen gas. The mixture was heated to 80° C. with stirring for 12 hours. The mixture was cooled down to 25° C. and poured into water (30 mL), and the aqueous phase was extracted with EA (30 mL×2). The combined organic phase was washed with water (50 mL) and saturated brine (40 mL), dried over anhydrous sodium sulfate, filtered and concentrated in vacuum to dryness, and concentrated under reduced pressure. The residue was purified by silica gel chromatography (100~200 mesh of silica gel, petroleum ether/ethyl acetate=3/1) to give the target product (700.00 mg, 78.17% yield) as a yellow solid. (MS: [M+1]=455.1).

Step B: Tris triphenylphosphine rhodium chloride (71.25 mg, 77 μmol) was added to a solution of 5-(2,4-dibenzyloxy-5-vinyl-phenyl)-N-ethyl-isoxazole-3-carboxamide (0.7 g, 1.54 mmol) in methanol (20 mL) at 25° C. under the protection of hydrogen gas. The mixture was heated to 50° C. and stirred at 50 psi for 12 hours. The mixture was cooled down to 25° C., filtered and concentrated under reduced pressure. The residue was diluted with water (20 mL) and the aqueous phase was extracted with EA (10 mL×2). The combined organic phase was washed with saturated brine (30 mL), dried with anhydrous sodium sulfate, filtered, and concentrated in vacuum to dryness. The residue was purified by silica gel chromatography (100~200 mesh of silica gel, petroleum ether/ethyl acetate=2/1) to give the target product (600.00 mg, 85.06% yield) as a yellow solid. (MS: [M+1]= 457.1)

Step C: Iodosuccinimide (442.09 mg, 1.96 mmol) was added to a solution of 5-(2,4-dibenzyloxy-5-ethyl-phenyl)-N-ethyl-isoxazole-3-carboxamide (0.6 g, 1.31 mmol) in acetonitrile (20 mL) at 25° C. under the protection of nitrogen gas. The mixture was stirred at 25° C. for 12 hours. The mixture was cooled down to 25° C. After the mixture was filtered and concentrated under reduced pressure, sodium thiosulfate (30 mL) was added. The aqueous phase was extracted with EA (20 mL×2). The combined organic phase was washed with saturated brine (40 mL), dried with anhydrous sodium sulfate, filtered, and concentrated in vacuum to dryness. The residue was purified by silica gel chromatography (100~200 mesh of silica gel, petroleum ether/ethyl acetate=3/1) to give the target product (420.00 mg, 55.05% yield) as a yellow solid. (MS: [M+1]=583.1)

Step D: NaHCO$_3$ (184 mg, 220 μmol, 4.0 eq.), H$_2$O (1.0 mL) and Pd(PPh$_3$)$_2$Cl$_2$ (39 mg, 55 μmol, 0.10 eq.) were added to a mixed solution of 5-(2,4-dibenzyloxy-5-ethyl-phenyl)-N-ethyl-4-iodo-isoxazole-3-carboxamide (320 mg, 549 μmol, 1 eq.) and 2-methyl-6-(4,4,5,5-tetramethyl-1,3,2-dioxaborolan-2-yl)-1,2,3,4-tetrahydroisoquinoline (250 mg, 549 μmol, 1.0 eq.) in dioxane (5.0 mL) at 25° C. under the protection of nitrogen gas. The mixture was heated to 80° C. with stirring for 12 hours. The mixture was filtered through diatomaceous earth and concentrated under reduced pressure. The residue was purified by preparative TLC (dichloromethane/methanol=10/1) to give 5-(5-ethyl-2,4-dibenzyloxy-phenyl)-N-ethyl-4-(2-methyl-1,2,3,4-tetrahydroisoquinolin-6-yl)isoxazole-3-carboxamide (67.00 mg, 111 μmol, 20% yield) as a brown solid. MS: [M+1]= 602.3

Step E: BCl$_3$/DCM (5 mL, 1.0 mol/L) was added dropwise to a mixed solution of 5-(5-ethyl-2,4-dibenzyloxy-phenyl)-N-ethyl-4-(2-methyl-1,2,3,4-tetrahydroisoquinolin-6-yl)isoxazole-3-carboxamide (100.00 mg, 166 μmol) in dichloromethane (10.00 mL) at 25° C. under the protection of nitrogen gas. The mixture was stirred at 25° C. for 0.5 hour. The mixture was added dropwise with methanol (10 mL) and concentrated under reduced pressure. The residue was purified by preparative HPLC to give 5-(5-ethyl-2,4-dihydroxyl-phenyl)-N-ethyl-4-(2-methyl-1,2,3,4-tetrahydroisoquinolin-6-yl)isoxazole-3-carboxamide (15 mg, 36 μmol, 21% yield). $^1$H NMR (400 MHz, DMSO-d$_6$) δ=8.90 (t, J=5.52 Hz, 1 H), 7.14 (s, 1 H), 7.09 (br. s., 2 H), 6.85 (s, 1 H), 6.43 (s, 1 H), 3.50 (br. s., 2 H), 3.18-3.25 (m, 2 H), 2.89 (s, 3 H), 2.46 (br. s., 2 H), 2.30-2.41 (m, 4 H), 1.08 (t, J=7.15 Hz, 3 H), 0.98 (t, J=7.40 Hz, 3 H). MS (ESI) M/Z: 422 (M+1).

EXAMPLE 35

5-(5-cyclopropyl-2,4-dihydroxyl-phenyl)-N-ethyl-4-(2-methyl-1,2,3,4-tetrahydroisoquinolin-6-yl)isoxazole-3-carboxamide

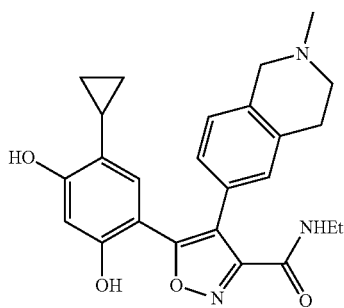

Reaction scheme:

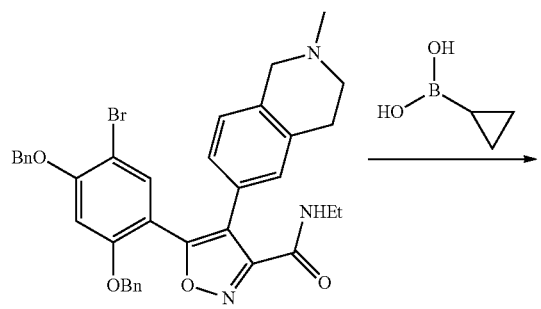

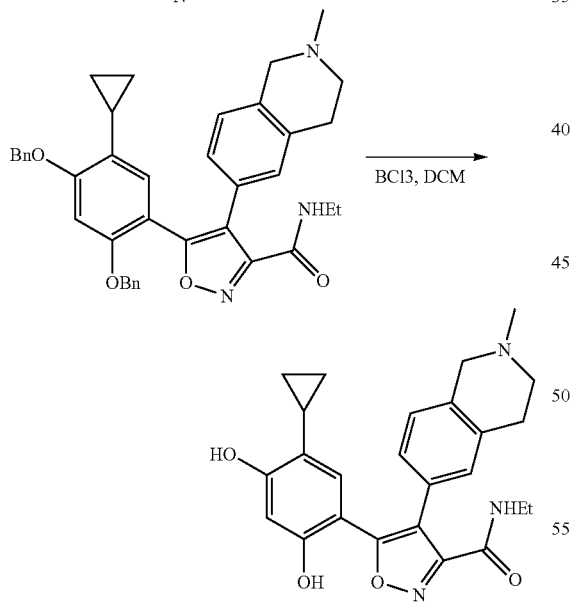

Step A: Cyclopropylboronic acid (217.76 mg, 2.54 mmol, 1.50 eq.), K₃PO₄ (717.47 mg, 3.38 mmol, 2.00 eq.) and Pd(OAc)₂ (75.88 mg, 338.00 μmol, 0.20 eq.) were added to a mixed solution of 5-(2, 4-benzyloxy-5-bromo-phenyl)-N-ethyl-4-(2-methyl-1,2,3,4-tetrahydroisoquinolin-6-yl)-isoxazole-3-carboxamide (1.10 g, 1.69 mmol, 1.00 eq.) dissolved in PhMe (10.00 mL) and H₂O (2.1 mL) at 25° C. under the protection of nitrogen gas. The mixture was stirred at 25° C. for 20 min and then heated to 90° C. with stirring for 12 hours. The mixture was cooled down to 25° C., and the reaction solution was poured into ammonium chloride solution (20 mL), with stirring for 10 min. The aqueous phase was extracted with ethyl acetate (10 mL×L). The combined organic phase was washed with saturated brine (10 mL×L), dried with anhydrous sodium sulfate, filtered and concentrated in vacuum. The residue was purified by a thin layer chromatography plate (dichloromethane:ethyl acetate=100/1 to 10/1) to give 5-(2, 4-benzyloxy-5-cyclopropyl-phenyl)-N-ethyl-4-(2-methyl-1,2,3,4-tetrahydroisoquinolin-6-yl)-isoxazole-3-carboxamide (300.00 mg, 488.81 μmol, 28.92% yield) as a black oil.

Step B: BCl₃/DCM (1.9 mL, 1 mol/L) was added dropwise to a mixed solution of 5-(2,4-benzyloxy-5-cyclopropyl-phenyl)-N-ethyl-4-(2-methyl-1,2,3,4-tetrahydroisoquinolin-6-yl)-isoxazole-3-carboxamide (300 mg, 489 μmol) in dichloromethane (30.00 mL) at 0° C. under the protection of nitrogen gas. The mixture was stirred at 0° C. for 1 hour. The mixture was added dropwise with methanol (4 mL) and concentrated under reduced pressure. The residue was purified by preparative HPLC (formic acid, Column: Phenomenex Synergi Max-RP 250×80 10 μm, Condition: 0.225% FA-ACN) to give 5-(2,4-dihydroxyl-5-cyclopropyl-phenyl)-N-ethyl-4-(2-methyl-1,2,3,4-tetrahydroisoquinolin-6-yl)-isoxazole-3-carboxamide (22 mg, 10% yield). ¹H NMR (DMSO-d₆, 400 MHz) δ: ¹H NMR (400 MHz, DMSO-d₆) δ=8.80-8.86 (m, 1 H), 6.90-7.01 (m, 3 H), 6.51 (s, 1 H), 6.42 (s, 1 H), 3.44 (s, 2 H), 3.16-3.27 (m, 2 H), 2.67-2.76 (m, 3 H), 2.55-2.60 (m, 3 H), 2.32 (s, 3 H), 2.27 (br. s., 1 H), 1.08 (t, J=7.16 Hz, 3 H), 0.70 (d, J=8.29 Hz, 2 H), 0.28 (d, J=4.14 Hz, 2 H). MS (ESI) M/Z: 434 (M+1).

EXAMPLE 36

5-(2,4-dihydroxyl-5-isopropylphenyl)-N-methyl-4-(2-methyl-1,2,3,4-tetrahydroisoquinolin-6-yl)isoxazole-3-carboxamide

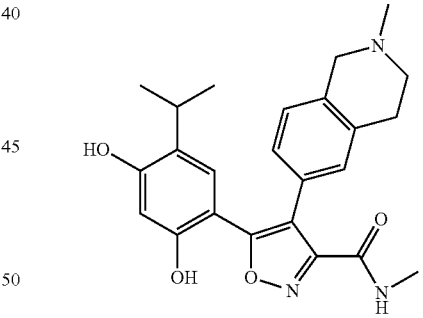

Reaction scheme:

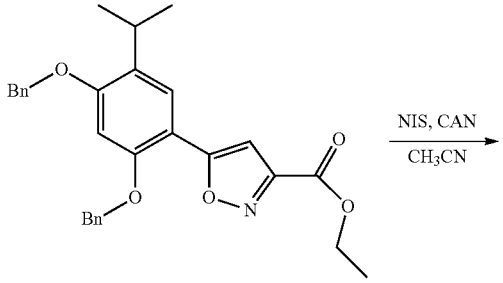

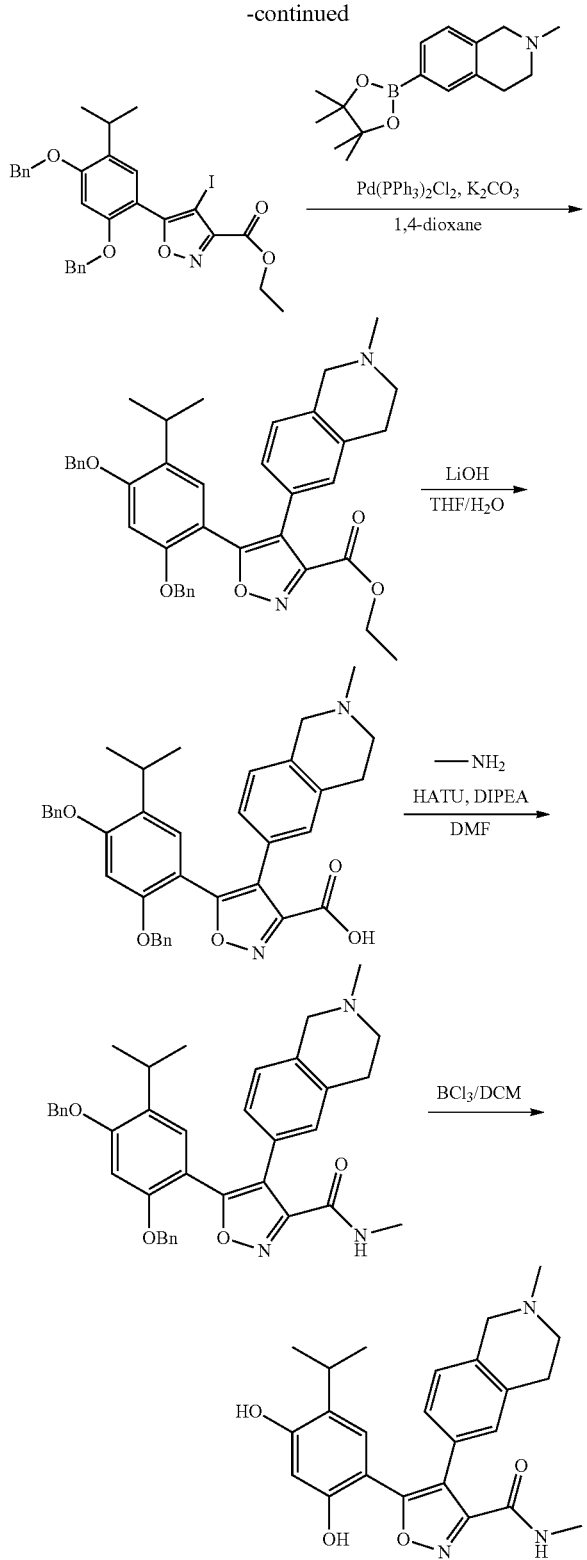

Step A: CAN (465 mg, 848 μmol, 0.1 eq.) and NIS (7.63 g, 34.0 mmol, 4.0 eq.) were added to a solution of ethyl-5-(2,4-dibenzyloxy-5-isopropyl-phenyl)isoxazole-3-formate (4.00 g, 8.5 mmol, 1.0 eq.) in MeCN (50 mL) at room temperature under N₂ protection. The mixture was heated to 90° C. with stirring for 12 hours. The mixture was cooled down to room temperature and poured into water (40 mL), and the aqueous phase was extracted with EA (50 mL×2). The combined organic phase was washed with saturated brine (20 mL×2), dried with anhydrous sodium sulfate, filtered and concentrated in vacuum to dryness. The residue was purified by silica gel chromatography (PE/EA=10/1 to 4/1) to give ethyl-5-(2,4-dibenzyloxy-5-isopropyl-phenyl)-4-iodo-isoxazole-3-carboxylate (3.40 g) as a yellow solid. MS (ESI) M/Z: (M+1).

Step B: NaHCO₃ (1.52 g, 18.0 mmol), H₂O (6.0 mL) and Pd(PPh₃)₄ (1.26 g, 1.80 mmol) were added to a mixed solution of 2-methyl-6-(4,4,5,5-tetramethyl-1,3,2-dioxaborolan-2-yl)-1,2,3,4-tetrahydroisoquinoline (2.47 g, 9.0 mmol) and ethyl-5-(2,4-dibenzyloxy-5-isopropyl-phenyl)-4-iodo-isoxazole-3-carboxylate (2.70 g, 4.5 mmol) in dioxane (30 mL) at 25° C. under the protection of nitrogen gas. The mixture was stirred at 25° C. for 10 min and then heated to 110° C. with stirring for 18 hours. The mixture was cooled down to 25° C. and concentrated under reduced pressure. The residue was purified by silica gel chromatography (200~300 mesh of silica gel, petroleum ether/ethyl acetate, dichloromethane/methanol=5/1, 10/1) to give ethyl-5-(2,4-dibenzyloxy-5-isopropyl-phenyl)-4-(2-methyl-1,2,3,4-tetrahydroisoquinolin-6-yl)isoxazole-3-formate (1.4 g) as a yellow oil. MS (ESI) M/Z: 617 (M+1).

Step C: LiOH (101 mg, 4.2 mmol) was added to a mixed solution of ethyl-5-(2,4-dibenzyloxy-5-isopropyl-phenyl)-4-(2-methyl-1,2,3,4-tetrahydrofluoquinolin-6-yl)isoxazole-3-carboxylate in THF (15 mL)/H₂O (15 mL) at 20° C. The mixture was stirred at 20° C. for 2 hours. The mixture was adjusted to pH 6 with HCl and extracted with EA (30 mL×3). The combined organic phase was dried with anhydrous sodium sulfate, filtered and concentrated in vacuum to dryness. The crude product 5-(2,4-dibenzyloxy-5-isopropyl-phenyl)-4-(2-methyl-1,2,3,4-tetrahydroisoquinolin-6-yl)isoxazole-3-formic acid (1 g) was obtained as a brown solid. MS (ESI) M/Z: 589 (M+1).

Step D: DIPEA (220 mg, 1.7 mmol) and HATU (194 mg, 510 μmol) were added to a solution of 5-(2,4-dibenzyloxy-5-isopropyl-phenyl)-4-(2-methyl-1,2,3,4-tetrahydroisoquinolin-6-yl)isoxazole-3-formic acid (200 mg, 340 μmol) in DMF (5 mL) at 20° C. The mixture was stirred at 20° C. for 0.5 hour. Subsequently, methylamine hydrochloride (30 mg, 441 μmol) was added, and the reaction solution was stirred at 20° C. for 1 hour. To the reaction solution, H₂O (20 mL) was added to precipitate a solid. The solid was collected by filtration, washed with water (5 mL) and dried to give 5-(2,4-dibenzyloxy-5-isopropyl-phenyl)-N-methyl-4-(2-methyl-1,2,3,4-tetrahydroisoquinolin-6-yl)isoxazole-3-carboxamide (120 g) as a yellow solid. MS (ESI) M/Z: 602 (M+1).

Step E: BCl₃ (1 M, 2 mL, 10.0 eq.) was added to a solution of 5-(2,4-dibenzyloxy-5-isopropyl-phenyl)-N-methyl-4-(2-methyl-1,2,3,4-tetrahydroisoquinolin-6-yl)isoxazole-3-carboxamide (120 mg, 199 μmol, 1.0 eq.) in DCM (5 mL) at 0° C. After the mixture was stirred at 20° C. for 12 hours, 5 mL of MeOH was added to quench, and the mixture was concentrated in vacuum to give a crude product. The crude product was purified by preparative HPLC to give 5-(2,4-hydroxyl-5-isopropyl-phenyl)-N-methyl-4-(2-methyl-1,2,3,4-tetraisoquinolin-6-yl)isoxazole-3-carboxamide (38 mg, 34% yield). ¹HNMR (400 MHz, DMSO-d₆) δ 10.75 (s, 1H), 9.85 (s, 1H), 9.72 (s, 1H), 8.81 (s, 1H), 7.14-7.08 (m, 3H), 6.86 (s, 1H), 6.46 (s, 1H), 4.41-4.23 (m, 2H), 3.59 (brs, 1H), 3.04-2.99 (m, 4H), 2.87 (s, 3H), 2.73 (s, 3H), 1.00 (d, J=6.8 Hz, 6H). MS (ESI) M/Z: 422 (M+1).

EXAMPLE 37

5-(2,4-dihydroxyl-5-isopropylphenyl)-N-propyl-4-(2-methyl-1,2,3,4-tetrahydroisoquinolin-6-yl)isoxazole-3-carboxamide

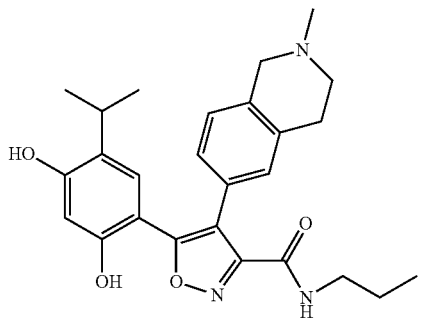 [SMILES: CCCNC(=O)c1noc(-c2cc(C(C)C)c(O)cc2O)c1-c1ccc2c(c1)CCN(C)C2]

Reaction scheme:

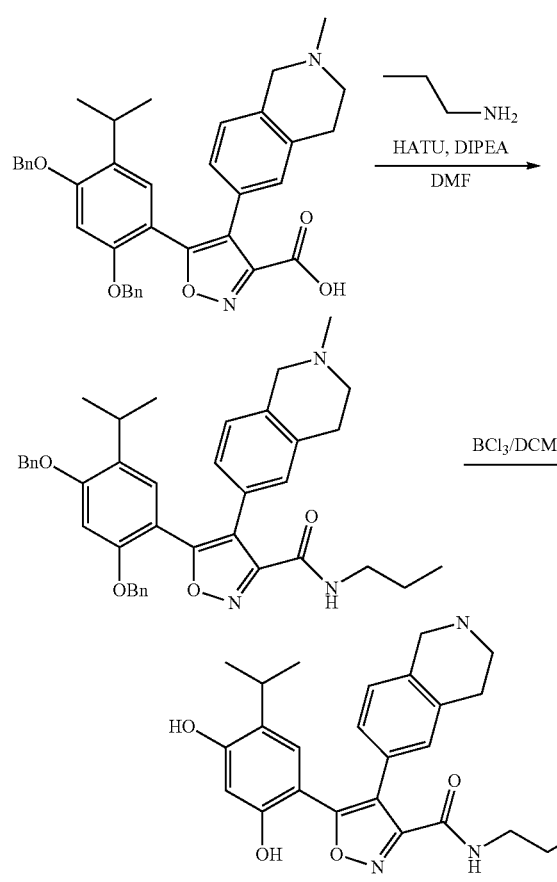

Step A: The title compound of this Example was prepared according to the order of steps D and E in Example 36, wherein methylamine hydrochloride in step D was replaced with propylamine, and the product was a pale yellow solid. $^1$H NMR (400 MHz, DMSO-d$_6$) δ 10.87 (s, 1H), 9.84 (s, 1H), 9.71 (s, 1H), 8.89 (t, J=6.0 Hz, 1H), 7.14-7.08 (m, 3H), 6.88 (s, 1H), 6.48 (s, 1H), 4.45-4.21 (m, 2H), 3.58 (brs, 1H), 3.19-3.14 (m, 4H), 3.05-3.01 (m, 2H), 2.86 (s, 3H), 1.52-1.46 (m, 2H), 1.01 (d, J=6.8 Hz, 6H), 0.86 (t, J=7.2 Hz, 3H). MS (ESI) M/Z: 450 (M+1).

EXAMPLE 38

5-(2,4-dihydroxyl-5-isopropylphenyl)-N-isopropyl-4-(2-methyl-1,2,3,4-tetrahydroisoquinolin-6-yl)isoxazole-3-carboxamide

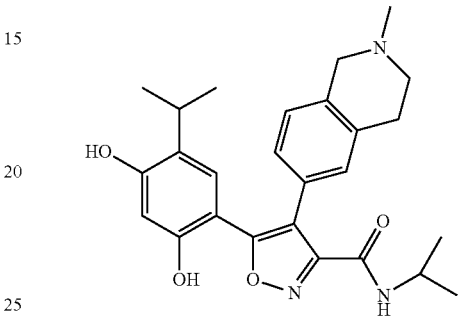

Reaction scheme:

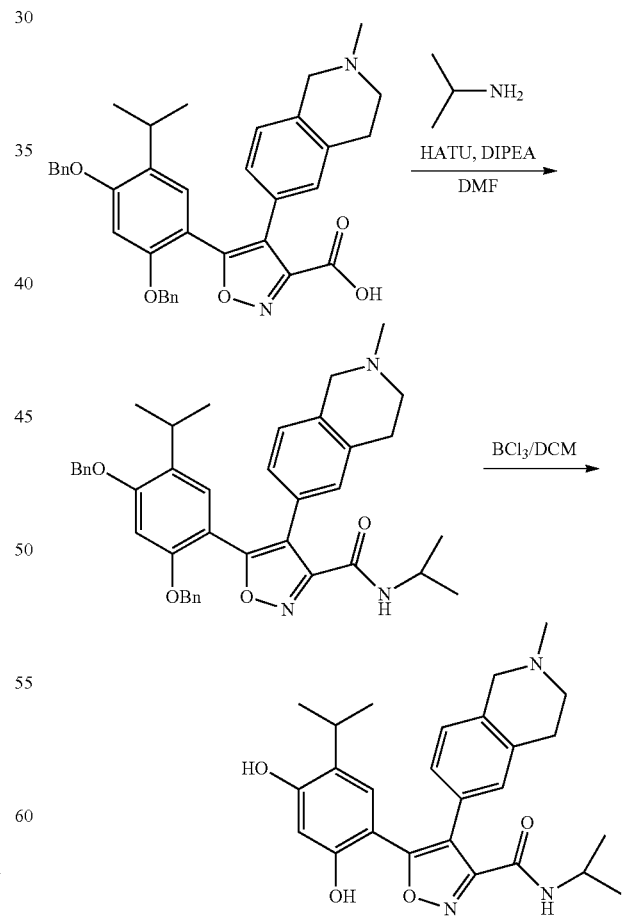

Step A: The title compound of this Example was prepared according to the order of steps D and E in Example 36, wherein methylamine hydrochloride in step D was replaced with propane-2-amine, and the product was a pale yellow solid. $^1$H NMR (400 MHz, DMSO-$d_6$) δ10.41 (s, 1H), 9.80 (s, 1H), 9.66 (s, 1H), 8.81 (d, J=7.6 Hz, 1H), 7.14-7.08 (m, 3H), 6.87 (s, 1H), 6.45 (s, 1H), 4.46-4.24 (m, 2H), 4.01 (q, J=6.8 Hz, 1H), 3.60 (brs, 1H), 3.06-2.99 (m, 2H), 2.89 (brs, 5H), 1.13 (d, J=6.4 Hz, 6 H), 1.01 (d, J=7.2 Hz, 6 H). MS (ESI) M/Z: 450 (M+1).

EXAMPLE 39

5-(2,4-dihydroxyl-5-isopropylphenyl)-N-(2,2, 2-trifluoroethyl)-4-(2-methyl-1,2,3,4-tetrahydroisoquinolin-6-yl)isoxazole-3-carboxamide

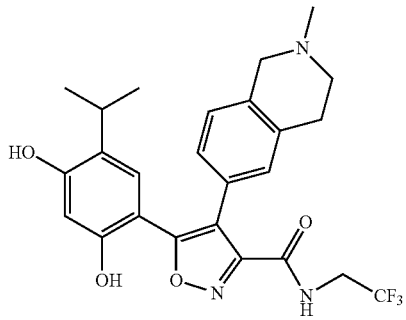 [SMILES: CC(C)c1cc(-c2onc(C(=O)NCC(F)(F)F)c2-c2ccc3c(c2)CCN(C)C3)c(O)cc1O]

Reaction scheme:

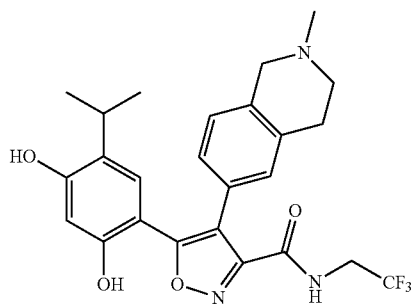

Step A: The title compound of this Example was prepared according to the order of steps D and E in Example 36, wherein methylamine hydrochloride in step D was replaced with 2,2,2-trifluoroethylamine. $^1$H NMR (400 MHz, DMSO-$d_6$) δδ 10.85 (brs, 1H), 9.88 (s, 1H), 9.76 (s, 1H), 9.64 (t, J=6.4 Hz, 1H), 7.11-7.06 (m, 3H), 6.89 (s, 1H), 6.48 (s, 1H), 4.23 (brs, 2H), 4.09-4.05 (m, 2H), 3.04-2.96 (m, 3H), 2.81 (s, 3H), 1.01 (d, J=6.8 Hz, 6 H). MS (ESI) M/Z: 490 (M+1).

EXAMPLE 40

5-(2,4-dihydroxyl-5-isopropylphenyl)-N-(2-fluoroethyl)-4-(2-methyl-1,2,3,4-tetrahydroisoquinolin-6-yl)isoxazole-3-carboxamide

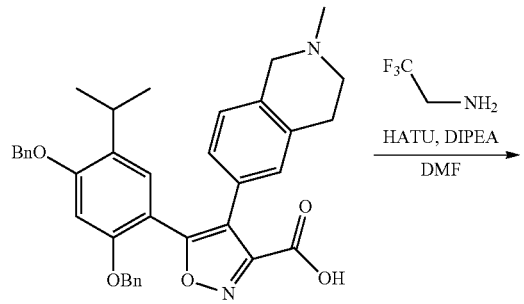

Reaction scheme:

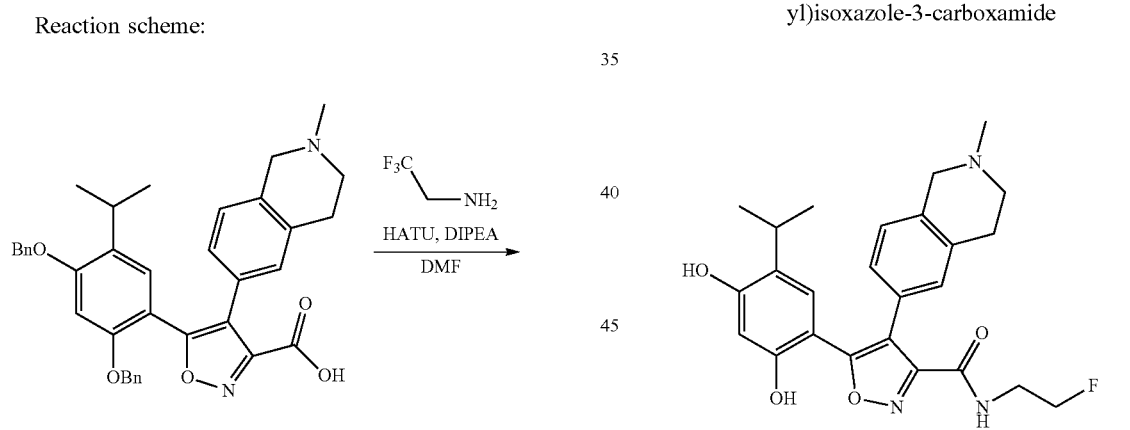

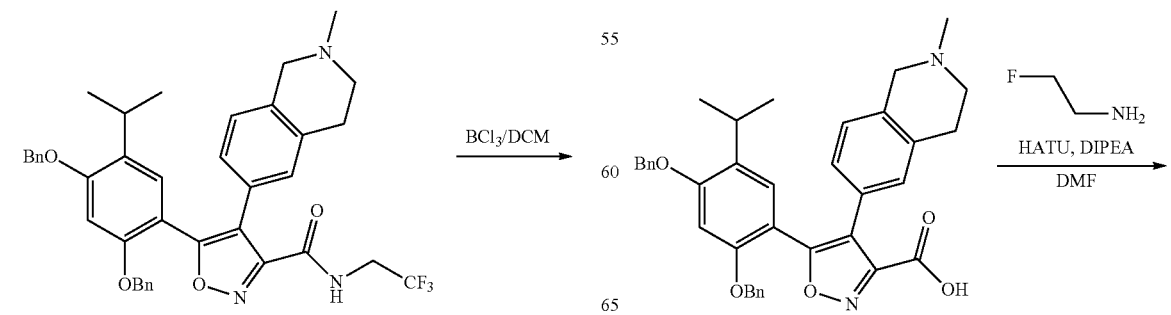

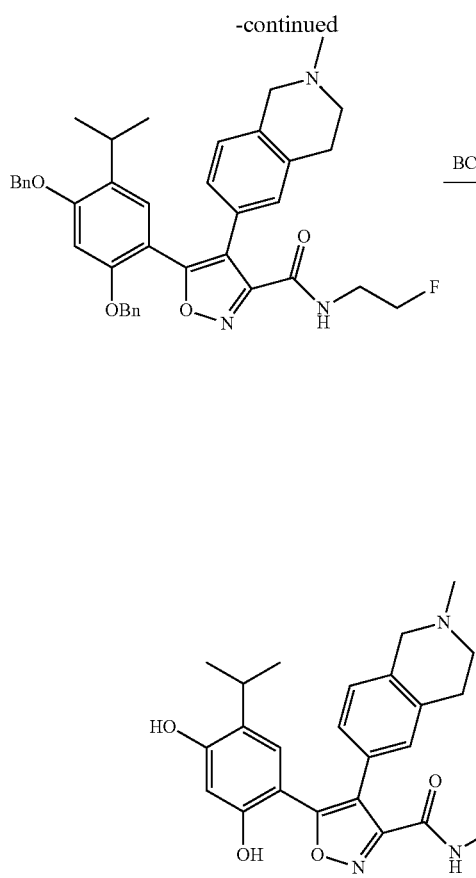

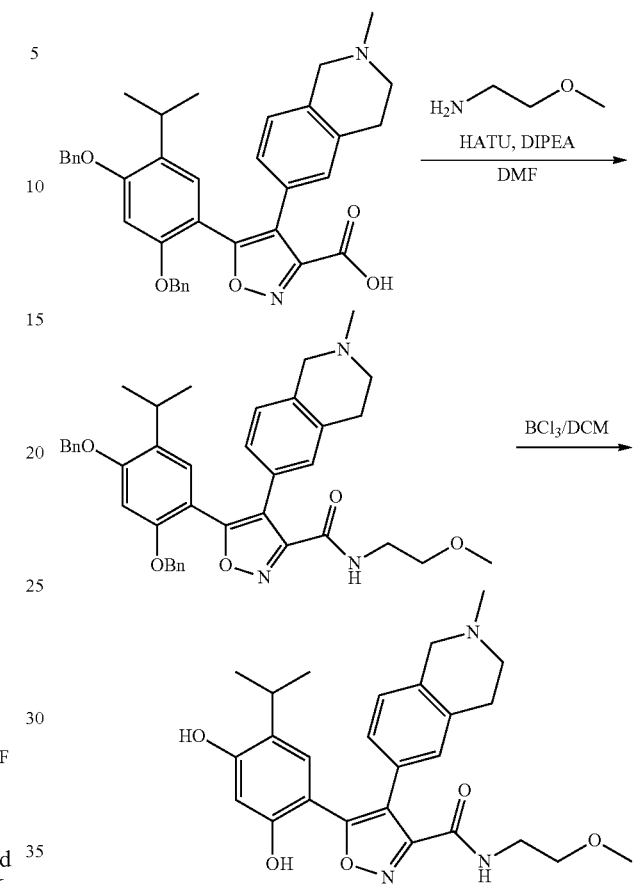

Step A: The title compound of this Example was prepared according to the order of steps D and E in Example 36, wherein methylamine hydrochloride in step D was replaced with 2-fluoroethylamine. $^1$H NMR (400 MHz, DMSO-d$_6$) δ 10.37 (brs, 1H), 9.83 (s, 1H), 9.70 (s, 1H), 9.13 (t, J=5.6 Hz, 1H), 7.15-7.08 (m, 3H), 6.87 (s, 1H), 6.45 (s, 1H), 4.58-4.44 (m, 2H), 4.22 (brs, 1H), 3.56-3.36 (m, 2H), 3.20-3.00 (m, 4H), 2.90 (brs, 5H), 1.00 (d, J=6.8 Hz, 6 H). MS (ESI) M/Z: 454 (M+1).

EXAMPLE 41

5-(2,4-dihydroxyl-5-isopropylphenyl)-N-(2-methoxyethyl)-4-(2-methyl-1,2,3,4-tetrahydroisoquinolin-6-yl)isoxazole-3-carboxamide

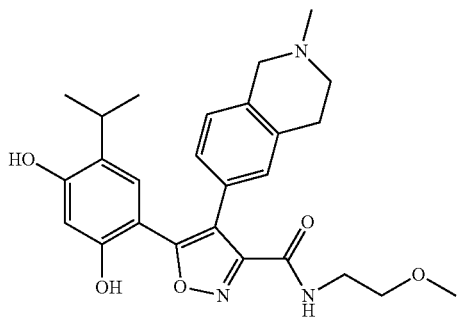 [SMILES: COCCNC(=O)c1noc(-c2cc(C(C)C)c(O)cc2O)c1-c1ccc2c(c1)CCN(C)C2]

Step A: The title compound of this Example was prepared according to the order of steps D and E in Example 36, wherein methylamine hydrochloride in step D was replaced with 2-methoxyethylamine. $^1$H NMR (400 MHz, DMSO-d$_6$) δ10.55 (brs, 1H), 9.84 (s, 1H), 9.71 (s, 1H), 8.92 (t, J=5.6 Hz, 1H), 7.14-7.10 (m, 3H), 6.87 (s, 1H), 6.46 (s, 1H), 4.28 (brs, 3H), 3.44-3.37 (m, 6H), 3.26 (s, 3H), 3.03-2.98 (m, 2H), 2.87 (s, 3H), 1.00 (d, J=6.8 Hz, 6 H). MS (ESI) M/Z: 466 (M+1).

EXAMPLE 42

5-(2,4-dihydroxyl-5-isopropylphenyl)-N-(3-methoxypropyl)-4-(2-methyl-1,2,3,4-tetrahydroisoquinolin-6-yl)isoxazole-3-carboxamide

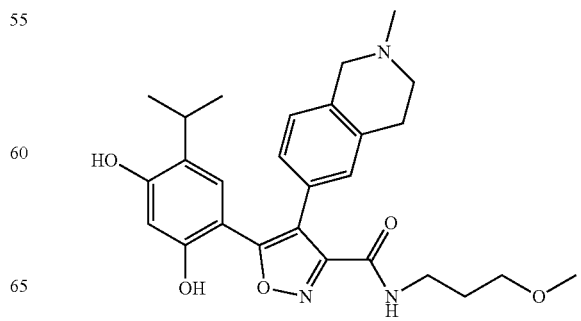

Reaction scheme:

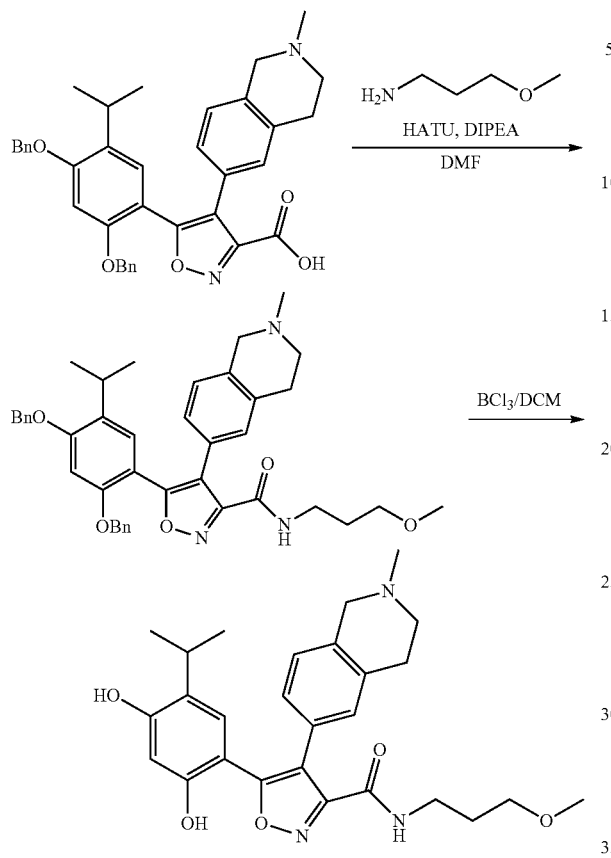

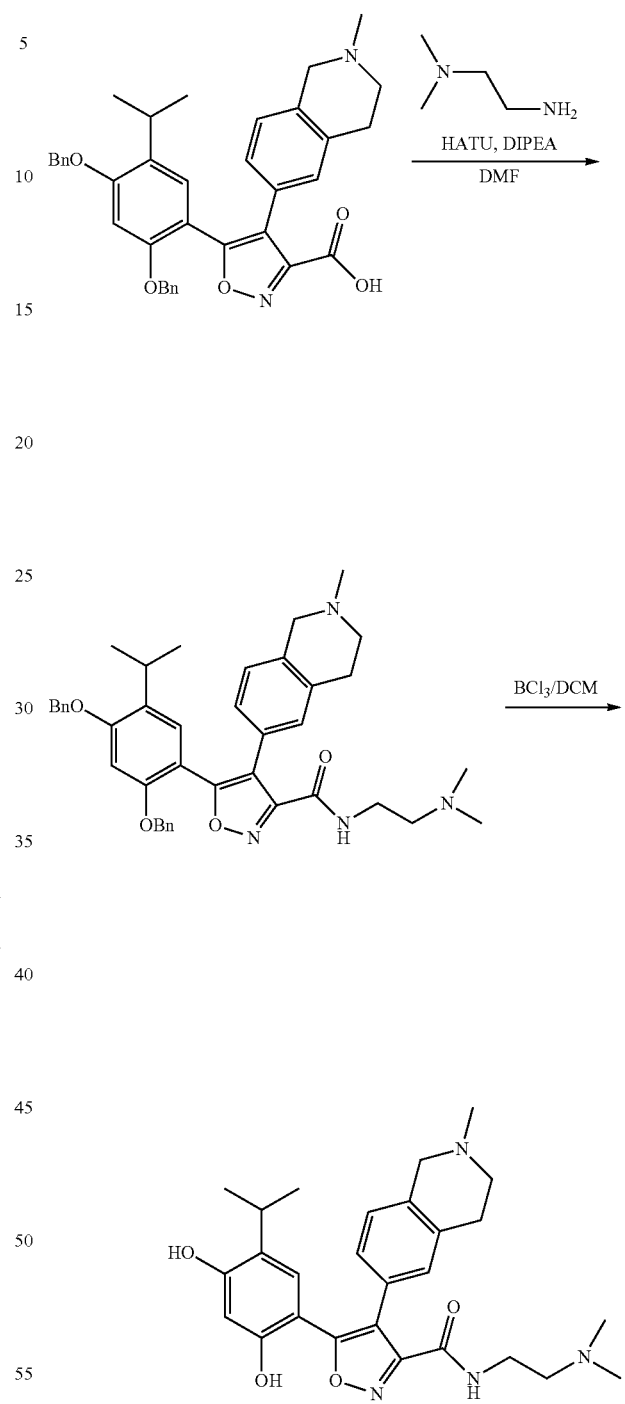

Step A: The title compound of this Example was prepared according to the order of steps D and E in Example 36, wherein methylamine hydrochloride in step D was replaced with 3-methoxypropan-1-amine. $^1$H NMR (400 MHz, DMSO-d$_6$) δ 10.77 (brs, 1H), 9.83 (s, 1H), 9.71 (s, 1H), 8.89 (t, J=5.6 Hz, 1H), 7.14-7.08 (m, 3H), 6.87 (s, 1H), 6.47 (s, 1H), 4.45-4.20 (m, 2H), 3.58 (brs, 1H), 3.32-3.21 (m, 7H), 3.19-2.99 (m, 3H), 2.87 (brs, 4H), 1.72-1.69 (m, 2H), 1.01 (d, J=6.8 Hz, 6 H). MS (ESI) M/Z: 480 (M+1).

EXAMPLE 43

5-(2,4-dihydroxyl-5-isopropylphenyl)-N-[2-(dimethylamino)ethyl]-4-(2-methyl-1,2,3,4-tetrahydroisoquinolin-6-yl)isoxazole-3-carboxamide

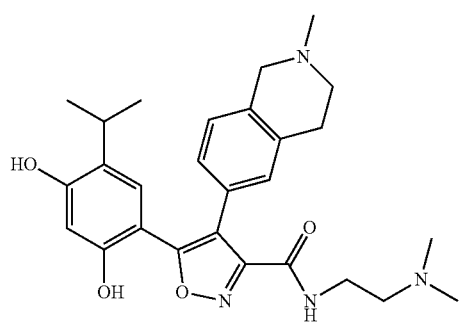 [SMILES: CC(C)c1cc(-c2onc(C(=O)NCCN(C)C)c2-c2ccc3c(c2)CCN(C)C3)c(O)cc1O]

Step A: The title compound of this Example was prepared according to the order of steps D and E in Example 36, wherein the methylamine hydrochloride in step D was replaced with N',N'-dimethylethane-1,2-diamine. $^1$H NMR (400 MHz, DMSO-d$_6$) δ 9.83 (s, 1H), 9.72 (s, 1H), 9.05 (t, J=5.6 Hz, 1H), 7.17-7.09 (m, 3H), 6.84 (s, 1H), 6.46 (s, 1H), 4.24 (brs, 2H), 3.59-3.58 (m, 3H), 3.19 (brs, 4H), 3.02-2.99 (m, 2H), 2.85 (s, 3H), 2.77 (s, 6H), 0.99 (d, J=6.8 Hz, 6 H). MS (ESI) M/Z: 479 (M+1), 240 (M/2+1).

EXAMPLE 44
5-(2,4-dihydroxyl-5-isopropylphenyl)-N-ethyl-4-(2-(2-hydroxyethyl)-1,2,3,4-tetrahydroisoquinolin-6-yl)isoxazole-3-carboxamide
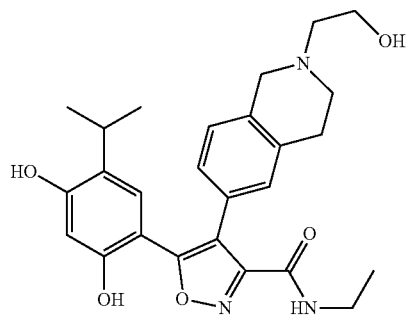 [SMILES: CCNC(=O)c1noc(-c2cc(C(C)C)c(O)cc2O)c1-c1ccc2c(c1)CCN(CCO)C2]
Reaction scheme:
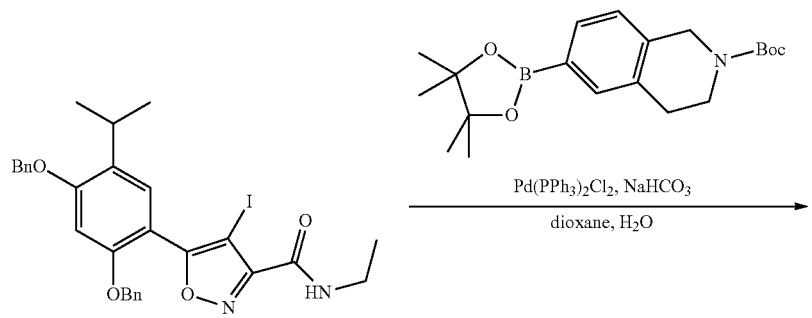
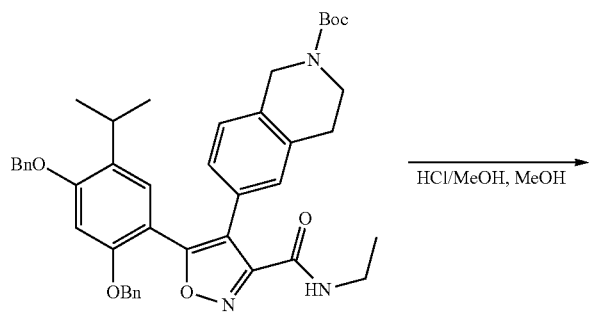
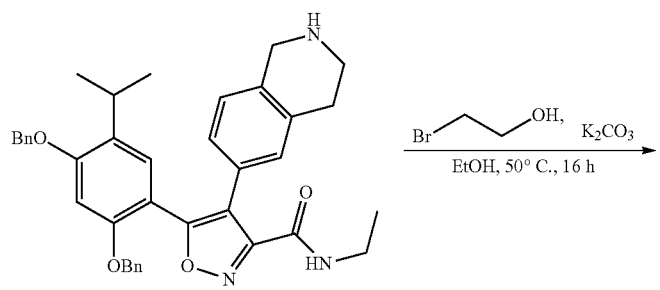

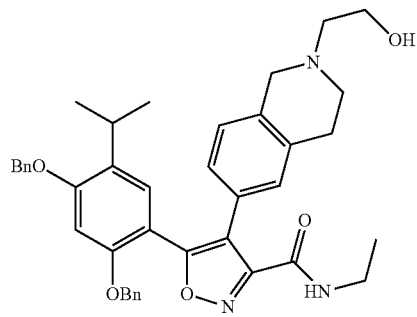 → 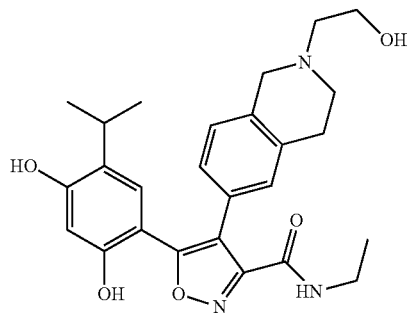

BCl₃
DCM, r.t, 16 h

Step A: t-Butyl-6-(4,4,5,5-tetramethyl-1, 3,2-dioxaborolan-2-yl)-1,2,3,4-tetrahydroisoquinoline-2-formate (4.00 g, 11.1 mmol, 1.6 eq.), ethyl 5-(2,4-dibenzyloxy-5-isopropyl-phenyl)-4-iodo-isoxazole-3-carboxylate (4.10 g, 6.9 mmol, 1.0 eq.), Pd(PPh₃)₂Cl₂ (723 mg, 1.0 mmol, 0.15 eq.) and NaHCO₃ (2.31 g, 27.5 mmol, 4.0 eq.) were added to a mixed solution of dioxane (40 mL) and water (8 mL) under the protection of nitrogen gas. The mixture was heated to 80° C. with stirring for 16 hours under N₂ protection. After cooling, the reaction mixture was poured into water (50 mL) and extracted with ethyl acetate (40 mL×3). The organic phase was washed with saturated brine (50 mL), dried over anhydrous Na₂SO₄ and concentrated in vacuum to give a residue. The residue was purified by silica gel chromatography (petroleum ether/ethyl acetate=50/1 to 3/1) to give t-butyl 6-[5-(2,4-dibenzyloxy-5-isopropyl-phenyl)-3-(ethylcarbamoyl)isoxazol-4-yl]-(3,4-dihydroisoquinoline)-2(1H)-formate (4.8 g, 6.8 mmol, 99% yield) as a yellow solid. MS: [M-56]=646.

Step B: A mixture of t-butyl 6-[5-(2,4-dibenzyloxy-5-isopropyl-phenyl)-3-(ethylcarbamoyl)isoxazol-4-yl]-(3,4-dihydroisoquinoline)-2(1H)-formate (750 mg, 1.07 mmol, 1.00 eq.) in HCl/MeOH (4 M, 6.00 mL) was stirred at 25° C. for 30 min. The mixture was concentrated at 40° C. to give the product 5-(2,4-dibenzyloxy-5-isopropyl-phenyl)-N-ethyl-4-(1,2,3,4-tetrahydroisoquinolin-6-yl)isoxazole-3-carboxamide (630 mg, 1.07 mmol, 98% yield) as a yellow solid.

Step C: 5-(2,4-Dibenzyloxy-5-isopropyl-phenyl)-N-ethyl-4-(1,2,3,4-tetrahydroisoquinolin-6-yl)isoxazole-3-carboxamide (4.00 g, 382 µmol, 1.0 eq.), K₂CO₃ (158 mg, 1.2 mmol, 3.0 eq.) and 2-bromoethanol (72 mg, 570 µmol, 1.5 eq.) were added to ethanol (5 mL). The mixture was heated to 50° C. with stirring for 12 hours. After cooling, the reaction mixture was concentrated to dryness, added with water (10 mL) and extracted with ethyl acetate (10 mL×2). The organic phase was washed with saturated brine (20 mL), dried over anhydrous Na₂SO₄ and concentrated in vacuum to give a residue. The residue was purified by silica gel chromatography (dichloromethane/methanol=50/1 to 15/1) to give 5-(2,4-dibenzyloxy-5-isopropyl-phenyl)-N-ethyl-4-[2-(2-hydroxyethyl)-(1,2,3,4-tetrahydroisoquinolin-6-yl)]isoxazole-3-carboxamide (132 mg, 204 µmol, 53% yield) as a white solid. MS: [M+1]=646.3.

Step D: A solution of BCl₃ in DCM (1 M, 2.0 mL, 10.0 eq.) was added dropwise to a solution of 5-(2,4-dibenzyloxy-5-isopropyl-phenyl)-N-ethyl-4-[2-(2-hydroxyethyl)-(1,2,3,4-tetrahydroisoquinolin-6-yl)]isoxazole-3-carboxamide (132 mg, 204 µmol, 1.0 eq.) in DCM (5.0 mL) at 0° C. over a course of 5 min. The suspension was stirred at 0° C. for 30 min, and then heated to 25° C. with stirring for 2 hours. The mixture was cooled down to 0° C., quenched by slowly adding MeOH (1 mL) and concentrated in vacuum to give a residue. The residue was purified by preparative HPLC to give 5-(2,4-dihydroxyl-5-isopropyl-phenyl)-N-ethyl-4-[2-(2-hydroxyethyl)-(1,2,3,4-tetrahydroisoquinolin-6-yl)]isoxazole-3-carboxamide (51 mg, 110 µmol, 53.6% yield). ¹H NMR (400 MHz, DMSO-d₆) δ=8.85 (t, J=5.52 Hz, 1 H), 8.21 (s, 1 H), 6.94-7.01 (m, 3 H), 6.86 (s, 1 H), 6.42 (s, 1 H), 3.54-3.60 (m, 4 H), 3.24 (dd, J=13.18, 6.90 Hz, 5 H), 3.02 (dt, J=13.80, 6.90 Hz, 2 H), 2.68 (br. s., 4 H), 2.34 (br. s., 1 H), 1.09 (t, J=7.15 Hz, 3 H), 1.00 (d, J=6.78 Hz, 6 H). MS (ESI) M/Z: 466 (M+1).

EXAMPLE 45

5-(2,4-dihydroxyl-5-isopropylphenyl)-N-ethyl-4-(2-(2-methoxyethyl)-1,2,3,4-tetrahydroisoquinolin-6-yl)isoxazole-3-carboxamide

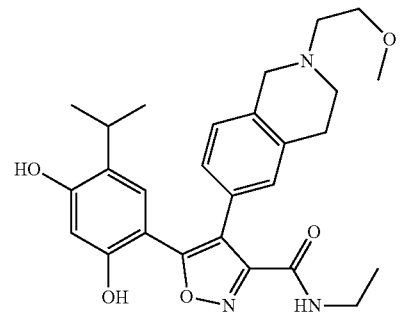 [SMILES: CCNC(=O)c1noc(-c2cc(C(C)C)c(O)cc2O)c1-c1ccc2c(c1)CCN(CCOC)C2]

Reaction scheme:

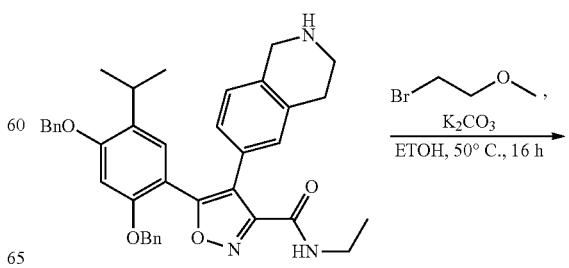

Br⁓⁓O⁓,
K₂CO₃
ETOH, 50° C., 16 h

145

-continued

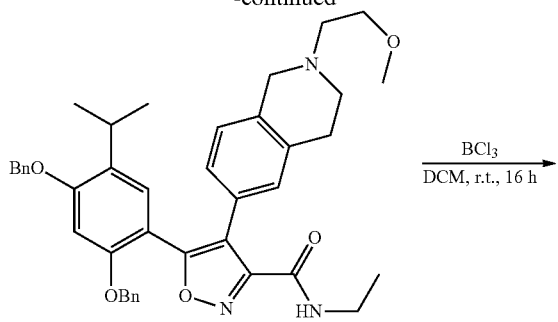

Step A: The title compound of this Example was prepared according to the order of steps C and D in Example 44, wherein 2-bromoethanol in step C was replaced with 1-bromo-2-methoxyethane. ¹H NMR (400 MHz, DMSO-d₆) δ=10.59 (br. s., 1 H), 9.85 (s, 1 H), 9.71 (s, 1 H), 8.91 (t, J=5.65 Hz, 1 H), 7.05-7.20 (m, 3 H), 6.83-6.93 (m, 1 H), 6.48 (s, 1 H), 4.43-4.52 (m, 1 H), 4.26-4.36 (m, 1 H), 3.63-3.83 (m, 3 H), 3.38-3.44 (m, 2 H), 3.32 (s, 4 H), 3.23 (quin, J=6.78 Hz, 2 H), 3.08-3.18 (m, 1 H), 3.02 (dt, J=13.74, 6.81 Hz, 1 H), 2.84-2.95 (m, 1 H), 1.09 (t, J=7.15 Hz, 3 H), 1.01 (d, J=6.78 Hz, 6 H). MS (ESI) M/Z: 480 (M+1).

EXAMPLE 46

5-(2,4-dihydroxyl-5-isopropylphenyl)-N-ethyl-4-(2-(2-fluoroethyl)-1,2,3,4-tetrahydroisoquinolin-6-yl)isoxazole-3-carboxamide

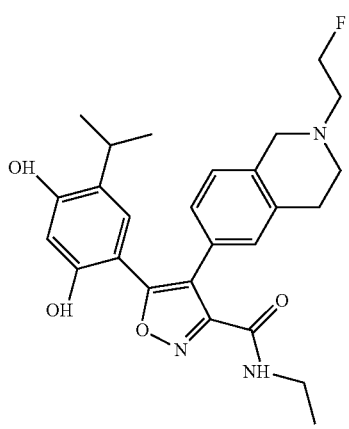 [SMILES: CCNC(=O)c1noc(-c2cc(C(C)C)c(O)cc2O)c1-c1ccc2c(c1)CCN(CCF)C2]

146

Reaction scheme:

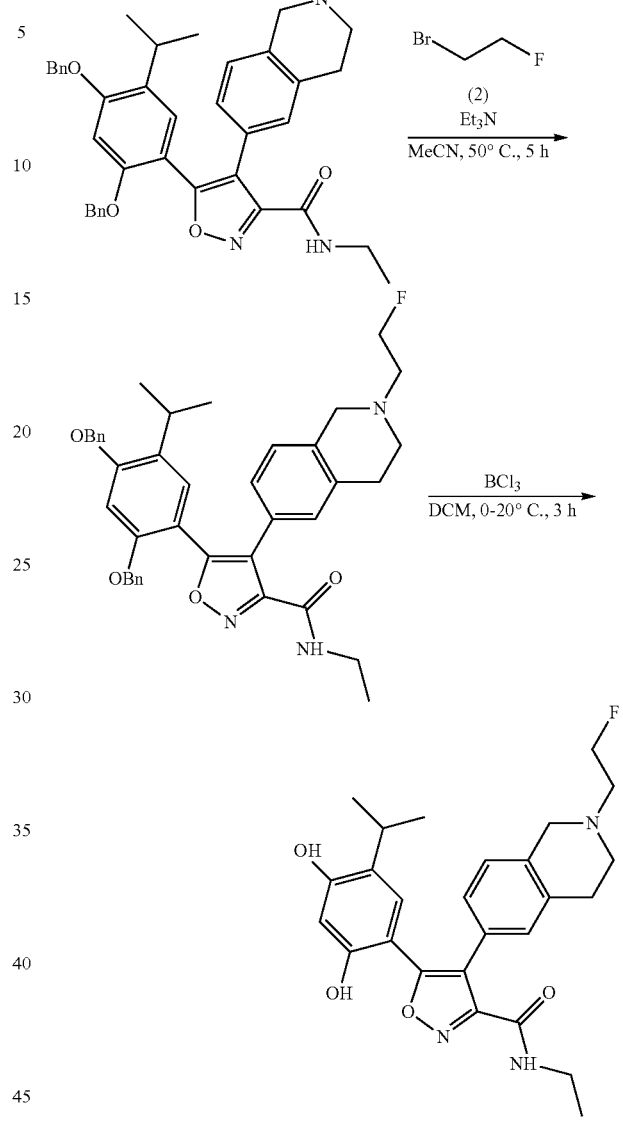

Step A: 5-(2,4-Dibenzyloxy-5-isopropyl-phenyl)-N-ethyl-4-(1,2,3,4-tetrahydroisoquinolin-6-yl)isoxazole-3-carboxamide (150 mg, 250 µmol, 1.0 eq.), triethylamine (63 mg, 623 µmol, 2.5 eq) and 1-bromo-2-fluoroethane (44 mg, 350 µmol, 1.4 eq) were added to acetonitrile (3 mL). The mixture was heated to 50° C. with stirring for 5 hours. After cooling, the reaction mixture was concentrated in vacuum to give a residue. The residue was purified by preparative TLC to give 5-(2,4-dibenzyloxy-5-isopropyl-phenyl)-N-ethyl-4-[2-(2-fluoroethyl)-(1,2,3,4-tetrahydroisoquinolin-6-yl)]isoxazole-3-carboxamide (120 mg, 185 µmol, 74% yield) as a yellow solid. MS: [M+1]=646.3.

Step B: A solution of BCl₃ in DCM (1 M, 1.9 mL, 10.0 eq.) were added dropwise to a solution of 5-(2,4-dibenzyloxy-5-isopropyl-phenyl)-N-ethyl-4-[2-(2-fluoroethyl)-(1,2,3,4-tetrahydroisoquinolin-6-yl)]isoxazole-3-carboxamide (120 mg, 185 µmol, 1.0 eq.) in DCM (8.0 mL) at 0° C. over a course of 5 min. The suspension was stirred at 0° C. for 30 min, and then heated to 25° C. with stirring for 2 hours. The mixture was cooled down to 0° C., quenched by slowly adding MeOH (4 mL) and concentrated in vacuum to give a residue. The residue was purified by preparative HPLC to give 5-(2,4-dihydroxyl-5-isopropyl-phenyl)-N-ethyl-4-[2-(2-fluoroethyl)-(1,2,3,4-tetrahydroisoquinolin-6-yl)]isoxazole-3-carboxamide (48 mg, 96 μmol, 52% yield). $^1$H NMR (400 MHz, DMSO-$d_6$) ppm: 1.01 (d, J=6.90 Hz, 6 H); 1.08 (t, J=7.22 Hz, 3 H); 2.91 (d, J=15.69 Hz, 1 H); 3.01 (dt, J=13.77, 6.85 Hz, 1 H); 3.08-3.28 (m, 3 H); 3.37-3.41 (m, 1 H); 3.49-3.82 (m, 3 H); 4.24-4.62 (m, 2 H); 4.79-5.10 (m, 2 H); 6.46 (s, 1 H); 6.88 (s, 1 H); 7.05-7.19 (m, 3 H); 8.91 (t, J=5.65 Hz, 1 H); 9.70 (s, 1 H); 9.83 (s, 1 H); 11.01 (br. s., 1 H). MS (ESI) M/Z: 468 (M+1).

EXAMPLE 47

5-(2,4-dihydroxyl-5-isopropylphenyl)-N-ethyl-4-(2-(3-methoxypropyl)-1,2,3,4-tetrahydroisoquinolin-6-yl)isoxazole-3-carboxamide

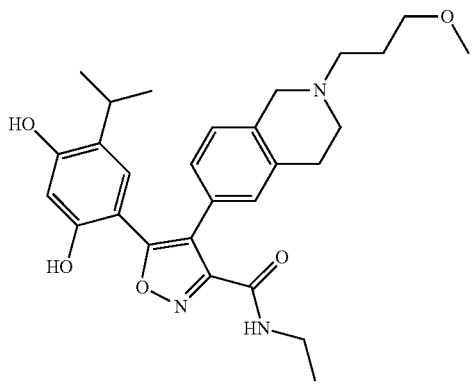 [SMILES: CCNC(=O)c1noc(-c2cc(C(C)C)c(O)cc2O)c1-c1ccc2c(c1)CCN(CCCOC)C2]

Reaction scheme:

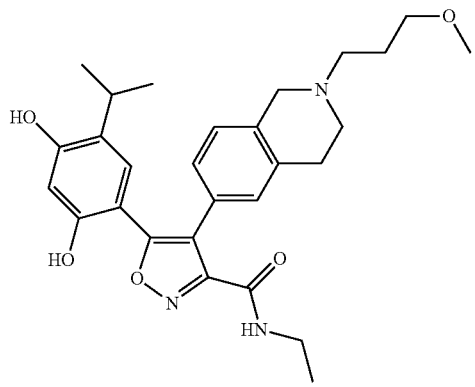

Step A: The title compound of this Example was prepared according to the order of steps A and B in Example 46, wherein 1-bromo-2-fluoroethane was replaced with 1-bromo-3-methoxypropane, and triethylamine was replaced with cesium carbonate in step A. $^1$H NMR (400 MHz, DMSO-$d_6$) ppm: 1.01 (d, J=6.90 Hz, 6 H); 1.09 (t, J=7.15 Hz, 3 H); 1.96-2.08 (m, 2 H); 2.89 (d, J=17.32 Hz, 1 H); 2.97-3.17 (m, 2 H); 3.19-3.27 (m, 8 H); 3.41 (t, J=5.90 Hz, 3 H); 3.67 (d, J=10.67 Hz, 1 H); 4.25 (dd, J=15.56, 8.03 Hz, 1 H); 4.50 (d, J=15.18 Hz, 1 H); 6.47 (s, 1 H); 6.88 (s, 1 H); 7.07-7.18 (m, 3 H); 8.91 (t, J=5.65 Hz, 1 H); 9.70 (s, 1 H); 9.83 (s, 1 H); 10.53 (br. s., 1 H). MS (ESI) M/Z: 494 (M+1).

EXAMPLE 48

5-(2,4-dihydroxyl-5-isopropylphenyl)-N-ethyl-4-(2-(2-ethylsulfonyl)ethyl-1,2,3,4-tetrahydroisoquinolin-6-yl)isoxazole-3-carboxamide

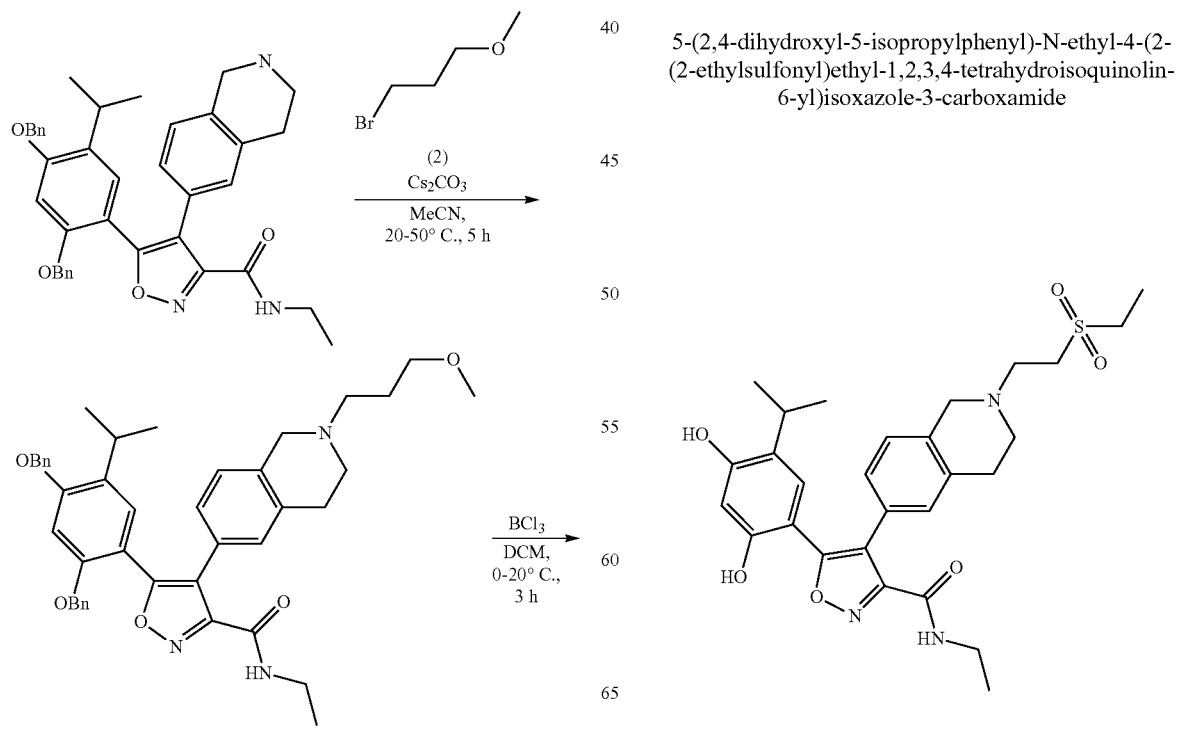

Reaction scheme:

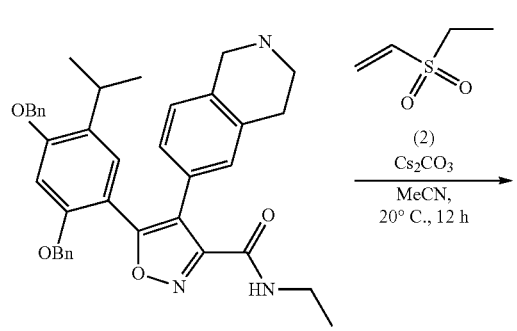

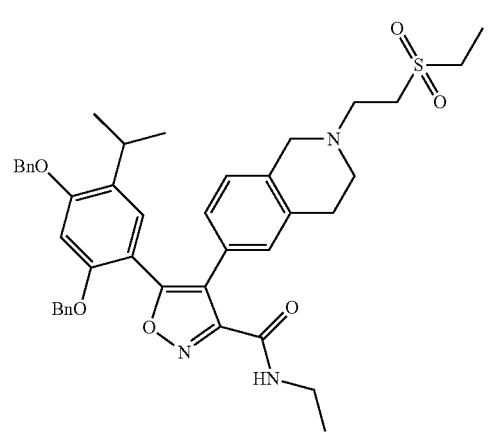

Step A: The title compound of this Example was prepared according to the order of steps A and B in Example 46, wherein 1-bromo-2-fluoroethane was replaced with 1-vinyl-sulfonylethane in step A. $^1$H NMR (400 MHz, DMSO-$d_6$) ppm: 0.96-1.13 (m, 9 H); 1.28 (t, J=7.44 Hz, 3 H); 2.86-3.16 (m, 3 H); 3.16-3.31 (m, 5 H); 3.52-3.97 (m, 5 H); 4.18-4.72 (m, 2 H); 6.46 (s, 1 H); 6.89 (s, 1 H); 7.04-7.20 (m, 3 H); 8.91 (t, J=5.65 Hz, 1 H); 9.60-9.94 (m, 2 H); 11.20 (br. s., 1 H). MS (ESI) M/Z: 542 (M+1).

EXAMPLE 49

5-(2,4-dihydroxyl-5-isopropylphenyl)-N-ethyl-4-(2-ethyl-1,2,3,4-tetrahydroisoquinolin-6-yl)isoxazole-3-carboxamide

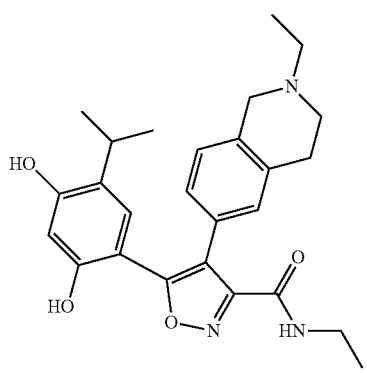 [SMILES: CCNC(=O)c1noc(-c2cc(C(C)C)c(O)cc2O)c1-c1ccc2c(c1)CCN(CC)C2]

Reaction scheme:

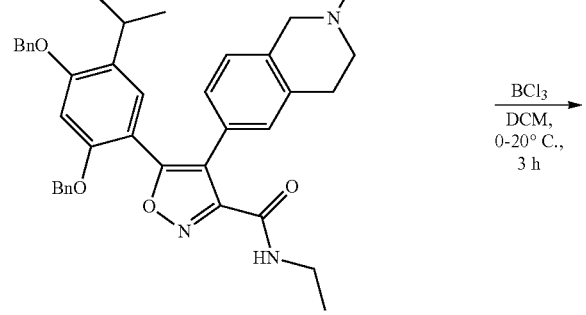

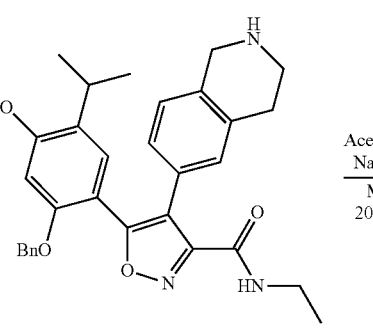

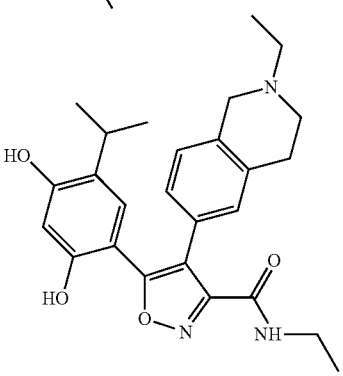

Step A: Acetaldehyde (274 mg, 433.3 µmol, 10.00 eq.), acetic acid (1.3 mg, 21.7 µmol, 0.50 eq.) and titanium tetraisopropoxide (6.2 mg, 2.5 mmol, 10 eq.) were added to a solution of 5-(2,4-dibenzyloxy-5-isopropyl-phenyl)-N-ethyl-4-(1,2,3,4-tetrahydroisoquinolin-6-yl)isoxazole-3-carboxamide (150 mg, 250 µmol, 1.0 eq.) in methanol (3 mL). After the mixture was stirred at 30° C. for 0.5 hour, NaBH$_3$CN (78 mg, 1.3 mmol, 5.0 eq.) was added, and the mixture was stirred for an additional 12 hours. The reaction solution was added with water (10 mL) and filtered, and the filtrate was extracted with DCM (10 mL×3). The organic layers were combined, washed with brine (5 mL×2), dried with anhydrous sodium sulfate, filtered and concentrated in vacuum. The residue was purified by preparative TLC to give 5-(2,4-dibenzyloxy-5-isopropyl-phenyl)-N-ethyl-4-(2-ethyl-1,2,3,4-tetrahydroisoquinolin-6-yl)isoxazole-3-carboxamide (60 mg, 95 µmol, 38% yield) as a colorless oil.

Step B: A solution of BCl$_3$ in DCM (1 M, 1.0 mL, 10.0 eq.) was added dropwise to a solution of 5-(2,4-dibenzyloxy-5-isopropyl-phenyl)-N-ethyl-4-(2-ethyl-1,2,3,4-tetrahydroisoquinolin-6-yl)isoxazole-3-carboxamide (60 mg, 95 µmol, 1.0 eq.) in anhydrous DCM (8 mL) at 0° C. over a course of 5 min. The suspension was stirred at 0° C. for 30 min, and then heated to 25° C. with stirring for 2 hours. The mixture was cooled down to 0° C., quenched by slowly adding MeOH (2 mL) and concentrated in vacuum to give a residue. The residue was purified by preparative HPLC to give 5-(2,4-dihydroxyl-5-isopropyl-phenyl)-N-ethyl-4-(2-ethyl-1,2,3,4-tetrahydroisoquinolin-6-yl)isoxazole-3-carboxamide (15 mg, 30 µmol, 32% yield). $^1$H NMR (400 MHz, DMSO-d$_6$) ppm: 1.02 (d, J=6.90 Hz, 6 H); 1.09 (t, J=7.15 Hz, 3 H); 1.32 (t, J=7.22 Hz, 3 H); 2.89 (d, J=17.07 Hz, 1 H); 3.03 (dt, J=13.71, 6.89 Hz, 1 H); 3.08-3.29 (m, 7 H); 3.65 (d, J=11.17 Hz, 1 H); 4.22 (dd, J=15.31, 8.16 Hz, 1 H); 4.48 (d, J=15.06 Hz, 1 H); 6.48 (s, 1 H); 6.89 (s, 1 H); 7.06-7.18 (m, 3 H); 8.91 (t, J=5.71 Hz, 1 H); 9.71 (s, 1 H); 9.85 (s, 1H); 10.61 (br. s., 1H). MS (ESI) M/Z: 450 (M+1).

EXAMPLE 50

5-(2,4-dihydroxyl-5-isopropylphenyl)-N-ethyl-4-(2-propyl-1,2,3,4-tetrahydroisoquinolin-6-yl)isoxazole-3-carboxamide

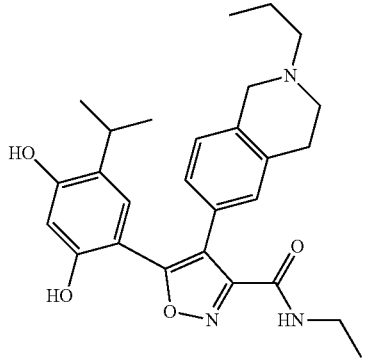 [SMILES: CCCN1CCc2cc(-c3c(C(=O)NCC)noc3-c3cc(C(C)C)c(O)cc3O)ccc2C1]

Reaction scheme:

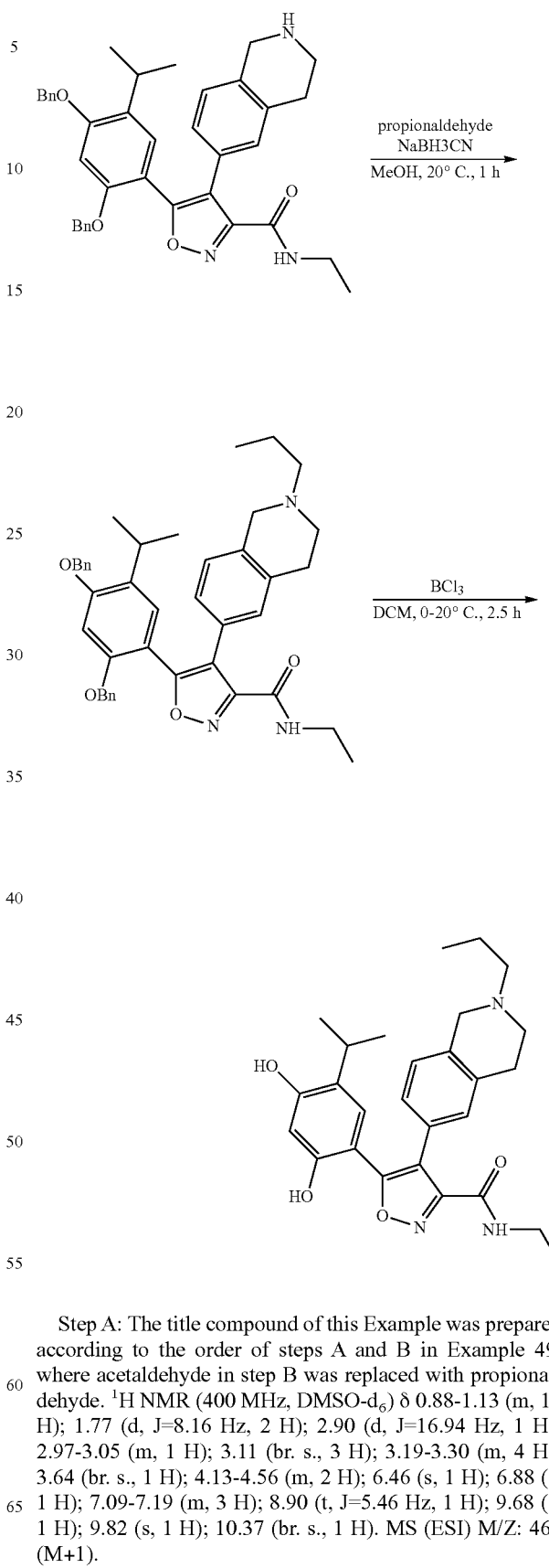

Step A: The title compound of this Example was prepared according to the order of steps A and B in Example 49, where acetaldehyde in step B was replaced with propionaldehyde. $^1$H NMR (400 MHz, DMSO-d$_6$) δ 0.88-1.13 (m, 12 H); 1.77 (d, J=8.16 Hz, 2 H); 2.90 (d, J=16.94 Hz, 1 H); 2.97-3.05 (m, 1 H); 3.11 (br. s., 3 H); 3.19-3.30 (m, 4 H); 3.64 (br. s., 1 H); 4.13-4.56 (m, 2 H); 6.46 (s, 1 H); 6.88 (s, 1 H); 7.09-7.19 (m, 3 H); 8.90 (t, J=5.46 Hz, 1 H); 9.68 (s, 1 H); 9.82 (s, 1 H); 10.37 (br. s., 1 H). MS (ESI) M/Z: 464 (M+1).

EXAMPLE 51

5-(2,4-dihydroxyl-5-isopropylphenyl)-N-ethyl-4-(2-isopropyl-1,2,3,4-tetrahydroisoquinolin-6-yl)isoxazole-3-carboxamide

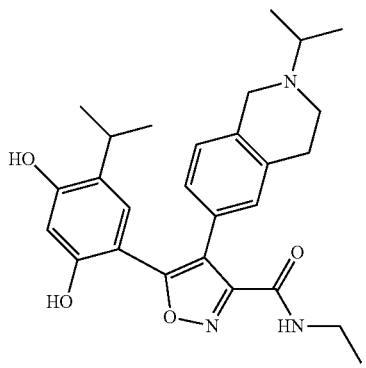 [SMILES: CCNC(=O)c1noc(-c2cc(C(C)C)c(O)cc2O)c1-c1ccc2c(c1)CCN(C(C)C)C2]

Reaction scheme:

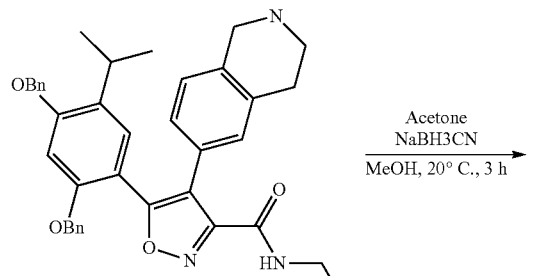

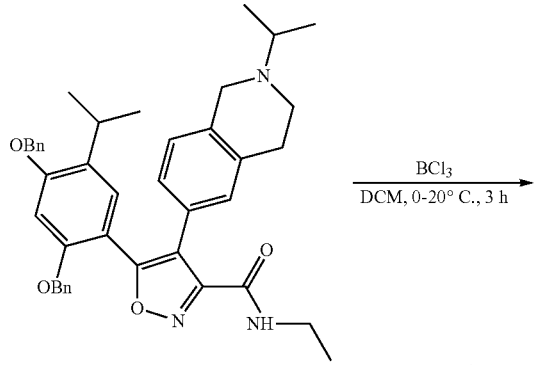

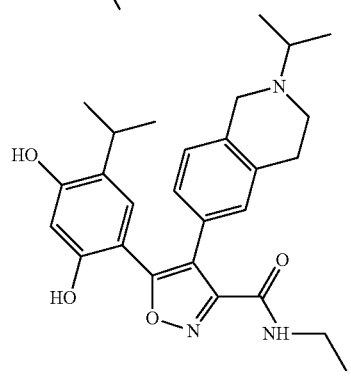

Step A: The title compound of this Example was prepared according to the order of steps A and B in Example 49, wherein acetaldehyde in step B was replaced with acetone. $^1$H NMR (400 MHz, DMSO-$d_6$) δ 0.97-1.13 (m, 9 H); 1.25-1.41 (m, 6 H); 2.82-2.93 (m, 1 H); 2.97-3.08 (m, 1 H); 3.13-3.28 (m, 4 H); 3.60 (br. s., 2 H); 4.23-4.43 (m, 2 H); 6.49 (s, 1 H); 6.91 (s, 1 H); 7.06-7.24 (m, 3 H); 8.92 (t, J=5.58 Hz, 1 H); 9.58-9.95 (m, 2 H); 10.53 (br. s., 1 H). MS (ESI) M/Z: 464 (M+1).

EXAMPLE 52

5-(2,4-dihydroxyl-5-isopropylphenyl)-N-ethyl-4-(2-isobutyl-1,2,3,4-tetrahydroisoquinolin-6-yl)isoxazole-3-carboxamide

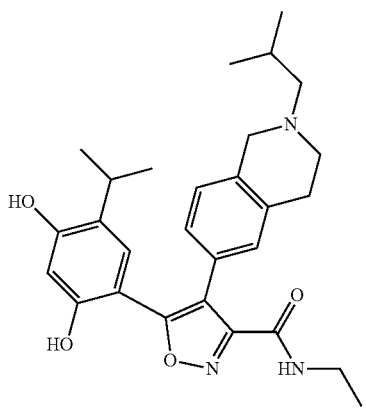 [SMILES: CCNC(=O)c1noc(-c2cc(C(C)C)c(O)cc2O)c1-c1ccc2c(c1)CCN(CC(C)C)C2]

Reaction scheme:

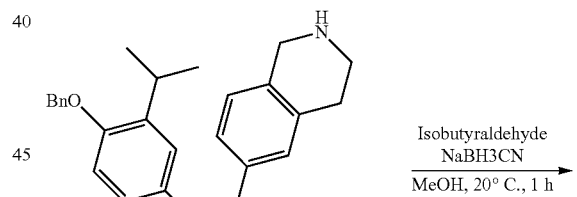

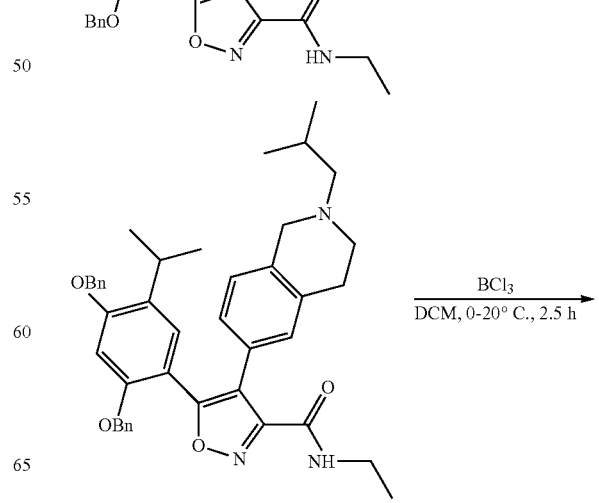

155

-continued

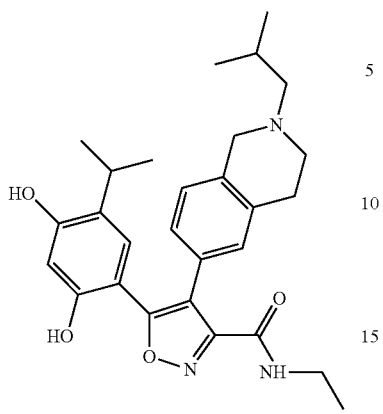

Step A: The title compound of this Example was prepared according to the order of steps A and B in Example 49, wherein acetaldehyde in step B was replaced with 2-methylpropionaldehyde. $^1$H NMR (400 MHz, DMSO-$d_6$) δ 0.94-1.13 (m, 15 H); 2.05-2.26 (m, 1H); 2.91 (d, J=17.57 Hz, 1 H); 2.99-3.08 (m, 3 H); 3.19-3.27 (m, 3 H); 3.66 (br. s., 1 H); 4.26 (dd, J=15.75, 7.47 Hz, 1 H); 4.51 (d, J=15.43 Hz, 1 H); 6.46 (s, 1H); 6.88 (s, 1 H); 7.05-7.21 (m, 3 H); 8.89 (t, J=5.14 Hz, 1 H); 9.61-9.87 (m, 3 H). MS (ESI) M/Z: 478 (M+1).

EXAMPLE 53

4-(2-(2-acetylaminoethyl)-1,2,3,4-tetrahydroisoquinolin-6-yl)-5-(2,4-dihydroxyl-5-isopropylphenyl)-N-ethylisoxazole-3-carboxamide

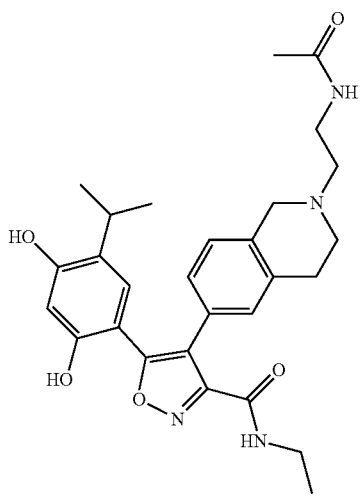 [SMILES: CCNC(=O)c1noc(-c2cc(C(C)C)c(O)cc2O)c1-c1ccc2c(c1)CCN(CCNC(C)=O)C2]

156

Reaction scheme:

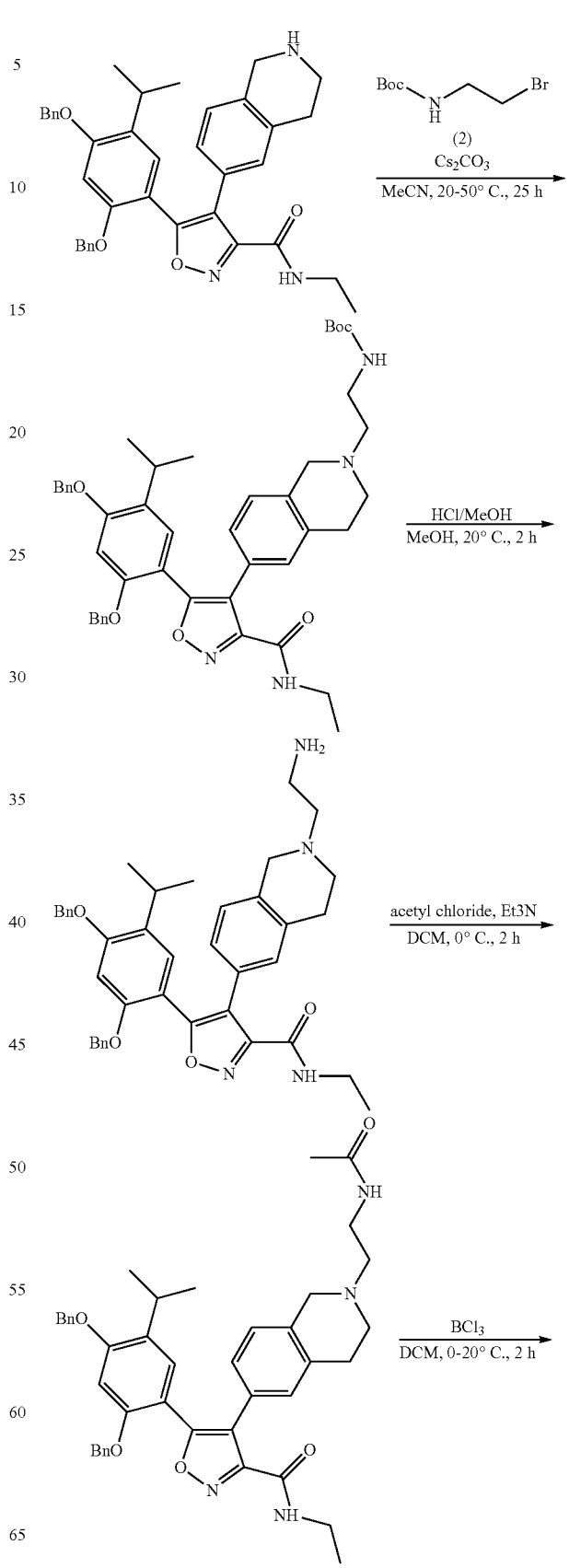

-continued

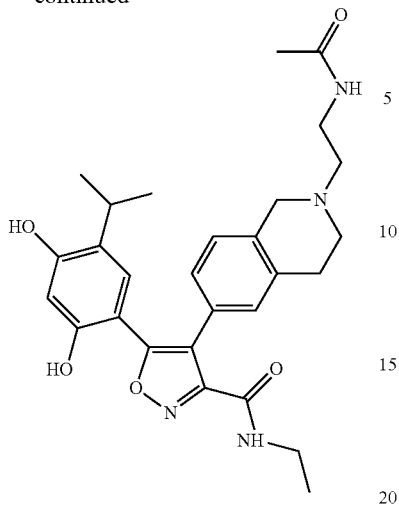

Step A. 5-(2,4-Dibenzyloxy-5-isopropyl-phenyl)-N-ethyl-4-(1,2,3,4-tetrahydroisoquinolin-6-yl)isoxazole-3-carboxamide (300 mg, 499 μmol, 1.0 eq.), cesium carbonate (244 mg, 748 μmol, 1.5 eq) and t-butyl N-(2-bromoethyl) carbamate (168 mg, 748 μmol, 1.5 eq) were added to acetonitrile (5 mL). The mixture was heated to 50° C. with stirring for 25 hours. After cooling, the reaction mixture was concentrated in vacuum to give a residue. The residue was purified by preparative TLC to give t-butyl N-[2-[6-[5-(2,4-benzyloxy-5-isopropylphenyl)-3-(ethylcarbamoyl)isoxazol-4-yl]-1,2,3,4-tetrahydroisoquinolin-2-yl]ethyl]formate (250 mg, 336 μmol, 67% yield) as a brown solid.

Step B: A mixture of t-butyl N-[2-[6-[5-(2,4-benzyloxy-5-isopropylphenyl)-3-(ethylcarbamoyl)isoxazol-4-yl]-1,2,3,4-tetrahydroisoquinolin-2-yl]ethyl]formate (250 mg, 336 μmol, 1.00 eq.) in HCl/MeOH (4 M, 6.00 mL) was stirred at 25° C. for 2 hours. The mixture was concentrated at 40° C. to give the product 4-(2-(2-aminoethyl)-1,2,3,4-tetrahydroisoquinolin-2-yl)-5-(2,4-benzyloxy-5-isopropylphenyl)-N-ethylisoxazole-3-carboxamide (250 mg, a crude product) as a brown solid.

Step C: Acetyl chloride (39 mg, 496 μmol, 2.0 eq.) was added to a solution of 4-(2-(2-aminoethyl)-1,2,3,4-tetrahydroisoquinolin-2-yl)-5-(2,4-benzyloxy-5-isopropylphenyl)-N-ethylisoxazole-3-carboxamide (170 mg, 248 μmol, 1.0 eq.) and triethylamine (100 mg, 991 μmol, 4.0 eq.) in DCM (6 mL) at 0° C. The mixture was stirred at 0° C. for 2 hours. The reaction mixture was concentrated in vacuum to give a residue. The residue was purified by preparative TLC to give 4-(2-(2-acetylaminoethyl)-1,2,3,4-tetrahydroisoquinolin-2-yl)-5-(2,4-benzyloxy-5-isopropylphenyl)-N-ethylisoxazole-3-carboxamide (150 mg, 218 μmol, 88% yield) as a yellow solid.

Step D: To a solution of 4-(2-(2-acetylaminoethyl)-1,2,3,4-tetrahydroisoquinolin-2-yl)-5-(2,4-benzyloxy-5-isopropylphenyl)-N-ethylisoxazole-3-carboxamide (100 mg, 146 μmol, 1.0 eq.) in DCM (5.0 mL), a solution of BCl$_3$ in DCM (1 M, 1.5 mL, 10.0 eq.) was added at 0° C. over a course of 5 min. The suspension was stirred at 0° C. for 30 min, and then warmed up to 25° C. with stirring for 2 hours. The mixture was cooled down to 0° C., quenched by slowly adding MeOH (3 mL) and concentrated in vacuum to give a residue. The residue was purified by preparative HPLC to give 4-(2-(2-acetylaminoethyl)-1,2,3,4-tetrahydroisoquinolin-6-yl)-5-(2,4-dihydroxyl-5-isopropylphenyl)-N-ethylisoxazole-3-carboxamide (60 mg, 118 μmol, 81% yield). $^1$H NMR (400 MHz, DMSO-d$_6$) ppm: 0.95-1.14 (m, 9 H); 1.79-1.88 (m, 3 H); 2.90 (d, J=16.94 Hz, 1 H); 2.97-3.07 (m, 1 H); 3.10-3.34 (m, 6 H); 3.51 (d, J=5.65 Hz, 2 H); 3.71 (d, J=10.67 Hz, 1 H); 4.28 (dd, J=15.75, 7.72 Hz, 1 H); 4.55 (d, J=15.31 Hz, 1 H); 6.43-6.52 (m, 1 H); 6.84-6.92 (m, 1 H); 7.06-7.20 (m, 3 H); 8.30 (t, J=5.58 Hz, 1 H); 8.90 (t, J=5.71 Hz, 1 H); 9.56-9.95 (m, 2 H); 10.52 (br. s., 1 H). MS (ESI) M/Z: 507 (M+1).

EXAMPLE 54

4-(2-(2-acetylaminopropyl)-1,2,3,4-tetrahydroisoquinolin-6-yl)-5-(2,4-dihydroxyl-5-isopropylphenyl)-N-ethylisoxazole-3-carboxamide

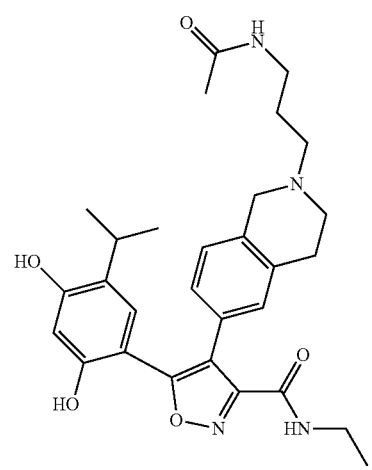 [SMILES: CCNC(=O)c1noc(-c2cc(C(C)C)c(O)cc2O)c1-c1ccc2c(c1)CCN(CCCNC(C)=O)C2]

Reaction scheme:

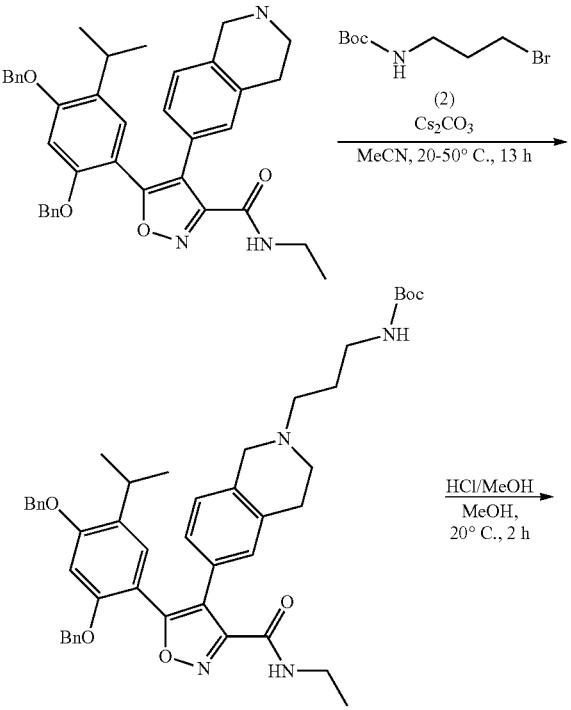

159

-continued

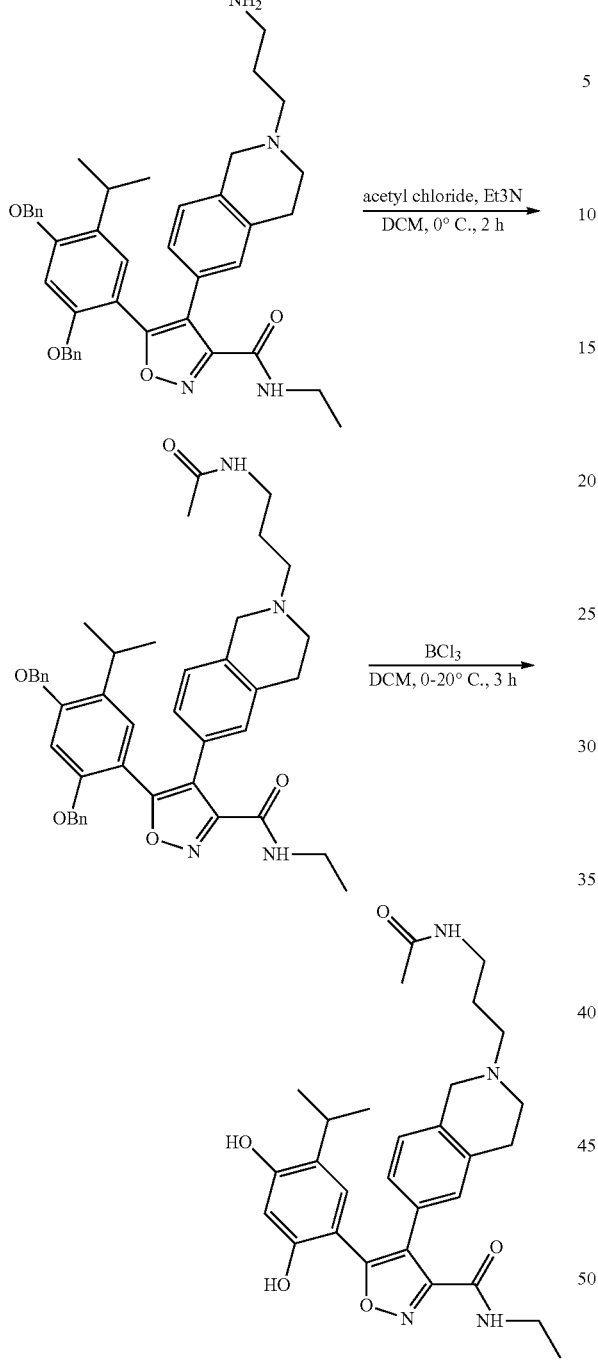

Step A: The title compound of this Example was prepared according to the order of steps A, B and C in Examples 53, wherein t-butyl N-(2-bromoethyl)carbamate in step A was replaced with t-butyl N-(3-bromopropyl) carbamate. ¹H NMR (400 MHz, DMSO-d₆) • ppm: 1.01 (d, J=6.90 Hz, 6 H); 1.08 (t, J=7.22 Hz, 3 H); 1.81 (s, 3 H); 1.86-1.96 (m, 2 H); 2.88 (d, J=17.19 Hz, 1 H); 2.96-3.34 (m, 10 H); 4.23 (dd, J=15.62, 7.97 Hz, 1 H); 4.47 (d, J=14.18 Hz, 1 H); 6.48 (s, 1 H); 6.88 (s, 1 H); 7.07-7.17 (m, 3 H); 8.10 (t, J=5.71 Hz, 1 H); 8.90 (t, J=5.65 Hz, 1 H); 9.52-10.02 (m, 2 H); 10.69 (br. s., 1 H). MS (ESI) M/Z: 521 (M+1).

160

EXAMPLE 55

5-(2,4-dihydroxyl-5-isopropylphenyl)-4-(2-(2-(dimethylamino)-2-oxoethyl)-1,2,3,4-tetrahydroisoquinolin-6-yl)-N-ethylisoxazole-3-carboxamide

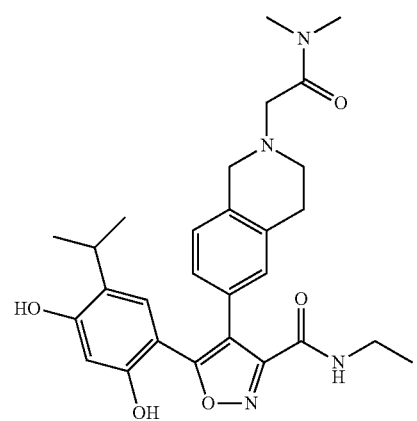 [SMILES: CCNC(=O)c1noc(-c2cc(C(C)C)c(O)cc2O)c1-c1ccc2c(c1)CCN(CC(=O)N(C)C)C2]

Reaction scheme:

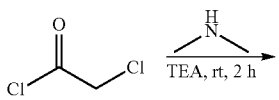

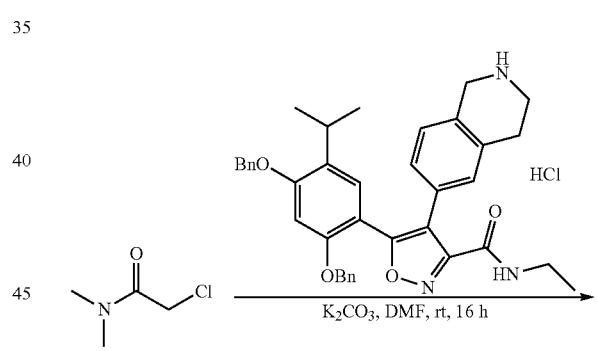

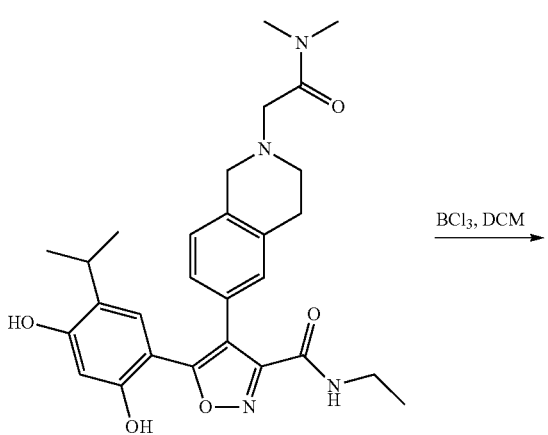

161

-continued

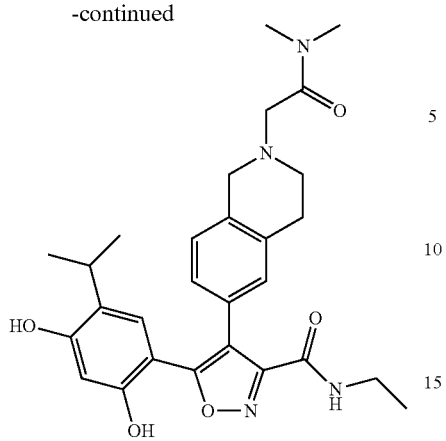

Step A: 2-Chloroacetyl chloride (3.00 g, 26.6 mmol, 1.6 eq.), dimethylamine hydrochloride (2.38 g, 29.2 mmol, 1.1 eq.) and triethylamine (8.0 g, 79.7 mmol, 3.0 eq.) were added to DCM (30 mL). The mixture was stirred at 15° C. for 3 hours. The reaction mixture was poured into water (30 mL) and extracted with DCM (50 mL×2). The organic phase was washed with dilute hydrochloric acid (30 mL×2, 1 M), dried over anhydrous $Na_2SO_4$ and concentrated in vacuum to give 2-chloro-N,N-dimethylacetamide (2.5 g, 20.6 mmol, 77% yield) as a yellow oil.

Step B: 5-(2,4-Dibenzyloxy-5-isopropyl-phenyl)-N-ethyl-4-(1,2,3,4-tetrahydroisoquinolin-6-yl)isoxazole-3-carboxamide (200 mg, 313 μmol, 1.0 eq.), $K_2CO_3$ (130 mg, 940 μmol, 3.0 eq) and 2-chloro-N,N-dimethylacetamide (114 mg, 940 μmol, 3.0 eq.) were added to DMF (4 mL). The mixture was stirred at 15° C. for 16 hours. The reaction mixture was added to water (30 mL) and filtered to collect a solid, to give 5-(2,4-dibenzyloxy-5-isopropyl-phenyl)-4-(2-(2-(dimethylamino)-2-oxoethyl)-(1,2,3,4-tetrahydroisoquinolin-6-yl)-N-ethylisoxazole-3-carboxamide (195 mg, a crude product, 74% of purity) as a white solid.

Step C: A solution of $BCl_3$ in DCM (1 M, 3.0 mL, 10.0 eq.) was added dropwise to a solution of 5-(2,4-dibenzyloxy-5-isopropyl-phenyl)-4-(2-(2-(dimethylamino)-2-oxoethyl)-(1,2,3,4-tetrahydroisoquinolin-6-yl)-N-ethylisoxazole-3-carboxamide (190 mg, 277 μmol, 1.0 eq.) in DCM (10.0 mL) at 0° C. over a course of 5 min. The suspension was stirred at 0° C. for 30 min and then warmed up to 25° C. with stirring for 2 hours. The mixture was cooled down to 0° C., quenched by slowly adding MeOH (6 mL), and concentrated in vacuum to give a residue. The residue was purified by preparative HPLC to give 5-(2,4-dihydroxyl-5-isopropylphenyl)-4-(2-(2-(dimethylamino)-2-oxoethyl)-1,2,3,4-tetrahydroisoquinolin-6-yl)-N-ethylisoxazole-3-carboxamide (78 mg, 138 μmol, 49.8% yield). $^1$H NMR (400 MHz, DMSO-$d_6$): δ10.22 (s, 1H), 9.86 (s, 1H), 9.72 (s, 1H), 8.92 (t, J=5.2 Hz, 1H), 7.10-7.16 (m, 3H), 6.86 (s, 1H), 6.48 (s, 1H), 4.32-4.55 (m, 4H), 3.63 (brs, 2H), 3.20-3.25 (m, 2H), 3.10-3.14 (m, 1H), 2.67-3.00 (m, 7 H), 0.99-1.15 (m, 9 H). MS (ESI) M/Z: 507 (M+1).

EXAMPLE 56

5-(2,4-dihydroxyl-5-isopropylphenyl)-4-(2-(2-(dimethylamino)-3-oxopropyl)-1,2,3,4-tetrahydroisoquinolin-6-yl)-N-ethylisoxazole-3-carboxamide

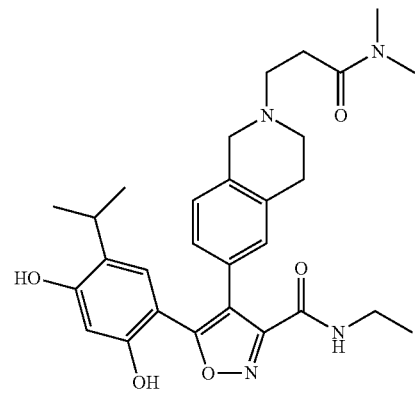 [SMILES: CCNC(=O)c1noc(-c2cc(C(C)C)c(O)cc2O)c1-c1ccc2c(c1)CCN(CCC(=O)N(C)C)C2]

Reaction scheme:

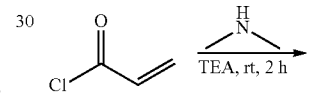

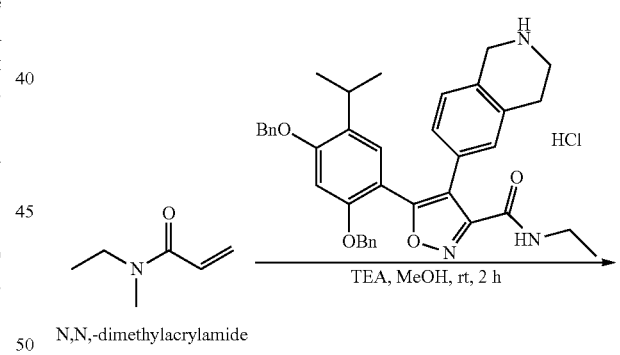

N,N,-dimethylacrylamide

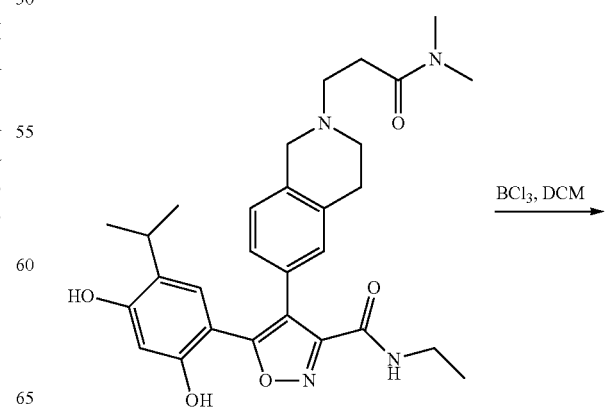

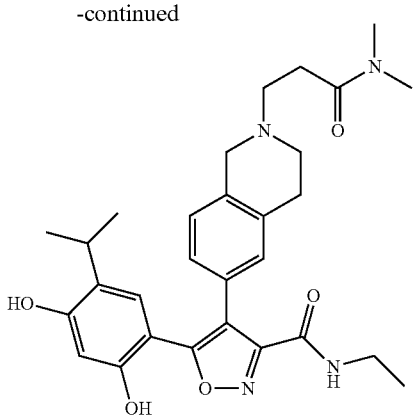

Step A: Acryloyl chloride (5.0 g, 55 mmol, 1.0 eq.), dimethylamine hydrochloride (4.95 g, 60.8 mmol, 1.1 eq.) and triethylamine (16.8 g, 166 mmol, 3.0 eq.) were added to DCM (50 mL). The mixture was stirred at 15° C. for 3 hours. The reaction mixture was poured into water (30 mL) and extracted with DCM (50 mL×2). The organic phase was washed with dilute hydrochloric acid (30 mL×2, 1 M), dried over anhydrous $Na_2SO_4$ and concentrated in vacuum to give N,N-dimethylacrylamide (3.0 g, 30 mmol, 55% yield) as a yellow oil.

Step B: 5-(2,4-Dibenzyloxy-5-isopropyl-phenyl)-N-ethyl-4-(1,2,3,4-tetrahydroisoquinolin-6-yl)isoxazole-3-carboxamide (100 mg, 157 μmol, 1.0 eq.), triethylamine (48 mg, 470 μmol, 3.0 eq.) and N,N-dimethylacrylamide (155 mg, 1.57 mmol, 10.0 eq.) were added to ethanol (2 mL). The mixture was stirred at 15° C. for 2 hours. The reaction mixture was added to water (30 mL) and extracted with EA (30 mL×2). The organic phase was dried over anhydrous $Na_2SO_4$ and concentrated in vacuum to give 5-(2, 4-dibenzyloxy-5-isopropylphenyl)-4-(2-(2-(dimethylamino)-3-oxopropyl)-1,2,3,4-tetrahydroisoquinolin-6-yl)-N-ethylisoxazole-3-carboxamide (195 mg, a crude product, 74% of purity) as a yellow oil.

Step C: A solution of $BCl_3$ in DCM (1 M, 3.0 mL, 20.0 eq) was added dropwise to a solution of 5-(2, 4-dibenzyloxy-5-isopropylphenyl)-4-(2-(2-(dimethylamino)-3-oxopropyl)-1,2,3,4-tetrahydroisoquinolin-6-yl)-N-ethylisoxazole-3-carboxamide (105 mg, 149 μmol, 1.0 eq.) in DCM (15.0 mL) at 0° C. over a course of 5 min. The suspension was stirred at 0° C. for 30 min, and then warmed up to 25° C. with stirring for 2 hours. The mixture was cooled down to 0° C., quenched by slowly adding MeOH (6 mL) and concentrated in vacuum to give a residue. The residue was purified by preparative HPLC to give 5-(2,4-dihydroxyl-5-isopropylphenyl)-4-(2-(2-(dimethylamino)-3-oxopropyl)-1,2,3,4-tetrahydroisoquinolin-6-yl)-N-ethylisoxazole-3-carboxamide (28 mg, 46 μmol, 31% yield). $^1$H NMR (400 MHz, DMSO-$d_6$): δ 10.49 (s, 1H), 9.85 (s, 1H), 9.71 (s, 1H), 8.91 (t, J=5.6 Hz, 1H), 7.10-7.15 (m, 3H), 6.88 (s, 1H), 6.47 (s, 1H), 4.51-4.55 (m, 1 H), 4.31-4.34 (m, 2 H), 3.68-3.72 (m, 1H), 3.30-3.42 (m, 4H), 3.21-3.30 (m, 1 H), 3.00-3.20 (m, 4 H), 2.93-3.00 (m, 3 H), 2.85 (s, 4 H), 3.00-3.20 (m, 4 H), 1.09 (t, J=7.6 Hz, 3H), 1.01 (d, J=3.6 Hz, 6 H). MS (ESI) M/Z: 521 (M+1).

EXAMPLE 57

5-(2,4-dihydroxyl-5-isopropylphenyl)-4-(2-(3-(dimethylamino)propionyl)-1,2,3,4-tetrahydroisoquinolin-6-yl)-N-ethylisoxazole-3-carboxamide

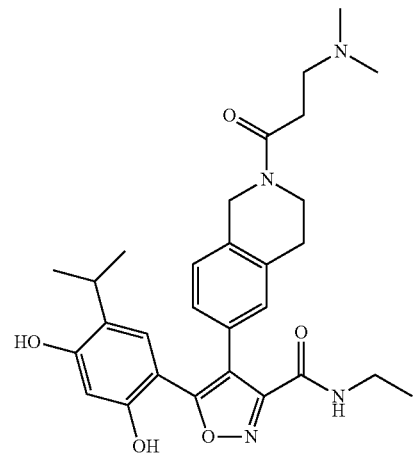 [SMILES: CCNC(=O)c1noc(-c2cc(C(C)C)c(O)cc2O)c1-c1ccc2c(c1)CCN(C(=O)CCN(C)C)C2]

Reaction scheme:

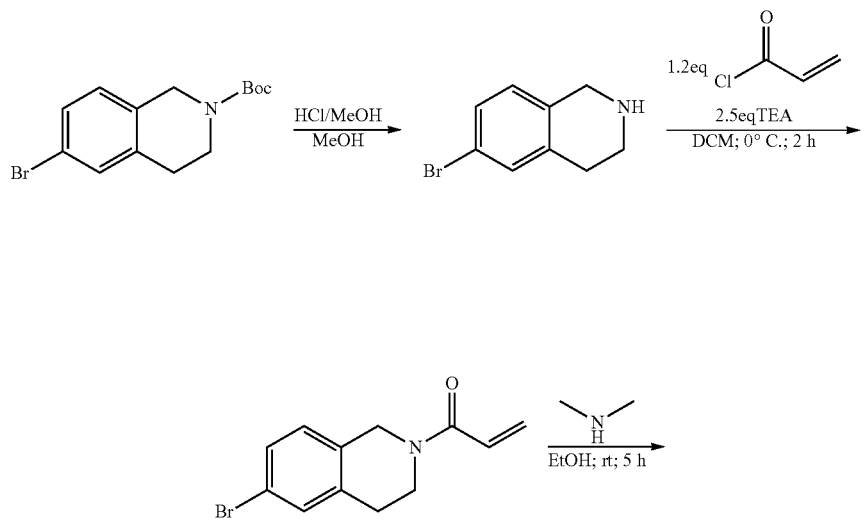

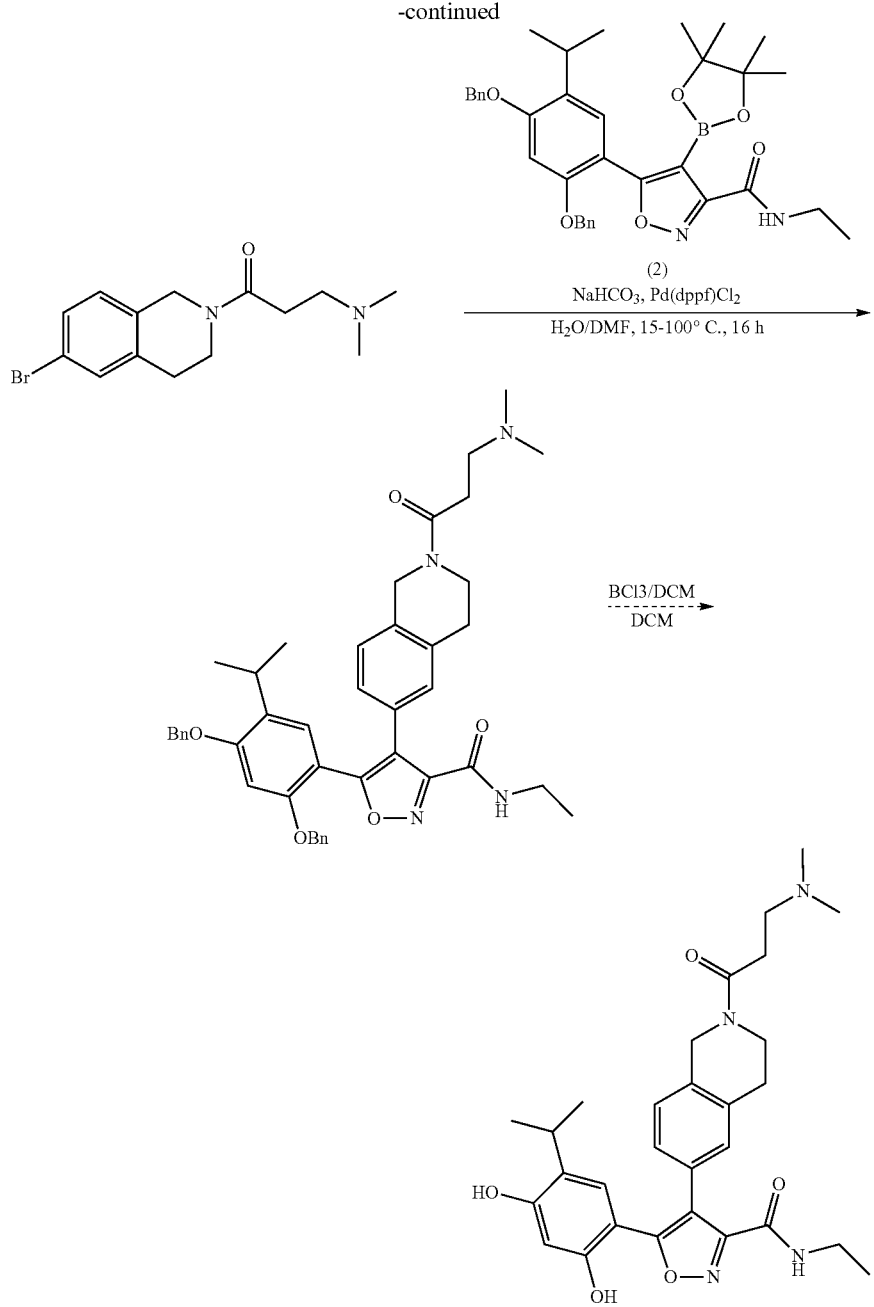

Step A: HCl/MeOH (4M, 30.00 mL) was added to a solution of t-butyl-6-bromo-1,2,3,4-tetrahydroisoquinolin-2-formate (5.0 g, 16 mmol, 1.00 eq.) in MeOH (20.0 mL) at 20° C., and the mixture was stirred at 25° C. for 2 hours. The mixture was concentrated at 40° C. to give the product 6-bromo-1,2,3,4-tetrahydroisoquinoline hydrochloride (4.5 g, a crude product).

Step B: Acryloyl chloride (1.0 g, 11 mmol, 1.2 eq.) was added to a solution of 6-bromo-1,2,3,4-tetrahydroisoquinoline hydrochloride (2.0 g, 9 mmol, 1 eq.) and triethylamine (2.9 g, 28 mmol, 3.0 eq) in DCM (40 mL) at 0° C. The mixture was stirred at 15° C. for 14 hours. The reaction mixture was poured into water (30 mL) and extracted with DCM (50 mL×2). The organic phase was dried with anhydrous $Na_2SO_4$ and concentrated in vacuum. The residue was purified by column chromatography to give 1-(6-bromo-1,2,3,4-tetrahydroisoquinolin-yl)propyl-2-en-1-one (1.4 g, 5 mmol, 56% yield) as a yellow oil. MS (ESI) m/z: 266 (M+1).

Step C: 1-(6-Bromo-1,2,3,4-tetrahydroisoquinolin-yl)propyl-2-en-1-one (700 mg, 2.6 mmol, 1.0 eq.) and dimethylamine (1.1 g, 7.9 mmol, 3.0 eq) were added to ethanol (10 mL). The mixture was stirred at 15° C. for 12 hours. The reaction mixture was concentrated in vacuum. The residue was purified by column chromatography to give 1-(6-bromo-1,2,3,4-tetrahydroisoquinolin-yl)-3-(dimethylamino)propan-1-one (700 mg, 2.3 mmol, 86% yield) as a yellow oil.

Step D: 1-(6-bromo-1,2,3,4-tetrahydroisoquinolin-yl)-3-(dimethylamino)propan-1-one (200 mg, 643 μmol, 1.0 eq.) and $NaHCO_3$ (216 mg, 2.6 mmol, 4.0 eq.) were added to a mixed solution of 5-(2,4-dibenzyloxy-5-isopropyl-phenyl)-N-ethyl-4-(4,4,5,5-tetramethyl-1,3,2-dioxaborolan-2-yl)isoxazole-3-carboxamide (767 mg, 771 μmol, 1.0 eq.) in DMF (2.5 mL) and water (0.5 mL). The atmosphere of the mixture was replaced with a nitrogen atmosphere, followed by adding Pd(dppf)Cl$_2$ (47 mg, 641 mol, 0.1 eq.). The mixture was stirred at 100° C. for 16 hours, and the reaction substance was diluted with 20 mL of water and filtered through diatomaceous earth. The filtrate was extracted with EA (20 mL×3), and the combined organic phase was washed with water (20 mL×L), dried over anhydrous Na$_2$SO$_4$, filtered and concentrated in vacuum to give a crude product. The crude product was purified by preparative TLC (DCM:methanol 10:1) to give 5-(2,4-dibenzyloxy-5-isopropylphenyl)-4-(2-(3-(dimethylamino)propionyl)-1,2,3,4-tetrahydroisoquinolin-6-yl)-N-ethylisoxazole-3-carboxamide (220 mg, 314 μmol, 49% yield) as a white solid. MS (ESI) m/z: 701 (M+1).

Step E: A solution of BCl$_3$ in DCM (1 M, 2.4 mL, 10.0 eq.) was added dropwise to a solution of 5-(2,4-dibenzyloxy-5-isopropylphenyl)-4-(2-(3-(dimethylamino)propionyl)-1,2,3,4-tetrahydroisoquinolin-6-yl)-N-ethylisoxazole-3-carboxamide (170 mg, 243 μmol, 1.0 eq.) in DCM (12.0 mL) at 0° C. over a course of 5 min. The suspension was stirred at 0° C. for 30 min, and then warmed up to 25° C. with stirring for 2 hours. The mixture was cooled down to 0° C., quenched by slowly adding MeOH (6 mL), and concentrated in vacuum to give a residue. The residue was purified by preparative HPLC to give 5-(2,4-dihydroxyl-5-isopropylphenyl)-4-(2-(3-(dimethylamino)propionyl)-1,2,3,4-tetrahydroisoquinolin-6-yl)-N-ethylisoxazole-3-carboxamide (65 mg, 117 μmol, 48% yield). 1H NMR (400 MHz, DMSO-d6) ppm 8.89 (t, J=5.65 Hz, 1 H) 7.11-7.20 (m, 1 H) 6.99-7.10 (m, 2 H) 6.84 (s, 1 H) 6.48 (d, J=1.88 Hz, 1 H) 4.54-4.72 (m, 2 H) 3.65 (t, J=5.65 Hz, 2 H) 3.16-3.37 (m, 4 H) 2.98-3.07 (m, 1 H) 2.94 (t, J=7.15 Hz, 2 H) 2.63-2.83 (m, 8 H) 1.08 (t, J=7.22 Hz, 3 H) 0.98 (d, J=6.78 Hz, 6 H). MS (ESI) M/Z: 521 (M+1).

EXAMPLE 58

5-(2,4-dihydroxyl-5-isopropylphenyl)-N-ethyl-4-(2-(3-morpholino-4-yl-propionyl)-1,2,3,4-tetrahydroisoquinolin-6-yl)isoxazole-3-carboxamide

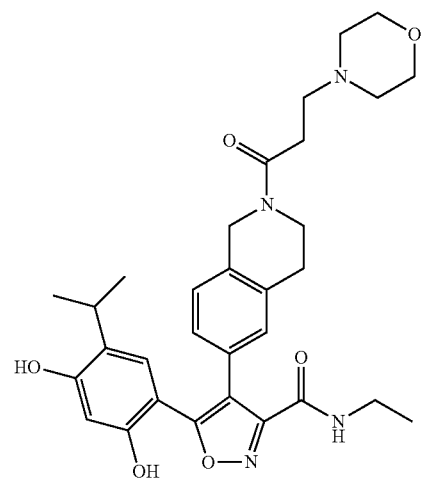 [SMILES: CCNC(=O)c1noc(-c2cc(C(C)C)c(O)cc2O)c1-c1ccc2c(c1)CCN(C(=O)CCN1CCOCC1)C2]

Reaction scheme:

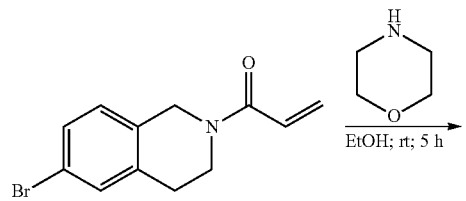

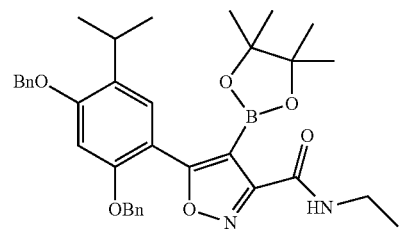

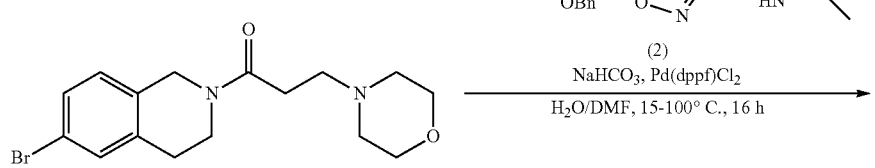

-continued
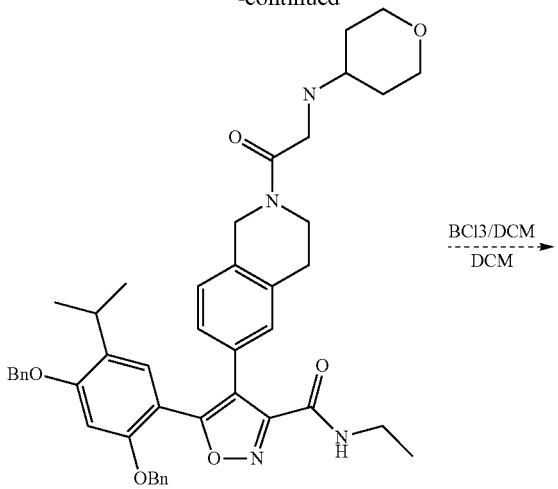
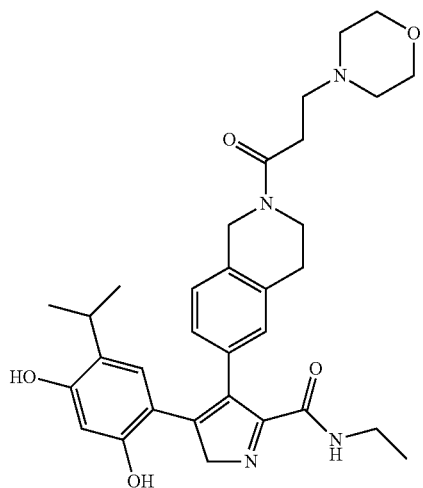
Step A: The title compound of this Example was prepared according to the order of steps C, D and E in Example 57, wherein dimethylamine in step C was replaced with morpholine. 1H NMR (400 MHz, DMSO-6) ppm: 8.89 (t, J=5.65 Hz, 1 H), 7.13 (t, J=7.78 Hz, 1 H), 7.00-7.10 (m, 2 H), 6.85 (s, 1 H), 6.44 (d, J=1.76 Hz, 1 H), 4.62 (d, J=19.58 Hz, 2 H), 3.95 (d, J=11.92 Hz, 2 H), 3.74 (t, J=12.11 Hz, 2 H), 3.62-3.69 (m, 2 H), 3.45 (d, J=12.17 Hz, 3 H), 3.28-3.38 (m, 2 H), 3.16-3.27 (m, 2 H), 2.92-3.15 (m, 5 H), 2.79 (t, J=5.65 Hz, 1 H), 2.63-2.71 (m, 1 H), 1.08 (t, J=7.15 Hz, 3 H), 0.98 (d, J=6.90 Hz, 6 H). MS (ESI) M/Z: 563 (M+1).

EXAMPLE 59
5-(2,4-dihydroxyl-5-isopropylphenyl)-4-(2-(2-(dimethylamino)acetyl)-1,2,3,4-tetrahydroisoquinolin-6-yl)-N-ethylisoxazole-3-carboxamide
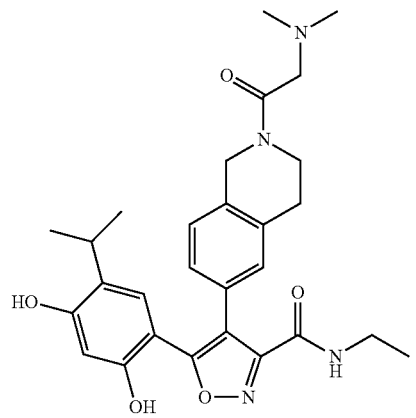 [SMILES: CCNC(=O)c1noc(-c2cc(C(C)C)c(O)cc2O)c1-c1ccc2c(c1)CCN(C(=O)CN(C)C)C2]
Reaction scheme:
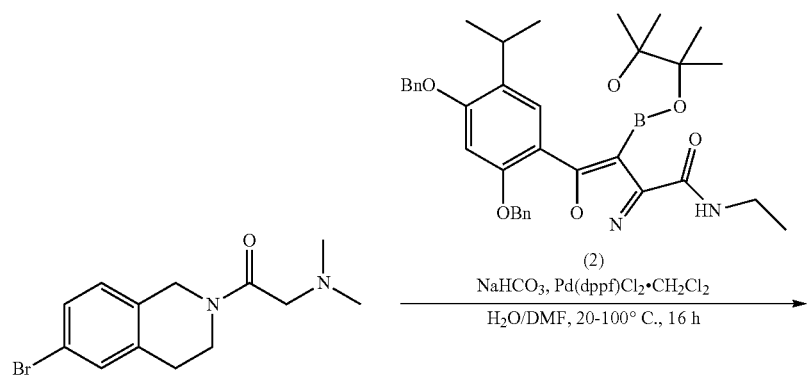
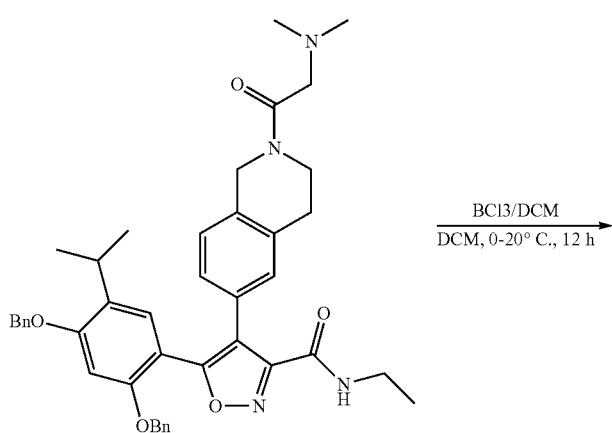

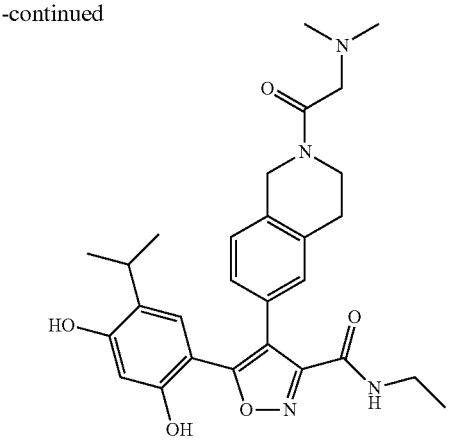

Step A: The title compound of this Example was prepared according to the order of steps D and E in Example 57, wherein 1-(6-bromo-1,2,3,4-tetrahydroisoquinolin-yl)-3-(dimethylamino)propan-1-one in step D was replaced with 1-(6-bromo-1,2,3,4-tetrahydroisoquinolin-yl)-2-(dimethylamino)ethanone. $^1$H NMR (400 MHz, DMSO-$d_6$) ppm: 0.98 (d, J=6.90 Hz, 6H); 1.04-1.14 (m, 3 H); 2.52 (br. s., 1 H); 2.71 (t, J=5.77 Hz, 1 H); 2.81 (d, J=4.64 Hz, 7 H); 3.00 (dt, J=13.65, 6.79 Hz, 1 H); 3.22 (quin, J=6.71 Hz, 2 H); 3.53 (t, J=5.83 Hz, 1 H); 3.69 (t, J=5.77 Hz, 1 H); 4.37 (d, J=4.52 Hz, 2 H); 4.50-4.69 (m, 2 H); 6.48 (d, J=2.64 Hz, 1 H); 6.84 (s, 1 H); 7.01-7.13 (m, 2 H); 7.17 (d, J=8.03 Hz, 1 H); 8.89 (t, J=5.65 Hz, 1 H); 9.47-10.00 (m, 3 H). MS (ESI) M/Z: 507 (M+1).

EXAMPLE 60

5-(2,4-dihydroxyl-5-isopropylphenyl)-N-ethyl-4-(2-(2-morpholino-4-yl-acetyl)-1,2,3,4-tetrahydroisoquinolin-6-yl)isoxazole-3-carboxamide

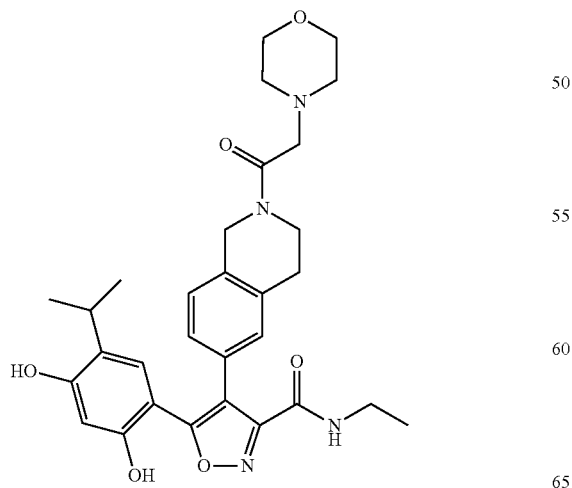

Reaction scheme:

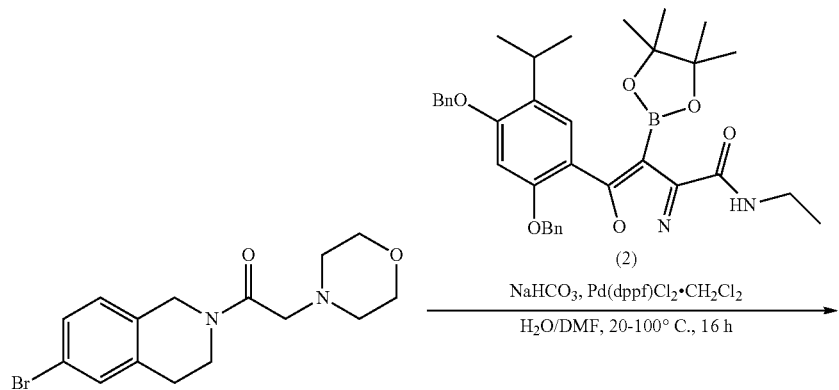

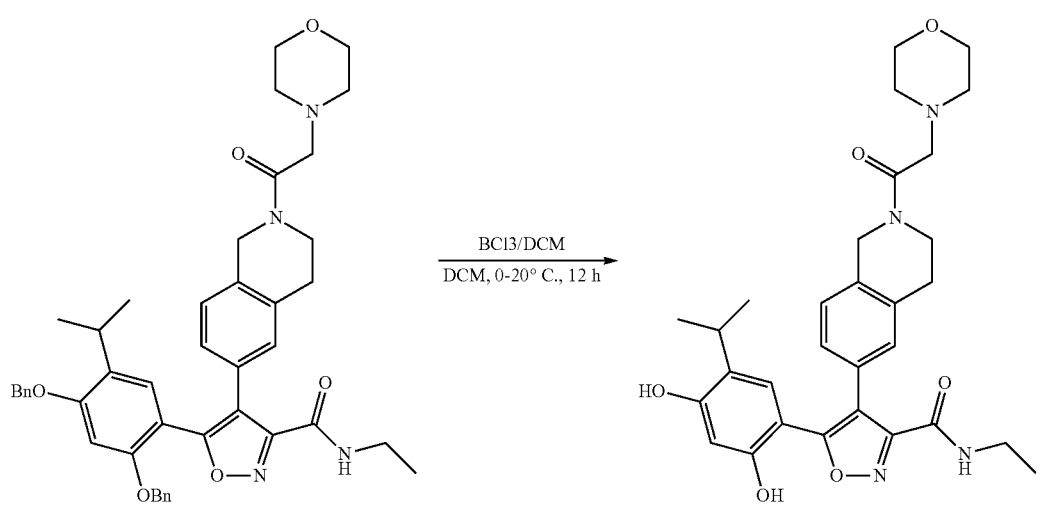

Step A: The title compound of this Example was prepared according to the order of steps D and E in Example 57, wherein 1-(6-bromo-1,2,3,4-tetrahydroisoquinolin-yl)-3-(dimethylamino)propan-1-one in step D was replaced with 1-(6-bromo-1,2,3,4-tetrahydroisoquinolin-yl)-2-morpholinylethanone. $^1$H NMR (400 MHz, DMSO-$d_6$) ppm: 0.94-1.01 (m, 6 H); 1.08 (td, J=7.15, 1.38 Hz, 3 H); 2.69-2.87 (m, 2 H); 3.01 (dt, J=13.71, 6.76 Hz, 1 H); 3.09-3.27 (m, 4 H); 3.42 (d, J=11.67 Hz, 2 H); 3.55-3.58 (m, 1 H); 3.70 (t, J=5.96 Hz, 1 H); 3.75-3.86 (m, 2 H); 3.87-4.01 (m, 2 H); 4.45 (br. s., 2H); 4.53-4.67 (m, 2 H); 6.48 (d, J=2.76 Hz, 1 H); 6.84 (s, 1 H); 7.03-7.14 (m, 2 H); 7.17 (d, J=8.03 Hz, 1 H); 8.90 (t, J=5.52 Hz, 1 H); 9.63-9.95 (m, 2 H); 10.27 (br. s., 1 H). MS (ESI) M/Z: 549 (M+1).

EXAMPLE 61

3-(2,4-dihydroxyl-5-isopropylphenyl)-4-(2-methyl-1,2,3,4-tetrahydroisoquinolin-6-yl)isoxazol-5-carboxamide

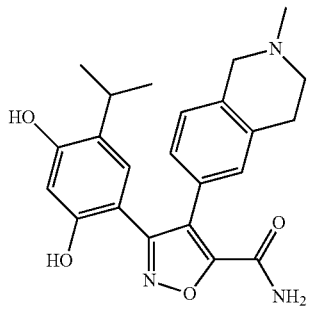 [SMILES: CC(C)c1cc(-c2noc(C(N)=O)c2-c2ccc3c(c2)CCN(C)C3)c(O)cc1O]

Reaction scheme:

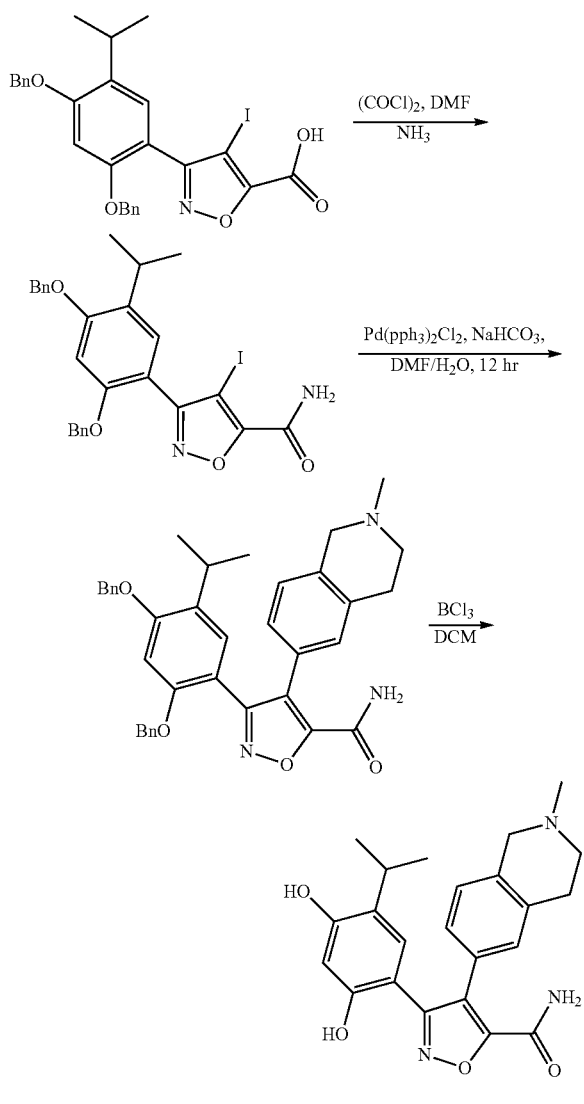

Step A: (COCl)$_2$ (134 mg, 1050 μmol, 2 eq) and DMF (100.00 μL) were added to a solution of 3-(2, 4-dibenzyloxyl-5-isopropylphenyl)-4-iodo-isoxazole-5-formic acid (300 mg, 527 μmol, 1.0 eq) in DCM (10 mL) at 0° C. The mixture was stirred at 0° C. for 1 hour, and then the reaction solution was concentrated in vacuum to give an intermediate. The intermediate was dissolved in DCM (10 mL) at 0° C. and NH$_3$/THF (4 M, 1.32 mL, 10.00 eq) was added to the solution. The mixture was stirred at 0° C. for 1 hour and poured into 15 mL water. The mixture was then extracted with DCM (15 mL×2), and the combined organic phase was dried with anhydrous Na$_2$SO$_4$, filtered and concentrated in vacuum, to give a crude product. The residue was purified by silica gel chromatography (200~300 mesh of silica gel, petroleum ether/ethyl acetate=20/1 to 5/1) to give 3-(2,4-dibenzyloxy-5-isopropylphenyl)-4-iodide-isoxazole-5-carboxamide (140 mg, 47% yield) as a yellow solid. MS (ESI) M/Z: 569 (M+1).

Step B: NaHCO$_3$ (40 mg, 472 μmol), H$_2$O (1.0 mL) and Pd(PPh$_3$)$_2$Cl$_2$ (17 mg, 24 μmol) were added to a mixed solution of 2-methyl-6-(4,4,5,5-tetramethyl-1,3,2-dioxaborolan-2-yl)-1,2,3,4-tetrahydroisoquinoline (103 mg, 377 μmol) and 3-(2,4-dibenzyloxy-5-isopropylphenyl)-4-iodo-isoxazole-5-carboxamide (134 mg, 236 μmol) in DMF (4 mL) at 25° C. under the protection of nitrogen gas. The mixture was stirred at 25° C. for 10 min and then heated to 80° C. with stirring for 12 hours. The mixture was cooled down to 25° C. and concentrated under reduced pressure. The residue was purified by silica gel chromatography (200~300 mesh of silica gel, dichloromethane/methanol=20/1 to 10/1) to give 3-(2, 4-dibenzyloxy-5-isopropylphenyl)-4-(2-methyl-1,2,3,4-tetrahydroisoquinolin-6-yl)isoxazole-3-carboxamide (80 mg, 51% yield) as a yellow solid. MS (ESI) M/Z: 588 (M+1).

Step C: BCl$_3$ (2 mL, 1 mol in DCM solution) was added slowly to a solution of 3-(2, 4-dibenzyloxy-5-isopropylphenyl)-4-(2-methyl-1,2,3,4-tetrahydroisoquinolin-6-yl)isoxazole-3-carboxamide (80 mg, 136 μmol) in DCM (15.00 mL) at 0° C. under the protection of nitrogen gas. The reaction mixture was stirred at 0° C. for 1 hour, and then warmed up to room temperature with stirring for 2 hours. The reaction solution was cooled down to 0° C. and then the reaction was quenched by adding MeOH (20 mL). The reaction mixture was concentrated in vacuum to give a crude product. The residue was purified by preparative HPLC (HCl method: Phenomenex Synergi C18 150×30 mm×4 μm, water (0.05% HCl)-ACN) to give 3-(2,4-dihydroxyl-5-isopropylphenyl)-4-(2-methyl-1,2,3,4-tetrahydroisoquinolin-6-yl)isoxazole-5-carboxamide hydrochloride (9 mg, 15% yield). MS (ESI) M/Z: 408 (M+1). $^1$H NMR (400 MHz, DMSO-d$_6$) • NMR (400 MHz, DMSO-dnomenex Synergi C18 150×30 mm×41 μm, water (0.05% HCl)-ACN) 2 H); 4.53-4.67 (m, 2 H); 6.48 (d, ), 3.30-3.42 (m, 4H), 3.21-3.30 (m, 1 H), 3.00-3.20 (m, 4 H), 2.93-3.00 (m, 3 H), 2.85 (s, 4 H), 3.00-3.20 (m, 4 H), 1.09 (t, =8.29 Hz, 2 H) J=6.8 Hz, 6H).

EXAMPLE 62

3-(2,4-dihydroxyl-5-isopropylphenyl)-N-methyl-4-(2-methyl-1,2,3,4-tetrahydroisoquinolin-6-yl)isoxazole-5-carboxamide

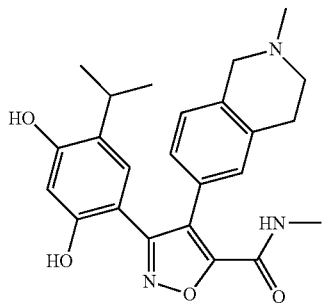 [SMILES: CNC(=O)c1onc(-c2cc(C(C)C)c(O)cc2O)c1-c1ccc2c(c1)CCN(C)C2]

Reaction scheme:

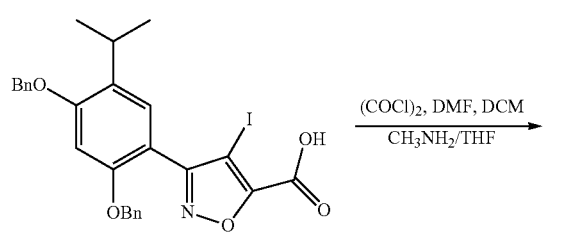

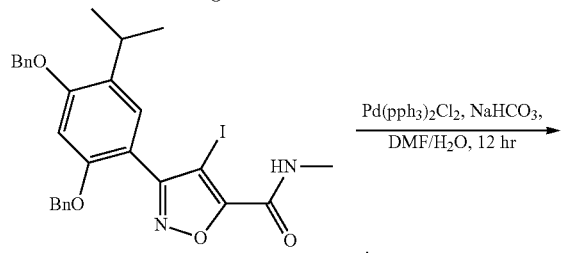

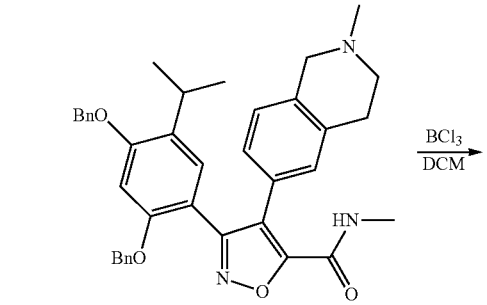

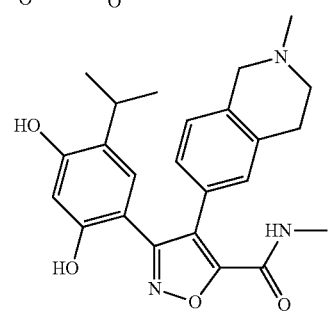

Step A: The title compound of this Example was prepared according to the order of steps A, B and C in Example 61, where NH$_3$/THF in step A was replaced with methylamine. $^1$H NMR (400 MHz, DMSO-d$_6$) δ 9.64 (s, 1H), 9.36 (s, 1H), 8.91 (d, J=4.8 Hz, 1H), 7.19 (s, 1H), 7.09 (s, 2H), 6.89 (s, 1H), 6.44 (s, 1H), 4.08 (br. s., 2H), 3.19 (br. s., 2H), 3.14-3.04 (m, 1H), 2.95 (br. s., 2H), 2.81 (d, J=4.5 Hz, 3H), 2.75 (br. s., 3H), 1.15-1.06 (m, 6H). MS (ESI) M/Z: 422 (M+1).

EXAMPLE 63

3-(2,4-dihydroxyl-5-isopropylphenyl)-N-isopropyl-4-(2-methyl-1,2,3,4-tetrahydroisoquinolin-6-yl)isoxazole-5-carboxamide

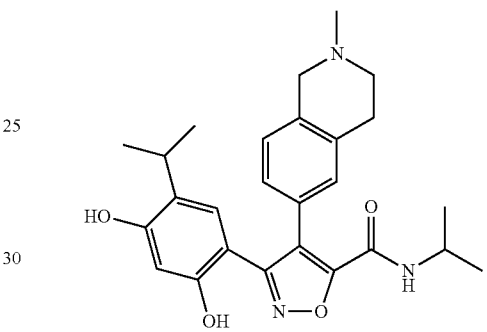

Reaction scheme:

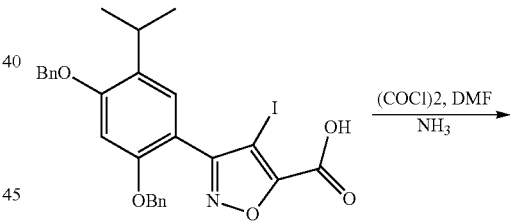

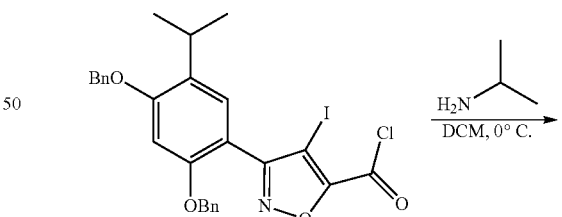

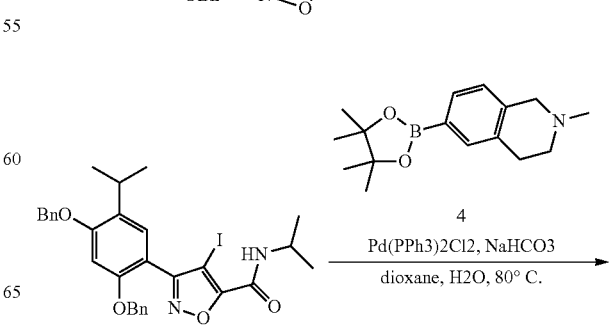

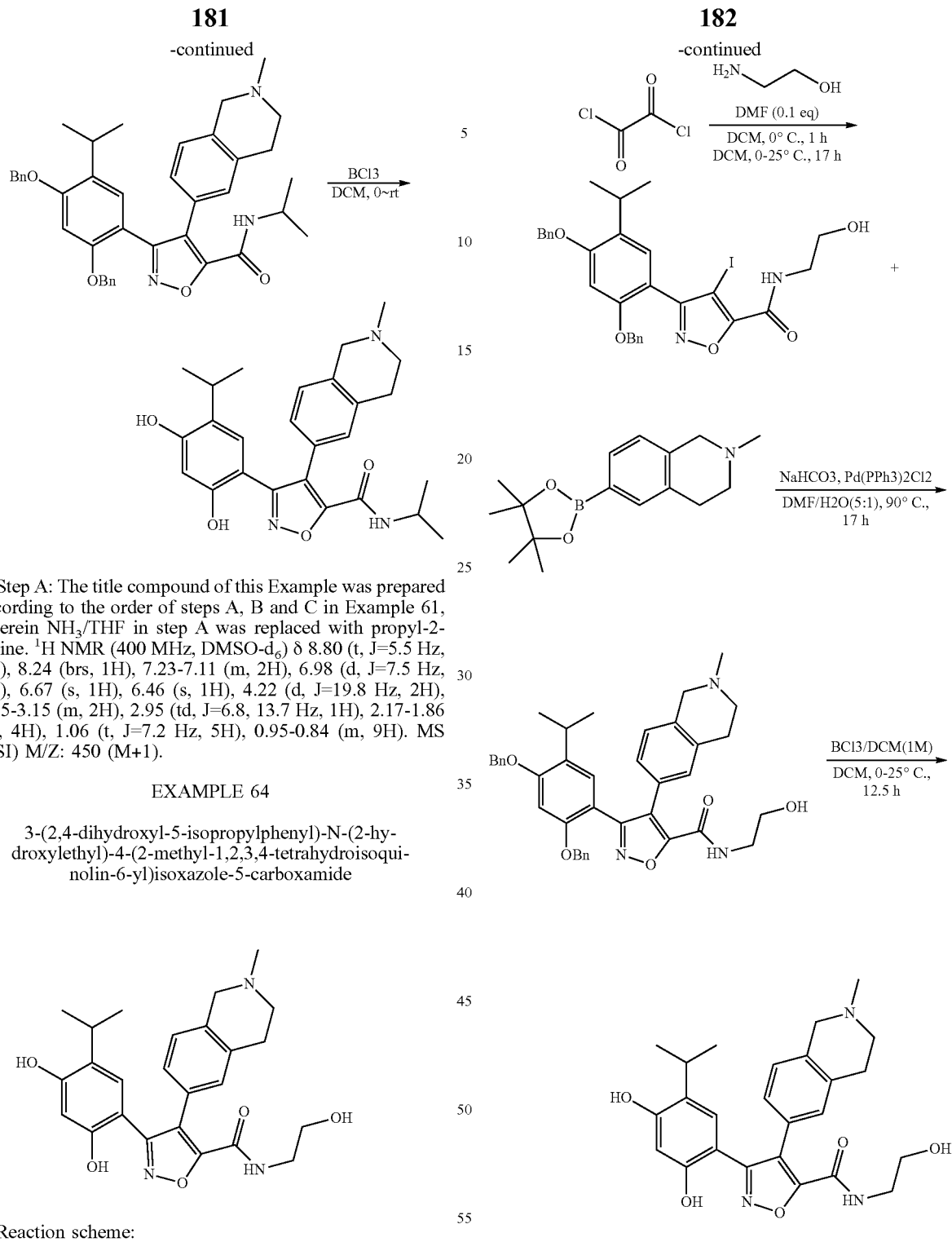

Step A: The title compound of this Example was prepared according to the order of steps A, B and C in Example 61, wherein NH$_3$/THF in step A was replaced with propyl-2-amine. $^1$H NMR (400 MHz, DMSO-d$_6$) δ 8.80 (t, J=5.5 Hz, 1H), 8.24 (brs, 1H), 7.23-7.11 (m, 2H), 6.98 (d, J=7.5 Hz, 1H), 6.67 (s, 1H), 6.46 (s, 1H), 4.22 (d, J=19.8 Hz, 2H), 3.25-3.15 (m, 2H), 2.95 (td, J=6.8, 13.7 Hz, 1H), 2.17-1.86 (m, 4H), 1.06 (t, J=7.2 Hz, 5H), 0.95-0.84 (m, 9H). MS (ESI) M/Z: 450 (M+1).

EXAMPLE 64

3-(2,4-dihydroxyl-5-isopropylphenyl)-N-(2-hydroxylethyl)-4-(2-methyl-1,2,3,4-tetrahydroisoquinolin-6-yl)isoxazole-5-carboxamide Reaction scheme:

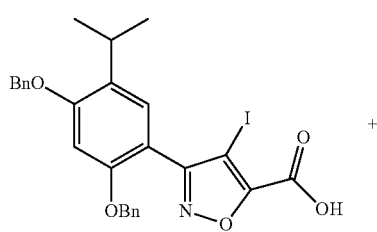

Step A: The title compound of this Example was prepared according to the order of steps A, B and C in Example 61, wherein NH$_3$/THF in step A was replaced with 2-aminoethanol. $^1$H NMR (400 MHz, DMSO-d$_6$) δ 1.05 (d, J=6.90 Hz, 6 H); 2.87 (s, 3 H); 3.04 (dt, J=13.71, 6.76 Hz, 2 H); 3.28 (q, J=5.86 Hz, 3 H); 3.45-3.50 (m, 2 H); 3.58 (br. s., 1 H); 4.10-4.52 (m, 2 H); 4.80 (br. s., 1 H); 6.39 (s, 1 H); 6.86 (s, 1 H); 7.07 (s, 2 H); 7.16-7.26 (m, 1 H); 8.83 (t, J=5.58 Hz, 1 H); 9.36 (s, 1 H); 9.62 (s, 1 H); 10.54-11.07 (m, 1 H). MS (ESI) M/Z: 452 (M+1).

EXAMPLE 65

3-(2,4-dihydroxyl-5-isopropylphenyl)-N-(2-fluoro-ethyl)-4-(2-methyl-1,2,3,4-tetrahydroisoquinolin-6-yl)isoxazole-5-carboxamide

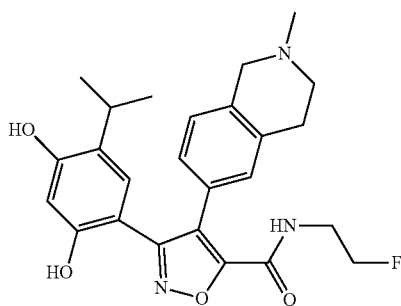 [SMILES: CC(C)c1cc(-c2noc(C(=O)NCCF)c2-c2ccc3c(c2)CCN(C)C3)c(O)cc1O]

Reaction scheme:

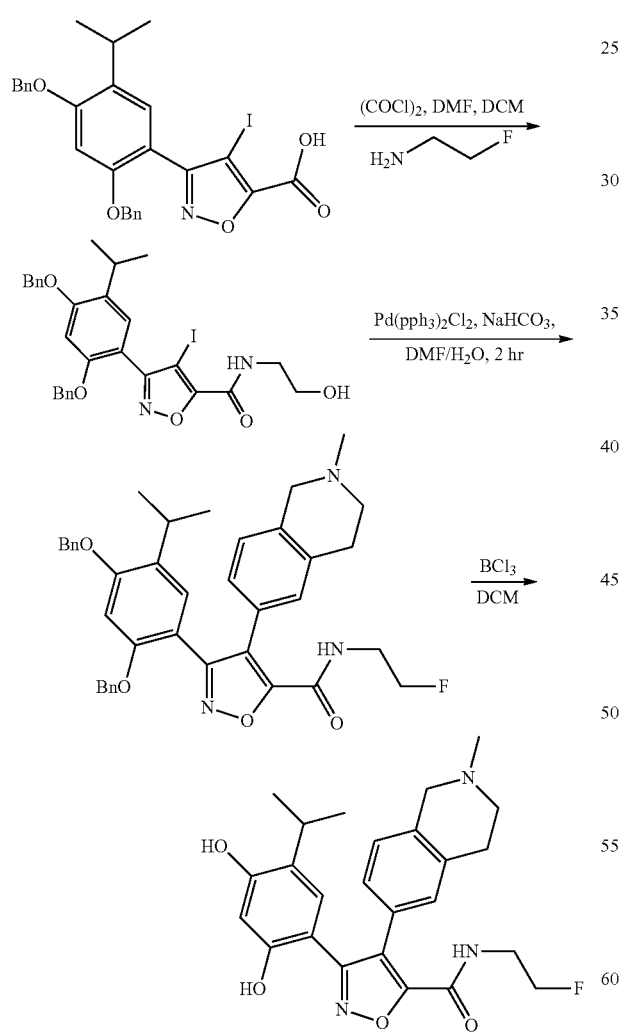

Step A: The title compound of this Example was prepared according to the order of steps A, B and C in Example 61, wherein NH$_3$/THF in step A was replaced with 2-fluoroethylamine. $^1$H NMR (400 MHz, DMSO-d$_6$) δ 9.63 (s, 1H), 9.37 (s, 1H), 9.15 (t, J=5.4 Hz, 1H), 7.19 (s, 1H), 7.08 (s, 2H), 6.87 (s, 1H), 6.39 (s, 1H), 4.58 (t, J=4.8 Hz, 1H), 4.46 (t, J=4.9 Hz, 1H), 4.31 (br. s., 1H), 3.60-3.52 (m, 2H), 3.51 (br. s., 4H), 3.10-2.96 (m, 2H), 2.87 (s, 3H), 2.11-2.05 (m, 1H), 1.06 (d, J=6.8 Hz, 6H). MS (ESI) M/Z: 454 (M+1).

EXAMPLE 66

3-(2,4-dihydroxyl-5-isopropylphenyl)-N-(3-hydroxylpropyl)-4-(2-methyl-1,2,3,4-tetrahydroisoquinolin-6-yl)isoxazole-5-carboxamide

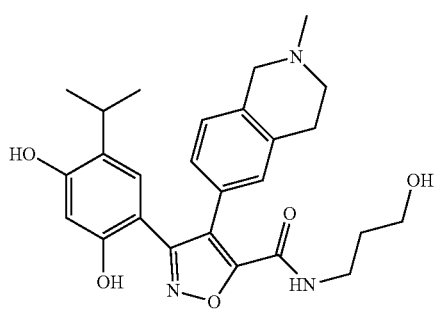 [SMILES: CC(C)c1cc(-c2noc(C(=O)NCCCO)c2-c2ccc3c(c2)CCN(C)C3)c(O)cc1O]

Reaction scheme:

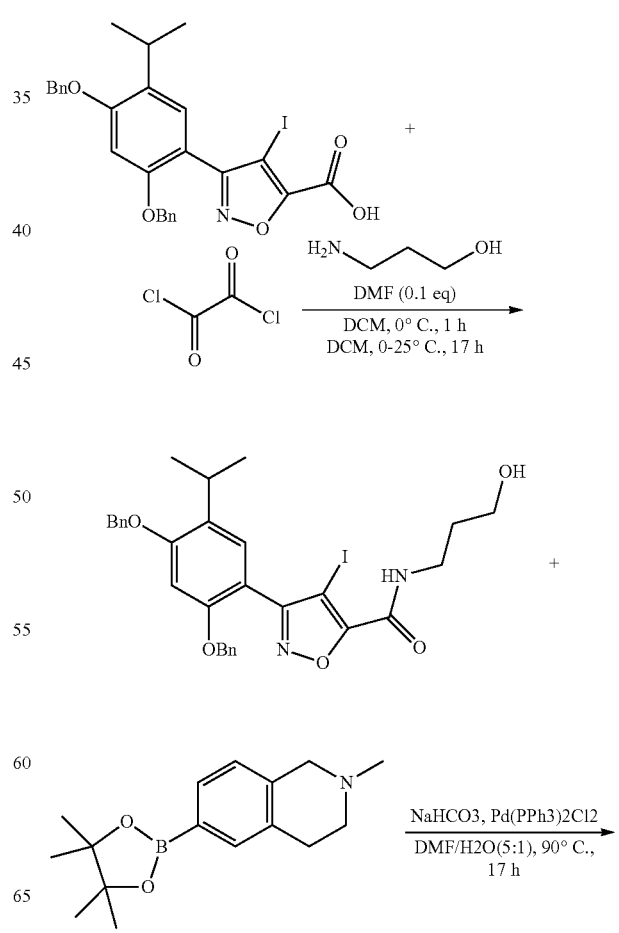

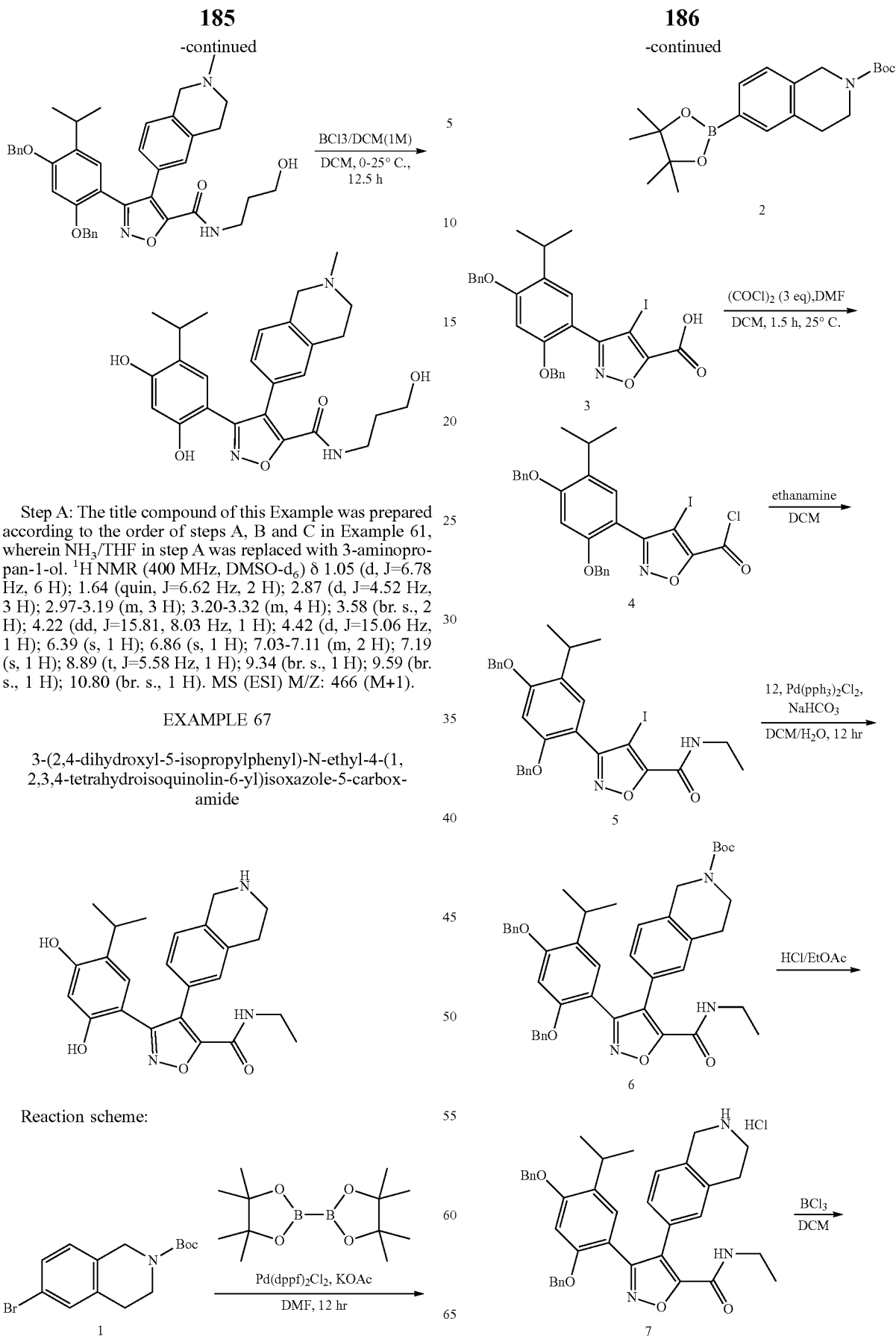

Step A: The title compound of this Example was prepared according to the order of steps A, B and C in Example 61, wherein NH$_3$/THF in step A was replaced with 3-aminopropan-1-ol. $^1$H NMR (400 MHz, DMSO-d$_6$) δ 1.05 (d, J=6.78 Hz, 6 H); 1.64 (quin, J=6.62 Hz, 2 H); 2.87 (d, J=4.52 Hz, 3 H); 2.97-3.19 (m, 3 H); 3.20-3.32 (m, 4 H); 3.58 (br. s., 2 H); 4.22 (dd, J=15.81, 8.03 Hz, 1 H); 4.42 (d, J=15.06 Hz, 1 H); 6.39 (s, 1 H); 6.86 (s, 1 H); 7.03-7.11 (m, 2 H); 7.19 (s, 1 H); 8.89 (t, J=5.58 Hz, 1 H); 9.34 (br. s., 1 H); 9.59 (br. s., 1 H); 10.80 (br. s., 1 H). MS (ESI) M/Z: 466 (M+1).

EXAMPLE 67

3-(2,4-dihydroxyl-5-isopropylphenyl)-N-ethyl-4-(1,2,3,4-tetrahydroisoquinolin-6-yl)isoxazole-5-carboxamide Reaction scheme:

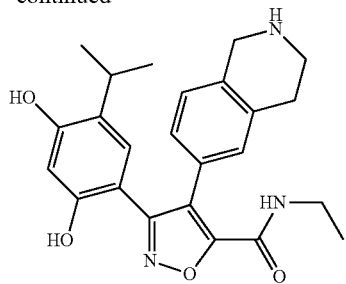

Step A: Bis(pinacolato)diboron (7.3 g, 29 mmol) and KOAc (7.1 g, 72 mmol) were added to a solution of t-butyl-6-bromo-1,2,3,4-tetrahydroisoquinolin-2-formate (7.5 g, 24 mmol) in DMF (100 mL) at 25° C. under the protection of nitrogen gas, followed by adding a catalyst Pd(dppf)Cl$_2$CH$_2$Cl$_2$ (5.3 g, 7 mmol). The mixture was stirred at 25° C. for 10 min and then heated to 80° C. with stirring for 12 hours. The mixture was cooled down to 25° C. and poured into water (600 mL). The mixture was then extracted with EA (200 mL×2). The combined organic phase was dried with anhydrous Na$_2$SO$_4$, filtered and concentrated in vacuum to give a crude product. The residue was purified by silica gel chromatography (petroleum ether/ethyl acetate=20/1 to 10/1) to give t-butyl-6-(4,4,5,5-tetramethyl-1,3,2-dioxaborolan-2-yl)-1,2,3,4-tetrahydroisoquinolin-2-formate (7.4 g, 21 mmol, 86% yield) as a white solid.

Step B: (COCl)$_2$ (2.2 g, 18 mmol, 1.5 eq) and DMF (100.00 μL) were added to a solution of 3-(2,4-dibenzyloxy-5-isopropylphenyl)-4-iodo-isoxazole-5-formic acid (5 g, 9 mmol, 1.0 eq.) in DCM (60 mL) at 0° C. The mixture was stirred at 0° C. for 1 hour, and then the reaction solution was concentrated in vacuum to give an intermediate. The intermediate was dissolved in DCM (80 mL) and at 0° C. ethylamine (1.9 g, 2.8 mL, 5.00 eq.) was added to the solution. The mixture was stirred at 0° C. for 1 hour and poured into 100 mL of water. The mixture was then extracted with DCM (80 mL×2), and the combined organic phase was dried with anhydrous Na$_2$SO$_4$, filtered and concentrated in vacuum to give 3-(2,4-dibenzyloxy-5-isopropylphenyl)-N-ethyl-4-iodo-isoxazole-5-carboxamide (3.8 g, 75% yield) as a yellow solid.

Step C: NaHCO$_3$ (1.6 g, 19 mmol), H$_2$O (17.0 mL) and Pd(PPh$_3$)$_2$Cl$_2$ (447 mg, 637 μmol) were added to a mixed solution of t-butyl-6-(4,4,5,5-tetramethyl-1,3,2-dioxaborolan-2-yl)-1,2,3,4-tetrahydroisoquinolin-2-formate (3.2 g, 9 mmol) and 3-(2,4-dibenzyloxy-5-isopropylphenyl)-N-ethyl-4-iodo-isoxazole-5-carboxamide (3.8 g, 6 mmol) in DMF (50 mL) at 25° C. under the protection of nitrogen gas. The mixture was stirred at 25° C. for 10 min and then heated to 80° C. with stirring for 12 hours. The mixture was cooled down to 25° C. and poured into water (100 mL). The mixture was then extracted with EA (150 mL×2), and the combined organic phase was washed with water (100 mL), dried over anhydrous Na$_2$SO$_4$, filtered and concentrated in vacuum. The residue was purified by silica gel chromatography (200~300 mesh of silica gel, PE/EA=10/1 to 5/1) to give t-butyl 6-(3-(2,4-dibenzyloxy-5-isopropyl-phenyl)-5-(ethyl-formamyl)isoxazol-4-yl)-1,2,3,4-tetrahydroisoquinoline-2-formate (2.6 g, 3.7 mmol, 58% yield) as a yellow solid. MS (ESI) M/Z: 588 (M+1).

Step D: HCl/MeOH (4 M, 20.00 mL) was added to a solution of t-butyl 6-(3-(2,4-dibenzyloxy-5-isopropyl-phenyl)-5-(ethylformamyl)isoxazol-4-yl)-1,2,3,4-tetrahydroisoquinoline-2-formate (2.6 g, 3.7 mmol, 1.00 eq.) in MeOH (20.00 mL) at 25° C., and the mixture was stirred at 25° C. for 30 min. The mixture was concentrated at 40° C. to give the product 3-(2, 4-dibenzyloxy-5-isopropylphenyl)-N-ethyl-4-(1,2,3,4-tetrahydroisoquinolin-6-yl)isoxazole-5-carboxamide (2.5 g, a crude product) as a yellow solid.

Step E: BCl$_3$ (9.5 mL, 1 mol in DCM solution) was slowly added to a solution of 3-(2, 4-dibenzyloxy-5-isopropylphenyl)-N-ethyl-4-(1,2,3,4-tetrahydroisoquinolin-6-yl)isoxazole-5-carboxamide (1.0 g, 1.6 mmol) in DCM (50.00 mL) at 0° C. under the protection of nitrogen gas. The reaction mixture was stirred at 0° C. for 1 hour, and then warmed up to room temperature with stirring for 2 hours. The reaction solution was cooled down to 0° C. and then the reaction was quenched by the addition of MeOH (20 mL). The reaction mixture was concentrated in vacuum to give a crude product. The residue was purified by preparative HPLC (HCl method: Phenomenex Synergi C18 150×30 mm×4 μm, water (0.05% HCl)-ACN) to give 3-(2,4-dihydroxyl-5-isopropylphenyl)-N-ethyl-4-(1,2,3,4-tetrahydroisoquinolin-6-yl)isoxazole-5-carboxamide hydrochloride (315 mg, 685 μmol, 44% yield). $^1$H NMR (400 MHz, DMSO-d$_6$): δ9.57 (s, 1 H), 9.38 (s, 2 H), 9.31 (s, 1 H), 8.94 (t, J=5.6 Hz, 1 H), 7.15 (s, 1H), 7.05-7.12 (m, 2 H), 6.86 (s, 1H), 6.38 (s, 1H), 4.21 (s, 2 H), 3.21-3.33 (m, 4 H), 3.03-3.10 (m, 1 H), 2.56-2.90 (m, 2 H), 1.05-1.11 (m, 9 H). MS (ESI) M/Z: 422 (M+1).

EXAMPLE 68

3-(2,4-dihydroxyl-5-isopropylphenyl)-N-ethyl-4-(2-isopropyl-1,2,3,4-tetrahydroisoquinolin-6-yl)isoxazole-5-carboxamide

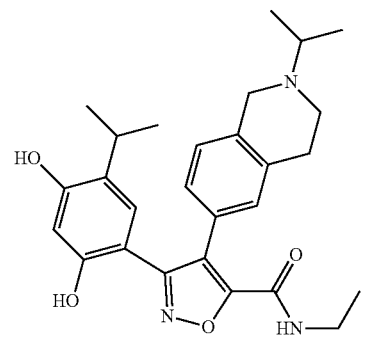 [SMILES: CCNC(=O)c1onc(-c2cc(C(C)C)c(O)cc2O)c1-c1ccc2c(c1)CCN(C(C)C)C2]

Reaction scheme:

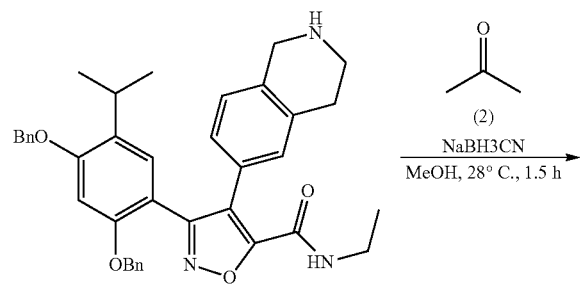

-continued

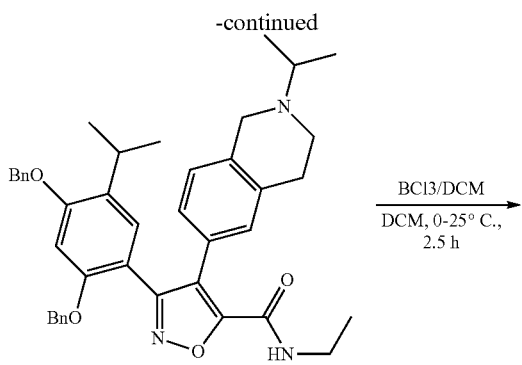

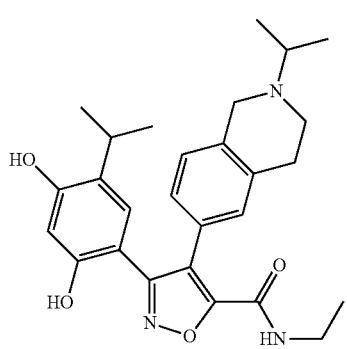

Step A: Acetone (97 mg, 2 mmol, 10.00 eq.) and acetic acid (5 mg, 8 μmol, 0.50 eq.) were added to a solution of 3-(2, 4-dibenzyloxy-5-isopropylphenyl)-N-ethyl-4-(1,2,3,4-tetrahydroisoquinolin-6-yl)isoxazole-5-carboxamide (100 mg, 166 μmol, 1.0 eq.) in methanol (3 mL). After the mixture was stirred at 30° C. for 0.5 hour, NaBH₃CN (31 mg, 499 μmol, 3.0 eq.) was added and the mixture was stirred for an additional hour. The reaction solution was concentrated in vacuum. The residue was purified by preparative TLC to give 3-(2,4-dibenzyloxy-5-isopropylphenyl)-N-ethyl-4-(2-isopropyl-1,2,3,4-tetrahydroisoquinolin-6-yl)isoxazole-5-carboxamide (80 mg, 124 μmol, 75% yield) as a yellow oil.

Step B: A solution of BCl₃ in DCM (1 M, 1.2 mL, 10.0 eq.) was added slowly dropwise to a solution of 3-(2,4-dibenzyloxy-5-isopropylphenyl)-N-ethyl-4-(2-isopropyl-1,2,3,4-tetrahydroxyquinolin-6-yl)isoxazole-5-carboxamide (80 mg, 124 mol, 1.0 eq.) in anhydrous DCM (8 mL) at 0° C. over a course of 5 min. The suspension was stirred at 0° C. for 30 min, and then warmed up to 25° C. with stirring for 2 hours. The mixture was cooled down to 0° C., quenched by slowly adding MeOH (3 mL) and concentrated in vacuum to give a residue. The residue was purified by preparative HPLC to give 3-(2,4-dihydroxyl-5-isopropylphenyl)-N-ethyl-4-(2-isopropyl-1,2,3,4-tetrahydroisoquinolin-6-yl)isoxazole-5-carboxamide (25 mg, 48 mol, 39% yield). ¹H NMR (400 MHz, DMSO-d₆) ppm: 1.02-1.11 (m, 15 H); 2.64-2.69 (m, 4 H); 2.85 (dt, J=13.05, 6.53 Hz, 1 H); 3.04 (dt, J=13.71, 6.89 Hz, 1 H); 3.18-3.29 (m, 4 H); 3.61 (s, 2 H); 6.33 (s, 1 H); 6.81 (s, 1 H); 6.93-6.96 (m, 2 H); 6.98 (s, 1 H); 8.20 (s, 1 H); 8.85 (t, J=5.71 Hz, 1 H). MS (ESI) M/Z: 464 (M+1).

EXAMPLE 69

3-(2,4-dihydroxyl-5-isopropylphenyl)-N-ethyl-4-(2-(2-hydroxylethyl)-(1,2,3,4-tetrahydroisoquinolin-6-yl)isoxazole-5-carboxamide

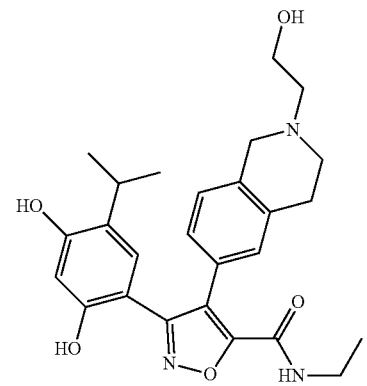 [SMILES: CCNC(=O)c1onc(-c2cc(C(C)C)c(O)cc2O)c1-c1ccc2c(c1)CCN(CCO)C2]

Reaction scheme:

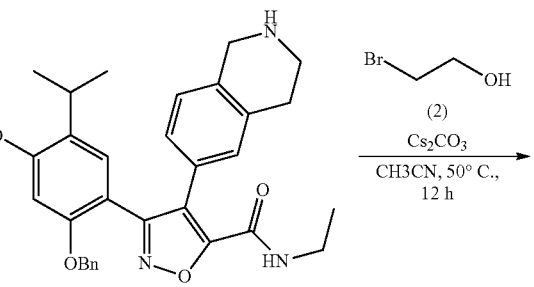

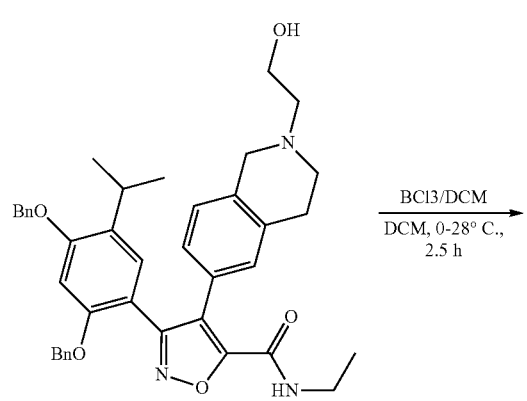

-continued

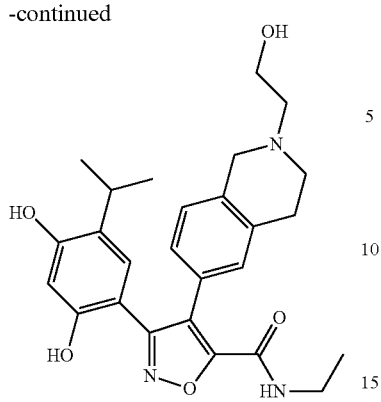

Step A: 3-(2,4-dibenzyloxy-5-isopropylphenyl)-N-ethyl-4-(1,2,3,4-tetrahydroisoquinolin-6-yl)isoxazole-5-carboxamide (150 mg, 249 μmol, 1.0 eq.), Cs$_2$CO$_3$ (122 mg, 374 μmol, 1.5 eq.) and 2-bromoethanol (32 mg, 249 μmol, 1.0 eq.) were added to acetonitrile (3 mL). The mixture was heated to 50° C. with stirring for 12 hours. After cooling, the reaction mixture was concentrated to dryness. The residue was purified by preparative TLC (dichloromethane/methanol=15:1) to give 3-(2,4-dibenzyloxyl-5-isopropylphenyl)-N-ethyl-4-(2-(2-hydroxylethyl)-(1,2,3,4-tetrahydroisoquinolin-6-yl)isoxazole-5-carboxamide (120 mg, 185 μmol, 74% yield) as a colorless oil.

Step B: BCl$_3$ (1.9 mL, 1 mol in DCM solution) was slowly added to a solution of 3-(2,4-dibenzyloxyl-5-isopropylphenyl)-N-ethyl-4-(2-(2-hydroxylethyl)-(1,2,3,4-tetrahydroisoquinolin-6-yl)isoxazole-5-carboxamide (120 mg, 186 μmol) in DCM (8.00 mL) at 0° C. under the protection of nitrogen gas. The reaction mixture was stirred at 0° C. for 1 hour, and then warmed up to room temperature with stirring for two hours. The reaction solution was cooled down to 0° C. and then the reaction was quenched by adding MeOH (4 mL). The reaction mixture was concentrated in vacuum to give a crude product. The residue was purified by preparative HPLC to give 3-(2,4-dihydroxyl-5-isopropylphenyl)-N-ethyl-4-(2-(2-hydroxylethyl)-(1,2,3,4-tetrahydroisoquinolin-6-yl)isoxazole-5-carboxamide hydrochloride (39 mg, 77 μmol, 41% yield). $^1$H NMR (400 MHz, DMSO-d$_6$) ppm: 1.03-1.12 (m, 9 H); 2.88 (d, J=17.32 Hz, 1 H); 3.00-3.18 (m, 2 H); 3.21-3.31 (m, 5 H); 3.71 (d, J=11.67 Hz, 1 H); 3.84 (t, J=4.96 Hz, 2 H); 4.32 (dd, J=15.69, 7.91 Hz, 1 H); 4.51 (d, J=15.18 Hz, 1 H); 6.39 (s, 1 H); 6.85 (s, 1 H); 7.10 (s, 2 H); 7.18 (s, 1 H); 8.95 (t, J=5.71 Hz, 1 H); 9.32 (br. s., 1 H); 9.58 (br. s., 1 H); 10.43 (br. s., 1 H). MS (ESI) M/Z: 466 (M+1).

EXAMPLE 70

3-(2,4-dihydroxyl-5-isopropylphenyl)-N-ethyl-4-(2-(2-methoxyethyl)-(1,2,3,4-tetrahydroisoquinolin-6-yl)isoxazole-5-carboxamide

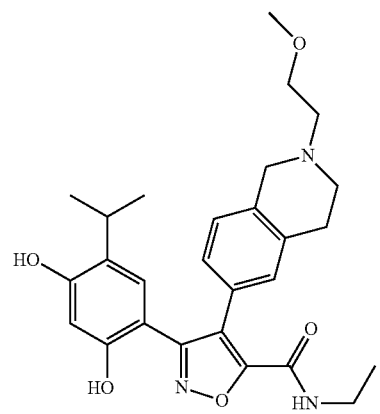 [SMILES: CCNC(=O)c1onc(-c2cc(C(C)C)c(O)cc2O)c1-c1ccc2c(c1)CCN(CCOC)C2]

Reaction scheme:

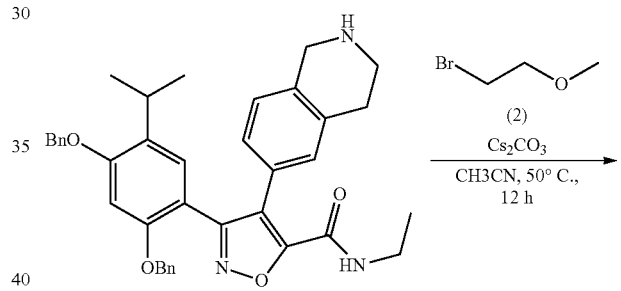

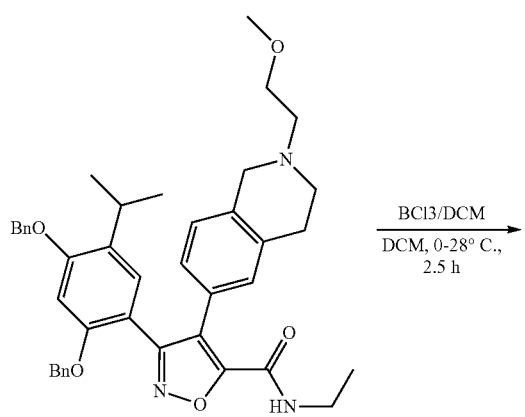

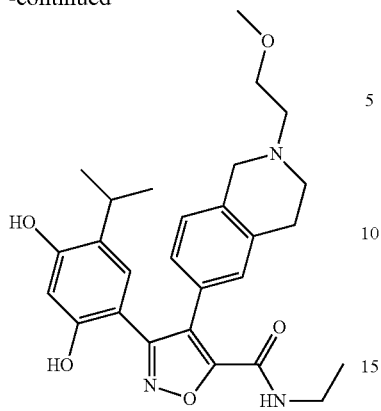

Step A: The title compound of this Example was prepared according to the order of steps A and B in Example 69, wherein 2-bromoethanol in step A was replaced with 1-bromo-2-methoxyethane. $^1$H NMR (400 MHz, DMSO-d$_6$) ppm: 0.99-1.12 (m, 9 H); 2.61-2.68 (m, 6 H); 3.04 (dt, J=13.77, 6.85 Hz, 1 H); 3.19-3.24 (m, 2 H); 3.47-3.60 (m, 7 H); 6.33 (s, 1 H); 6.81 (s, 1 H); 6.90-6.96 (m, 2 H); 6.98 (s, 1 H); 8.18 (s, 1 H); 8.85 (t, J=5.71 Hz, 1H). MS (ESI) M/Z: 480 (M+1).

EXAMPLE 71

3-(2,4-dihydroxyl-5-isopropylphenyl)-N-ethyl-4-(2-(2-fluoroethyl)-(1,2,3,4-tetrahydroisoquinolin-6-yl)isoxazole-5-carboxamide

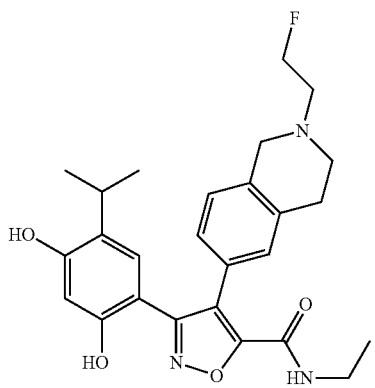 [SMILES: CCNC(=O)c1onc(-c2cc(C(C)C)c(O)cc2O)c1-c1ccc2c(c1)CCN(CCF)C2]

Reaction scheme:

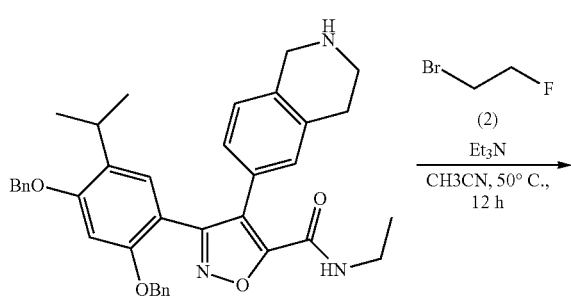

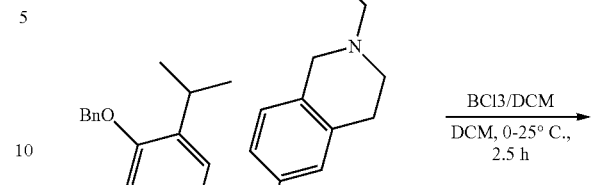

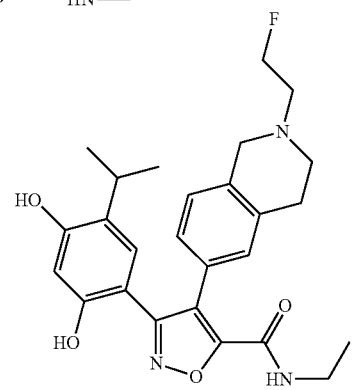

Step A: The title compound of this Example was prepared according to the order of steps A and B in Example 69, wherein 2-bromoethanol in step A was replaced with 1-bromo-2-fluoroethane. $^1$H NMR (400 MHz, DMSO-d$_6$) ppm: 1.02-1.11 (m, 9 H); 2.89 (d, J=16.56 Hz, 1 H); 2.99-3.18 (m, 2 H); 3.19-3.28 (m, 2 H); 3.30-3.44 (m, 1 H); 3.66-3.75 (m, 2 H); 4.28-4.41 (m, 1 H); 4.45-4.57 (m, 1 H); 4.88 (t, J=4.14 Hz, 1 H); 5.00 (t, J=4.27 Hz, 1 H); 6.37 (s, 1 H); 6.85 (s, 1 H); 7.10 (s, 2 H); 7.19 (s, 1 H); 8.94 (t, J=5.71 Hz, 1 H); 9.18-9.76 (m, 2 H); 10.97 (br. s., 1 H). MS (ESI) M/Z: 468 (M+1);

EXAMPLE 72

Determination of the Activity of Compound at Enzyme Level

In the present invention, the method of fluorescence polarization (FP) was used to establish the screening platform for HSP90-alpha inhibitors. The principle based on is to calculate fluorescence polarization values in horizontal and vertical directions by detecting molecular weight changes before and after interaction of fluorescent labeled small molecules with other molecules, in use for correlation analysis. If binding equilibria between the fluorescent labeled small molecule and the macromolecule is established, it moves slowly when excited, and the fluorescence polarization values measured will increase. If the fluorescent labeled small molecule binding to the macromolecule is replaced with other ligands, its rotational or inversional speed in free state will become faster, the emitted light would be depolarized with respect to the exciting light plane, and thus the polarized light value measured will decrease, so as to calculate the polarization value of the sample (the unit of polarization value is mP).

The fluorescent labeled small molecule used in the present invention was VER-00051001 (synthesized by reference to the synthetic method described in JMC, 2008, 51, 196-218). The reaction was carried out in a 384-well black plate, using the reaction hydrophobic protein HFB buffer: 100 mM Tris.Cl pH 7.4, 20 mM KCl, 6 mM $MgCl_2$, 5 μg/mL BSA, 25 nM full-length Hsp90U, 10 nM VER-51001. The volume of the reaction system was 50 mL, containing 5 nM GM-BODIPY (geldanamycin), 30 nM HSP90 and the test small molecular compound or DMSO (dimethyl sulfoxide), wherein the DMSO content was 2‰. Additional two group wells were established, wherein the wells only added with HFB buffer were used as blank controls, and the wells further added with 5 nM GM-BODIPY were used as negative controls. The reaction was carried out at 4° C. for 12-16 hours. The mP value was measured by Biotek microplate reader at 485 nm of excitation wavelength and 535 nm of emission wavelength. The inhibition rate was calculated using the following equation:

(Compound-free mP−Compound mP)/(Compound-free mP−negative control mP)×100%

After the inhibitory rates of the compound at different concentrations were calculated, the IC50 of the compound can be calculated, and the IC50 values for the compounds each were shown in Table 1 below.

EXAMPLE 73

Activity Measurement of Compound at Cell Level

The growth inhibition assay of tumor cells was detected by sulforhodamine B (SRB) staining method. The specific steps were as follows: inoculating human colon cancer cell line HCT116 and human lung cancer cell line A549 (purchased from American Type Culture Collection, ATCC) at the logarithmic growth phase into a 96-well micro culture plate at an appropriate concentration of 4000 cells/well, 100 μL for each well; after culturing overnight, adding with the compound at different concentrations (100, 10, 1, 0.1, 0.01 μM) to react for 72 h, wherein triplicate wells were set up for each concentration, and solvent control wells with the corresponding concentration and zero wells without cells were also set up. After the completion of the reaction, the culture medium was removed from the adherent cells, the later was added with 10% (w/v) trichloroacetic acid (100 μL/well) at 4° C. to fix for 1 h, and then washed five times with distilled water. After drying at room temperature, 100 μL of SRB solution (4 mg/mL, dissolved in 1% glacial acetic acid) was added into each well, followed by incubation and staining for 15 min at room temperature. The uncombined SRB was removed by washing five times with 1% glacial acetic acid. After drying at room temperature, 100 μL of 10 mM Tris solution was added into each well, and the optical density (OD) at 515 nm was measured by a VERSMax microplate reader. The inhibition rate of the drug to tumor cell growth was calculated according to the following equation:

Inhibition rate (%)=(OD of control well−OD of drug well)/OD of control well×100%.

The experiment was repeated twice.

The inhibition rate (%) of the compounds to HCT116 and A549 cells was shown in Table 1 below:

TABLE 1

In vitro screening test results of the compounds of the present invention

| Test samples (the title compounds obtained in the Examples) | Target binding ability HSP90α FP IC50 (nM) | Colon cancer cell HCT116 Cell EC50 (nM) | Lung cancer cell A549 Cell EC50 (nM) |
|---|---|---|---|
| 1 | A | A | A |
| 2 | B | B | ND |
| 3 | B | B | ND |
| 4 | B | ND | B |
| 5 | B | ND | A |
| 6 | B | ND | A |
| 7 | B | ND | A |
| 8 | B | ND | A |
| 9 | B | ND | B |
| 10 | B | ND | B |
| 11 | B | ND | A |
| 12 | A | ND | A |
| 13 | C | C | ND |
| 14 | A | A | ND |
| 15 | B | ND | C |
| 16 | B | ND | A |
| 17 | B | ND | B |
| 18 | A | ND | B |
| 19 | B | ND | C |
| 20 | B | ND | C |
| 21 | A | ND | C |
| 22 | A | ND | B |
| 23 | A | ND | B |
| 24 | B | ND | B |
| 25 | A | ND | B |
| 26 | A | ND | B |
| 27 | A | ND | A |
| 28 | A | ND | A |
| 29 | A | ND | B |
| 30 | B | ND | C |
| 31 | B | ND | C |
| 32 | A | ND | C |
| 33 | B | ND | C |
| 34 | A | ND | B |
| 35 | A | ND | B |
| 36 | A | ND | A |
| 37 | B | ND | B |
| 38 | B | ND | B |
| 39 | B | ND | B |
| 40 | A | ND | A |
| 41 | A | ND | B |
| 42 | B | ND | B |
| 43 | B | ND | C |
| 44 | A | ND | B |
| 45 | A | ND | B |
| 46 | B | ND | A |
| 47 | B | ND | B |
| 48 | B | ND | B |
| 49 | A | ND | B |
| 50 | B | ND | A |
| 51 | B | ND | B |
| 52 | B | ND | B |
| 53 | B | ND | C |
| 54 | B | ND | C |
| 55 | B | ND | C |
| 56 | B | ND | C |
| 57 | B | ND | C |
| 58 | B | ND | C |
| 59 | B | ND | C |
| 60 | B | ND | C |
| 61 | A | ND | A |
| 62 | A | ND | A |
| 63 | A | ND | A |
| 64 | A | ND | A |
| 65 | A | ND | A |
| 66 | A | ND | A |
| 67 | A | ND | A |
| 68 | A | ND | A |
| 69 | A | ND | A |

TABLE 1-continued

In vitro screening test results of the compounds of the present invention

| Test samples (the title compounds obtained in the Examples) | Target binding ability HSP90α FP IC50 (nM) | Colon cancer cell HCT116 Cell EC50 (nM) | Lung cancer cell A549 Cell EC50 (nM) |
|---|---|---|---|
| 70 | A | ND | B |
| 71 | A | ND | A |

Notes:
The above compounds in enzyme activity tests were divided into three parts of A~C according to the activity range, wherein A ≤ 20 nM; 20 nM < B ≤ 100 nM; C > 100 nM; ND indicates that the data was not detected.
Conclusions: Some compounds of the present invention have good activities in binding to HSP90 protein target and inhibiting the growth of HCT116 or A549 tumor cells, compared to the known HSP90 inhibitor Luminespib.

EXAMPLE 74

Efficacy Evaluation of the Compound in Animals

A549 tumor cells were subcutaneously inoculated in the right armpit of nude mice in 5×10$^6$ cells/mouse, to form a transplantion tumor. When the volume reached 100-200 mm$^3$, the animals were randomly divided according to tumor volume, into the negative control group (n=5), the positive control group groups (n=5 in each group), and the experimental groups (n=5 in each group). The experimental groups were respectively injected intravenously with the positive drug Luminespib (50 mg/kg) and compound 1 (50 mg/kg) at different concentrations, twice a week, and the negative control group was administrated an equal amount of solvent simultaneously. The length (A) and width (B) of the tumor were measured twice a week with a vernier caliper, and the tumor volume was calculated according to V=A×B$^2$/2. Relative tumor volume (RTV) was calculated as follows: RTV=V$_t$/V$_0$, wherein V$_t$ is the tumor volume at the end of the administration, and V$_0$ is the tumor volume measured before separation and administration. The pharmacodynamic evaluation index of antitumor activity is relative tumor proliferation rate T/C (%), and the calculation formula is: T/C (%)=T$_{RTV}$/C$_{RTV}$×100%, wherein T$_{RTV}$: RTV of the treatment group; C$_{RTV}$: RTV of the negative control group. Efficacy evaluation criteria: T/C %>60% is inefficient; T/C %≤60% and P<0.05 by statistical treatment is effective. The tumor growth inhibition rate (TGI) was calculated as follows:

$$TGI\ (\%) = \{[(CV_t - CV_0) - (TV_t - TV_0)]/(CV_t - CV_0)\} \times 100\%$$

Wherein, CV$_t$ is the tumor volume of the control group at the end of the administration; CV$_0$ is the tumor volume of the control group before separation and administration; TV$_t$ is the tumor volume of the administration group at the end of the administration; and TV$_0$ is the tumor volume of the administration group before separation and administration. The difference in tumor volume between the administration group and the control group was examined by t-test. At the same time, the body weights of nude mice in each group were weighed twice a week to preliminarily evaluate the toxic side effects of the drug. The efficacy results of the compounds in this model were shown in Table 2 below.

TABLE 2

Results of in vivo efficacy test of the compounds of the present invention

| Test samples (the title compounds obtained in the Examples) | TGI (%) | | | | | |
|---|---|---|---|---|---|---|
| | Day 0 | Day 7 | Day 11 | Day 14 (stopping administration) | Day 17 | Day 28 |
| Vehicle | — | — | — | — | — | — |
| Luminespib | — | 18 | 34 | 49 | 52 | 35 |
| Example 1 | — | 20 | 40 | 63 | 71 | 60 |

Conclusions: The compound in Example 1 of the present invention have slightly superior antitumor efficacy in the mouse model transplanted with A549 lung cancer cells, compared to the known HSP90 inhibitor Luminespib.

EXAMPLE 75

Tissue Distribution Study of the Compound

The tissue distribution study of Example 67 of the present invention

1. Summary

SD rats were used as the subject animals. The drug concentrations in plasma, lung and breast tissue were measured by LC/MS/MS method at different times after the compound of Example 67 was intravenously injected at the tails of rats. The tissue distribution of the compounds of the present invention in rats was studied and their pharmacokinetic characteristics were evaluated.

2. Test Protocol 2.1 Experimental Drugs: Luminespib, Ganetespib and the compound of Example 67.

2.2 Test Animals:

Healthy adult male SD rats, 100-200 g, 9 rats in total, purchased from Shanghai Slack Laboratory Animal Co., Ltd.

2.3 Drug Preparation:

The appropriate amounts of the samples were weighed. All of Luminespib, Ganetespib and the compound 67 of the present invention were formulated into clear solutions in 1 mg/mL in 0.5 mg/ml in 10% DMSO/14% Cremophor RH40/76% D5W, for intravenous injection.

2.4 Administration:

9 SD male rats were divided into three groups, three rats in each group. After normal feeding, administrations were carried out in tails by intravenous injection at the dose of 1 mg/kg.

3. Operation:

Samples were collected from blood, lung and breast tissues in three group rats at 0.5 h, 6 h and 24 h after administration. The blood samples were centrifuged at 4° C., 3000 rpm for 15 min within half an hour after collection, to separate and obtain plasma samples. The resulting plasma samples were placed in polypropylene tubes and stored at −80° C. for LC/MS/MS analysis. After the collection of the blood samples, the animals were sacrificed with CO$_2$, followed by collection of the tissue samples. Each of the tissue samples was washed twice with cold deionized water and adhered to filter papers. Each of the tissue samples was then homogenized several times in MeOH/15 mM PBS (1:2) (5 mL MeOH/15 mM PBS (1:2) per gram of tissue, with a dilution factor of 6) to ensure the formation of homogeneous phase. The whole process was carried out below freezing point temperature. The homogenized samples were quickly frozen by using dry ice and stored at −80° C. for bioanalysis.

The contents of the test compound in rat plasma, lung and breast tissue after injection administration were measured by LC/MS/MS.

4. Results of Pharmacokinetic Parameters

TABLE 3

Results of the tissue distribution of the compound of the present invention

| Tissues | time (h) | Luminespib | Ganetespib | Example 67 |
|---|---|---|---|---|
| plasma concentration (nM) | 0.5 | 67.1 | 267 | 115 |
|  | 6 | ND | 4.46 | 9.98 |
|  | 24 | ND | ND | 3.72 |
| plasma exposure dose (nM · h) |  | ND | ND | 415 |
| pulmonary concentration (nM) | 0.5 | 1002 | 1010 | 3036 |
|  | 6 | 257 | 101 | 1534 |
|  | 24 | 35.9 | ND | 613 |
| pulmonary exposure dose (nM · h) |  | 5284 | ND | 30933 |
| concentration in breast tissue (nM) | 0.5 | 104 | 352 | 395 |
|  | 6 | 61.4 | 70.9 | 376 |
|  | 24 | ND | ND | 199 |
| breast tissue exposure dose (nM · h) |  | ND | ND | 7226 |

Notes:
ND indicates that the detection limit was exceeded, and no relevant data was detected.
Conclusions: When the injection dose of the preferred compound of the present invention was 1 mg/kg, the blood concentrations in lung and breast tissues of rats at the same time were significantly higher than those of Luminespib and Ganetespib at the same dose, and the AUC value was also significantly larger, suggesting that the preferred compound of the present invention has better application prospect in cancer such as lung cancer, breast cancer and the like.

EXAMPLE 76

Efficacy Evaluation of the Compound in Breast Cancer Animals

BT-474 tumor cells were subcutaneously inoculated in the right armpit of nude mice in $5 \times 10^6$ cells/mouse, to form a transplantion tumor. When the volume reached 100-200 mm$^3$, the animals were randomly divided according to tumor volume, into the negative control group (n=6), the positive control group groups (n=6 in each group), and the experimental groups (n=6 in each group). The experimental groups were respectively injected intravenously with the positive drug Ganetespib (20 mg/kg) and compound 67 (10 mg/kg and 20 mg/kg) at different concentrations, three times a week, and the negative control group was administrated an equal amount of solvent simultaneously. The length (A) and width (B) of the tumor were measured twice a week with a vernier caliper, and the tumor volume was calculated according to $V = A \times B^2/2$. Relative tumor volume (RTV) was calculated as follows: $RTV = V_t/V_0$, wherein $V_t$ is the tumor volume at the end of the administration, and $V_0$ is the tumor volume measured before separation and administration. The pharmacodynamic evaluation index of antitumor activity is relative tumor proliferation rate T/C (%), and the calculation formula is: T/C (%)=$T_{RTV}/C_{RTV} \times 100\%$, wherein $T_{RTV}$: RTV of the treatment group; $C_{RTV}$: RTV of the negative control group. Efficacy evaluation criteria: T/C %>60% is inefficient; T/C %≤60% and P<0.05 by statistical treatment is effective. The tumor growth inhibition rate (TGI) was calculated as follows:

TGI (%)={[(CV$_t$-CV$_0$)-(TV$_t$-TV$_0$)]/(CV$_t$-CV$_0$)}×100%

Wherein, CV$_t$ is the tumor volume of the control group at the end of the administration; CV$_0$ is the tumor volume of the control group before separation and administration; TV$_t$ is the tumor volume of the administration group at the end of the administration; and TV$_0$ is the tumor volume of the administration group before separation and administration. The difference in tumor volume between the administration group and the control group was examined by t-test. At the same time, the body weights of nude mice in each group were weighed twice a week to preliminarily evaluate the toxic side effects of the drug. The efficacy results of the compounds in this model were shown in Table 4 below.

TABLE 4

Results of in vivo efficacy test of the compounds of the present invention

| Test sample (the title compound obtained in the Example) | TGI (%) | | | | | |
|---|---|---|---|---|---|---|
|  | Day 0 | Day 7 | Day 11 | Day 18 (stopping administration) | Day 21 | Day 35 |
| Vehicle | — | — | — | — | — | — |
| Ganetespib (20 mpk) | — | — | — | — | 124 | 108 |
| Example 67 (10 mpk) | — | — | — | — | 137 | 120 |
| Example 67 (20 mpk) | — | — | — | — | 135 | 129 |

Conclusions: The preferred compound of the present invention at 10 mpk has a significantly better anti-tumor efficacy in the mouse model transplanted with BT-474 breast cancer cells, compared to the known HSP90 inhibitor Ganetespib at 20 mpk.

EXAMPLE 77

Water Solubility Comparison

The compounds of the present invention, Ganetespib and Luminespib are used clinically as injections, and thus they need to have good water solubility to facilitate the development of related clinical preparations. All the unique fused ring structures in the compounds of the present invention contain basic nitrogen atom, and the compounds is easy to form salts and have a great advantage in water solubility. CN1771235A discloses HSP90 inhibitors containing fused ring structures, but they are structurally distinct from the compounds of the present invention and do not contain the groups easy to form a salt, which can be expected to exhibit poor water solubility.

What is claimed is:
1. A compound represented by formula (I), or a pharmaceutically acceptable salt thereof,

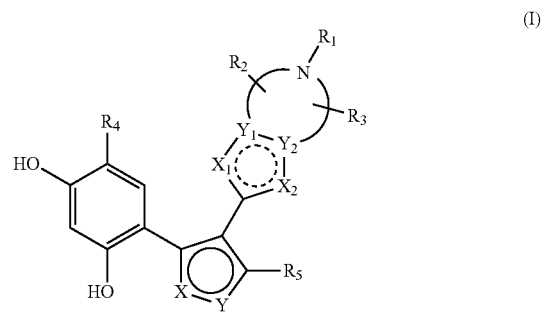

(I)

wherein:

X and Y are each independently selected from N, O or S;

$X_1$, $X_2$, $Y_1$, $Y_2$ and the carbon atom linking $X_1$ and $X_2$ together form a 5- to 7-membered aromatic ring, aliphatic saturated ring or aliphatic unsaturated ring;

$X_1$ and $X_2$ are each independently selected from C, O, S, N, —C=C—, —C=N—;

C in $X_1$ or $X_2$ may be unsubstituted, or may be substituted with $R_{01}$ or $R_{02}$;

$R_{01}$ and $R_{02}$ are each independently selected from halogen, CN, OH, SH, $NH_2$, CHO, COOH, $C_{1-10}$ alkyl, N—$C_{1-10}$ alkylamino, N,N-di($C_{1-10}$ alkyl)amino, $C_{1-10}$ alkoxy, $C_{1-10}$ alkanoyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ cycloalkoxy, $C_{3-10}$ cycloalkyl acyl, $C_{3-10}$ cycloalkoxycarbonyl, $C_{3-10}$ cycloalkylsulfonyl, $C_{3-10}$ cycloalkylsulfinyl, $C_{1-10}$ alkyl substituted with $C_{3-10}$ cycloalkyl;

$Y_1$ and $Y_2$ are each independently selected from C or N;

two substituents on $Y_1$ and $Y_2$ are linked together to form a five-, six- or seven-membered nitrogen-containing saturated ring or aromatic ring having substituents $R_1$, $R_2$ and $R_3$;

$R_1$, $R_2$ and $R_3$ are each independently selected from hydrogen, $C_{1-10}$ alkyl, hydroxyl $C_{1-10}$ alkyl, $C_{1-6}$ alkoxy-$C_{1-6}$ alkyl, halo $C_{1-10}$ alkyl, $C_{1-6}$ alkylsulfonyl-$C_{1-6}$ alkyl, $C_{1-6}$ alkylamido-$C_{1-6}$ alkyl, N,N-di($C_{1-6}$ alkyl)aminoacyl-$C_{1-6}$ alkyl, N,N-di($C_{1-6}$ alkyl)amino-$C_{1-6}$ alkanoyl, morpholinyl-$C_{1-6}$ alkanoyl, N-$C_{1-10}$ alkylamino, N,N-di($C_{1-10}$ alkyl)amino, $C_{1-10}$ alkoxy, $C_{1-10}$ alkanoyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ cycloalkyloxy, $C_{3-10}$ cycloalkyl acyl, $C_{3-10}$ cycloalkoxycarbonyl, $C_{3-10}$ cycloalkylsulfonyl, $C_{3-10}$ cycloalkylsulfinyl, $C_{3-10}$ cycloalkyl-$C_{1-5}$ alkyl;

or substituents of $R_2$ and $R_3$ are linked with each other by a covalent bond to form a five-, six- or seven-membered saturated ring with a substituent $R_{03}$ or without substituents;

$R_{03}$ is selected from $C_{1-6}$ alkyl or halogen;

$R_4$ is selected from H, halogen, $C_{1-6}$ alkyl, $C_{3-10}$ cycloalkoxy, phenyl substituted $C_{1-6}$ alkyl, phenyl substituted $C_{2-6}$ alkenyl, phenyl, $C_{1-6}$ alkyl substituted phenyl, $C_{3-6}$ cycloalkyl;

$R_5$ is selected from H, cyano, carboxyl, $C_{1-6}$ alkoxyacyl, $C_{1-7}$ alkylaminocarbonyl, halo $C_{1-6}$ alkylaminocarbonyl, $C_{1-6}$ alkoxy-$C_{1-6}$ alkylaminocarbonyl, N,N-di($C_{1-6}$ alkyl)amino-$C_{1-6}$ alkylaminocarbonyl, aminocarbonyl, hydroxy $C_{1-6}$ alkylaminocarbonyl, hydroxyl-substituted halo $C_{1-6}$ alkyl, nitrile group-substituted amidino, or selected from $C_{3-10}$ cycloalkyl, $C_{3-10}$ cycloalkenyl, or a 5- to 10-membered aromatic ring optionally substituted with one or more $R_{05}$;

$R_{05}$ is selected from $C_{1-6}$ alkyl, $C_{3-10}$ cycloalkyl.

2. The compound, or the pharmaceutically acceptable salt thereof according to claim 1, wherein $R_1$, $R_2$ and $R_3$ are each independently selected from hydrogen, $C_{1-10}$ alkyl, hydroxyl $C_{1-10}$ alkyl, $C_{3-10}$ cycloalkyl, $C_{1-6}$ alkoxy-$C_{1-6}$ alkyl, halo $C_{1-10}$ alkyl, $C_{1-6}$ alkylsulfonyl-$C_{1-6}$ alkyl, $C_{1-6}$ alkylamido-$C_{1-6}$ alkyl, N,N-di($C_{1-6}$ alkyl)aminoacyl-$C_{1-6}$ alkyl, N,N-di($C_{1-6}$ alkyl)amino-$C_{1-6}$ alkanoyl, morpholinyl-$C_{1-6}$ alkanoyl, $C_{3-10}$ cycloalkyl-$C_{1-5}$ alkyl, or the substituents of $R_2$ and $R_3$ are linked with each other by a covalent bond to form a five-, six- or seven-membered saturated ring with a substituent $R_{03}$ or without substituents.

3. The compound, or the pharmaceutically acceptable salt thereof according to claim 2, wherein $R_1$ is selected from hydrogen, $C_{1-6}$ alkyl, hydroxyl $C_{1-6}$ alkyl, $C_{3-10}$ cycloalkyl, $C_{1-4}$ alkoxy-$C_{1-4}$ alkyl, halo $C_{1-4}$ alkyl, $C_{1-4}$ alkylsulfonyl-$C_{1-4}$ alkyl, $C_{1-4}$ alkylamido-$C_{1-4}$ alkyl, N,N-di($C_{1-4}$ alkyl)aminoacyl-$C_{1-4}$ alkyl, N,N-di($C_{1-4}$ alkyl)amino-$C_{1-4}$ alkanoyl, morpholinyl-$C_{1-4}$ alkanoyl, $C_{3-6}$cycloalkyl-$C_{1-5}$ alkyl; $R_2$ and $R_3$ are selected from hydrogen or methyl; or the substituents of $R_2$ and $R_3$ are linked with each other by a covalent bond to form a five-, six- or seven-membered saturated ring without substituents.

4. The compound, or the pharmaceutically acceptable salt thereof according to claim 1, wherein $R_4$ is selected from H, $C_{1-6}$ alkyl, phenyl substituted $C_{1-6}$ alkyl, halogen, $C_{3-6}$ cycloalkyl.

5. The compound, or the pharmaceutically acceptable salt thereof according to claim 1, wherein $R_5$ is selected from cyano, $C_{1-6}$ alkylaminocarbonyl, halo $C_{1-4}$ alkylaminocarbonyl, $C_{1-4}$ alkoxy-$C_{1-4}$ alkylaminocarbonyl, N,N-di($C_{1-4}$ alkyl)amino-$C_{1-4}$ alkylaminocarbonyl, aminocarbonyl, hydroxy $C_{1-4}$ alkylaminocarbonyl, hydroxyl-substituted halo $C_{1-4}$ alkyl, nitrile group-substituted amidino, or selected from a 5- to 6-membered nitrogen-containing heteroaromatic ring optionally substituted with one or more $R_{05}$;

wherein $R_{05}$ is selected from $C_{1-6}$ alkyl.

6. The compound, or the pharmaceutically acceptable salt thereof according to claim 1, wherein $R_5$ is selected from

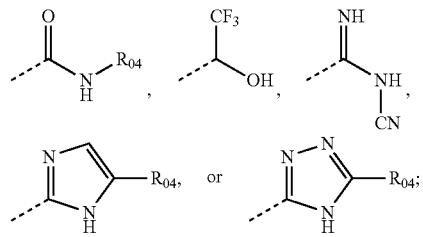

$R_{04}$ is selected from H, $C_{1-6}$ alkyl, halo $C_{1-4}$ alkyl, $C_{1-4}$ alkoxy-$C_{1-4}$ alkyl, N,N-di($C_{1-4}$ alkyl)amino-$C_{1-4}$ alkyl, hydroxy $C_{1-4}$ alkyl.

7. The compound, or the pharmaceutically acceptable salt thereof according to claim 1, wherein the structural unit

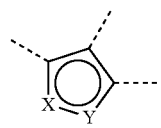

is selected from

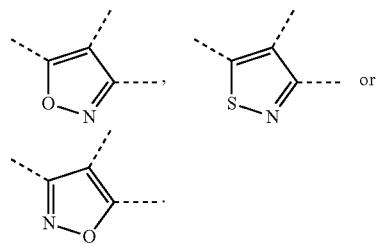

8. The compound, or the pharmaceutically acceptable salt thereof according to claim 1, wherein the structural unit

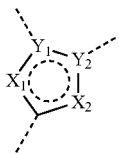

is selected from

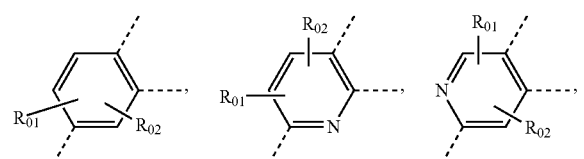

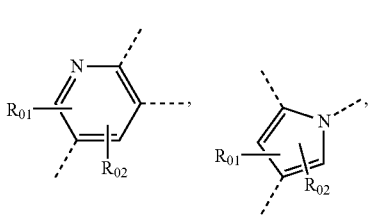

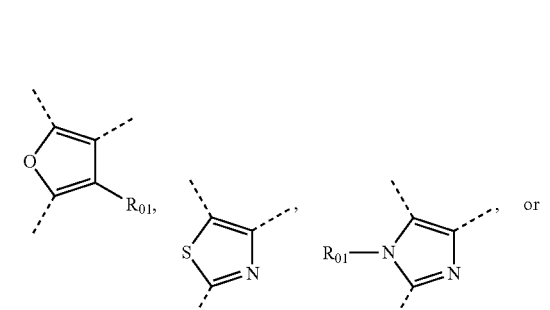

, or

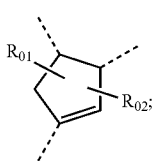

$R_{01}$ and $R_{02}$ are each independently selected from H, halogen, $C_{1-10}$ alkyl, $C_{3-10}$ cycloalkyl, $C_{1-10}$ alkyl substituted with $C_{3-10}$ cycloalkyl.

9. The compound, or the pharmaceutically acceptable salt thereof according to claim 8, wherein

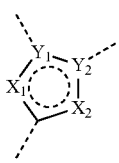

is selected from

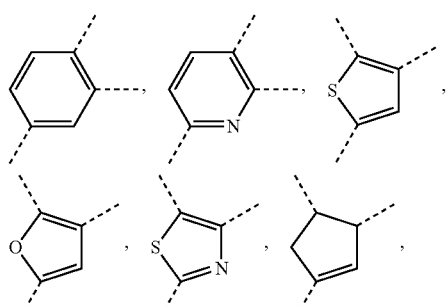

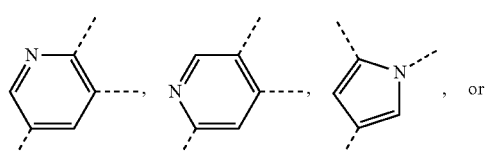

, or

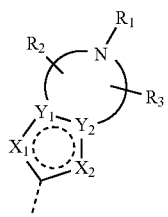

.

10. The compound, or the pharmaceutically acceptable salt thereof according to claim 1, wherein the structural unit

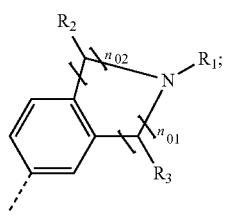

is selected from

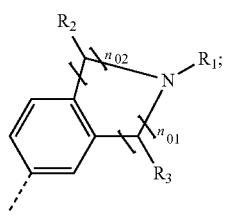

;

$n_{01}$ and $n_{02}$ are selected from 0, 1, 2 or 3, the sum of $n_{01}$ and $n_{02}$ is 2, 3 or 4, and $R_2$ and $R_3$ are not linked to form a ring.

11. The compound, or the pharmaceutically acceptable salt thereof according to claim 1, wherein the structural unit

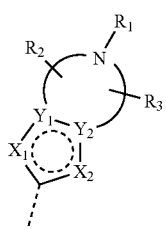
is selected from
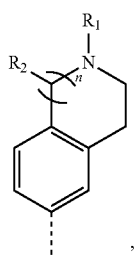,
wherein n=1 or 2.
12. The compound, or the pharmaceutically acceptable salt thereof according to claim 10, wherein the structural unit
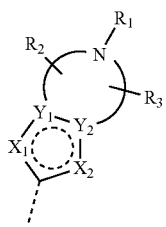
is selected from
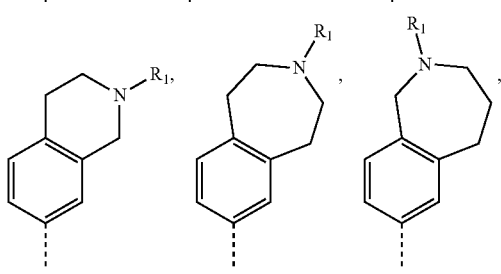
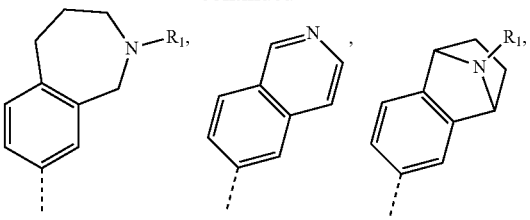
-continued
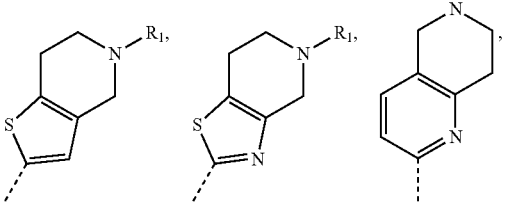
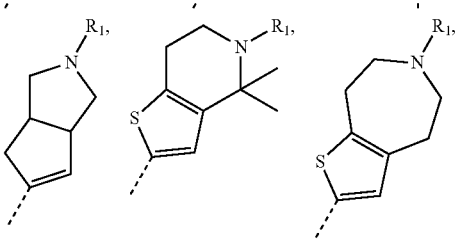
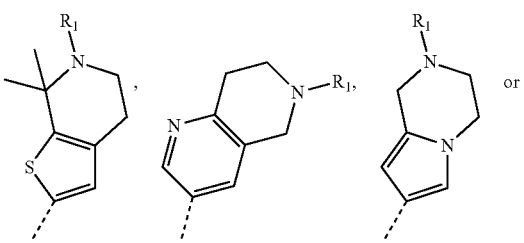 or
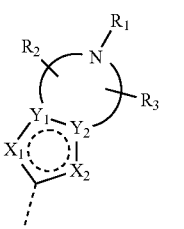
13. The compound, or the pharmaceutically acceptable salt thereof according to claim 1, wherein the structural unit
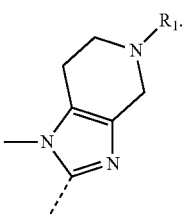

is selected from

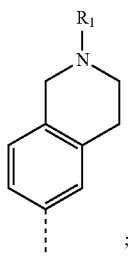

X and Y are each independently selected from N or O;

R₁ is selected from hydrogen or $C_{1-6}$ alkyl;

R₄ is selected from $C_{1-6}$ alkyl;

R₅ is selected from $C_{1-7}$ alkylaminocarbonyl.

14. The compound, or the pharmaceutically acceptable salt thereof according to claim 1, selected from the compound or the pharmaceutically acceptable salt thereof of the following structural formulas:

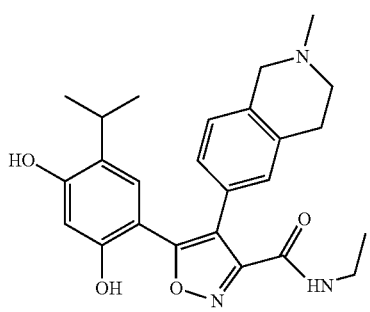

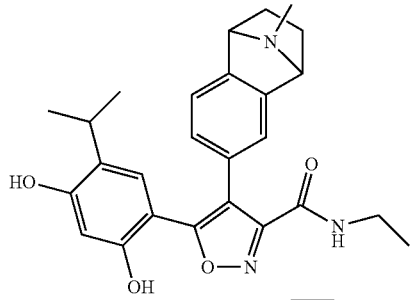

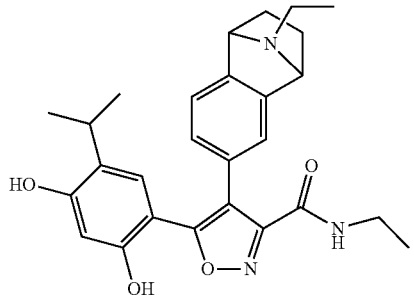

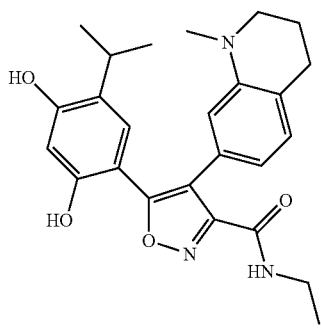

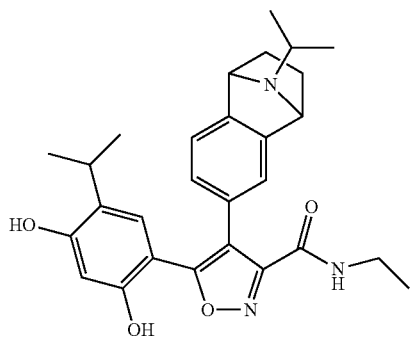

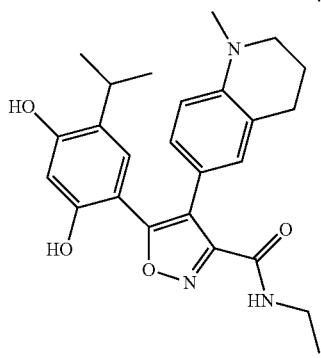

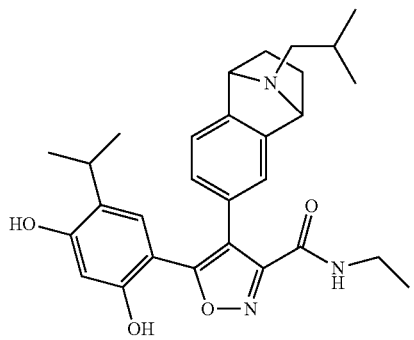

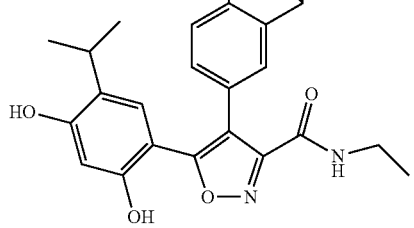

209
-continued
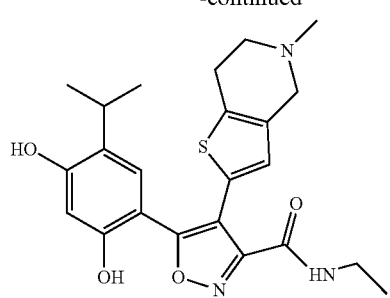
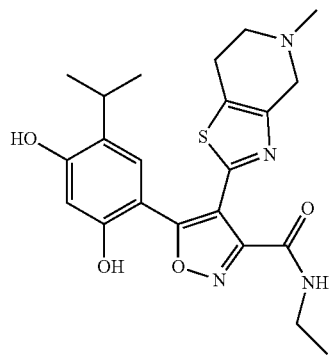
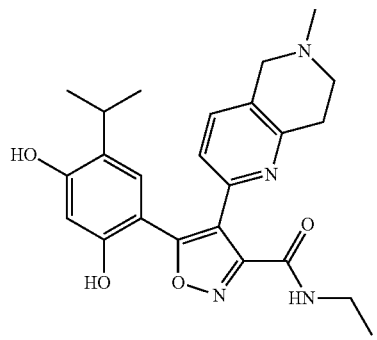
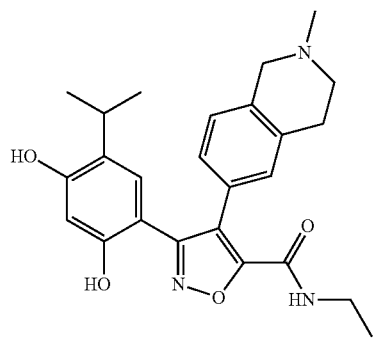
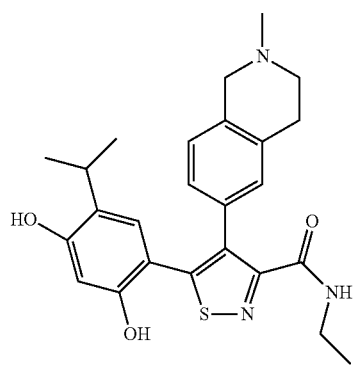
210
-continued
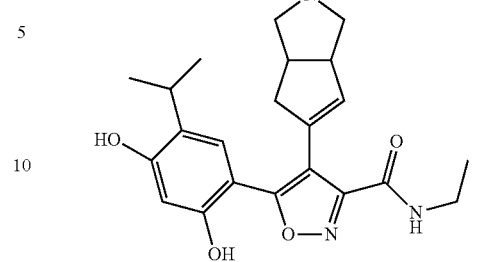
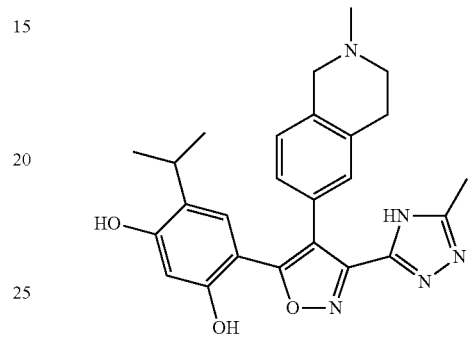
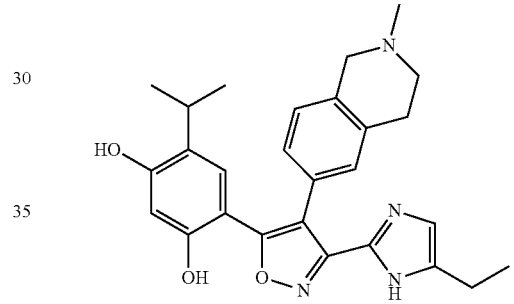
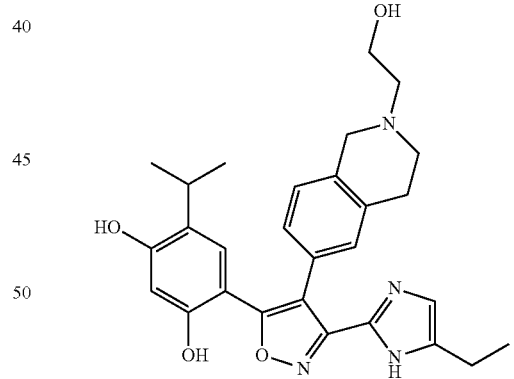

211
-continued
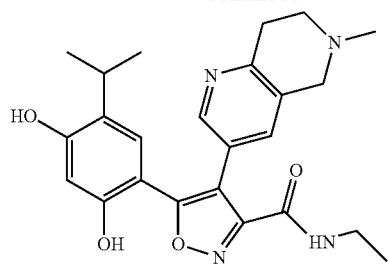
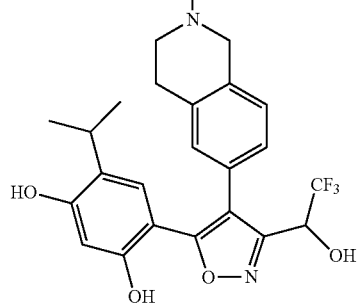
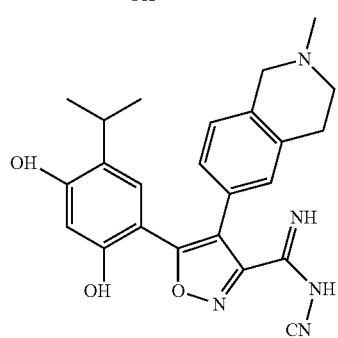
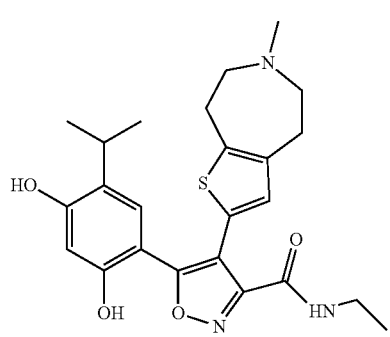
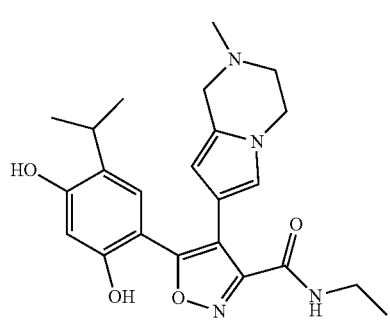
212
-continued
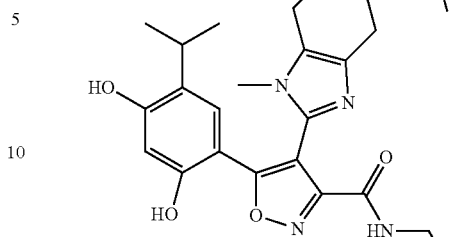
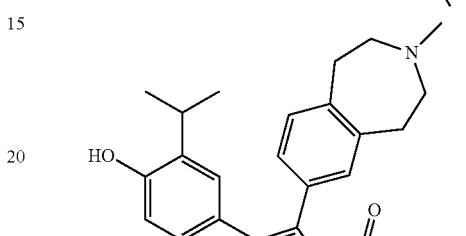
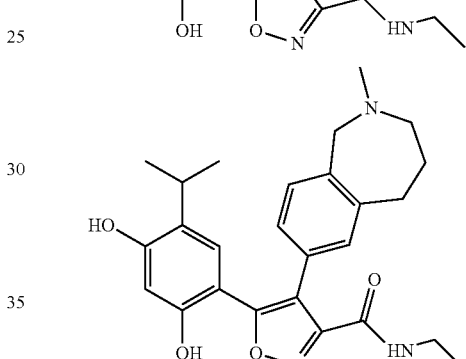
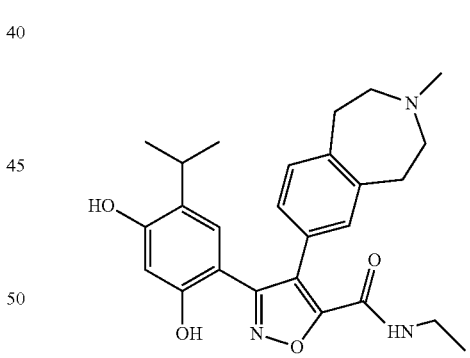
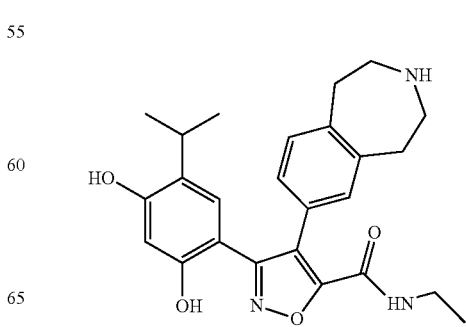

213
-continued
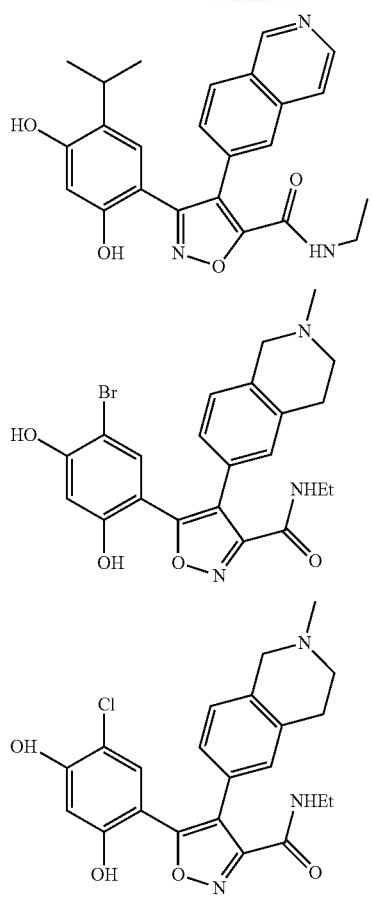
214
-continued
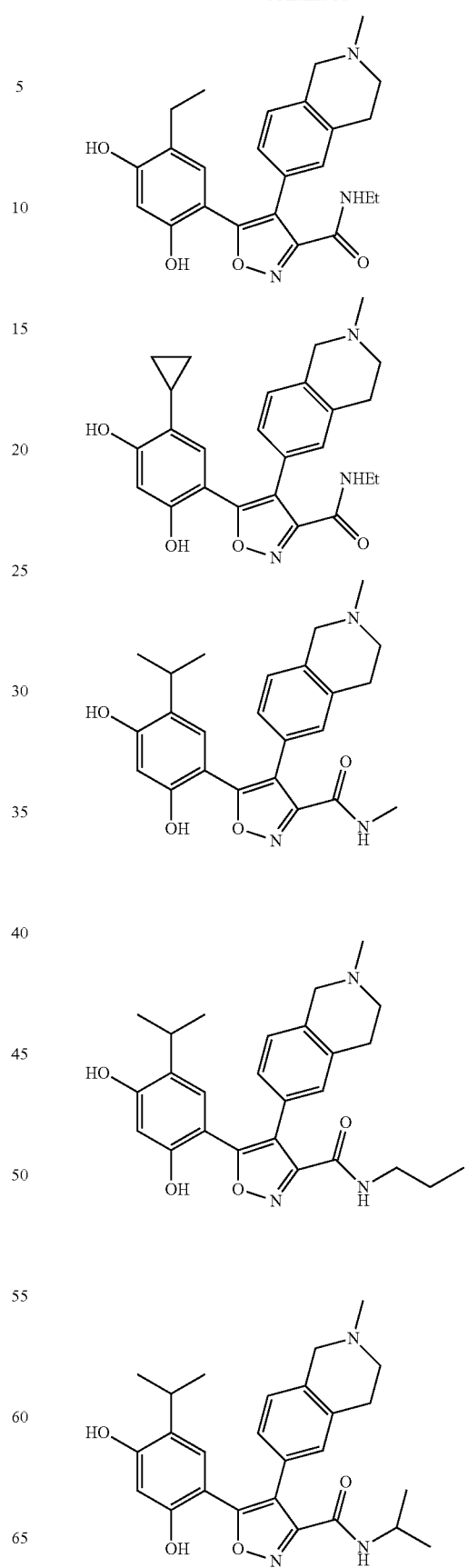

215
-continued
216
-continued
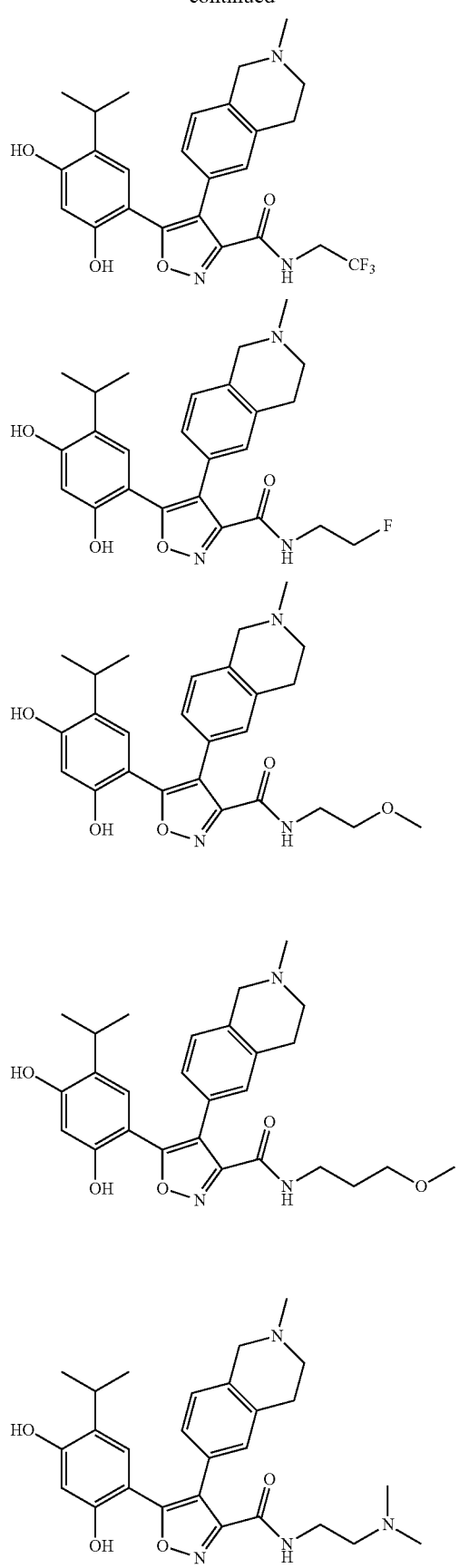
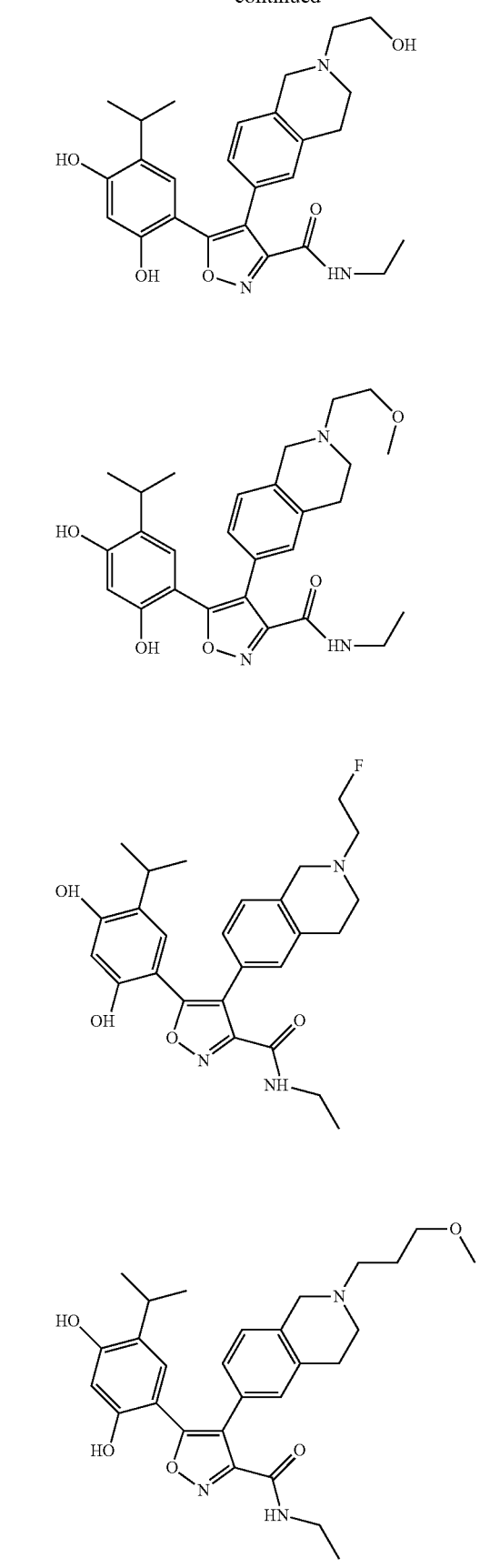

217
-continued
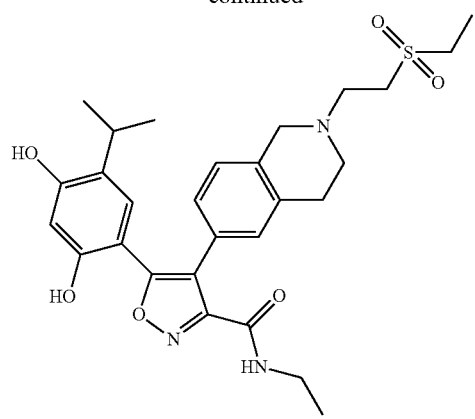
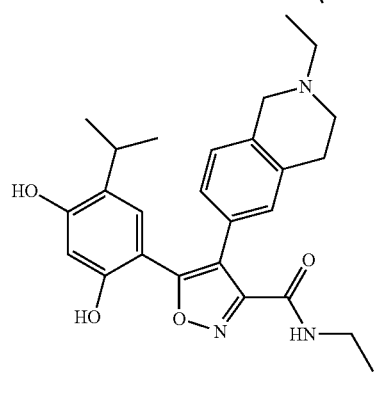
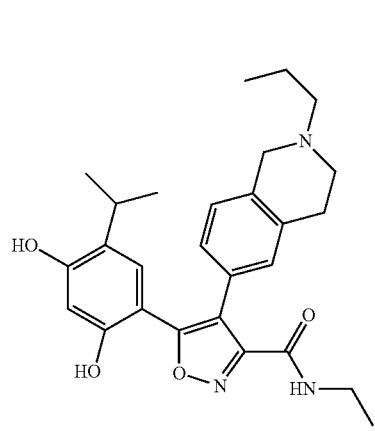
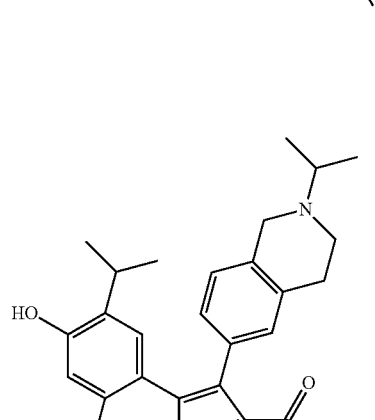
218
-continued
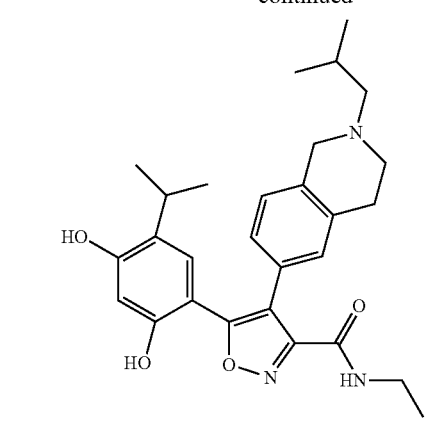
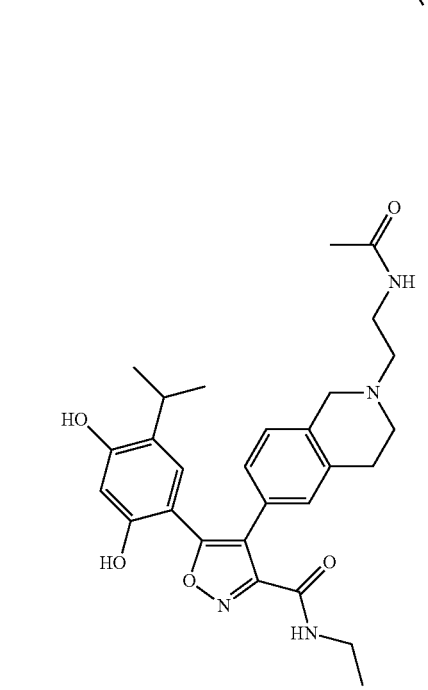
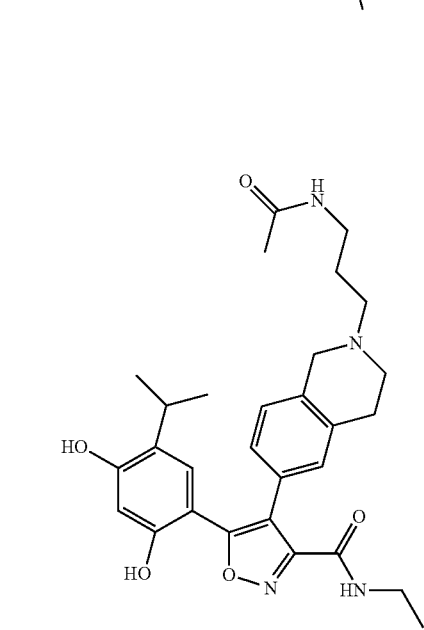

219
-continued
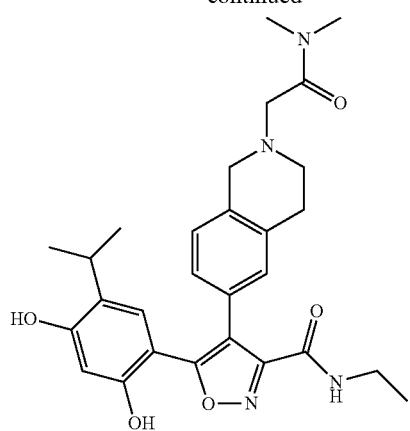
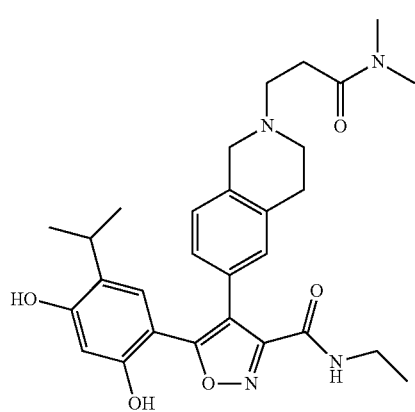
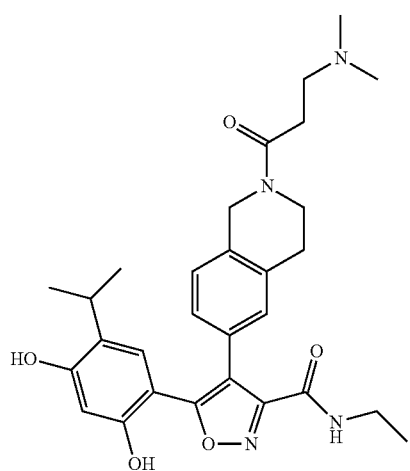
220
-continued
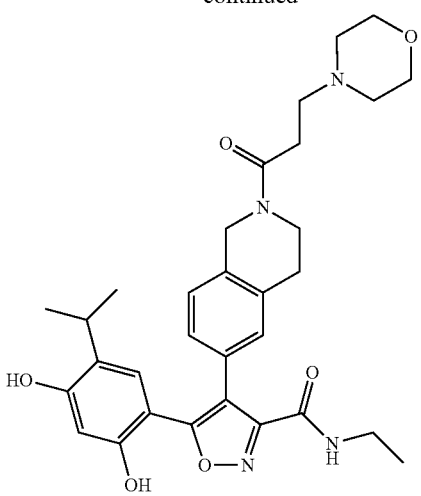
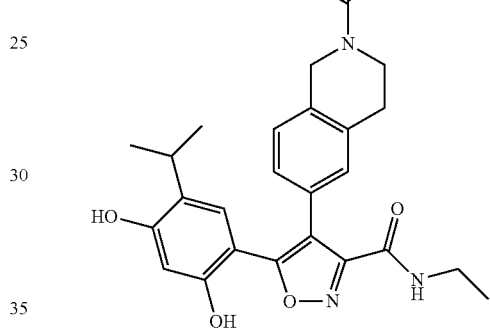
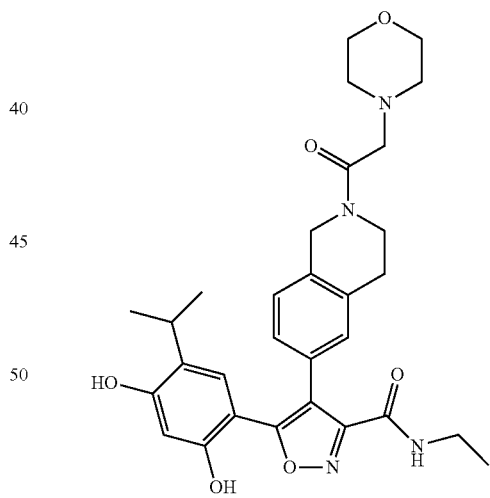
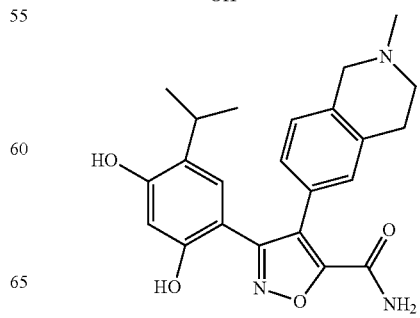

221
-continued
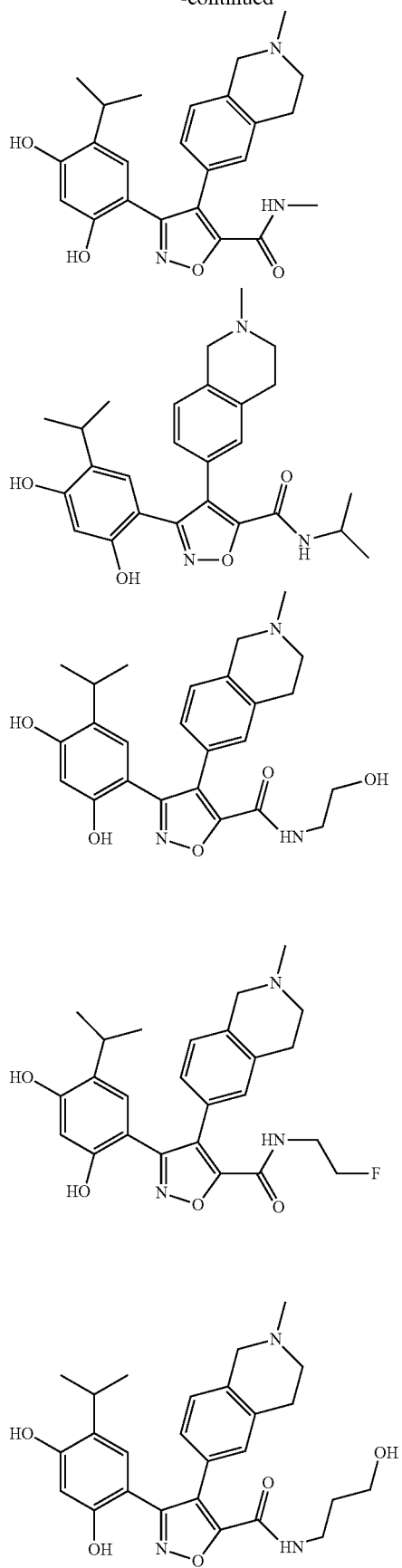
222
-continued
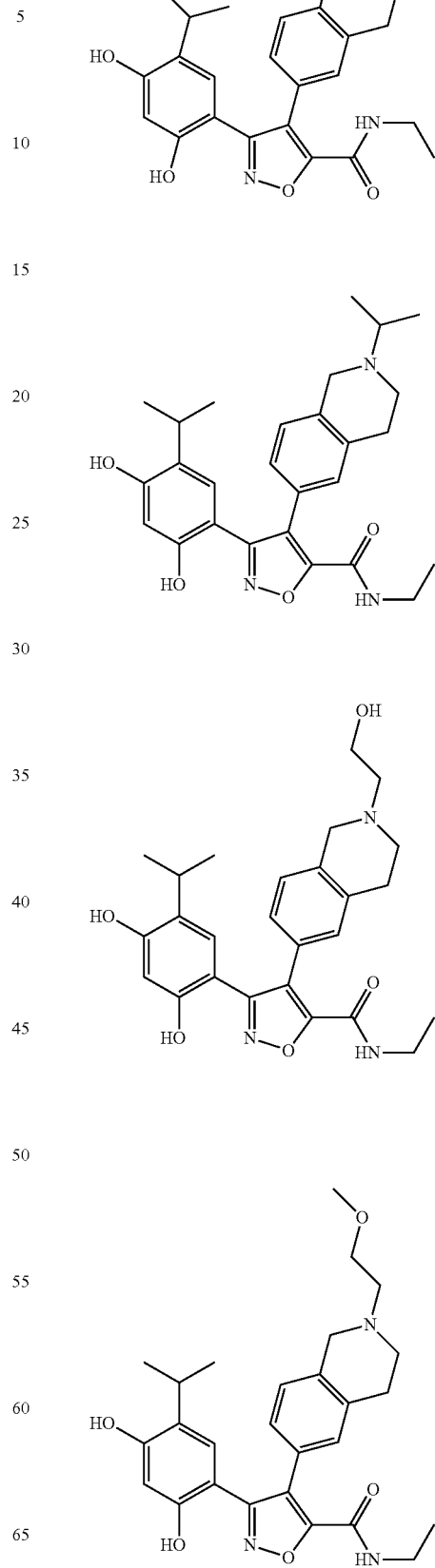

223
-continued

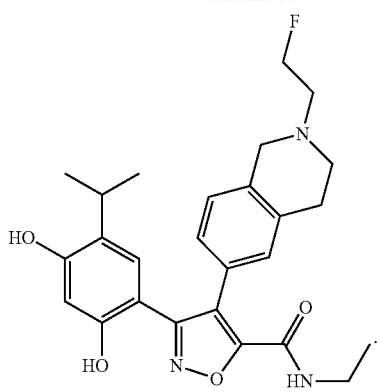

15. A method for preparing a compound of formula (I), comprising the following route:

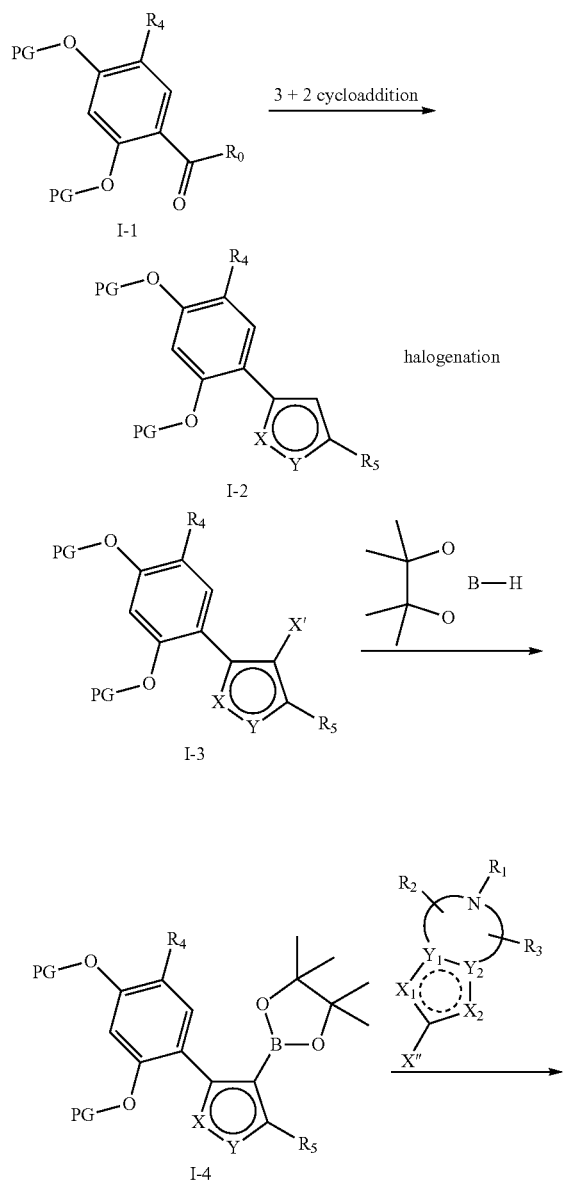

224
-continued

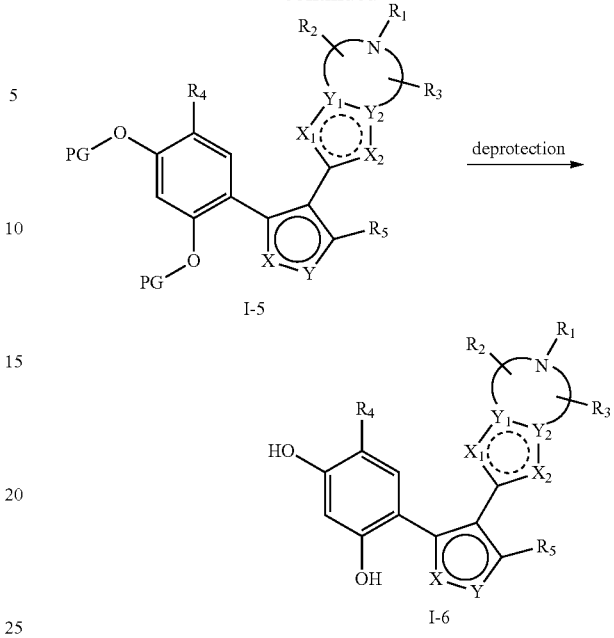

wherein
$R_0$ is selected from H, halogen, alkyl, heteroatom substituted alkyl, carboxylic acid, alkyl carboxylate;
PG is a hydroxyl-protecting group, selected from methyl, benzyl, 4-methoxybenzyl, 3,4-dimethoxybenzyl, methoxymethyl, 2-methoxyethoxymethyl, 2-tetrahydrofuryl, trimethylsilyl, triethylsilyl, triisopropylsilyl, t-butyldimethylsilyl, t-butyldiphenylsilyl, acetyl, benzoyl or pivaloyl;
X' is halogen;
X" is halogen or trifluoromethanesulfonic acid;
the other variables are defined as in claim 1.

16. A method for treating a HSP90 protein-mediated disease, the method comprising administering the compound of claim 1 to a subject in need thereof.

17. The method according to claim 16, wherein the HSP90 protein-mediated disease is selected from cancer and neurodegenerative disorders.

18. The method according to claim 17, wherein the HSP90 protein-mediated disease is cancer, the cancer being bladder cancer, breast cancer, colon cancer, kidney cancer, liver cancer, lung cancer including small cell lung cancer, esophagus cancer, gallbladder cancer, ovarian cancer, pancreatic cancer, gastric cancer, cervical cancer, thyroid cancer, prostate cancer, and skin cancer including squamous cell carcinoma; lymphoid hematopoietic tumor, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkitt's lymphoma; myeloid hematopoietic tumor, including acute and chronic myeloid leukemia, myelodysplastic syndrome and promyelocytic leukemia; mesenchyme-derived cancer including fibrosarcoma and rhabdomyosarcoma; cancer of the central and peripheral nervous system, including astrocytomas, neurocytomas, gliomas and neurilemmomas; and other cancers, including melanoma, seminoma, teratocarcinoma, osteosarcoma, xeroderma pigmentosum, keratoxanthoma, thyroid follicular carcinoma or Kaposi sarcoma.

19. The method according to claim 17, wherein the HSP90 protein-mediated disease is a neurodegenerative disorder, the neurodegenerative disorder includes Alzheimer's disease, Parkinson's disease, Huntington's disease, multiple sclerosis, or spinal and bulbar muscular atrophy.

20. The compound, or the pharmaceutically acceptable salt thereof according to claim 12, wherein, X and Y are each independently selected from N or O;

$R_1$ is selected from hydrogen, $C_{1-6}$ alkyl, hydroxyl $C_{1-6}$ alkyl, $C_{3-10}$ cycloalkyl, $C_{1-4}$ alkoxy-$C_{1-4}$ alkyl, halo $C_{1-4}$ alkyl, $C_{1-4}$ alkylsulfonyl-$C_{1-4}$ alkyl, $C_{1-4}$ alkylamido-$C_{1-4}$ alkyl, N,N-di($C_{1-4}$ alkyl)aminoacyl-$C_{1-4}$ alkyl, N,N-di($C_{1-4}$ alkyl)amino-$C_{1-4}$ alkanoyl, morpholinyl-$C_{1-4}$ alkanoyl, $C_{3-6}$ cycloalkyl-$C_{1-4}$ alkyl;

$R_4$ is selected from H, halogen, $C_{1-6}$ alkyl, $C_{3-6}$ cycloalkyl;

$R_5$ is selected from $C_{1-7}$ alkylaminocarbonyl, halo $C_{1-6}$ alkylaminocarbonyl, $C_{1-6}$ alkoxy-$C_{1-6}$ alkylaminocarbonyl, N,N-di($C_{1-6}$ alkyl)amino-$C_{1-6}$ alkylaminocarbonyl, aminocarbonyl, hydroxy $C_{1-6}$ alkylaminocarbonyl.

* * * * *